US012186376B2

(12) United States Patent
Bishai et al.

(10) Patent No.: US 12,186,376 B2
(45) Date of Patent: Jan. 7, 2025

(54) METHODS OF TREATING OR PREVENTING CANCER WITH AN AGENT THAT DEPLETES TREGS AND A CHECKPOINT INHIBITOR

(71) Applicant: THE JOHNS HOPKINS UNIVERSITY, Baltimore, MD (US)

(72) Inventors: William R. Bishai, Baltimore, MD (US); John R. Murphy, Tilghman, MD (US); Drew M. Pardoll, Brookeville, MD (US); Laurene Cheung, Baltimore, MD (US); Juan Fu, Lutherville, MD (US); Pankaj Kumar, New Delhi (IN); Amit Kumar, Baltimore, MD (US); Sadiya Parveen, Baltimore, MD (US); Cynthia Korin Bullen, Baltimore, MD (US); Vijayan Sambasivam, Puducherry (IN); Sumit Siddharth, Baltimore, MD (US); Dipali Sharma, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1027 days.

(21) Appl. No.: 16/978,949

(22) PCT Filed: Mar. 6, 2019

(86) PCT No.: PCT/US2019/020959

§ 371 (c)(1),
(2) Date: Sep. 8, 2020

(87) PCT Pub. No.: WO2019/173478

PCT Pub. Date: Sep. 12, 2019

(65) Prior Publication Data

US 2022/0023395 A1 Jan. 27, 2022

Related U.S. Application Data

(60) Provisional application No. 62/639,199, filed on Mar. 6, 2018.

(51) Int. Cl.
*A61K 39/395* (2006.01)
*A61K 38/20* (2006.01)
(Continued)

(52) U.S. Cl.
CPC .......... *A61K 38/45* (2013.01); *A61K 38/2013* (2013.01); *A61K 39/3955* (2013.01);
(Continued)

(58) Field of Classification Search
None
See application file for complete search history.

(56) References Cited

U.S. PATENT DOCUMENTS 5,399,363 A 3/1995 Liversidge et al.
5,466,468 A 11/1995 Schneider et al.
(Continued)

FOREIGN PATENT DOCUMENTS

WO WO 2013/148695 A1 10/2013
WO WO 2014/093240 A1 6/2014
(Continued)

OTHER PUBLICATIONS

EP Extended Search Report in European Application No. EP19764867, dated Nov. 9, 2021, 7 pages.
(Continued)

*Primary Examiner* — Michael D Pak
(74) *Attorney, Agent, or Firm* — DLA Piper LLP (US)

(57) ABSTRACT

The present invention is related to a method of treating or preventing cancer in a subject comprising administering to a subject having cancer or prone of getting cancer a first agent that depletes the subject's regulatory T cells (Tregs);
(Continued)

*toxO* sequence and mutations a) Mutant *toxO* in this invention report:

TTAGGATAGCTAAGTCCAT (altered bases shown in red)

b) Wild type *toxO*

TTAGGATAGCTTTACCTAA 19 bp imperfect palindrome around the large C followed by administering to the subject a second agent comprising a checkpoint inhibitor.

9 Claims, 238 Drawing Sheets

Specification includes a Sequence Listing.

(51) Int. Cl.
*A61K 38/45* (2006.01)
*A61P 35/00* (2006.01)
*C07K 16/28* (2006.01)

(52) U.S. Cl.
CPC .......... *A61P 35/00* (2018.01); *C07K 16/2818* (2013.01); *C12Y 204/02036* (2013.01)

(56) References Cited

U.S. PATENT DOCUMENTS

| | | | | |
|---|---|---|---|---|
| 5,543,158 | A | 8/1996 | Gref et al. | |
| 5,580,579 | A | 12/1996 | Ruddy et al. | |
| 5,629,001 | A | 5/1997 | Michael et al. | |
| 5,641,515 | A | 6/1997 | Ramtoola | |
| 5,725,871 | A | 3/1998 | Illum | |
| 5,756,353 | A | 5/1998 | Debs | |
| 5,780,045 | A | 7/1998 | Mcquinn et al. | |
| 5,792,451 | A | 8/1998 | Sarubbi et al. | |
| 5,804,212 | A | 9/1998 | Illum | |
| 6,613,308 | B2 | 9/2003 | Bartus et al. | |
| 8,865,866 | B2 | 10/2014 | Harrison et al. | |
| 2016/0030526 | A1 * | 2/2016 | Wang | A61K 45/06 435/254.2 |
| 2017/0233473 | A1 | 8/2017 | Cojocaru et al. | |

FOREIGN PATENT DOCUMENTS

| | | | |
|---|---|---|---|
| WO | 2016187122 | A1 | 11/2016 |
| WO | 2017156356 | A1 | 9/2017 |

OTHER PUBLICATIONS

Kotasek, et al., Mechanism of cultured endothelial injury induced by lymphokine-activated killer cells. Cancer Res. Oct. 1, 1988;48(19):5528-32.

Baluna, et al., Evidence for a structural motif in toxins and interleukin-2 that may be responsible for binding to endothelial cells and initiating vascular leak syndrome. Proc Natl Acad Sci U S A. Mar. 30, 1999; 96(7): 3957-3962.

Chen, et al., Regulatory T cells suppress tumor-specific CD8 T cell cytotoxicity through TGF-beta signals in vivo. Proc Natl Acad Sci U S A. Jan. 11, 2005;102(2):419-24.

Jang, et al., Crosstalk between Regulatory T Cells and Tumor-Associated Dendritic Cells Negates Anti-tumor Immunity in Pancreatic Cancer. Cell Rep. Jul. 18, 2017;20(3):558-571.

Ton-That, et al., Assembly of pili on the surface of Corynebacterium diphtheriae. Mol Microbiol. Nov. 2003;50(4):1429-38.

Allen, et al., HtaA is an iron-regulated hemin binding protein involved in the utilization of heme iron in Corynebacterium diphtheriae. J Bacteriol. Apr. 2009;191(8):2638-48.

Schafer, et al., Small mobilizable multi-purpose cloning vectors derived from the *Escherichia coli* plasmids pK18 and pK19: selection of defined deletions in the chromosome of Corynebacterium glutamicum. Gene. Jul. 22, 1994;145(1):69-73.

Rasku, et al., Transient T cell depletion causes regression of melanoma metastases. J Transl Med. 2008; 6: 12.

Topalian, et al., Safety, activity, and immune correlates of anti-PD-1 antibody in cancer. N Engl J Med. Jun. 28, 2012;366(26):2443-54.

Mandai, et al., Dual Faces of IFNγ in Cancer Progression: A Role of PD-L1 Induction in the Determination of Pro-and Antitumor Immunity. Clin Cancer Res. May 15, 2016;22(10):2329-34.

Erdag, et al., Immunotype and immunohistologic characteristics of tumor-infiltrating immune cells are associated with clinical outcome in metastatic melanoma. Cancer Res. Mar. 1, 2012;72(5):1070-80.

Padron, et al., Age effects of distinct immune checkpoint blockade treatments in a mouse melanoma model. Exp Gerontol. May 2018;105:146-154.

Gupta, et al., Suppressor Cell-Depleting Immunotherapy With Denileukin Diftitox is an Effective Host-Directed Therapy for Tuberculosis. J Infect Dis. Jun. 15, 2017;215(12):1883-1887.

Dey, et al., Inhibition of innate immune cytosolic surveillance by an M. tuberculosis phosphodiesterase. Nat Chem Biol. Feb. 2017;13(2):210-217.

Maiga, et al., Efficacy of Adjunctive Tofacitinib Therapy in Mouse Models of Tuberculosis. EBioMedicine. Aug. 2015;2(8):868-873.

Manoukian, et al., Denileukin diftitox: a novel immunotoxin. Expert Opin Biol Ther. Nov. 2009;9(11):1445-51.

Lansigan, et al., Role of denileukin diftitox in the treatment of persistent or recurrent cutaneous T-cell lymphoma. Cancer Manag Res. Feb. 5, 2010;2:53-9.

Olsen, et al., Pivotal phase III trial of two dose levels of denileukin diftitox for the treatment of cutaneous T-cell lymphoma. J Clin Oncol. Jan. 15, 2001;19(2):376-88.

Green, et al., CD4(+) regulatory T cells in a cynomolgus macaque model of *Mycobacterium tuberculosis* infection. J Infect Dis. Aug. 15, 2010;202(4):533-41.

Knol, et al., Prognostic value of tumor-infiltrating Foxp3+ T-cell subpopulations in metastatic melanoma. Exp Dermatol. May 2011;20(5):430-4.

Litzinger, et al., IL-2 immunotoxin denileukin diftitox reduces regulatory T cells and enhances vaccine-mediated T-cell immunity. Blood. Nov. 1, 2007;110(9):3192-201.

Gajewski, et al., Innate and adaptive immune cells in the tumor microenvironment. Nat Immunol. Oct. 2013;14(10):1014-22.

Hurez, et al., Mitigating age-related immune dysfunction heightens the efficacy of tumor immunotherapy in aged mice. Cancer Res. Apr. 15, 2012;72(8):2089-99.

Telang, et al., Phase II trial of the regulatory T cell-depleting agent, denileukin diftitox, in patients with unresectable stage IV melanoma. BMC Cancer. Dec. 13, 2011;11:515.

Pardoll, The blockade of immune checkpoints in cancer immunotherapy. Nat Rev Cancer. Mar. 22, 2012;12(4):252-64.

Topalian, et al., Targeting the PD-1/B7-H1(PD-L1) pathway to activate anti-tumor immunity. Curr Opin Immunol. Apr. 2012;24(2):207-12.

JP Report on Reconsideration before Appeal Proceedings in Japanese Application No. 2023-020984, dated Mar. 8, 2024, 3 pages (with English translation).

* cited by examiner

FIG. 1 *toxO* sequence and mutations a) Mutant *toxO* in this invention report:

TTAGGATAGCTAAGTCCAT (altered bases shown in red)

b) Wild type *toxO*

TTAGGATAGCTTTACCTAA 19 bp imperfect palindrome around the large C

FIG. 2 Addition of the *tox* promoter, mutant *tox* operator, and signal sequence in pKN2.6Z-LC127 a) Classic denileukin diftitox (c-denileukin diftitox) expression vector

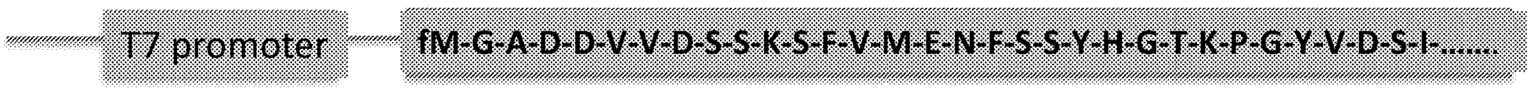

Classic Ontak® (c-Ontak®): Ontak® expressed in inclusion body form in the cytosol of recombinant *E. coli*. Must be denatured and refolded in the presence of Tween 20 to be active.

b) Secreted denileukin diftitox (s-denileukin difitox)expression vector

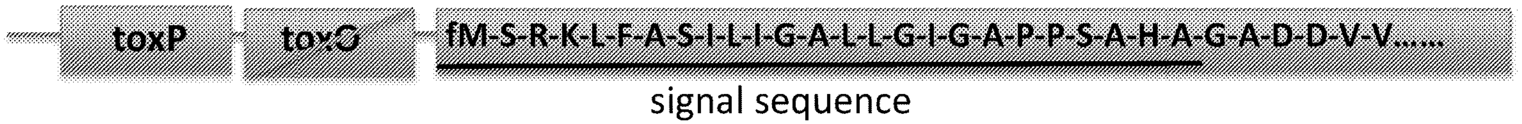

Secreted Ontak® (s-Ontak®): expressed as a secreted protein (i) into the periplasm of recombinant *E. coli*, or (ii) into the spent culture medium of recombinant *C. diphtheriae*, C7s(-)tox-, as a fully folded biologically active protein. The red slash indicates that the *toxO* operator sequence has been mutated to prevent DtxR repressor binding. The mutant *toxO* enables constitutive, iron-independent expression of the downstream gene.

c-denileukin diftitox-VLM : decreased vascular leak c-denileukin diftitox-VLM does not cause vascular leakage *in vitro*

FIG. 5 c-denileukin diftitox-VLM: Safety and Tolerability
c-denileukin diftitox-VLM has significantly less acute toxicity *in vivo* than c-denileukin diftitox
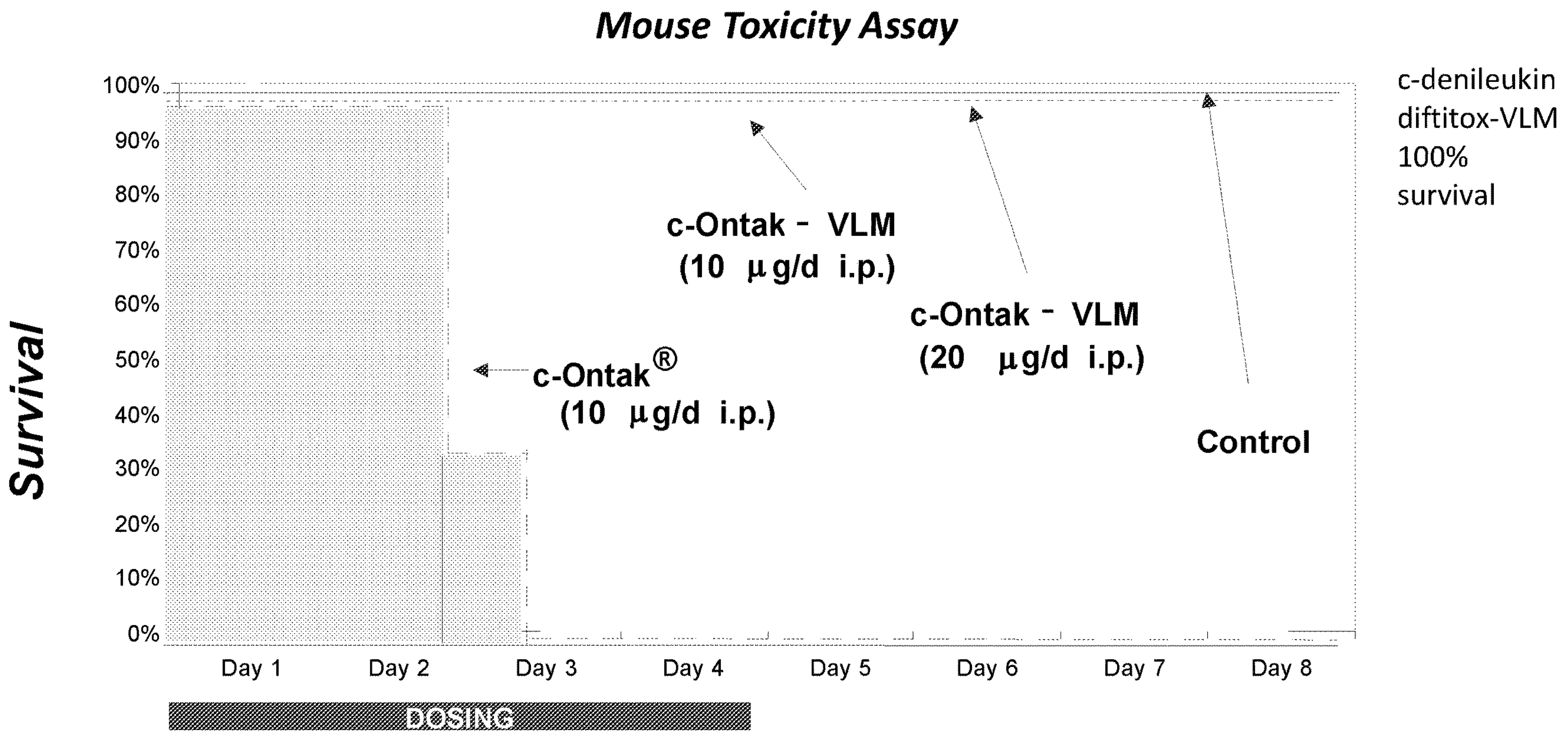

FIG. 6 Diphtheria toxin-based fusion protein toxin platform technology
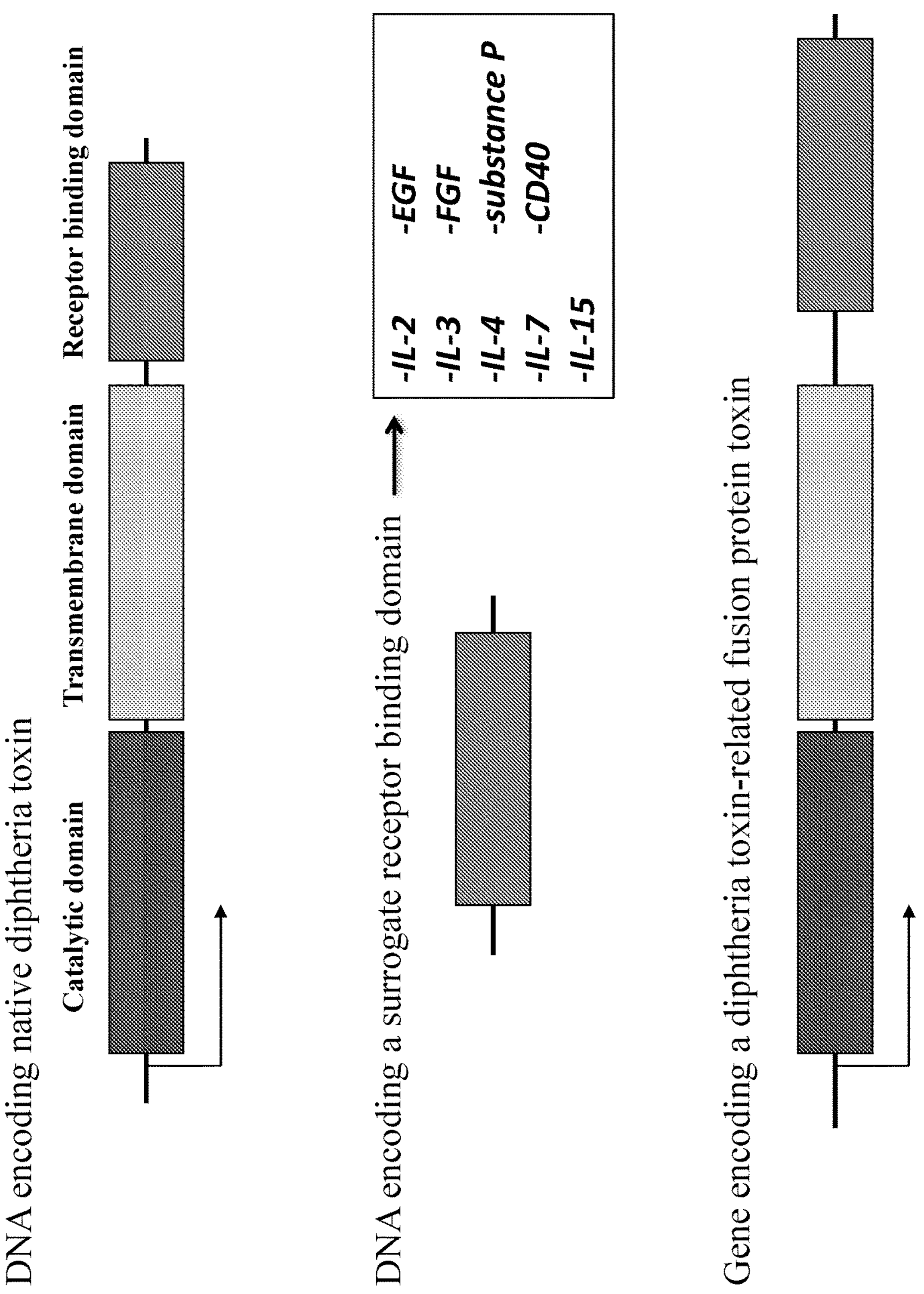
DNA encoding native diphtheria toxin
Catalytic domain | Transmembrane domain | Receptor binding domain
DNA encoding a surrogate receptor binding domain →
-IL-2     -EGF
-IL-3     -FGF
-IL-4     -substance P
-IL-7     -CD40
-IL-15
Gene encoding a diphtheria toxin-related fusion protein toxin

FIG. 7 Construct to express s-denileukin diftitox from *Corynebacterium diphtheriae* as a secreted protein into the culture medium in an iron-independent manner
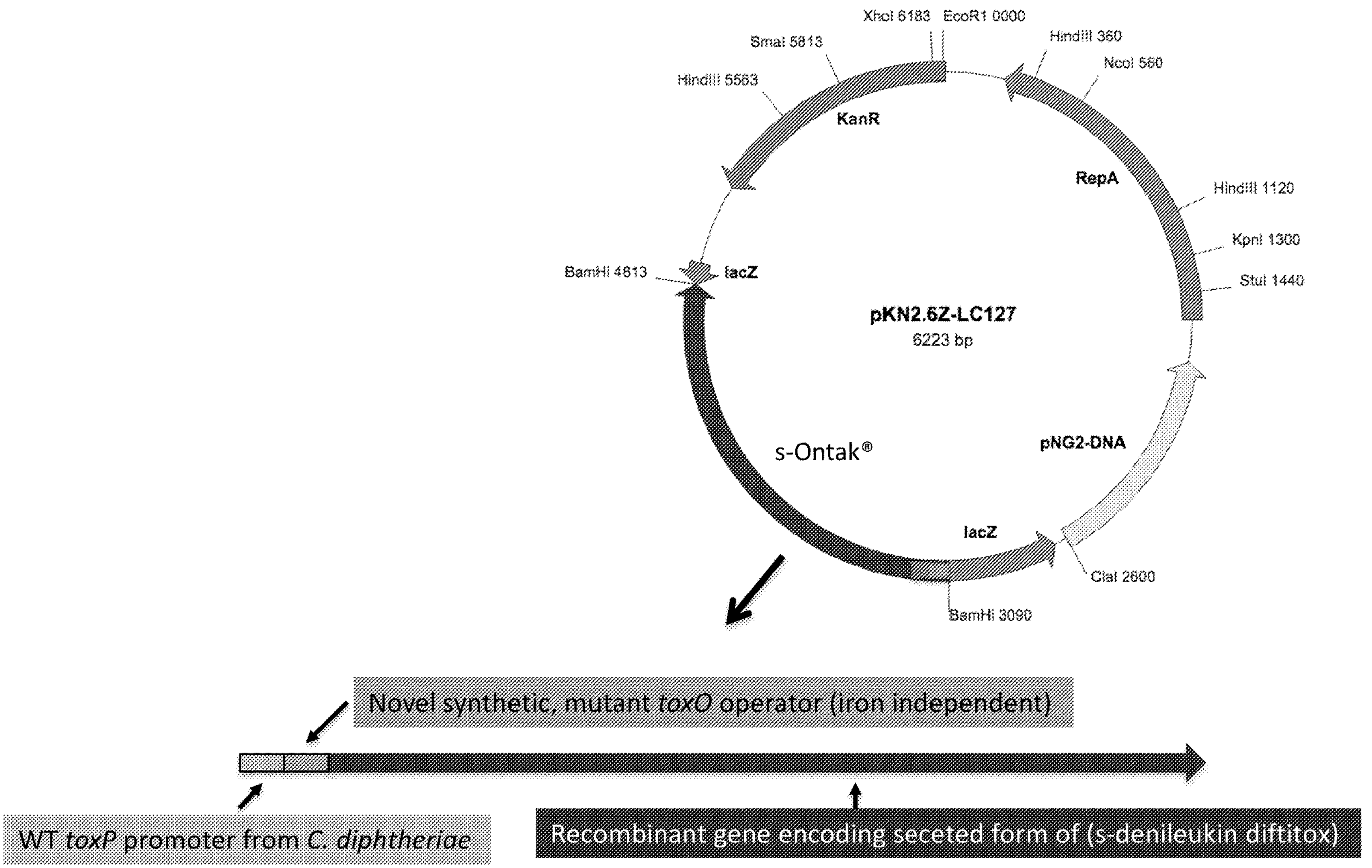

FIG. 8: Addressing the problems of inclusion body formation, denaturation, and refolding required for c-denileukin diftitox production a.

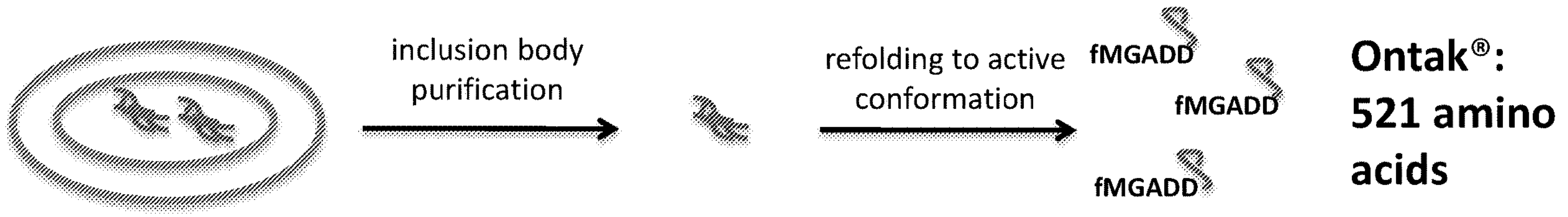

Ontak® is expressed in the *E. coli* cytoplasm and forms inclusion bodies; these must be denatured and refolded. Residual DNA, detergent, and protein aggregates are a limitation. Ontak® is 521 amino acids in length. Blue ovals indicate the gram-negative envelope of *E. coli.* fMGADD represent the first 5 amino acids of the N-terminus of Ontak®.

b.

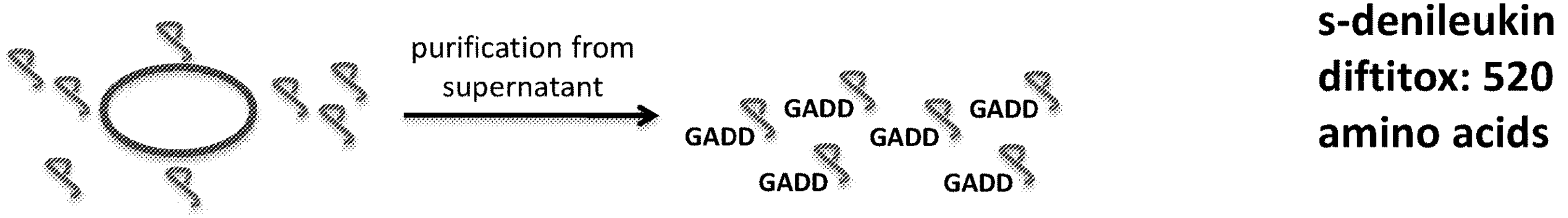

s-denileukin diftitox is expressed by *C. diphtheriae* as a secreted protein into the cell free culture supernatant fluid in biologically active form. Mature s-denileukin diftitox is 520 amino acids in length. Red oval indicates the gram-positive envelop of *C. diphtheriae.* GADD represent the first 4 amino acids of the N-terminus of s-denileukin diftitox of the present invention.

FIG. 9 s-denilekin diftitox: expressed as a secreted protein into the culture medium of *Corynebacterium diphtheriae* strain C7(-) *tox*-
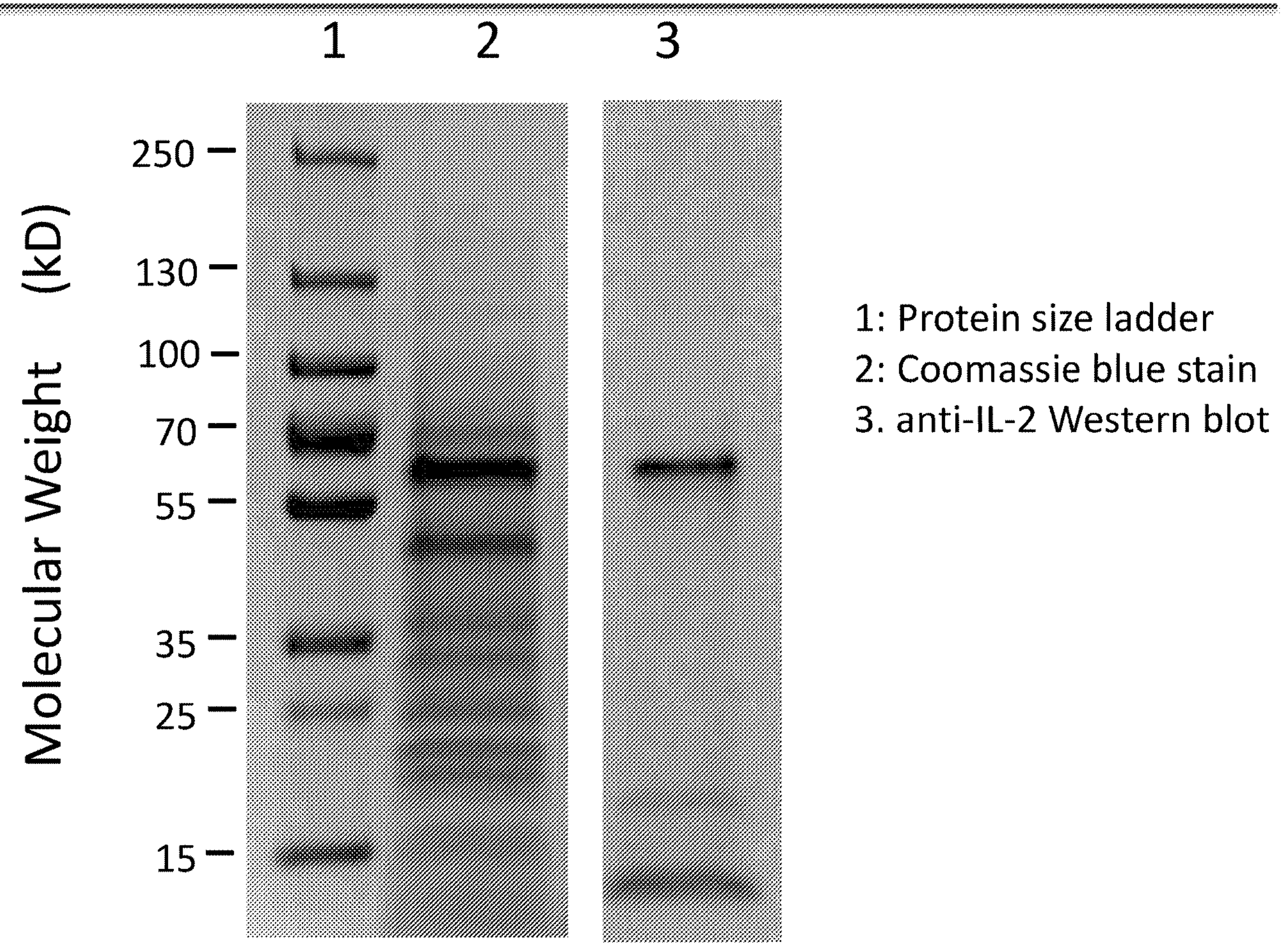
supernatant was concentrated 10x and 23 microliters of concentrate was loaded onto the gel FIG. 10 Ontak® ($DAB_{389}$IL-2) is expected to deplete IL-2R-bearing (CD25+) T cells ($T_{regs}$) within the tuberculous granuloma. $T_{regs}$ are immunosuppressive by their inhibition of $T_{eff}$ cells
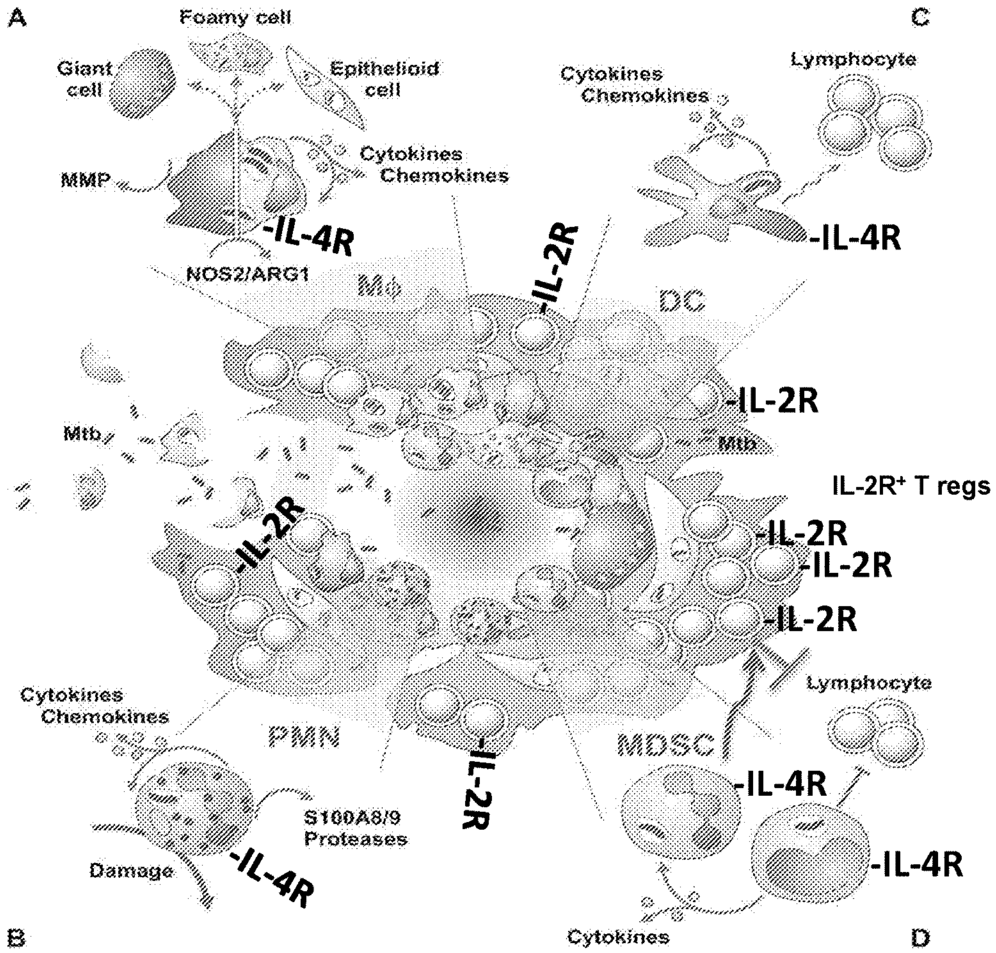

FIG 11. ONTAK for TB. Mouse TB Model. Experimental Scheme

| Treatment | Week 0 No. of mice sacrificed for CFU counts | Week 2 No. of mice sacrificed for CFU counts | Week 5 No. of mice sacrificed for CFU counts |
|---|---|---|---|
| Grp 1. No treatment | 5 | 5 | 5 |
| Grp 2. Ont-2x IP | 5 | 5 | 5 |
| Grp 3. Ont-2x IV | | 5 | 5 |
| Grp 4. Ont-1x IP | | 5 | 5 |
| Grp 5. RHZ | | | 5 |
| Grp 6. RHZ + Ont-1x IP | | | 5 |

Mice were infected with *M. tb.* strain H37Rv by aerosol infection giving an initial implantation of ~2.8 $log_{10}$ CFU counts in lungs on day 0. The groups of mice were treated with 750 ng of c-denileukin diftitox intraperitoneally (IP) or intravenously (IV) as one treatment cycle (1x, dosed at week 2 post-infection) or two treatment cycles (2x, dosed at ~day 3 pre-infection and week 2 post-infection). A treatment cycle of c-denileukin diftitox is defined as 35 μg/kg (750 ng for a typical mouse) given two times, two days apart. RHZ daily treatment by oral gavage was started at week 2. R = rifampin 10 mg/kg, H = isoniazid 10 mg/kg, Z = pyrazinamide 150 mg/kg.

FIG. 12 Ontak to treat TB. Mouse TB Model
Lung CFUs during treatment with different ONTAK regimens
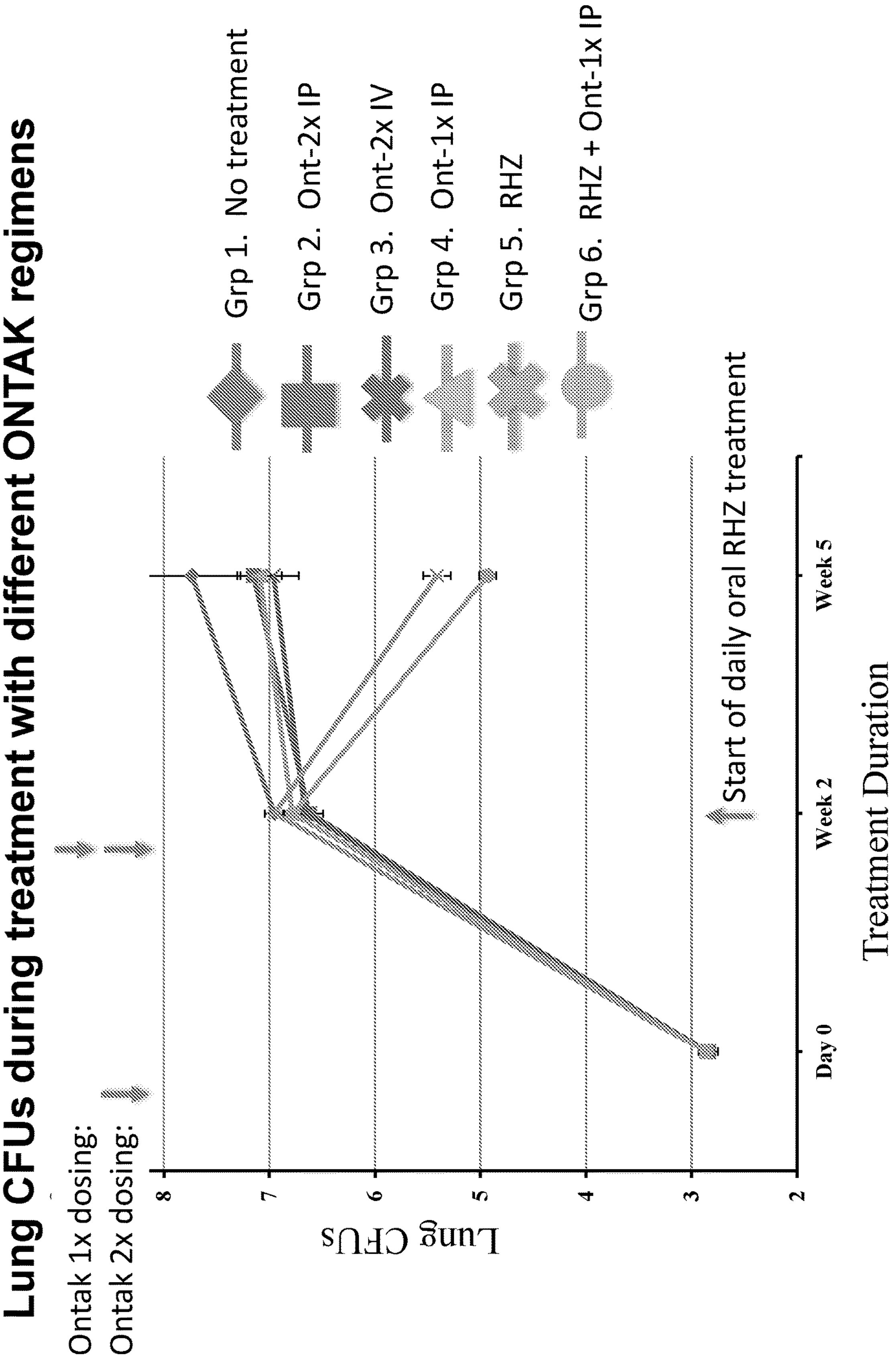

FIG 13. Ontak to treat TB. Mouse TB Model

Lung CFUs during treatment with different c-denileukin diftitox regimens

Data from Figure 12 with just Group 1 (no treatment) and Group 4 (c-denileukin diftitox 1x or one treatment cycle as monotherapy IP at week 2 post-infection)

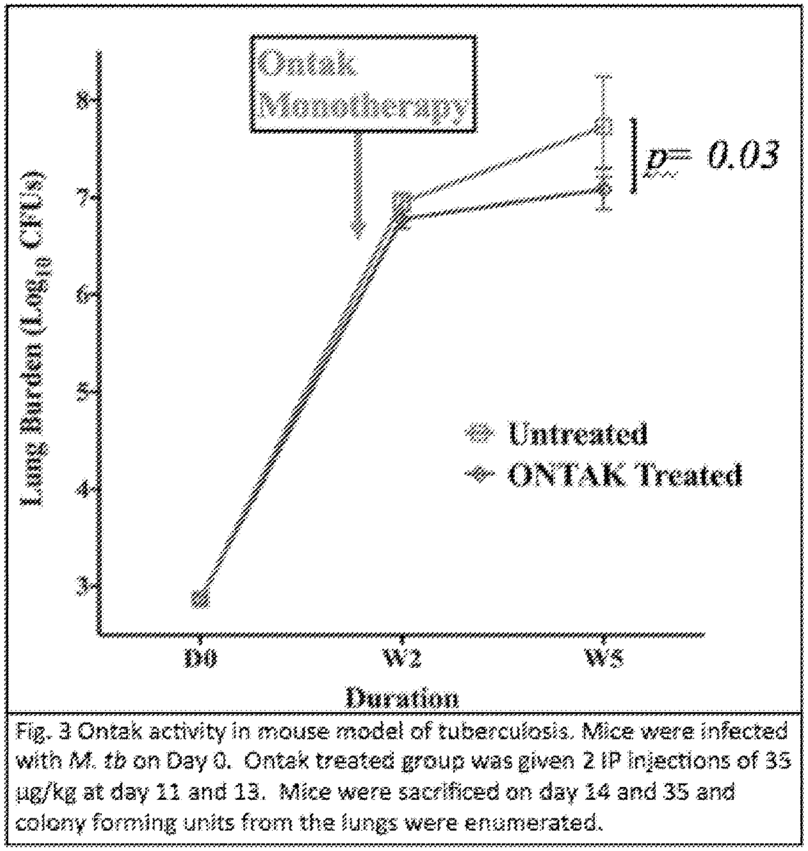

Fig. 3 Ontak activity in mouse model of tuberculosis. Mice were infected with *M. tb* on Day 0. Ontak treated group was given 2 IP injections of 35 µg/kg at day 11 and 13. Mice were sacrificed on day 14 and 35 and colony forming units from the lungs were enumerated.

FIG. 14 c-denileukin diftitox as an immunotherapeutic agent: Malignant Melanoma
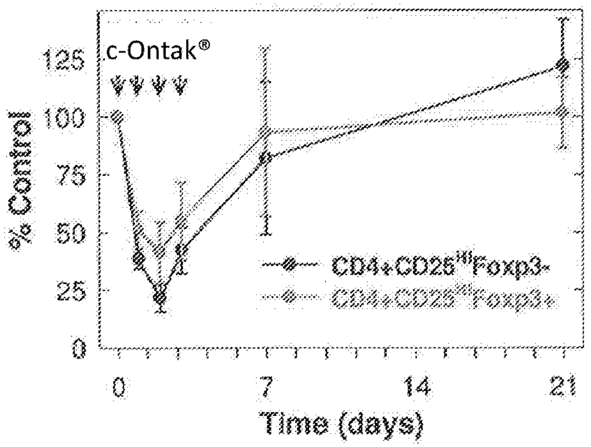
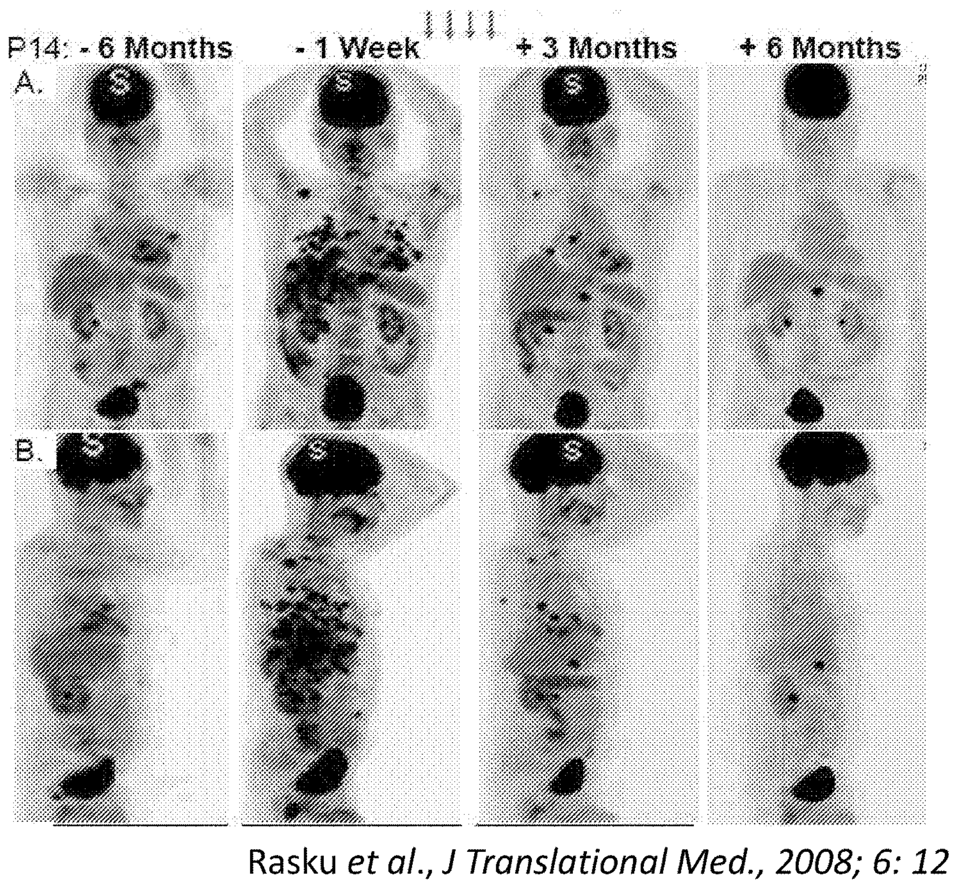
Rasku *et al.*, *J Translational Med., 2008; 6: 12*
1 cycle = 12 μg/kg QD x 4; rest 21 days

FIG. 15 Ontak production: His tag
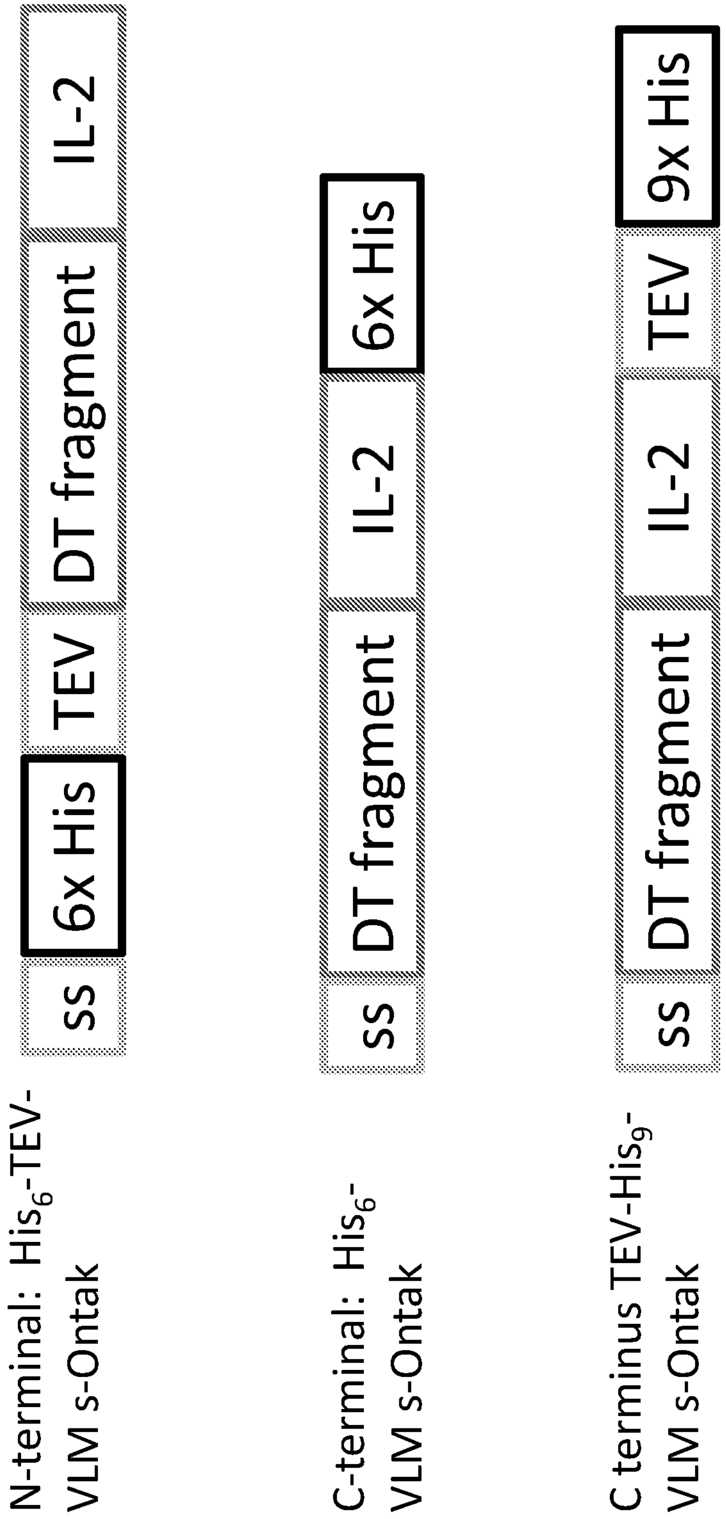

FIG 16. *VLM s-Ontak:*
*Purification to > 97% with C-terminal His6-tagged VLM s-Ontak*
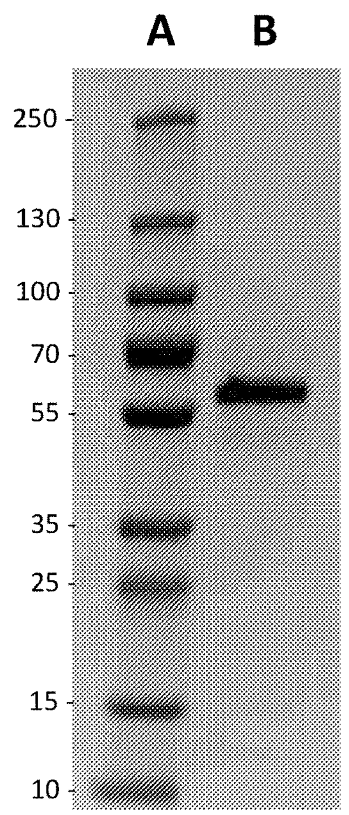
Coomassie-Blue stained SDS-PAGE
A. Molecular Weight Standards
B. purified VLM s-Ontak

Purified s-Ontak-$His_6$ (*C. diphtheriae*-derived)

Lanes

1 MW markers
2 Purified s-Ontak-$His_6$ (58kDa). Immediately after thaw. >97% pure.
3 Purified s-Ontak-$His_6$ (58kDa). Thawed, kept at 4°C for 3 days. >97% pure.

SDS-PAGE with Coomassie-blue staining

Purified VLM s-Ontak-$His_6$ (*C. diphtheriae*-derived)

SDS-PAGE with Coomassie-blue staining

Lanes

1 MW markers
2 Concentrated culture supernatant
3 Ni-column flow-through
4 Ni-column eluate with imidazole
5-6 S-100 gel filtration purified fractions

*C. diphtheriae*-derived SEQ ID NO: 43 shows reduced vascular leak by HUVEC monolayer permeation test C. *diphtheriae*-derived SEQ ID NO: 43 shows improved safety by mouse lethality & tolerability study Daily dosing of mice with
*C. diphtheriae*-derived SEQ ID NO: 43 or
*C. diphtheriae*-derived SEQ ID NO: 58

Abbreviations: *Cd*-der. = *C. diphtheriae*-derived

FIG. 22

*C. diphtheriae*-derived SEQ ID NO: 43 (V6A) is equivalent to *E. coli*-derived SEQ ID NO: 10 in *in vitro* cell killing and is equivalent to *C. diphtheriae*-derived SEQ ID NO: 58 in melanoma tumor growth inhibition *in vivo*

| $IC_{50}$ *in vitro* (pM) | |
|---|---|
| *Cd*-der. SEQ ID NO: 43 | *Ec*-der. SEQ ID NO: 10 |
| 3.5* | 1.8** |

*mean of 3 determinations
**mean of 2 determinations

Abbreviations:
*Cd*-der. = *C. diphtheriae*-derived
*Ec*-der. = *E. coli*-derived

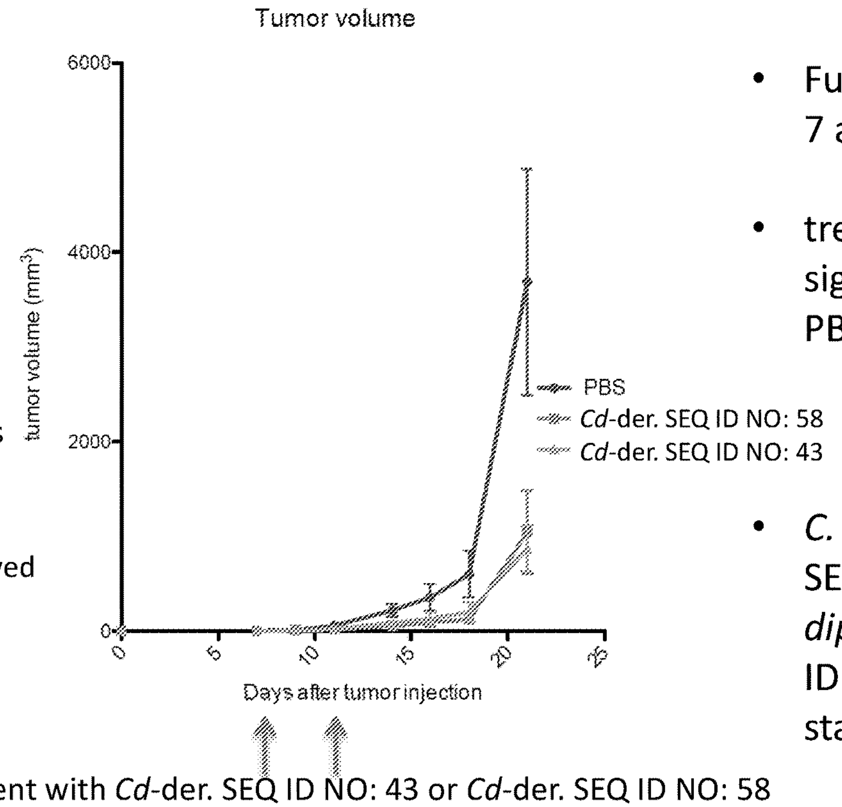

Treatment with *Cd*-der. SEQ ID NO: 43 or *Cd*-der. SEQ ID NO: 58

- Fusion toxin given on Day 7 and Day 10
- treatment groups are significantly better than PBS control $p<0.05$
- *C. diphtheriae*-derived SEQ ID NO: 43 and *C. diphtheriae*-derived SEQ ID NO: 58 are not statistically different

FIG. 23

*C. diphtheriae*-derived SEQ ID NO: 43 and *C. diphtheriae*-derived SEQ ID NO: 58 deplete Treg cells *in vivo* in mice

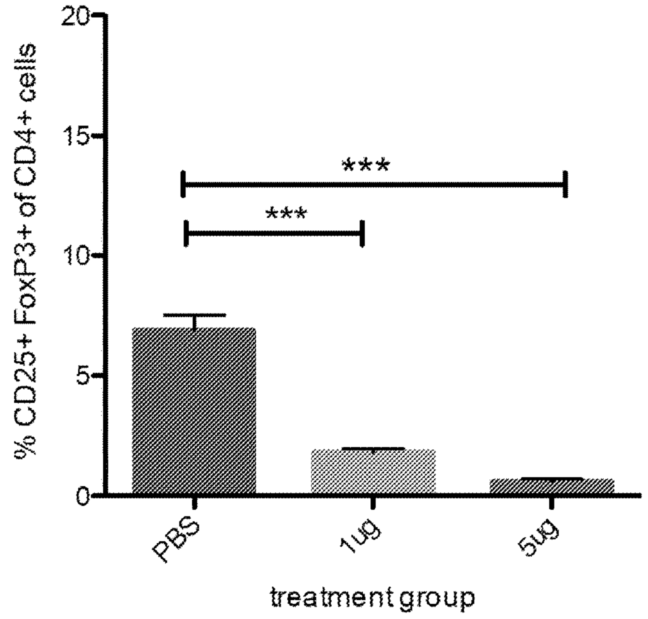

Tregs

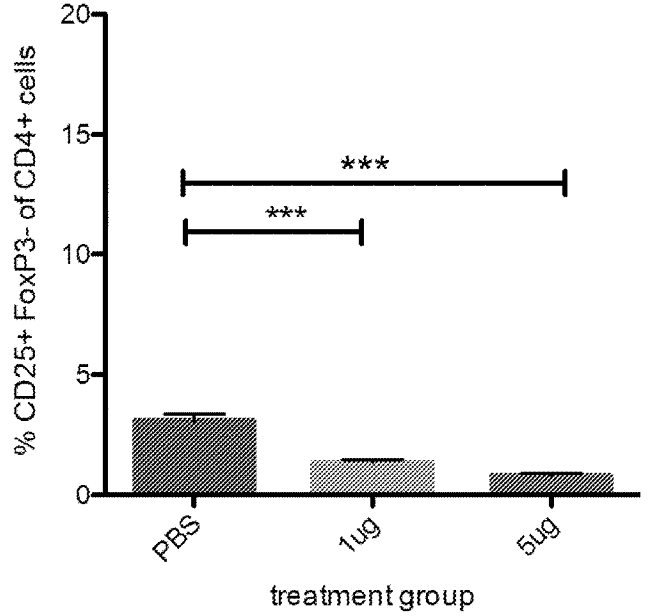

CD4+ CD25+ FoxP3-

Data shown are for *C. diphtheriae*-derived SEQ ID NO: 58 which was >97% pure. Mice were dosed with either 1 µg or 5 µg IP on day 1 and day 4. Mice were sacrificed, spleens were removed, and splenocytes prepared. The cell marker percentages were determined by flow cytometry. *** indicates $p < 0.05$

FIG. 24

Dual sequential therapy with *C. diphtheriae*-derived SEQ ID NO: 43 plus anti-PD1 demonstrates improved melanoma tumor growth inhibition compared with monotherapy

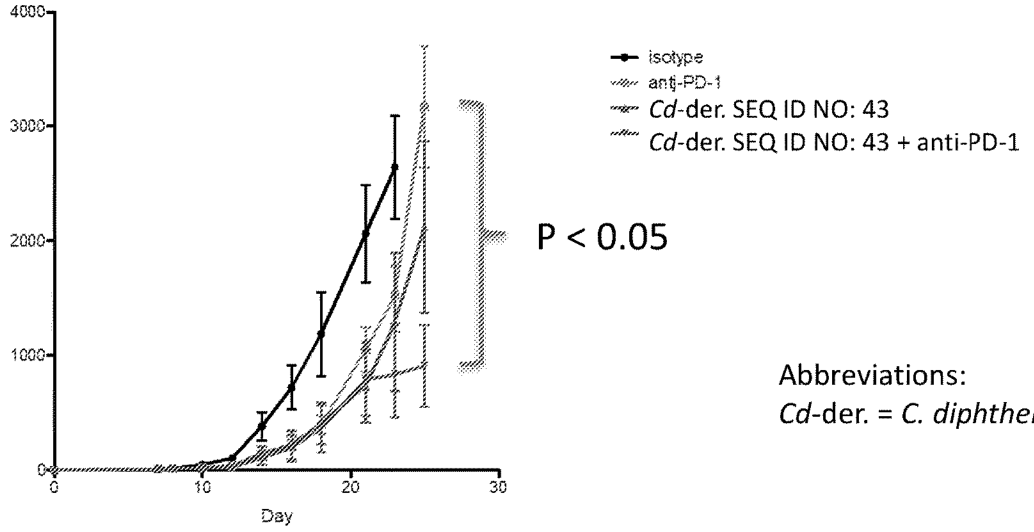

Abbreviations:
*Cd*-der. = *C. diphtheriae*-derived

*C. diphtheriae*-derived SEQ ID NO: 43 dosed at 10 μg given on Day 8 and on Day 11
anti PD-1 started on day 9 and day 12 and twice weekly until sacrifice

***C. diphtheriae*-derived SEQ ID NO: 43 inhibits B16F10 tumor growth in mice and enhances anti-tumor activity of anti-PD-1 treatment.**

C57BL/6 mice were treated with 10 μg of *C. diphtheriae*-derived SEQ ID NO: 43 on day 8 and day 11 post B16F10 inoculation. Isotype control or anti-PD-1 was begun on day 9 and given 2 times per week until sacrifice. (A-C) Tumors were measured with an electronic caliper. Experiment was ended on day 26 post tumor injection. Tumor growth curves for treatment groups are shown. On day 26, the tumors treated with *C. diphtheriae*-derived SEQ ID NO: 43 + anti-PD1 were statistically significantly smaller than those treated with anti-PD1 alone ($p < 0.05$)

FIG. 25

*C. diphtheriae*-derived SEQ ID NO: 58 treatment inhibits melanoma tumor growth and sequential combination therapy with *C. diphtheriae*-derived SEQ ID NO: 58 given first adds to effectiveness of anti-PD1. Treatment started on day 7

A

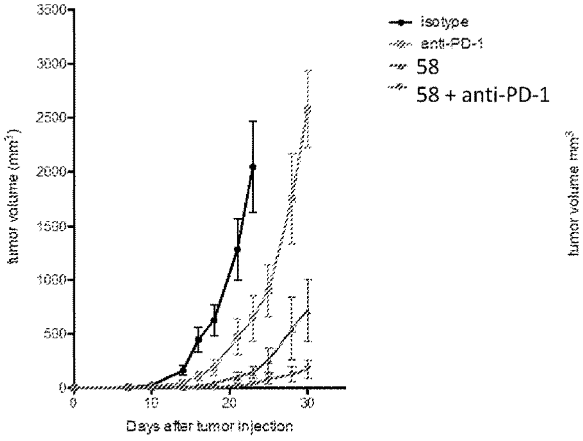

B

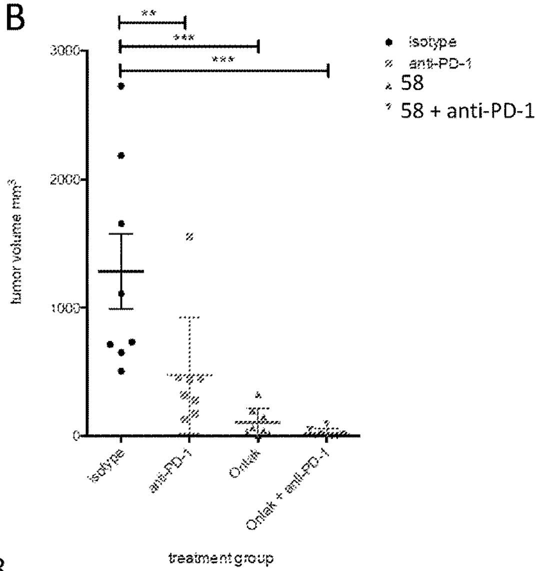

C

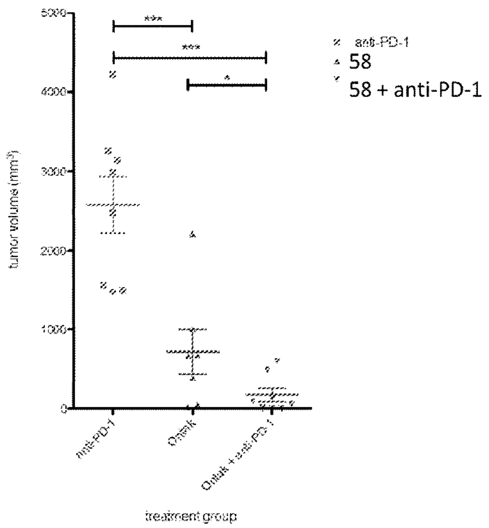

Abbreviations:
58 = *C. diphtheriae*-derived SEQ ID NO: 58

_C. diphtheriae_-derived SEQ ID NO: 58 inhibits B16F10 tumor growth in mice and enhances anti-tumor activity of anti-PD-1 treatment.

C57BL/6 mice were treated with 5 µg of *C. diphtheriae*-derived SEQ ID NO: 58 on day 7 and day 10 post B16F10 inoculation. Isotype control or anti-PD-1 was begun on day 8 and given 2 times per week until sacrifice. (A-C) Tumors were measured with an electronic caliper. Isotype control mice were euthanized on day 21 once tumors became too large, remaining groups were euthanized on day 30. (A) Growth curves for treatment groups. (B) Tumor volume on day 21. (C) Tumor volume on day 30. Data represent 8 mice per group and are shown as mean ± SEM. p values obtained by one-way ANOVA. * p<.05, p<0.01, * p<0.001

FIG. 26

Treatment with anti-PD-1 and *C. diphtheriae*-derived SEQ ID NO: 58 leads to increased frequency of CD8+ IFNγ+ lymphocytes in B16F10 tumors.

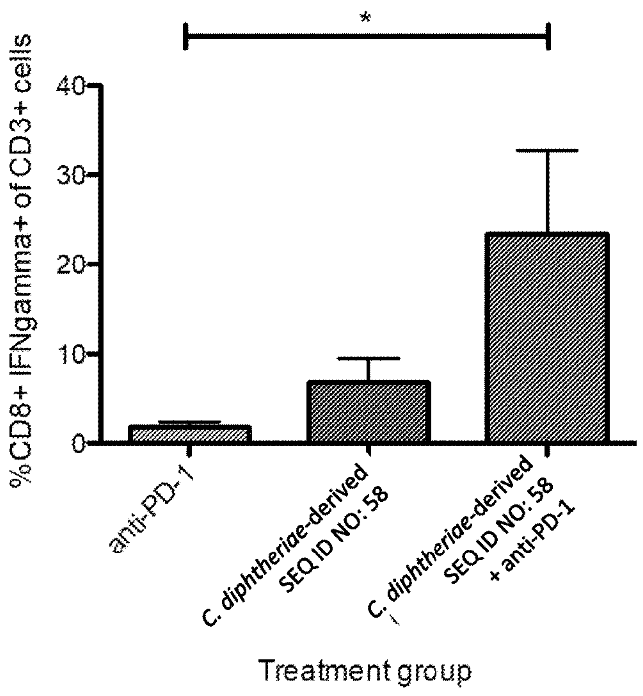

- Sacrificed on Day 30 post tumor injection.
- Tumors removed and homogenized
- Final *C. diphtheriae*-derived SEQ ID NO: 58 treatment given on Day 10
- *C. diphtheriae*-derived SEQ ID NO: 58 group: dosed on day 7 & day 10
- *C. diphtheriae*-derived SEQ ID NO: 58 + anti-PD-1 group: dosed with *C. diphtheriae*-derived SEQ ID NO: 58 on d7 & d10; dosed with anti-PD-1 on d8 and d11 and then twice weekly thereafter

**Treatment with anti-PD-1 and *C. diphtheriae*-derived SEQ ID NO: 58 leads to increased frequency of CD8+ IFNγ+ lymphocytes in B16F10 tumors.**

Tumor-infiltrating lymphocytes were isolated from tumors and stimulated with PMA + ionomycin and brefeldin A for 4 hours and analyzed by flow cytometry. Plots represent 7-8 animals per group. *$p<0.05$

FIG. 27

*C. diphtheriae*-derived SEQ ID NO: 58 treatment inhibits melanoma tumor growth and sequential combination therapy with *C. diphtheriae*-derived SEQ ID NO: 58 given first adds to effectiveness of anti-PD1. Treatment started on day 10

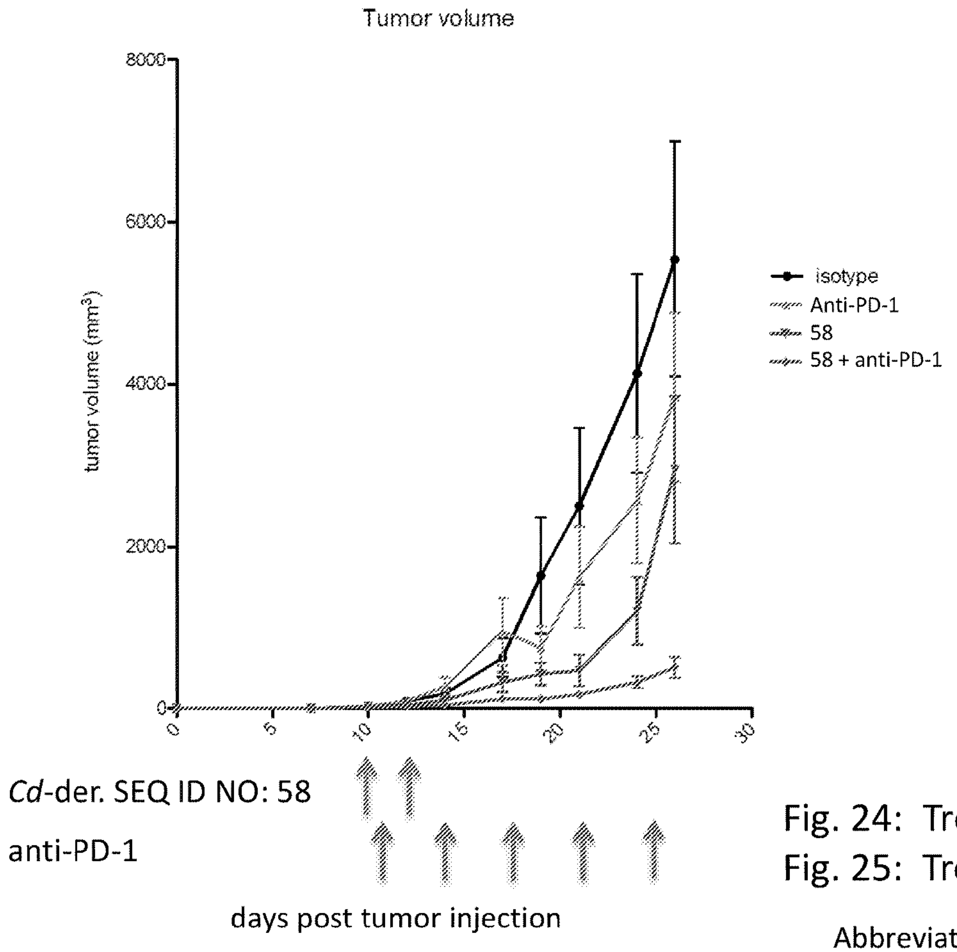

- *C. diphtheriae*-derived SEQ ID NO: 58 given on Day 10 and Day 13
- anti-PD-1 given 2x per week: starting on day 11
- *C. diphtheriae*-derived SEQ ID NO: 58 + anti-PD-1 tumors are significantly smaller than isotype control while single therapy are not
- Rate of growth of *C. diphtheriae*-derived SEQ ID NO: 58 + anti-PD-1 tumors is slower than isotype and single therapy groups Fig. 24: Treatment was started on day 8
Fig. 25: Treatment started on day 7

Abbreviations: 58 = *C. diphtheriae*-derived SEQ ID NO: 58

FIG. 28 Overcoming the double negative of tumor immunology provides the rationale for sequential immunotherapy
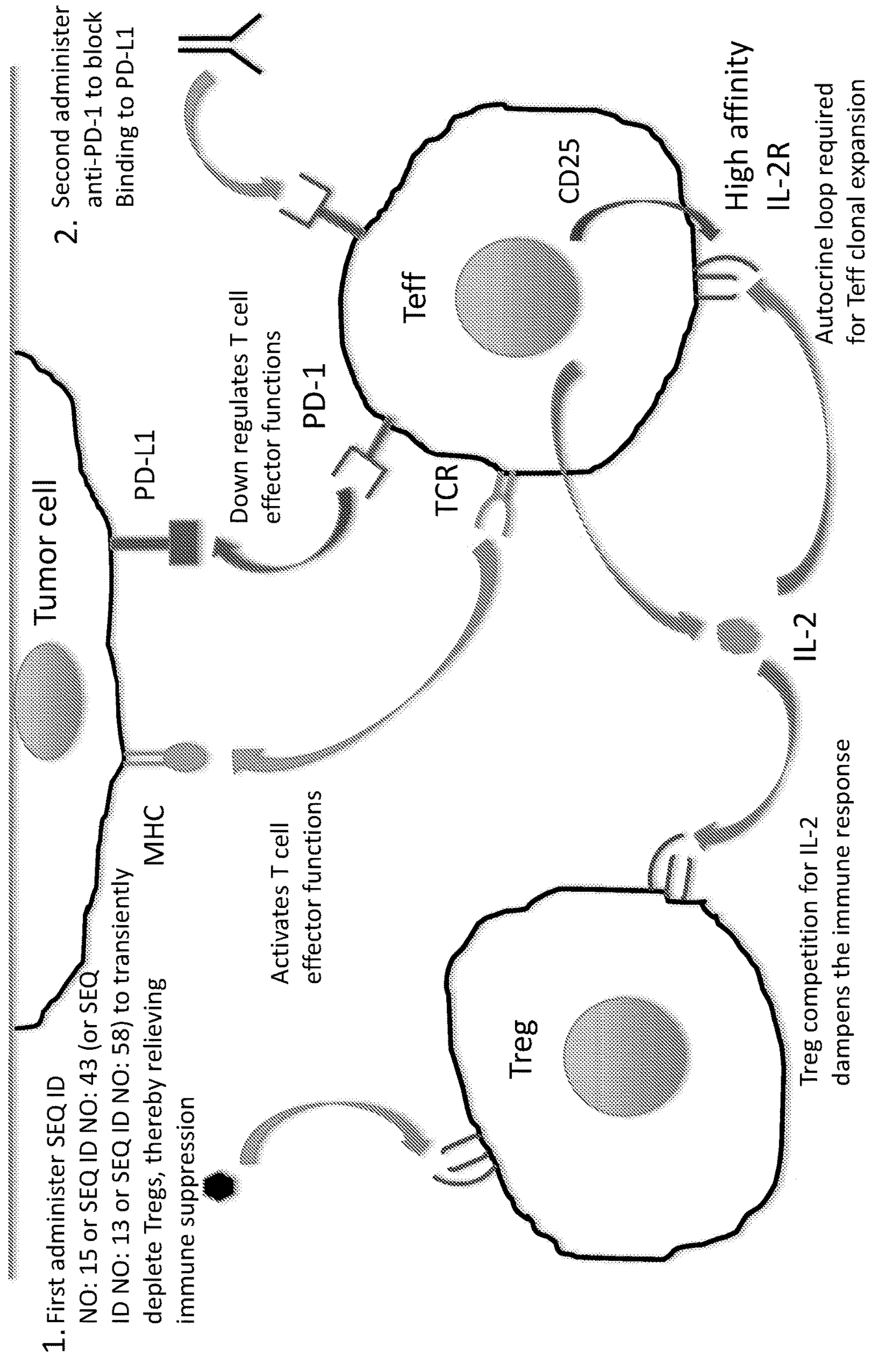

Protein being expressed is SEQ ID NO: 58 (s-Ontak-$His_6$)

SDS-PAGE gel subjected to Western immunoblotting with anti-IL-2 antibodies

Conclusion: Expression from Ptox (WT)-Operator (WT) or SEQ ID NO: 108 by the C7 ΔdtxR mutant strain gives ~50% higher protein yield than expression of from Ptox (WT)-Operator (Mutant) or SEQ ID NO: 2 from the C7 WT strain FIG. 30 Purification of DAB-IL2-V6A (SEQ ID NO: 15) by Hydrophobic interaction chromatography (HIC)

HiTrap Phenyl FF 5mL

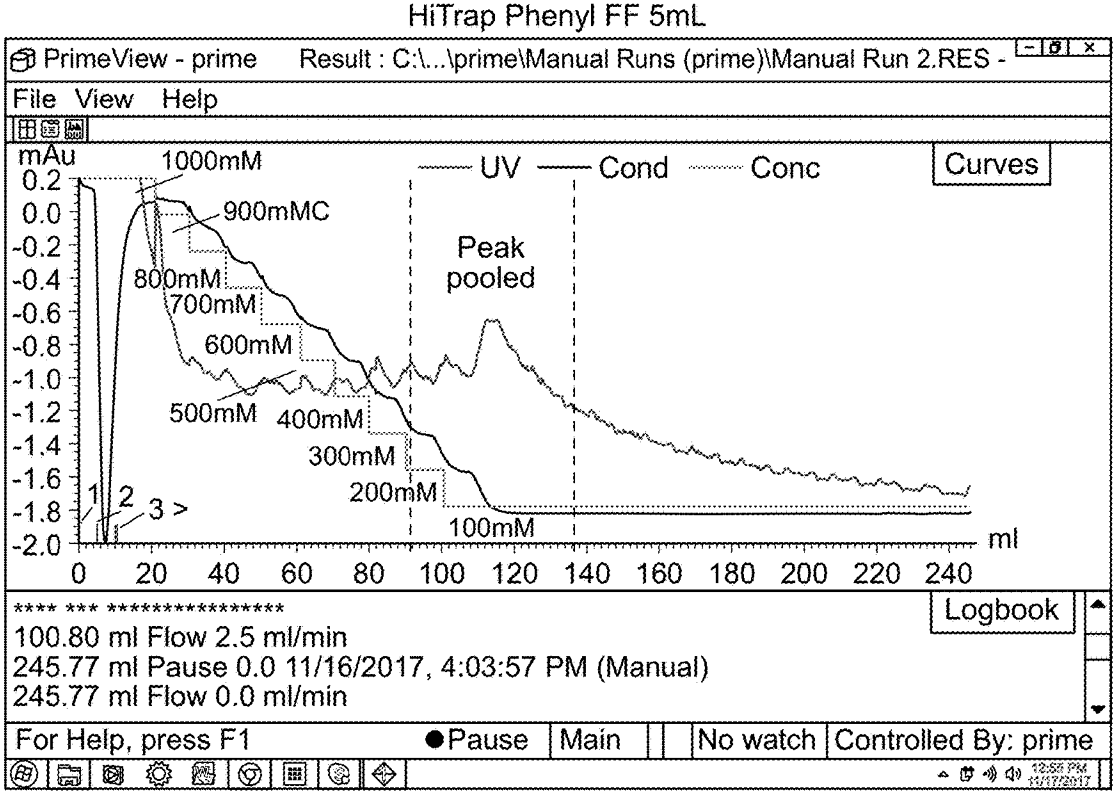

Protein concentrated to 100µl and run on SDS-PAGE

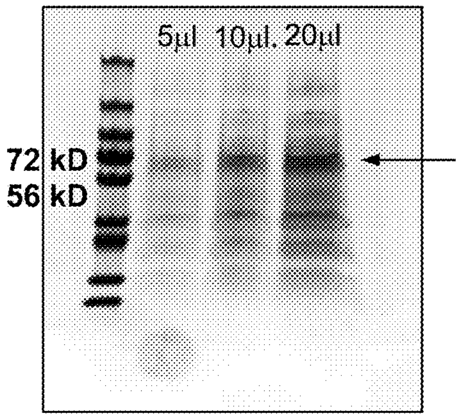

Methods

Protein was expressed in C. diphtheriae C7(-) at 37°C. Culture supernatant was concentrated by tangential flow ultrafiltration -and purified by hydrophobic interaction chromatography FPLC ((HiTrap Phenyl FF column, 5 ml) with a gradient of decreasing NaCL concentrations as shown. The fractions pooled at 100 mM NaCl are shown. Those fractions were concentrated and separated by SDS-PAGE. The red arrow indicates 58 kDa, the anticipated MW of SEQ ID NO: 15

Conclusions:

(1) Hydrophobic interaction chromatography leads to a significant partial purification of SEQ ID NO:15.
(2) Hydrophobic interaction chromatography combined with ion exchange chromatography or Mimetic Blue chromatography may yield highly purified preparations of SEQ ID NO: 15 and related proteins

FIG. 31

Depletion of Tregs and activated Tregs by SEQ ID NO: 43

Mice were inoculated with 4T1 triple negative breast cancer cells on day 0. They were treated with 3 doses on the indicated days with either (i) PBS or (ii) 10 micrograms of purified SEQ ID NO: 43 given intraperitoneally

5 mice per group

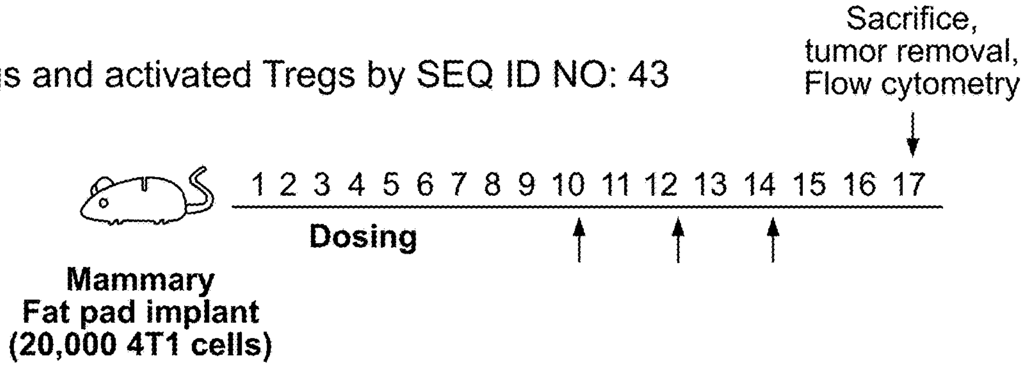

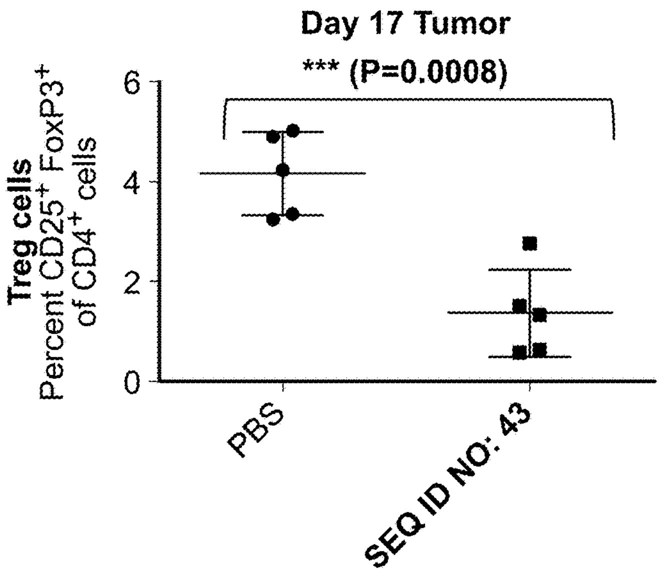

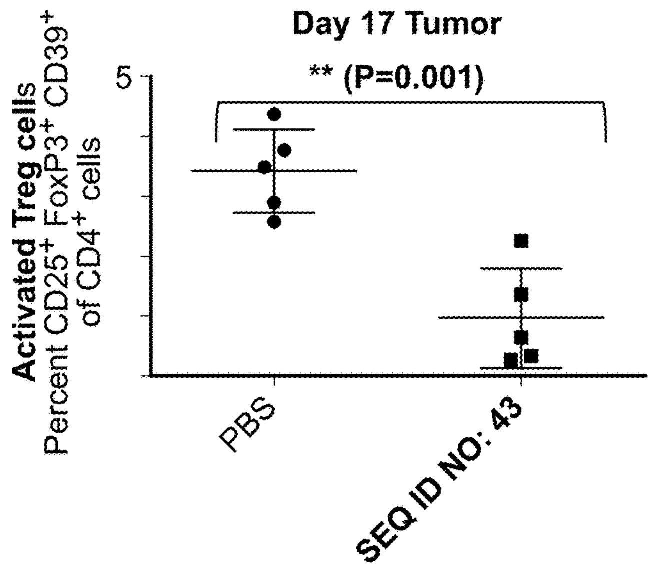

Conclusions:
SEQ ID NO: 43 (s-Ontak-V6A-$His_6$) leads to a significant reduction in tumor Treg and activated Treg cells

Fig. 32 Anti-tumor effects of SEQ ID NO: 43 (s-Ontak-V6A-$His_6$) when used as monotherapy and as dual sequential therapy with anti-PD1 in the mouse B16 melanoma model

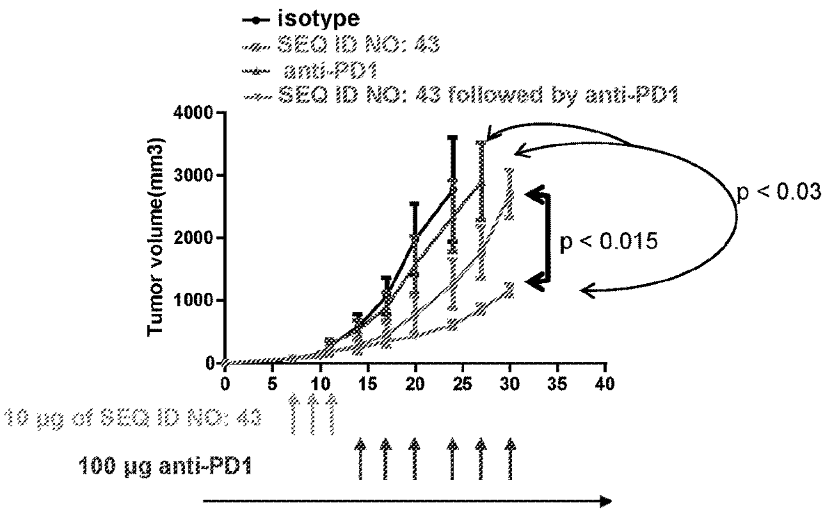

Mice were inoculated with B16 murine melanoma cells on day 0. They were treated with intraperitoneal doses on the indicated days of:

(i) anti-PD1 isotype control antibody
(ii) 10 microgram doses of purified SEQ ID NO: 43
(iii) 100 microgram doses of anti-PD1 antibody
(iv) a sequential combination of purified SEQ ID NO: 43 followed by anti-PD1 antibody

5 mice per group

Important note: in contrast to Fig 24, 25, & 27, treatment with SEQ ID NO: 43 and the anti-PD1 agent are non-overlapping in time. That is, therapy in this figure is fully sequential

Fig. 33 Anti-tumor effects of SEQ ID NO: 43 (s-Ontak-V6A-$His_6$) are retained even when used late in the course of tumor progression (day 10).

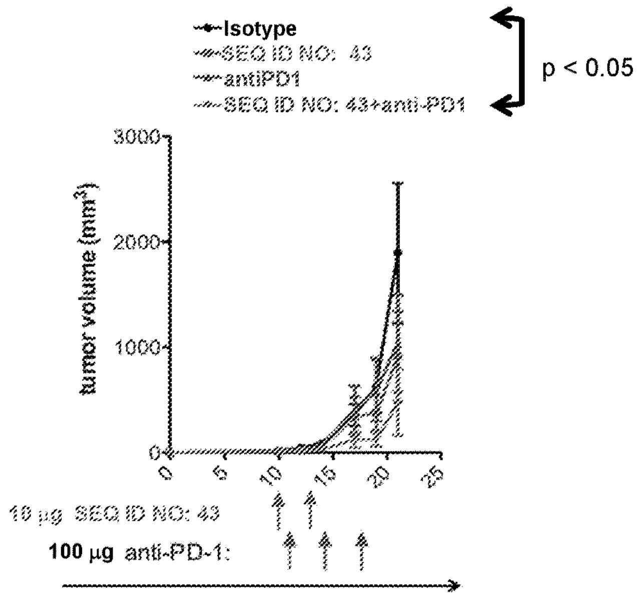

Mice were inoculated with B16 murine melanoma cells on day 0. They were treated with intraperitoneal doses on the indicated days of:

(i) anti-PD1 isotype control antibody
(ii) 10 microgram doses of purified SEQ ID NO: 43
(iii) 100 microgram doses of anti-PD1 antibody
(iv) An overlapping sequential combination of purified SEQ ID NO: 43 followed by anti-PD1 antibody

5 mice per group

Activity of SEQ ID NO: 58 as monotherapy or as fully sequential dual therapy with anti-PD1 in the CT26 colon carcinoma tumor model Activity vs colon carcinoma 5 mice per group

Fig. 35

Activity of SEQ ID NO: 58 (s-Ontak-His$_6$) as monotherapy or as fully sequential dual therapy with anti-PD1 in the RENCA renal carcinoma tumor model

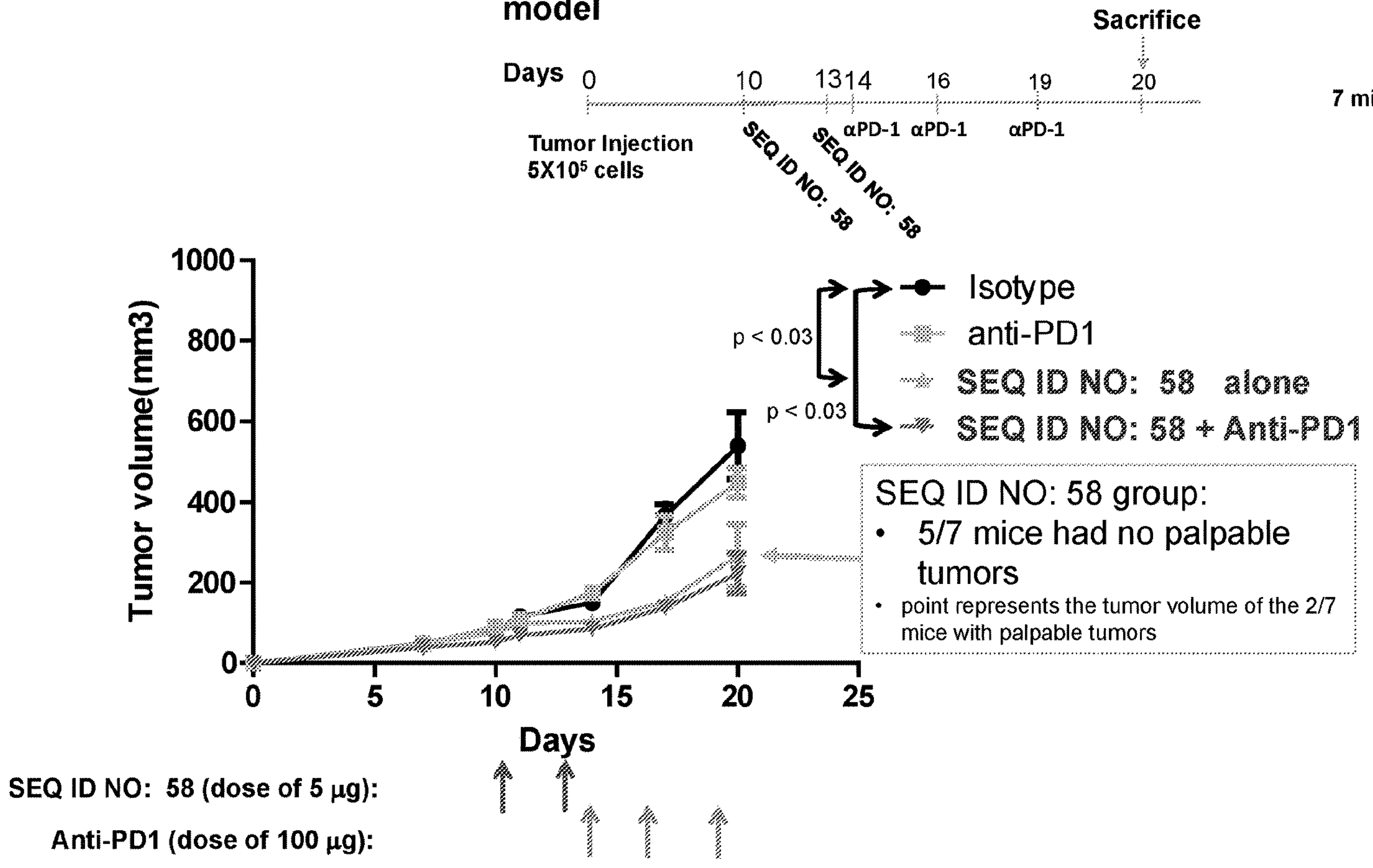

Mice were inoculated with RENCA renal cancer cells on day 0. They were treated with intraperitoneal doses on the indicated days of:

(i) anti-PD1 isotype control antibody
(ii) anti-PD1
(iii) 5 microgram doses of purified SEQ ID NO: 58
(iv) a sequential combination of purified SEQ ID NO: 58 followed by anti-PD1 antibody

Fig. 36

Energy minimization structural analysis indicates that D3E mutation will narrow the distance to VDS motif residue Serine 8 from 4.0 Å to 3.2 Å and thereby form a stronger hydrogen bond between residue E3 and residue S8

A

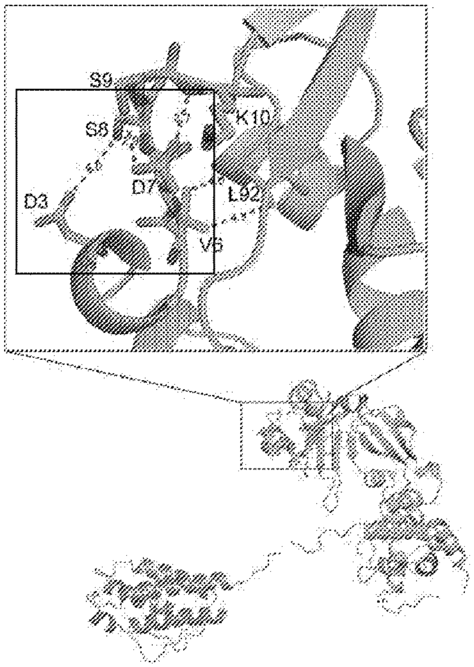

B SEQ ID NO: 13 (s-Ontak)

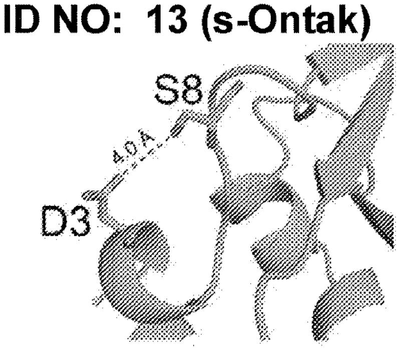

C SEQ ID NO: 60 (D3E)

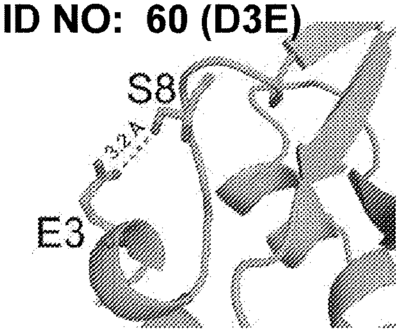

D
1. SEQ ID NO: 60 (D3E)
2. SEQ ID NO: 15 (V6A)
3. SEQ ID NO: 64 (D7E)
4. SEQ ID NO: 68 (S8T)

Protein structure simulation using Amber ff99SB Force field
Ref: PMID 16981200, Hornak V et al, Proteins 2006

Thermal shift analysis using SYPRO Orange release fluorimetry reveals enhanced thermal stability of the D3E mutant protein (SEQ ID NO: 60) compared with V6A (SEQ ID NO: 15) and D7E (SEQ ID NO: 64)

RFU = relative fluorescence units $T_m$ = melting temperature

Fig. 38 Thermal shift analysis of s-Ontak and mutants in the presences of varying amounts of substrate, NAD Increased secretion to the culture supernatant and greater protein yield with SEQ ID NO: 62 (D3E-His$_6$) compared to s-Ontak-His$_6$ and the other mutants.

Fig. 40

Cytotoxic activity of s-Ontak-$His_6$ and related mutant proteins for $CD25^+$ cells*

(*adult T-cell leukemia MT-2 cells, NIH AIDS Reagent Program Catalog number 237)

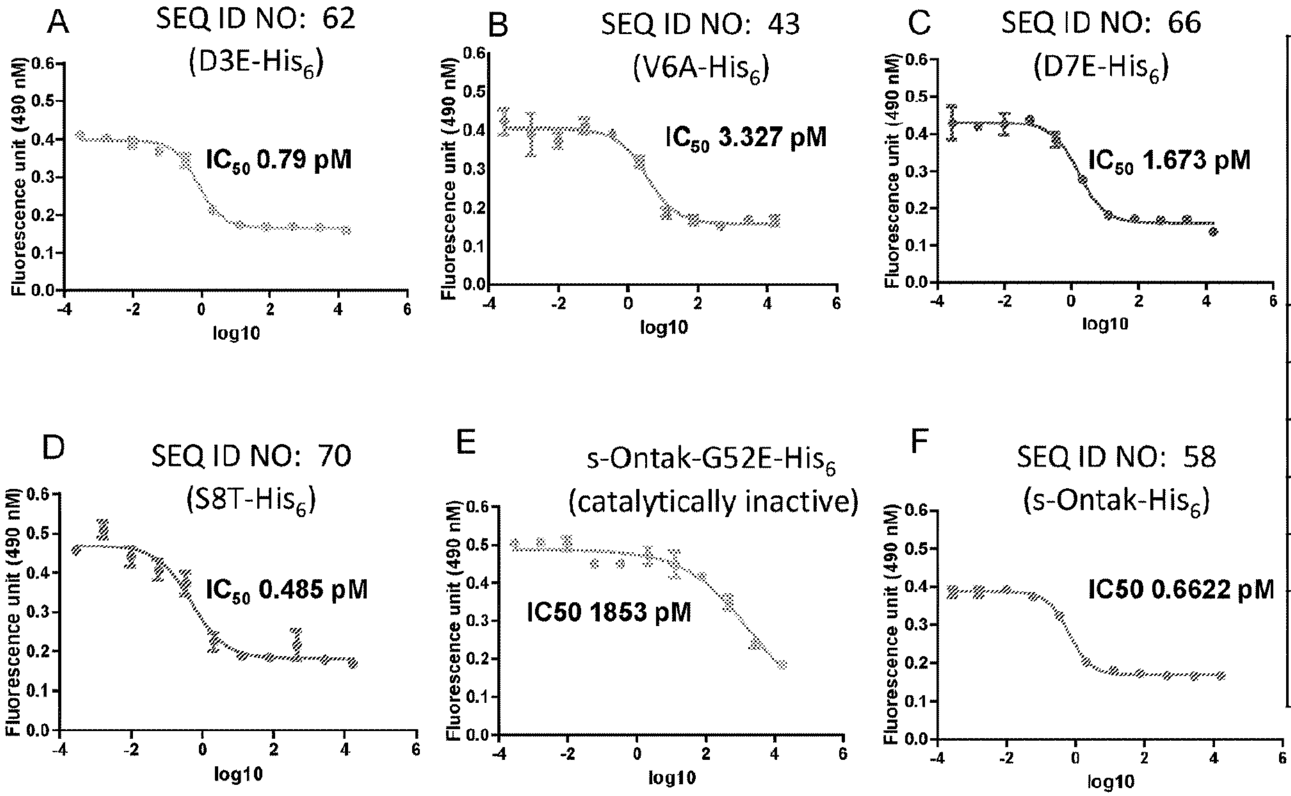

H

| Fusion Protein | $IC_{50}$ (M) | Potency relative to s-Ontak-$His_6$<br>Rreciprocal of ratio of $IC_{50}$ values (protein X/s-Ontak-$His_6$). Higher value means greater activity than s-Ontak-$His_6$ |
|---|---|---|
| SEQ ID NO: 58 (s-Ontak-$His_6$) | $6.22 \times 10^{-13}$ | 1.0 |
| SEQ ID NO: 62 (D3E-$His_6$) | $7.9 \times 10^{-13}$ | 0.84 |
| SEQ ID NO: 43 (V6A-$His_6$) | $33.27 \times 10^{-13}$ | 0.20 |
| SEQ ID NO: 66 (D7E-$His_6$) | $16.73 \times 10^{-13}$ | 0.40 |
| SEQ ID NO: 70 (S8T-$His_6$) | $4.85 \times 10^{-13}$ | 1.40 |
| s-Ontak-G52E-$His_6$ (catalytically inactive) | $1.853 \times 10^{-9}$ | 0.00036 |

Fig. 41

Vascular leak induction by HUVEC monolayer permeation by s-Ontak and mutants

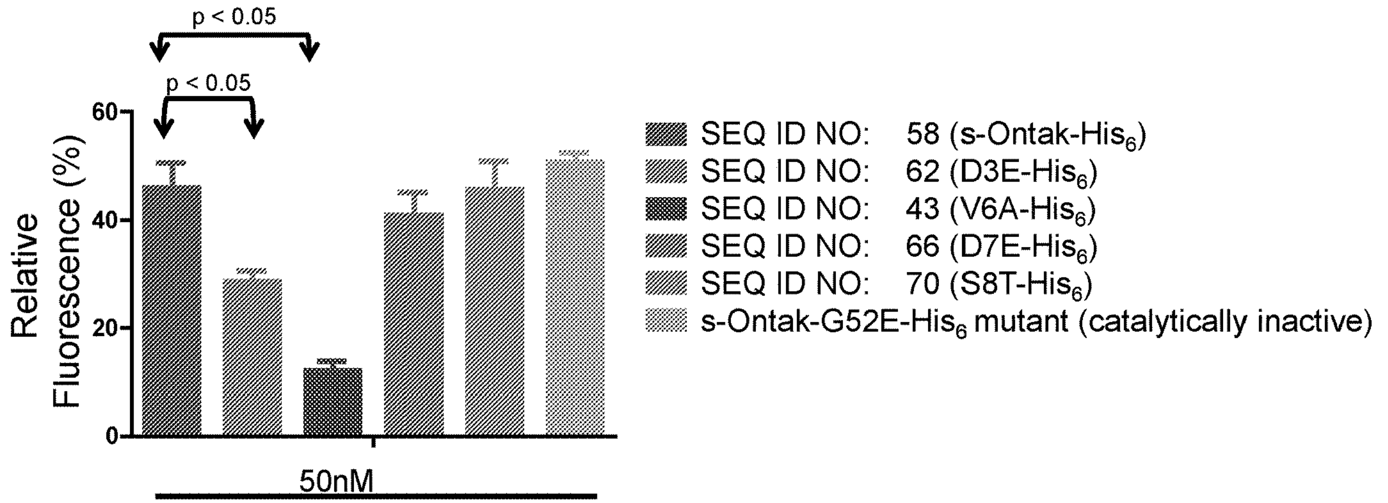

Method: A monolayer of HUVEC cells on culture inserts with 0.4-µm pores were treated with 50 nM s-Ontak and different mutant forms of s-Ontak (50nm) for 19 h and then with FITC-dextran for 30 min. The fluorescence intensity of FITC-dextran which diffused into the lower chamber was measured. PBS was used as the blank to determine baseline permeation, and LPS was used as the positive control (100% relative fluorescence). For each determination, there were three technical replicates. Data shown are the means of three biological replicates.

Conclusion: The D3E mutant, as well as the V6A mutant, give significantly lower levels of vascular leak than s-Ontak

Fig. 42 Vascular leak induction by HUVEC monolayer permeation by peptides corresponding to vascular leak-associated regions of s-Ontak

A

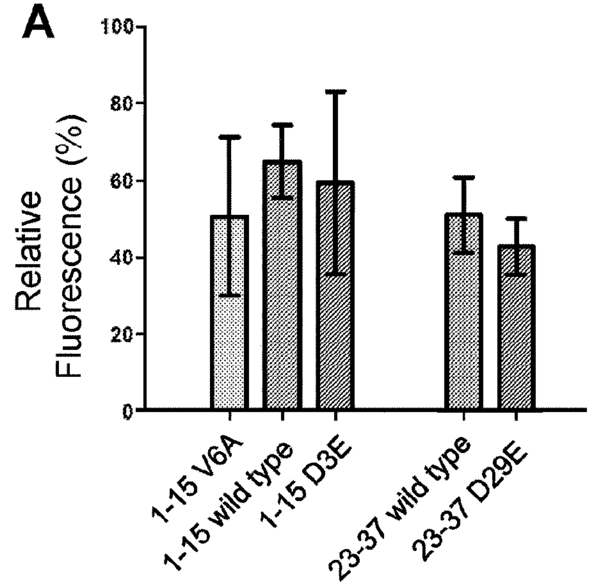

B

| Name of Peptide | Properties | Sequence |
|---|---|---|
| 1-15 wild type | WT residues 1-15 | GADDV**VDS**SKSFVME |
| 1-15 V6A | WT residues 1-15 with V6A substitution | GADDVADSSKSFVME |
| 1-15 D3E | WT residues 1-15 with D3E substitution | GAEDVVDSSKSFVME |
| 23-37 wild type | WT residues 1-15 | TKPGY**VDS**IQKGIQK |
| 23-37 D29E | WT residues 1-15 with D29E substitution | TKPGYVESIQKGIQK |

Panel A: A monolayer of HUVEC cells on culture inserts with 0.4-μm pores were treated with 50 nM of the indicated peptides for 19 h and then with FITC-dextran for 30 min. The fluorescence intensity of FITC-dextran which diffused into the lower chamber was measured. PBS was used as the blank to determine baseline permeation, and LPS was used as the positive control (100% relative fluorescence). For the determination shown, there were three technical replicates.

Panel B: Peptides 15 amino acids in length were synthesized and purified. The 15-mers span residues 1-15 and residues 23-37 of s-Ontak which contain the vascular leak associated-tripeptide motif (x)D(y) where x is valine, isoleucine, leucine, or glycine and y is serine, leucine, or valine. These tripeptide motifs are boldfaced The sequences of the wild type (WT) residues as well as the V6A, D3E, and D29E substitution versions is shown. The substitutions are shown in red.

Conclusion: Peptide 15-mers with D3E, V6A, and D29E substitutions give lower levels of vascular leak than the corresponding wild type 15-mers.

Fig. 43 Half lives ($T_{1/2}$) of s-Ontak-$His_6$, D3E-$His_6$, and V6A-$His_6$ biologic activity in circulation following IP challenge

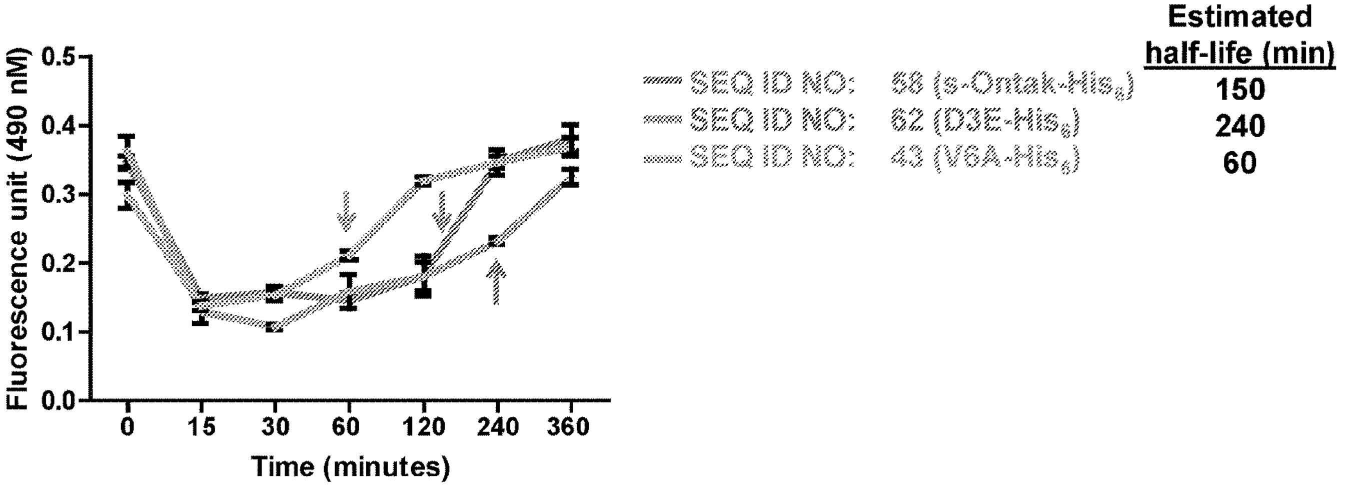

Method: Three groups of mice (3 mice per group) were given single dose of s-Ontak-$His_6$ (5μg), D3E-His6 (5μg) or V6A-$His_6$ (10μg) intraperitoneally. Blood were collected at 15, 30, 60, 120, 240, and 360 minutes post-treatment. Serum was prepared and used to determine growth inhibition of MT-2 cells ($CD25^+$ adult T-cell leukemia MT-2 cells, NIH AIDS Reagent Program Catalog number 237) using the MTS reagent (Promega).

Conclusions: The half-lives in mice of s-Ontak-$His_6$, D3E-$His_6$, and V6A-$His_6$ are 150 min, 240 min, and 60 min, respectively. These half-lives correspond to the protein stability of the respective proteins by thermal shift as shown in Fig 37 and Fig 38.

Fig. 44 s-Ontak-His$_6$ and s-Ontak-D3E-His$_6$) treatment induce similar toxicity in mice.

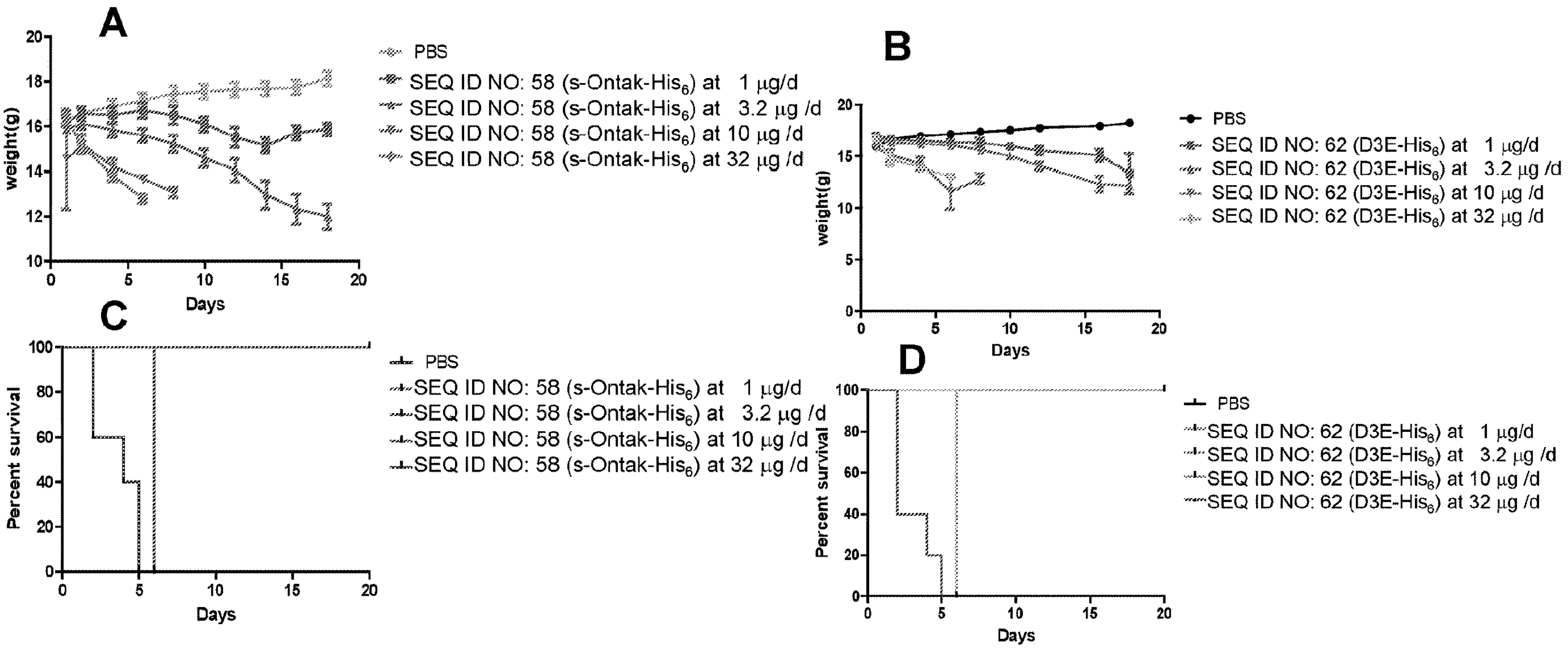

Method: Groups of mice were treated daily with s-Ontak-His$_6$ or D3E-His$_6$ at the indicated doses. Weights and mortality were monitored for 18 days

Conclusions: D3E-His$_6$ leads to weight loss and lethality in mice at the same doses as s-Ontak-His$_6$. Both s-Ontak-His$_6$, and D3E-His$_6$ lead to weight loss in mice when given at doses of 3.2 μg daily or greater. The minimal lethal dose for s-Ontak-His$_6$, and D3E-His$_6$ is between 3.2 and 10 μg daily.

Fig. 45 s-Ontak-D3E-His$_6$ shows anti-tumor activity in the mouse B16 melanoma models both as monotherapy and as dual sequential therapy with anti-PD1 antibody.

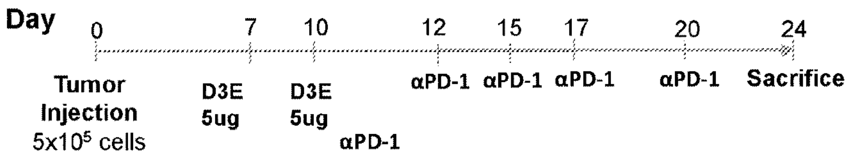

7 mice per group

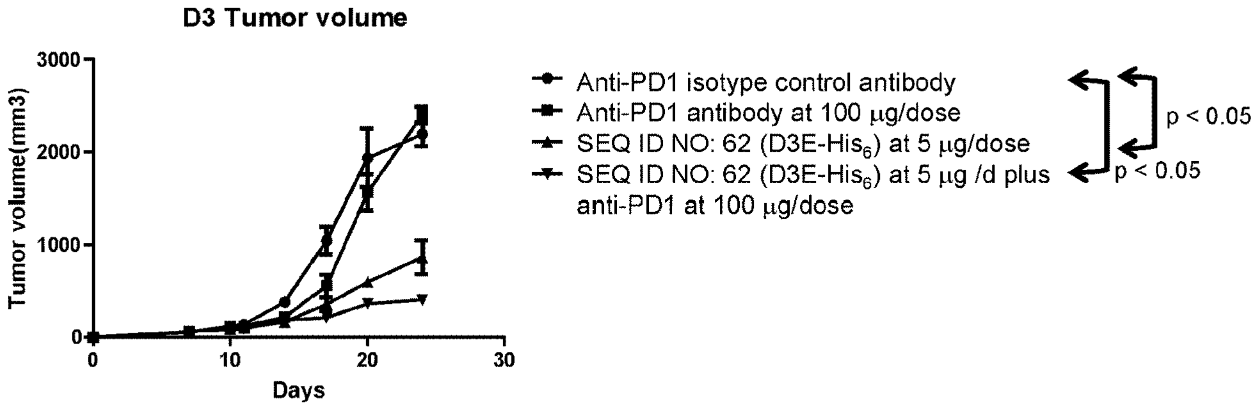

Mice were inoculated with B16 melanoma cancer cells on day 0. They were treated with intraperitoneal doses on the indicated days of:

(i) anti-PD1 isotype control antibody

(ii) anti-PD1

(iii) 5 microgram doses of purified SEQ ID NO: 62

(iv) a sequential combination of purified SEQ ID NO: 62 followed by anti-PD1 antibody

Fig. 46 SEQ ID NO: 134 (s-$DAB_{1\text{-}389}$-mIL4-$His_6$) is expressed from *C. diphtheriae* C7(-) and is readily purified from the culture supernatant
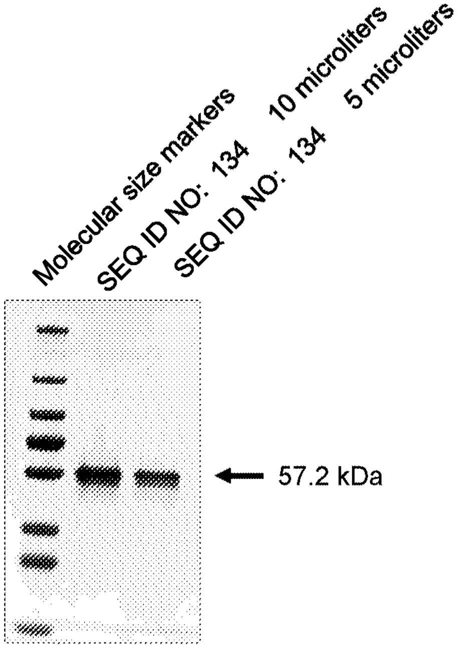
SEQ ID NO: 134 is >97% pure
Coomassie-blue stained SDS-PAGE gel

FIG. 47

SEQ ID NO: 134 (s-DAB$_{1-389}$-mIL4-His$_6$) is active in killing 4T1 triple-negative breast cancer cells and in inhibiting their migration

Mouse triple negative breast cancer cell line 4T1 was tested

A

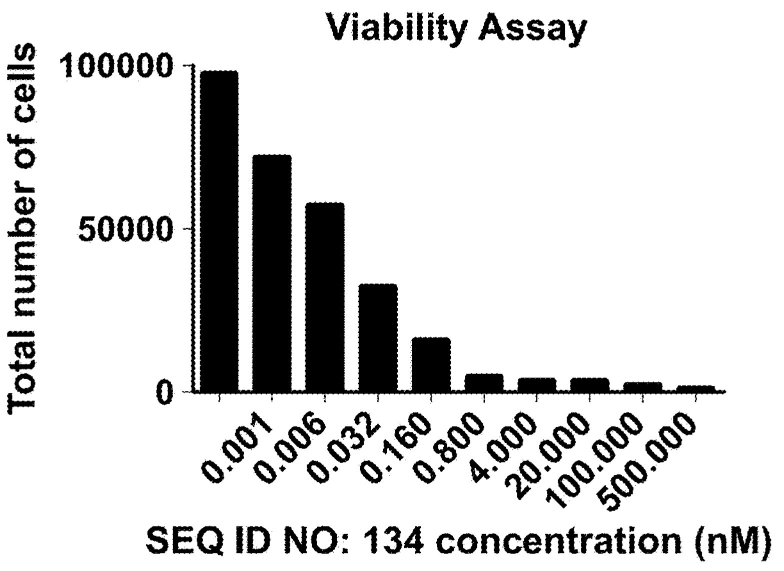

$IC_{50}$ 10 pM vs TNBC (4T1 cells)
- Trypan-blue cell killing assay
- Neutralized by anti-IL4

B

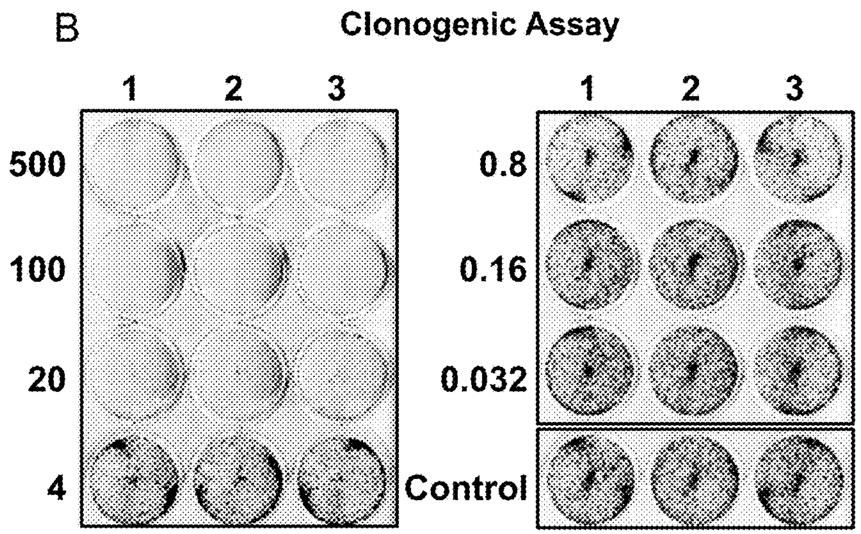

SEQ ID NO: 134 has an $IC_{50}$ of 800 pM for in vitro inhibition of 4T1 cell migration in a clonogenic assay
- Giemsa staining at 48 h
- Neutralized by anti-IL4

FIG. 48

SEQ ID NO: 134 (s-DAB$_{1-389}$-mIL4-His$_6$) is active in killing 4T1 triple-negative breast tumors in mice, depletes MDSCs, and reduces lung metastases

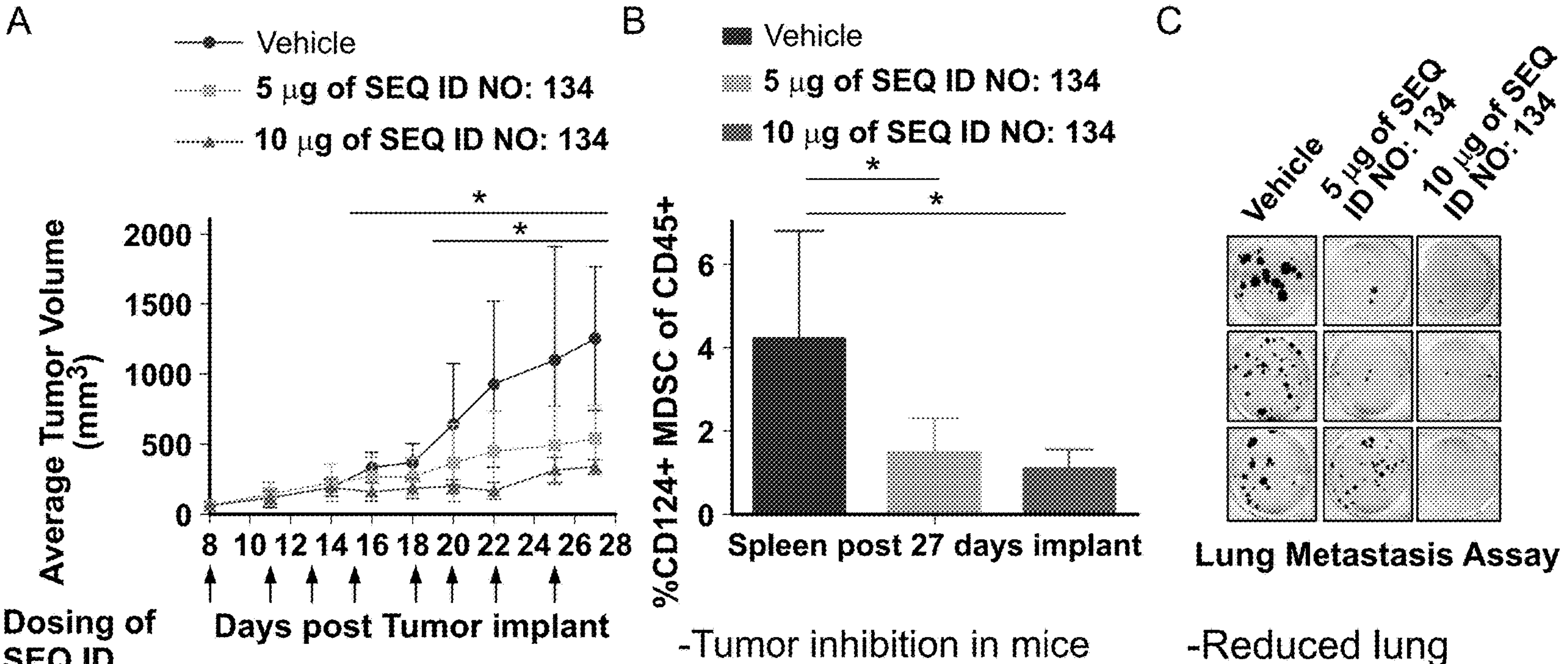

-Dose dependent tumor inhibition in mice
- 4T1 allograft model

-Tumor inhibition in mice correlates with MDSC depletion

-MDSCs defined as being CD45+ CD11b+ Gr1+ cells

-Reduced lung metastases
- 4T1 allograft model
- day 27
- 3 mice assayed per condition
- Similar results in a transwell assay

SEQ ID NO: 134 (s-DAB$_{1-389}$-mIL4-His$_6$) plus SEQ ID NO: 43 (s-DAB$_{1-389}$-IL2-V6A-His$_6$) have additive effects in killing 4T1 triple-negative breast tumors in mice

SEQ ID NO: 134 (s-DAB$_{1-389}$-mIL4-His$_6$), SEQ ID NO: 43 (s-DAB$_{1-389}$-IL2-V6A-His$_6$), and combination therapy deplete CD124+ tumor cells in a mouse model

*Tumor cells were CD45- CD3-

Fig. 51 SEQ ID NO: 134 (s-DAB$_{1-389}$-mIL-4-His$_6$), SEQ ID NO: 43 (s-DAB$_{1-389}$-IL2-V6A-His$_6$), and combination therapy deplete CD124$^+$ MDSCs in a mouse 4T1 orthotopic breast cancer model
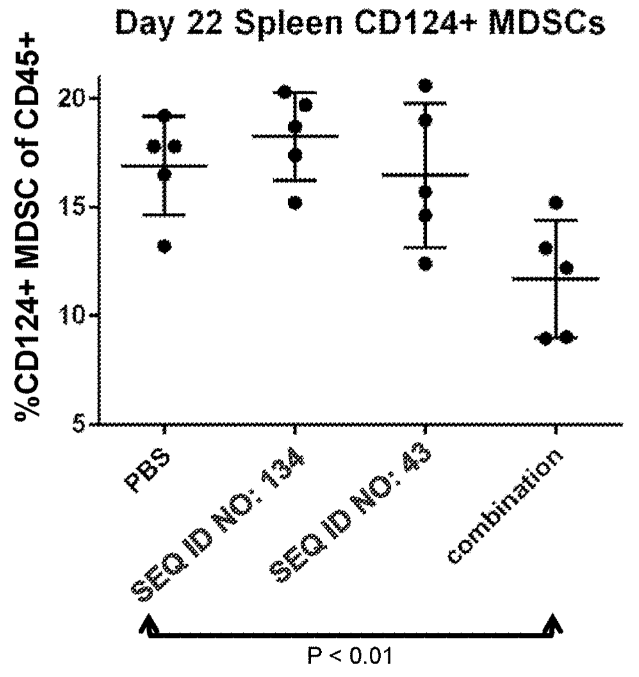
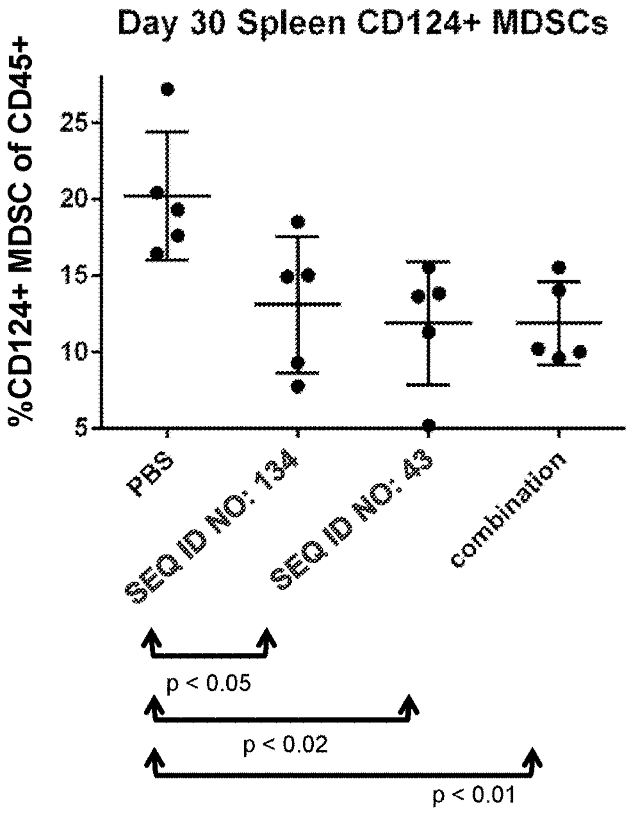
-MDSCs are defined as being CD45+ CD11b+ Gr1+ cells

Fig. 52 SEQ ID NO: 106 (s-DAB$_{1-389}$-EGF-V6A-His$_6$) is expressed from *C. diphtheriae* C7(-) and is readily purified from the culture supernatant
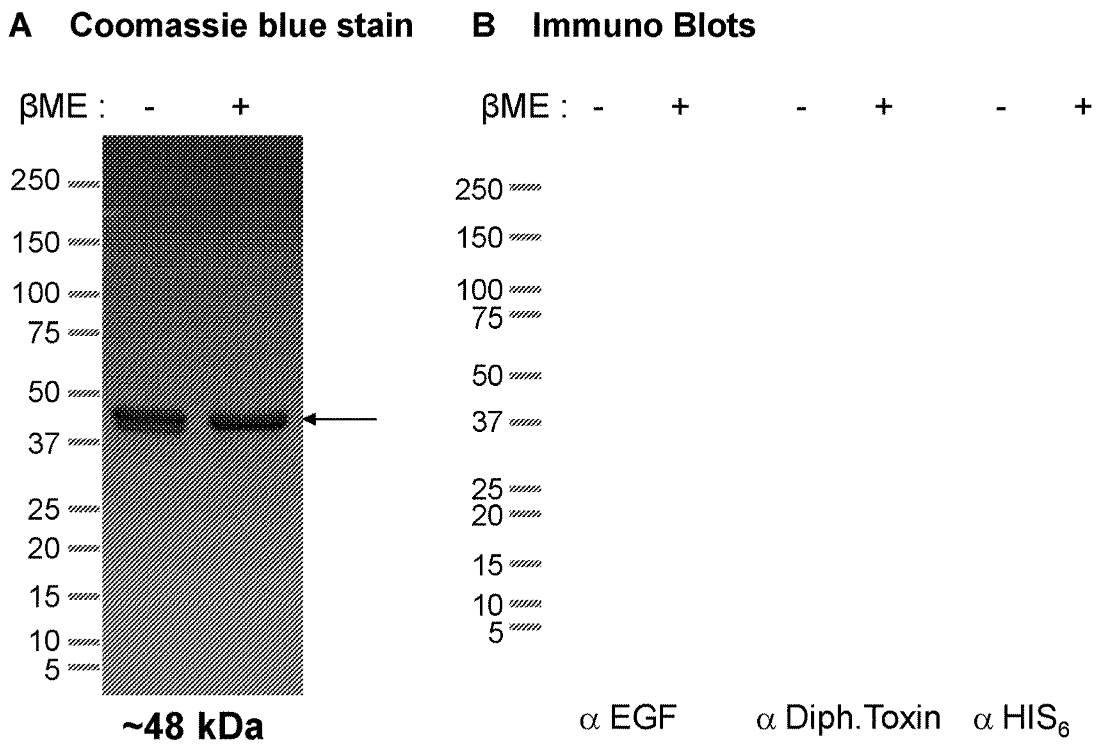
Estimated concentration: 0.3 μg/μL or 6.1 μM

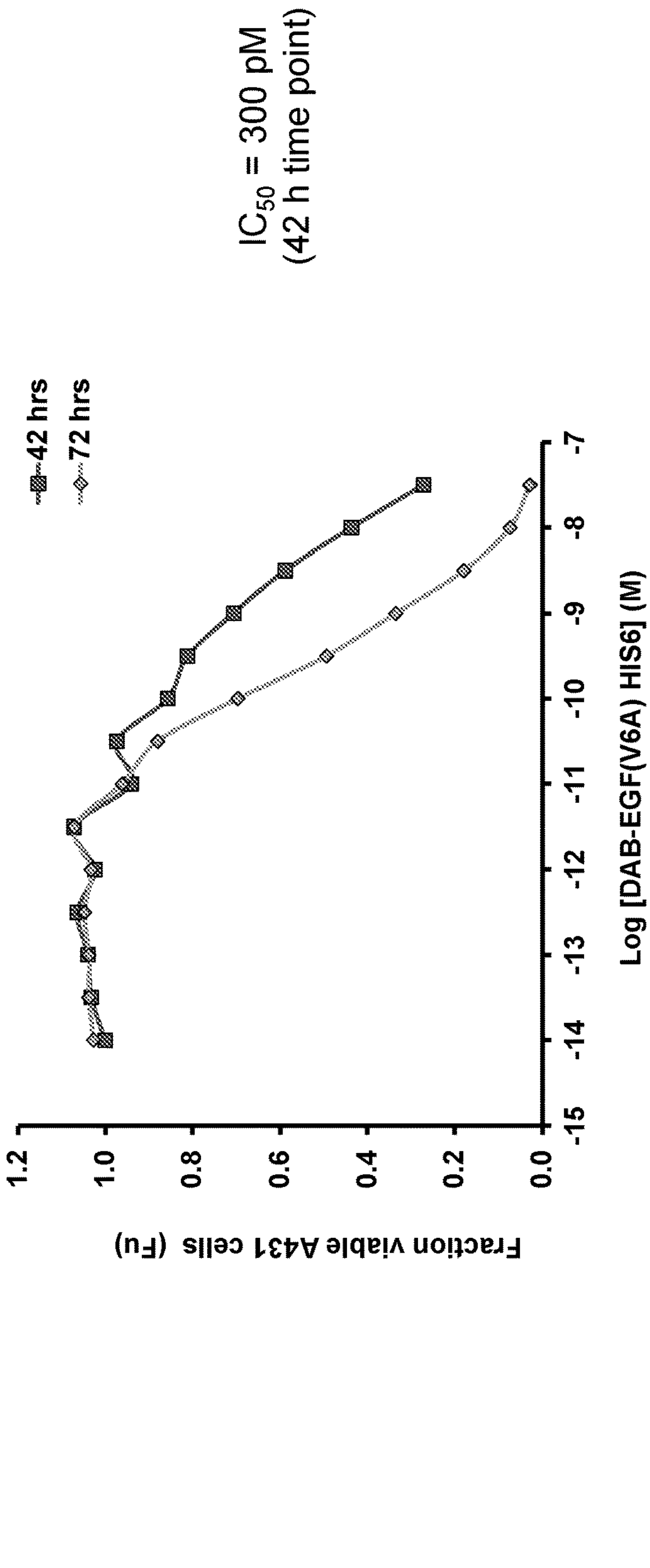
Fig. 53 SEQ ID NO: 106 (s-$DAB_{1\text{-}389}$-EGF-V6A-$His_6$) is active against A431 epidermoid carcinoma cell line ($EGFR^+$)

Fig. 54

<210> 1
<211> 19
<212> DNA
<213> Artificial Sequence

<220>
<223> Description of Artificial Sequence: Synthetic
oligonucleotide

<400> 1
ttaggatagc taagtccat 19

<210> 2
<211> 42
<212> DNA
<213> Artificial Sequence

<220>
<223> Description of Artificial Sequence: Synthetic
oligonucleotide

<400> 2
ttgatttcag agcaccctta taattaggat agctaagtcc at 42

<210> 3
<211> 1711
<212> DNA
<213> Artificial Sequence

<220>
<223> Description of Artificial Sequence: Synthetic
polynucleotide

<400> 3
ttgatttcag agcaccctta taattaggat agctaagtcc attattttat gagtcctggt 60
aaggggatac gttgtgagca gaaaactgtt tgcgtcaatc ttaatagggg cgctactggg 120
gataggggcc ccaccttcag cccatgcagg cgctgatgat gttgttgatt cttctaaatc 180
ttttgtgatg gaaaactttt cttcgtacca cgggactaaa cctggttatg tagattccat 240
tcaaaaaggt atacaaaagc caaaatctgg tacacaagga aattatgacg atgattggaa 300
agggttttat agtaccgaca ataaatacga cgctgcggga tactctgtag ataatgaaaa 360
cccgctctct ggaaaagctg gaggcgtggt caaagtgacg tatccaggac tgacgaaggt 420

Fig. 54 continued tctcgcacta aaagtggata atgccgaaac tattaagaaa gagttaggtt taagtctcac 480
tgaaccgttg atggagcaag tcggaacgga agagtttatc aaaaggttcg gtgatggtgc 540
ttcgcgtgta gtgctcagcc ttcccttcgc tgaggggagt tctagcgttg aatatattaa 600
taactgggaa caggcgaaag cgttaagcgt agaacttgag attaattttg aaacccgtgg 660
aaaacgtggc caagatgcga tgtatgagta tatggctcaa gcctgtgcag gaaatcgtgt 720
caggcgatca gtaggtagct cattgtcatg catcaacctg gattgggatg ttatccgtga 780
taaaactaaa actaagatcg aatctctgaa agaacacggt ccgatcaaaa acaaaatgag 840
cgaaagcccg aacaaaactg tatctgaaga aaaagctaaa cagtacctgg aagaattcca 900
ccagactgca ctggaacacc cggaactgtc tgaacttaag accgttactg gtaccaaccc 960
ggtattcgct ggtgctaact acgctgcttg ggcagtaaac gttgctcagg ttatcgatag 1020
cgaaactgct gataacctgg aaaaaactac cgcggctctg tctatcctgc cgggtatcgg 1080
tagcgtaatg ggcatcgcag acggcgccgt tcaccacaac actgaagaaa tcgttgcaca 1140
gtctatcgct ctgagctctc tgatggttgc tcaggccatc ccgctggtag gtgaactggt 1200
tgatatcggt ttcgctgcat acaacttcgt tgaaagcatc atcaacctgt tccaggttgt 1260
tcacaactct tacaaccgcc cggcttactc tccgggtcac aagacgcatg cacctacttc 1320
tagctctacc aagaaaaccc agctgcagct cgagcacctg ctgctggatt tgcagatgat 1380
cctgaacggt atcaacaatt acaagaaccc gaaactgacg cgtatgctga ccttcaagtt 1440
ctacatgccg aagaaggcca ccgaactgaa acacctgcag tgtctagaag aagaactgaa 1500
accgctggag gaagttctga acctggctca gtctaaaaac ttccacctgc ggccgcgtga 1560
cctgatctct aacatcaacg taatcgttct ggaactgaag ggctctgaaa ccaccttcat 1620
gtgtgaatac gctgatgaga ccgcaaccat cgtagaattc ctgaaccgtt ggatcacctt 1680
ctgtcagtct atcatctcta ccctgacctg a 1711

<210> 4
<211> 75
<212> DNA
<213> Artificial Sequence

<220>
<223> Description of Artificial Sequence: Synthetic
oligonucleotide

Fig. 54 continued

<400> 4
gtgagcagaa aactgtttgc gtcaatctta ataggggcgc tactggggat aggggcccca 60
ccttcagccc atgca 75

<210> 5
<211> 25
<212> PRT
<213> Artificial Sequence

<220>
<223> Description of Artificial Sequence: Synthetic peptide

<400> 5
Met Ser Arg Lys Leu Phe Ala Ser Ile Leu Ile Gly Ala Leu Leu Gly
1 5 10 15

Ile Gly Ala Pro Pro Ser Ala His Ala
20 25

<210> 6
<211> 1566
<212> DNA
<213> Artificial Sequence

<220>
<223> Description of Artificial Sequence: Synthetic polynucleotide

<400> 6
atgggcgctg atgatgttgt tgattcttct aaatcttttg tgatggaaaa cttttcttcg 60
taccacggga ctaaacctgg ttatgtagat tccattcaaa aaggtataca aaagccaaaa 120
tctggtacac aaggaaatta tgacgatgat tggaaagggt tttatagtac cgacaataaa 180
tacgacgctg cgggatactc tgtagataat gaaaacccgc tctctggaaa agctggaggc 240
gtggtcaaag tgacgtatcc aggactgacg aaggttctcg cactaaaagt ggataatgcc 300
gaaactatta agaaagagtt aggtttaagt ctcactgaac cgttgatgga gcaagtcgga 360
acggaagagt ttatcaaaag gttcggtgat ggtgcttcgc gtgtagtgct cagccttccc 420
ttcgctgagg ggagttctag cgttgaatat attaataact gggaacaggc gaaagcgtta 480
agcgtagaac ttgagattaa ttttgaaacc cgtggaaaac gtggccaaga tgcgatgtat 540
gagtatatgg ctcaagcctg tgcaggaaat cgtgtcaggc gatcagtagg tagctcattg 600

Fig. 54 continued tcatgcatca acctggattg ggatgttatc cgtgataaaa ctaaaactaa gatcgaatct 660
ctgaaagaac acggtccgat caaaaacaaa atgagcgaaa gcccgaacaa aactgtatct 720
gaagaaaaag ctaaacagta cctggaagaa ttccaccaga ctgcactgga acacccggaa 780
ctgtctgaac ttaagaccgt tactggtacc aacccggtat tcgctggtgc taactacgct 840
gcttgggcag taaacgttgc tcaggttatc gatagcgaaa ctgctgataa cctggaaaaa 900
actaccgcgg ctctgtctat cctgccgggt atcggtagcg taatgggcat cgcagacggc 960
gccgttcacc acaacactga agaaatcgtt gcacagtcta tcgctctgag ctctctgatg 1020
gttgctcagg ccatcccgct ggtaggtgaa ctggttgata tcggtttcgc tgcatacaac 1080
ttcgttgaaa gcatcatcaa cctgttccag gttgttcaca actcttacaa ccgcccggct 1140
tactctccgg gtcacaagac gcatgcacct acttctagct ctaccaagaa aacccagctg 1200
cagctcgagc acctgctgct ggatttgcag atgatcctga acggtatcaa caattacaag 1260
aacccgaaac tgacgcgtat gctgaccttc aagttctaca tgccgaagaa ggccaccgaa 1320
ctgaaacacc tgcagtgtct agaagaagaa ctgaaaccgc tggaggaagt tctgaacctg 1380
gctcagtcta aaaacttcca cctgcggccg cgtgacctga tctctaacat caacgtaatc 1440
gttctggaac tgaagggctc tgaaaccacc ttcatgtgtg aatacgctga tgagaccgca 1500
accatcgtag aattcctgaa ccgttggatc accttctgtc agtctatcat ctctaccctg 1560
acctga 1566

<210> 7
<211> 1566
<212> DNA
<213> Artificial Sequence

<220>
<223> Description of Artificial Sequence: Synthetic
polynucleotide

<400> 7
atgggcgctg atgatgttgc tgattcttct aaatcttttg tgatggaaaa cttttcttcg 60
taccacggga ctaaacctgg ttatgtagat tccattcaaa aaggtataca aaagccaaaa 120
tctggtacac aaggaaatta tgacgatgat tggaaagggt tttatagtac cgacaataaa 180
tacgacgctg cgggatactc tgtagataat gaaaacccgc tctctggaaa agctggaggc 240

Fig. 54 continued gtggtcaaag tgacgtatcc aggactgacg aaggttctcg cactaaaagt ggataatgcc 300
gaaactatta agaaagagtt aggtttaagt ctcactgaac cgttgatgga gcaagtcgga 360
acggaagagt ttatcaaaag gttcggtgat ggtgcttcgc gtgtagtgct cagccttccc 420
ttcgctgagg ggagttctag cgttgaatat attaataact gggaacaggc gaaagcgtta 480
agcgtagaac ttgagattaa ttttgaaacc cgtggaaaac gtggccaaga tgcgatgtat 540
gagtatatgg ctcaagcctg tgcaggaaat cgtgtcaggc gatcagtagg tagctcattg 600
tcatgcatca acctggattg ggatgttatc cgtgataaaa ctaaaactaa gatcgaatct 660
ctgaaagaac acggtccgat caaaaacaaa atgagcgaaa gcccgaacaa aactgtatct 720
gaagaaaaag ctaaacagta cctggaagaa ttccaccaga ctgcactgga acacccggaa 780
ctgtctgaac ttaagaccgt tactggtacc aacccggtat tcgctggtgc taactacgct 840
gcttgggcag taaacgttgc tcaggttatc gatagcgaaa ctgctgataa cctggaaaaa 900
actaccgcgg ctctgtctat cctgccgggt atcggtagcg taatgggcat cgcagacggc 960
gccgttcacc acaacactga agaaatcgtt gcacagtcta tcgctctgag ctctctgatg 1020
gttgctcagg ccatcccgct ggtaggtgaa ctggttgata tcggtttcgc tgcatacaac 1080
ttcgttgaaa gcatcatcaa cctgttccag gttgttcaca actcttacaa ccgcccggct 1140
tactctccgg gtcacaagac gcatgcacct acttctagct ctaccaagaa aacccagctg 1200
cagctcgagc acctgctgct ggatttgcag atgatcctga acggtatcaa caattacaag 1260
aacccgaaac tgacgcgtat gctgaccttc aagttctaca tgccgaagaa ggccaccgaa 1320
ctgaaacacc tgctgcagtg tctagaagaa gaactgaaac cgctggagga agttctgaac 1380
ctggctcagt ctaaaaactt ccacctgcgg ccgcgtgacc tgatctctaa catcaacgta 1440
atcgttctgg aactgaaggg ctctgaaacc accttcatgt gtgaatacgc tgatgagacc 1500
gcaaccatcg tagaattcct gaaccgttgg atcaccttct gtcagtctat catctctacc 1560
ctgacc 1566

<210> 8
<211> 1638
<212> DNA
<213> Artificial Sequence

<220>
<223> Description of Artificial Sequence: Synthetic polynucleotide

Fig. 54 continued

<400> 8
gtgagcagaa aactgtttgc gtcaatctta ataggggcgc tactggggat aggggcccca 60
ccttcagccc atgcaggcgc tgatgatgtt gctgattctt ctaaatcttt tgtgatggaa 120
aacttttctt cgtaccacgg gactaaacct ggttatgtag attccattca aaaaggtata 180
caaaagccaa aatctggtac acaaggaaat tatgacgatg attggaaagg gttttatagt 240
accgacaata aatacgacgc tgcgggatac tctgtagata atgaaaaccc gctctctgga 300
aaagctggag gcgtggtcaa agtgacgtat ccaggactga cgaaggttct cgcactaaaa 360
gtggataatg ccgaaactat taagaaagag ttaggtttaa gtctcactga accgttgatg 420
gagcaagtcg gaacggaaga gtttatcaaa aggttcggtg atggtgcttc gcgtgtagtg 480
ctcagccttc ccttcgctga ggggagttct agcgttgaat atattaataa ctgggaacag 540
gcgaaagcgt taagcgtaga acttgagatt aattttgaaa cccgtggaaa acgtggccaa 600
gatgcgatgt atgagtatat ggctcaagcc tgtgcaggaa atcgtgtcag gcgatcagta 660
ggtagctcat tgtcatgcat caacctggat tgggatgtta tccgtgataa aactaaaact 720
aagatcgaat ctctgaaaga acacggtccg atcaaaaaca aaatgagcga aagcccgaac 780
aaaactgtat ctgaagaaaa agctaaacag tacctggaag aattccacca gactgcactg 840
gaacacccgg aactgtctga acttaagacc gttactggta ccaacccggt attcgctggt 900
gctaactacg ctgcttgggc agtaaacgtt gctcaggtta tcgatagcga aactgctgat 960
aacctggaaa aaactaccgc ggctctgtct atcctgccgg gtatcggtag cgtaatgggc 1020
atcgcagacg gcgccgttca ccacaacact gaagaaatcg ttgcacagtc tatcgctctg 1080
agctctctga tggttgctca ggccatcccg ctggtaggtg aactggttga tatcggtttc 1140
gctgcataca acttcgttga aagcatcatc aacctgttcc aggttgttca caactcttac 1200
aaccgcccgg cttactctcc gggtcacaag acgcatgcac ctacttctag ctctaccaag 1260
aaaacccagc tgcagctcga gcacctgctg ctggatttgc agatgatcct gaacggtatc 1320
aacaattaca agaacccgaa actgacgcgt atgctgacct tcaagttcta catgccgaag 1380
aaggccaccg aactgaaaca cctgcagtgt ctagaagaag aactgaaacc gctggaggaa 1440
gttctgaacc tggctcagtc taaaaacttc cacctgcggc cgcgtgacct gatctctaac 1500
atcaacgtaa tcgttctgga actgaagggc tctgaaacca ccttcatgtg tgaatacgct 1560

Fig. 54 continued gatgagaccg caaccatcgt agaattcctg aaccgttgga tcaccttctg tcagtctatc 1620
atctctaccc tgacctga 1638

<210> 9
<211> 402
<212> DNA
<213> Artificial Sequence

<220>
<223> Description of Artificial Sequence: Synthetic
polynucleotide

<400> 9
gcacctactt ctagctctac caagaaaacc cagctgcagc tcgagcacct gctgctggat 60
ttgcagatga tcctgaacgg tatcaacaat tacaagaacc cgaaactgac gcgtatgctg 120
accttcaagt tctacatgcc gaagaaggcc accgaactga aacacctgca gtgtctagaa 180
gaagaactga aaccgctgga ggaagttctg aacctggctc agtctaaaaa cttccacctg 240
cggccgcgtg acctgatctc taacatcaac gtaatcgttc tggaactgaa gggctctgaa 300
accaccttca tgtgtgaata cgctgatgag accgcaacca tcgtagaatt cctgaaccgt 360
tggatcacct tctgtcagtc tatcatctct accctgacct ga 402

<210> 10
<211> 521
<212> PRT
<213> Artificial Sequence

<220>
<223> Description of Artificial Sequence: Synthetic
polypeptide

<400> 10
Met Gly Ala Asp Asp Val Val Asp Ser Ser Lys Ser Phe Val Met Glu
1 5 10 15

Asn Phe Ser Ser Tyr His Gly Thr Lys Pro Gly Tyr Val Asp Ser Ile
20 25 30

Gln Lys Gly Ile Gln Lys Pro Lys Ser Gly Thr Gln Gly Asn Tyr Asp
35 40 45

Asp Asp Trp Lys Gly Phe Tyr Ser Thr Asp Asn Lys Tyr Asp Ala Ala 50 55 60

Fig. 54 continued

Gly Tyr Ser Val Asp Asn Glu Asn Pro Leu Ser Gly Lys Ala Gly Gly
65 70 75 80

Val Val Lys Val Thr Tyr Pro Gly Leu Thr Lys Val Leu Ala Leu Lys
85 90 95

Val Asp Asn Ala Glu Thr Ile Lys Lys Glu Leu Gly Leu Ser Leu Thr
100 105 110

Glu Pro Leu Met Glu Gln Val Gly Thr Glu Glu Phe Ile Lys Arg Phe
115 120 125

Gly Asp Gly Ala Ser Arg Val Val Leu Ser Leu Pro Phe Ala Glu Gly
130 135 140

Ser Ser Ser Val Glu Tyr Ile Asn Asn Trp Glu Gln Ala Lys Ala Leu
145 150 155 160

Ser Val Glu Leu Glu Ile Asn Phe Glu Thr Arg Gly Lys Arg Gly Gln
165 170 175

Asp Ala Met Tyr Glu Tyr Met Ala Gln Ala Cys Ala Gly Asn Arg Val
180 185 190

Arg Arg Ser Val Gly Ser Ser Leu Ser Cys Ile Asn Leu Asp Trp Asp
195 200 205

Val Ile Arg Asp Lys Thr Lys Thr Lys Ile Glu Ser Leu Lys Glu His
210 215 220

Gly Pro Ile Lys Asn Lys Met Ser Glu Ser Pro Asn Lys Thr Val Ser
225 230 235 240

Glu Glu Lys Ala Lys Gln Tyr Leu Glu Glu Phe His Gln Thr Ala Leu
245 250 255

Glu His Pro Glu Leu Ser Glu Leu Lys Thr Val Thr Gly Thr Asn Pro
260 265 270

Fig. 54 continued

Val Phe Ala Gly Ala Asn Tyr Ala Ala Trp Ala Val Asn Val Ala Gln
275 280 285

Val Ile Asp Ser Glu Thr Ala Asp Asn Leu Glu Lys Thr Thr Ala Ala
290 295 300

Leu Ser Ile Leu Pro Gly Ile Gly Ser Val Met Gly Ile Ala Asp Gly
305 310 315 320

Ala Val His His Asn Thr Glu Glu Ile Val Ala Gln Ser Ile Ala Leu
325 330 335

Ser Ser Leu Met Val Ala Gln Ala Ile Pro Leu Val Gly Glu Leu Val
340 345 350

Asp Ile Gly Phe Ala Ala Tyr Asn Phe Val Glu Ser Ile Ile Asn Leu
355 360 365

Phe Gln Val Val His Asn Ser Tyr Asn Arg Pro Ala Tyr Ser Pro Gly
370 375 380

His Lys Thr His Ala Pro Thr Ser Ser Ser Thr Lys Lys Thr Gln Leu
385 390 395 400

Gln Leu Glu His Leu Leu Leu Asp Leu Gln Met Ile Leu Asn Gly Ile
405 410 415

Asn Asn Tyr Lys Asn Pro Lys Leu Thr Arg Met Leu Thr Phe Lys Phe
420 425 430

Tyr Met Pro Lys Lys Ala Thr Glu Leu Lys His Leu Gln Cys Leu Glu
435 440 445

Glu Glu Leu Lys Pro Leu Glu Glu Val Leu Asn Leu Ala Gln Ser Lys
450 455 460

Asn Phe His Leu Arg Pro Arg Asp Leu Ile Ser Asn Ile Asn Val Ile
465 470 475 480

Val Leu Glu Leu Lys Gly Ser Glu Thr Thr Phe Met Cys Glu Tyr Ala 485 490 495

Fig. 54 continued

Asp Glu Thr Ala Thr Ile Val Glu Phe Leu Asn Arg Trp Ile Thr Phe
500 505 510

Cys Gln Ser Ile Ile Ser Thr Leu Thr
515 520

<210> 11
<211> 560
<212> PRT
<213> Corynebacterium diphtheriae

<400> 11
Met Ser Arg Lys Leu Phe Ala Ser Ile Leu Ile Gly Ala Leu Leu Gly
1 5 10 15

Ile Gly Ala Pro Pro Ser Ala His Ala Gly Ala Asp Asp Val Val Asp
20 25 30

Ser Ser Lys Ser Phe Val Met Glu Asn Phe Ser Ser Tyr His Gly Thr
35 40 45

Lys Pro Gly Tyr Val Asp Ser Ile Gln Lys Gly Ile Gln Lys Pro Lys
50 55 60

Ser Gly Thr Gln Gly Asn Tyr Asp Asp Asp Trp Lys Gly Phe Tyr Ser
65 70 75 80

Thr Asp Asn Lys Tyr Asp Ala Ala Gly Tyr Ser Val Asp Asn Glu Asn
85 90 95

Pro Leu Ser Gly Lys Ala Gly Gly Val Val Lys Val Thr Tyr Pro Gly
100 105 110

Leu Thr Lys Val Leu Ala Leu Lys Val Asp Asn Ala Glu Thr Ile Lys
115 120 125

Lys Glu Leu Gly Leu Ser Leu Thr Glu Pro Leu Met Glu Gln Val Gly
130 135 140

Thr Glu Glu Phe Ile Lys Arg Phe Gly Asp Gly Ala Ser Arg Val Val

Fig. 54 continued 145 150 155 160

Leu Ser Leu Pro Phe Ala Glu Gly Ser Ser Ser Val Glu Tyr Ile Asn
165 170 175

Asn Trp Glu Gln Ala Lys Ala Leu Ser Val Glu Leu Glu Ile Asn Phe
180 185 190

Glu Thr Arg Gly Lys Arg Gly Gln Asp Ala Met Tyr Glu Tyr Met Ala
195 200 205

Gln Ala Cys Ala Gly Asn Arg Val Arg Arg Ser Val Gly Ser Ser Leu
210 215 220

Ser Cys Ile Asn Leu Asp Trp Asp Val Ile Arg Asp Lys Thr Lys Thr
225 230 235 240

Lys Ile Glu Ser Leu Lys Glu His Gly Pro Ile Lys Asn Lys Met Ser
245 250 255

Glu Ser Pro Asn Lys Thr Val Ser Glu Glu Lys Ala Lys Gln Tyr Leu
260 265 270

Glu Glu Phe His Gln Thr Ala Leu Glu His Pro Glu Leu Ser Glu Leu
275 280 285

Lys Thr Val Thr Gly Thr Asn Pro Val Phe Ala Gly Ala Asn Tyr Ala
290 295 300

Ala Trp Ala Val Asn Val Ala Gln Val Ile Asp Ser Glu Thr Ala Asp
305 310 315 320

Asn Leu Glu Lys Thr Thr Ala Ala Leu Ser Ile Leu Pro Gly Ile Gly
325 330 335

Ser Val Met Gly Ile Ala Asp Gly Ala Val His His Asn Thr Glu Glu
340 345 350

Ile Val Ala Gln Ser Ile Ala Leu Ser Ser Leu Met Val Ala Gln Ala
355 360 365

Fig. 54 continued

Ile Pro Leu Val Gly Glu Leu Val Asp Ile Gly Phe Ala Ala Tyr Asn
370 375 380

Phe Val Glu Ser Ile Ile Asn Leu Phe Gln Val Val His Asn Ser Tyr
385 390 395 400

Asn Arg Pro Ala Tyr Ser Pro Gly His Lys Thr Gln Pro Phe Leu His
405 410 415

Asp Gly Tyr Ala Val Ser Trp Asn Thr Val Glu Asp Ser Ile Ile Arg
420 425 430

Thr Gly Phe Gln Gly Glu Ser Gly His Asp Ile Lys Ile Thr Ala Glu
435 440 445

Asn Thr Pro Leu Pro Ile Ala Gly Val Leu Leu Pro Thr Ile Pro Gly
450 455 460

Lys Leu Asp Val Asn Lys Ser Lys Thr His Ile Ser Val Asn Gly Arg
465 470 475 480

Lys Ile Arg Met Arg Cys Arg Ala Ile Asp Gly Asp Val Thr Phe Cys
485 490 495

Arg Pro Lys Ser Pro Val Tyr Val Gly Asn Gly Val His Ala Asn Leu
500 505 510

His Val Ala Phe His Arg Ser Ser Ser Glu Lys Ile His Ser Asn Glu
515 520 525

Ile Ser Ser Asp Ser Ile Gly Val Leu Gly Tyr Gln Lys Thr Val Asp
530 535 540

His Thr Lys Val Asn Ser Lys Leu Ser Leu Phe Phe Glu Ile Lys Ser
545 550 555 560

<210> 12
<211> 545
<212> PRT
<213> Artificial Sequence

Fig. 54 continued

<220>
<223> Description of Artificial Sequence: Synthetic
polypeptide

<400> 12
Met Ser Arg Lys Leu Phe Ala Ser Ile Leu Ile Gly Ala Leu Leu Gly
1 5 10 15

Ile Gly Ala Pro Pro Ser Ala His Ala Gly Ala Asp Asp Val Val Asp
20 25 30

Ser Ser Lys Ser Phe Val Met Glu Asn Phe Ser Ser Tyr His Gly Thr
35 40 45

Lys Pro Gly Tyr Val Asp Ser Ile Gln Lys Gly Ile Gln Lys Pro Lys
50 55 60

Ser Gly Thr Gln Gly Asn Tyr Asp Asp Asp Trp Lys Gly Phe Tyr Ser
65 70 75 80

Thr Asp Asn Lys Tyr Asp Ala Ala Gly Tyr Ser Val Asp Asn Glu Asn
85 90 95

Pro Leu Ser Gly Lys Ala Gly Gly Val Val Lys Val Thr Tyr Pro Gly
100 105 110

Leu Thr Lys Val Leu Ala Leu Lys Val Asp Asn Ala Glu Thr Ile Lys
115 120 125

Lys Glu Leu Gly Leu Ser Leu Thr Glu Pro Leu Met Glu Gln Val Gly
130 135 140

Thr Glu Glu Phe Ile Lys Arg Phe Gly Asp Gly Ala Ser Arg Val Val
145 150 155 160

Leu Ser Leu Pro Phe Ala Glu Gly Ser Ser Ser Val Glu Tyr Ile Asn
165 170 175

Asn Trp Glu Gln Ala Lys Ala Leu Ser Val Glu Leu Glu Ile Asn Phe
180 185 190

Glu Thr Arg Gly Lys Arg Gly Gln Asp Ala Met Tyr Glu Tyr Met Ala 195 200 205

Fig. 54 continued

Gln Ala Cys Ala Gly Asn Arg Val Arg Arg Ser Val Gly Ser Ser Leu
210 215 220

Ser Cys Ile Asn Leu Asp Trp Asp Val Ile Arg Asp Lys Thr Lys Thr
225 230 235 240

Lys Ile Glu Ser Leu Lys Glu His Gly Pro Ile Lys Asn Lys Met Ser
245 250 255

Glu Ser Pro Asn Lys Thr Val Ser Glu Glu Lys Ala Lys Gln Tyr Leu
260 265 270

Glu Glu Phe His Gln Thr Ala Leu Glu His Pro Glu Leu Ser Glu Leu
275 280 285

Lys Thr Val Thr Gly Thr Asn Pro Val Phe Ala Gly Ala Asn Tyr Ala
290 295 300

Ala Trp Ala Val Asn Val Ala Gln Val Ile Asp Ser Glu Thr Ala Asp
305 310 315 320

Asn Leu Glu Lys Thr Thr Ala Ala Leu Ser Ile Leu Pro Gly Ile Gly
325 330 335

Ser Val Met Gly Ile Ala Asp Gly Ala Val His His Asn Thr Glu Glu
340 345 350

Ile Val Ala Gln Ser Ile Ala Leu Ser Ser Leu Met Val Ala Gln Ala
355 360 365

Ile Pro Leu Val Gly Glu Leu Val Asp Ile Gly Phe Ala Ala Tyr Asn
370 375 380

Phe Val Glu Ser Ile Ile Asn Leu Phe Gln Val Val His Asn Ser Tyr
385 390 395 400

Asn Arg Pro Ala Tyr Ser Pro Gly His Lys Thr His Ala Pro Thr Ser
405 410 415

Fig. 54 continued

Ser Ser Thr Lys Lys Thr Gln Leu Gln Leu Glu His Leu Leu Leu Asp
420 425 430

Leu Gln Met Ile Leu Asn Gly Ile Asn Asn Tyr Lys Asn Pro Lys Leu
435 440 445

Thr Arg Met Leu Thr Phe Lys Phe Tyr Met Pro Lys Lys Ala Thr Glu
450 455 460

Leu Lys His Leu Gln Cys Leu Glu Glu Glu Leu Lys Pro Leu Glu Glu
465 470 475 480

Val Leu Asn Leu Ala Gln Ser Lys Asn Phe His Leu Arg Pro Arg Asp
485 490 495

Leu Ile Ser Asn Ile Asn Val Ile Val Leu Glu Leu Lys Gly Ser Glu
500 505 510

Thr Thr Phe Met Cys Glu Tyr Ala Asp Glu Thr Ala Thr Ile Val Glu
515 520 525

Phe Leu Asn Arg Trp Ile Thr Phe Cys Gln Ser Ile Ile Ser Thr Leu
530 535 540

Thr
545

<210> 13
<211> 520
<212> PRT
<213> Artificial Sequence

<220>
<223> Description of Artificial Sequence: Synthetic
polypeptide

<400> 13
Gly Ala Asp Asp Val Val Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Fig. 54 continued

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly
210 215 220

Pro Ile Lys Asn Lys Met Ser Glu Ser Pro Asn Lys Thr Val Ser Glu
225 230 235 240

Glu Lys Ala Lys Gln Tyr Leu Glu Glu Phe His Gln Thr Ala Leu Glu 245 250 255

Fig. 54 continued

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

Ile Asp Ser Glu Thr Ala Asp Asn Leu Glu Lys Thr Thr Ala Ala Leu
290 295 300

Ser Ile Leu Pro Gly Ile Gly Ser Val Met Gly Ile Ala Asp Gly Ala
305 310 315 320

Val His His Asn Thr Glu Glu Ile Val Ala Gln Ser Ile Ala Leu Ser
325 330 335

Ser Leu Met Val Ala Gln Ala Ile Pro Leu Val Gly Glu Leu Val Asp
340 345 350

Ile Gly Phe Ala Ala Tyr Asn Phe Val Glu Ser Ile Ile Asn Leu Phe
355 360 365

Gln Val Val His Asn Ser Tyr Asn Arg Pro Ala Tyr Ser Pro Gly His
370 375 380

Lys Thr His Ala Pro Thr Ser Ser Ser Thr Lys Lys Thr Gln Leu Gln
385 390 395 400

Leu Glu His Leu Leu Leu Asp Leu Gln Met Ile Leu Asn Gly Ile Asn
405 410 415

Asn Tyr Lys Asn Pro Lys Leu Thr Arg Met Leu Thr Phe Lys Phe Tyr
420 425 430

Met Pro Lys Lys Ala Thr Glu Leu Lys His Leu Gln Cys Leu Glu Glu
435 440 445

Glu Leu Lys Pro Leu Glu Glu Val Leu Asn Leu Ala Gln Ser Lys Asn
450 455 460

Fig. 54 continued

Phe His Leu Arg Pro Arg Asp Leu Ile Ser Asn Ile Asn Val Ile Val
465 470 475 480

Leu Glu Leu Lys Gly Ser Glu Thr Thr Phe Met Cys Glu Tyr Ala Asp
485 490 495

Glu Thr Ala Thr Ile Val Glu Phe Leu Asn Arg Trp Ile Thr Phe Cys
500 505 510

Gln Ser Ile Ile Ser Thr Leu Thr
515 520

<210> 14
<211> 545
<212> PRT
<213> Artificial Sequence

<220>
<223> Description of Artificial Sequence: Synthetic
polypeptide

<400> 14
Met Ser Arg Lys Leu Phe Ala Ser Ile Leu Ile Gly Ala Leu Leu Gly
1 5 10 15

Ile Gly Ala Pro Pro Ser Ala His Ala Gly Ala Asp Asp Val Ala Asp
20 25 30

Ser Ser Lys Ser Phe Val Met Glu Asn Phe Ser Ser Tyr His Gly Thr
35 40 45

Lys Pro Gly Tyr Val Asp Ser Ile Gln Lys Gly Ile Gln Lys Pro Lys
50 55 60

Ser Gly Thr Gln Gly Asn Tyr Asp Asp Asp Trp Lys Gly Phe Tyr Ser
65 70 75 80

Thr Asp Asn Lys Tyr Asp Ala Ala Gly Tyr Ser Val Asp Asn Glu Asn
85 90 95

Pro Leu Ser Gly Lys Ala Gly Gly Val Val Lys Val Thr Tyr Pro Gly
100 105 110

Fig. 54 continued

Leu Thr Lys Val Leu Ala Leu Lys Val Asp Asn Ala Glu Thr Ile Lys
115 120 125

Lys Glu Leu Gly Leu Ser Leu Thr Glu Pro Leu Met Glu Gln Val Gly
130 135 140

Thr Glu Glu Phe Ile Lys Arg Phe Gly Asp Gly Ala Ser Arg Val Val
145 150 155 160

Leu Ser Leu Pro Phe Ala Glu Gly Ser Ser Ser Val Glu Tyr Ile Asn
165 170 175

Asn Trp Glu Gln Ala Lys Ala Leu Ser Val Glu Leu Glu Ile Asn Phe
180 185 190

Glu Thr Arg Gly Lys Arg Gly Gln Asp Ala Met Tyr Glu Tyr Met Ala
195 200 205

Gln Ala Cys Ala Gly Asn Arg Val Arg Arg Ser Val Gly Ser Ser Leu
210 215 220

Ser Cys Ile Asn Leu Asp Trp Asp Val Ile Arg Asp Lys Thr Lys Thr
225 230 235 240

Lys Ile Glu Ser Leu Lys Glu His Gly Pro Ile Lys Asn Lys Met Ser
245 250 255

Glu Ser Pro Asn Lys Thr Val Ser Glu Glu Lys Ala Lys Gln Tyr Leu
260 265 270

Glu Glu Phe His Gln Thr Ala Leu Glu His Pro Glu Leu Ser Glu Leu
275 280 285

Lys Thr Val Thr Gly Thr Asn Pro Val Phe Ala Gly Ala Asn Tyr Ala
290 295 300

Ala Trp Ala Val Asn Val Ala Gln Val Ile Asp Ser Glu Thr Ala Asp
305 310 315 320

Asn Leu Glu Lys Thr Thr Ala Ala Leu Ser Ile Leu Pro Gly Ile Gly

Fig. 54 continued 325 330 335

Ser Val Met Gly Ile Ala Asp Gly Ala Val His His Asn Thr Glu Glu
340 345 350

Ile Val Ala Gln Ser Ile Ala Leu Ser Ser Leu Met Val Ala Gln Ala
355 360 365

Ile Pro Leu Val Gly Glu Leu Val Asp Ile Gly Phe Ala Ala Tyr Asn
370 375 380

Phe Val Glu Ser Ile Ile Asn Leu Phe Gln Val Val His Asn Ser Tyr
385 390 395 400

Asn Arg Pro Ala Tyr Ser Pro Gly His Lys Thr His Ala Pro Thr Ser
405 410 415

Ser Ser Thr Lys Lys Thr Gln Leu Gln Leu Glu His Leu Leu Leu Asp
420 425 430

Leu Gln Met Ile Leu Asn Gly Ile Asn Asn Tyr Lys Asn Pro Lys Leu
435 440 445

Thr Arg Met Leu Thr Phe Lys Phe Tyr Met Pro Lys Lys Ala Thr Glu
450 455 460

Leu Lys His Leu Gln Cys Leu Glu Glu Glu Leu Lys Pro Leu Glu Glu
465 470 475 480

Val Leu Asn Leu Ala Gln Ser Lys Asn Phe His Leu Arg Pro Arg Asp
485 490 495

Leu Ile Ser Asn Ile Asn Val Ile Val Leu Glu Leu Lys Gly Ser Glu
500 505 510

Thr Thr Phe Met Cys Glu Tyr Ala Asp Glu Thr Ala Thr Ile Val Glu
515 520 525

Phe Leu Asn Arg Trp Ile Thr Phe Cys Gln Ser Ile Ile Ser Thr Leu
530 535 540

Fig. 54 continued

Thr
545

<210> 15
<211> 520
<212> PRT
<213> Artificial Sequence

<220>
<223> Description of Artificial Sequence: Synthetic
polypeptide

<400> 15
Gly Ala Asp Asp Val Ala Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Fig. 54 continued

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly
210 215 220

Pro Ile Lys Asn Lys Met Ser Glu Ser Pro Asn Lys Thr Val Ser Glu
225 230 235 240

Glu Lys Ala Lys Gln Tyr Leu Glu Glu Phe His Gln Thr Ala Leu Glu
245 250 255

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

Ile Asp Ser Glu Thr Ala Asp Asn Leu Glu Lys Thr Thr Ala Ala Leu
290 295 300

Ser Ile Leu Pro Gly Ile Gly Ser Val Met Gly Ile Ala Asp Gly Ala
305 310 315 320

Val His His Asn Thr Glu Glu Ile Val Ala Gln Ser Ile Ala Leu Ser
325 330 335

Ser Leu Met Val Ala Gln Ala Ile Pro Leu Val Gly Glu Leu Val Asp
340 345 350

Ile Gly Phe Ala Ala Tyr Asn Phe Val Glu Ser Ile Ile Asn Leu Phe
355 360 365

Gln Val Val His Asn Ser Tyr Asn Arg Pro Ala Tyr Ser Pro Gly His 370 375 380

Fig. 54 continued

Lys Thr His Ala Pro Thr Ser Ser Ser Thr Lys Lys Thr Gln Leu Gln
385 390 395 400

Leu Glu His Leu Leu Leu Asp Leu Gln Met Ile Leu Asn Gly Ile Asn
405 410 415

Asn Tyr Lys Asn Pro Lys Leu Thr Arg Met Leu Thr Phe Lys Phe Tyr
420 425 430

Met Pro Lys Lys Ala Thr Glu Leu Lys His Leu Gln Cys Leu Glu Glu
435 440 445

Glu Leu Lys Pro Leu Glu Glu Val Leu Asn Leu Ala Gln Ser Lys Asn
450 455 460

Phe His Leu Arg Pro Arg Asp Leu Ile Ser Asn Ile Asn Val Ile Val
465 470 475 480

Leu Glu Leu Lys Gly Ser Glu Thr Thr Phe Met Cys Glu Tyr Ala Asp
485 490 495

Glu Thr Ala Thr Ile Val Glu Phe Leu Asn Arg Trp Ile Thr Phe Cys
500 505 510

Gln Ser Ile Ile Ser Thr Leu Thr
515 520

<210> 16
<211> 522
<212> PRT
<213> Artificial Sequence

<220>
<223> Description of Artificial Sequence: Synthetic
polypeptide

<400> 16
Met Gly Ala Asp Asp Val Ala Asp Ser Ser Lys Ser Phe Val Met Glu
1 5 10 15

Asn Phe Ser Ser Tyr His Gly Thr Lys Pro Gly Tyr Val Asp Ser Ile 20 25 30

Fig. 54 continued

Gln Lys Gly Ile Gln Lys Pro Lys Ser Gly Thr Gln Gly Asn Tyr Asp
35 40 45

Asp Asp Trp Lys Gly Phe Tyr Ser Thr Asp Asn Lys Tyr Asp Ala Ala
50 55 60

Gly Tyr Ser Val Asp Asn Glu Asn Pro Leu Ser Gly Lys Ala Gly Gly
65 70 75 80

Val Val Lys Val Thr Tyr Pro Gly Leu Thr Lys Val Leu Ala Leu Lys
85 90 95

Val Asp Asn Ala Glu Thr Ile Lys Lys Glu Leu Gly Leu Ser Leu Thr
100 105 110

Glu Pro Leu Met Glu Gln Val Gly Thr Glu Glu Phe Ile Lys Arg Phe
115 120 125

Gly Asp Gly Ala Ser Arg Val Val Leu Ser Leu Pro Phe Ala Glu Gly
130 135 140

Ser Ser Ser Val Glu Tyr Ile Asn Asn Trp Glu Gln Ala Lys Ala Leu
145 150 155 160

Ser Val Glu Leu Glu Ile Asn Phe Glu Thr Arg Gly Lys Arg Gly Gln
165 170 175

Asp Ala Met Tyr Glu Tyr Met Ala Gln Ala Cys Ala Gly Asn Arg Val
180 185 190

Arg Arg Ser Val Gly Ser Ser Leu Ser Cys Ile Asn Leu Asp Trp Asp
195 200 205

Val Ile Arg Asp Lys Thr Lys Thr Lys Ile Glu Ser Leu Lys Glu His
210 215 220

Gly Pro Ile Lys Asn Lys Met Ser Glu Ser Pro Asn Lys Thr Val Ser
225 230 235 240

Fig. 54 continued

Glu Glu Lys Ala Lys Gln Tyr Leu Glu Glu Phe His Gln Thr Ala Leu
245 250 255

Glu His Pro Glu Leu Ser Glu Leu Lys Thr Val Thr Gly Thr Asn Pro
260 265 270

Val Phe Ala Gly Ala Asn Tyr Ala Ala Trp Ala Val Asn Val Ala Gln
275 280 285

Val Ile Asp Ser Glu Thr Ala Asp Asn Leu Glu Lys Thr Thr Ala Ala
290 295 300

Leu Ser Ile Leu Pro Gly Ile Gly Ser Val Met Gly Ile Ala Asp Gly
305 310 315 320

Ala Val His His Asn Thr Glu Glu Ile Val Ala Gln Ser Ile Ala Leu
325 330 335

Ser Ser Leu Met Val Ala Gln Ala Ile Pro Leu Val Gly Glu Leu Val
340 345 350

Asp Ile Gly Phe Ala Ala Tyr Asn Phe Val Glu Ser Ile Ile Asn Leu
355 360 365

Phe Gln Val Val His Asn Ser Tyr Asn Arg Pro Ala Tyr Ser Pro Gly
370 375 380

His Lys Thr His Ala Pro Thr Ser Ser Ser Thr Lys Lys Thr Gln Leu
385 390 395 400

Gln Leu Glu His Leu Leu Leu Asp Leu Gln Met Ile Leu Asn Gly Ile
405 410 415

Asn Asn Tyr Lys Asn Pro Lys Leu Thr Arg Met Leu Thr Phe Lys Phe
420 425 430

Tyr Met Pro Lys Lys Ala Thr Glu Leu Lys His Leu Leu Gln Cys Leu
435 440 445

Glu Glu Glu Leu Lys Pro Leu Glu Glu Val Leu Asn Leu Ala Gln Ser 450 455 460

Fig. 54 continued

Lys Asn Phe His Leu Arg Pro Arg Asp Leu Ile Ser Asn Ile Asn Val
465 470 475 480

Ile Val Leu Glu Leu Lys Gly Ser Glu Thr Thr Phe Met Cys Glu Tyr
485 490 495

Ala Asp Glu Thr Ala Thr Ile Val Glu Phe Leu Asn Arg Trp Ile Thr
500 505 510

Phe Cys Gln Ser Ile Ile Ser Thr Leu Thr
515 520

<210> 17
<211> 535
<212> PRT
<213> Artificial Sequence

<220>
<223> Description of Artificial Sequence: Synthetic
polypeptide

<400> 17
Gly Ala Asp Asp Val Val Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Glu Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu

Fig. 54 continued 100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly
210 215 220

Pro Ile Lys Asn Lys Met Ser Glu Ser Pro Asn Lys Thr Val Ser Glu
225 230 235 240

Glu Lys Ala Lys Gln Tyr Leu Glu Glu Phe His Gln Thr Ala Leu Glu
245 250 255

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

Ile Asp Ser Glu Thr Ala Asp Asn Leu Glu Lys Thr Thr Ala Ala Leu
290 295 300

Ser Ile Leu Pro Gly Ile Gly Ser Val Met Gly Ile Ala Asp Gly Ala
305 310 315 320

Fig. 54 continued

Val His His Asn Thr Glu Glu Ile Val Ala Gln Ser Ile Ala Leu Ser
325 330 335

Ser Leu Met Val Ala Gln Ala Ile Pro Leu Val Gly Glu Leu Val Asp
340 345 350

Ile Gly Phe Ala Ala Tyr Asn Phe Val Glu Ser Ile Ile Asn Leu Phe
355 360 365

Gln Val Val His Asn Ser Tyr Asn Arg Pro Ala Tyr Ser Pro Gly His
370 375 380

Lys Thr Gln Pro Phe Leu His Asp Gly Tyr Ala Val Ser Trp Asn Thr
385 390 395 400

Val Glu Asp Ser Ile Ile Arg Thr Gly Phe Gln Gly Glu Ser Gly His
405 410 415

Asp Ile Lys Ile Thr Ala Glu Asn Thr Pro Leu Pro Ile Ala Gly Val
420 425 430

Leu Leu Pro Thr Ile Pro Gly Lys Leu Asp Val Asn Lys Ser Lys Thr
435 440 445

His Ile Ser Val Asn Gly Arg Lys Ile Arg Met Arg Cys Arg Ala Ile
450 455 460

Asp Gly Asp Val Thr Phe Cys Arg Pro Lys Ser Pro Val Tyr Val Gly
465 470 475 480

Asn Gly Val His Ala Asn Leu His Val Ala Phe His Arg Ser Ser Ser
485 490 495

Glu Lys Ile His Ser Asn Glu Ile Ser Ser Asp Ser Ile Gly Val Leu
500 505 510

Gly Tyr Gln Lys Thr Val Asp His Thr Lys Val Asn Ser Lys Leu Ser
515 520 525

Leu Phe Phe Glu Ile Lys Ser 530 535

Fig. 54 continued

<210> 18
<211> 560
<212> PRT
<213> Artificial Sequence

<220>
<223> Description of Artificial Sequence: Synthetic
polypeptide

<400> 18
Met Ser Arg Lys Leu Phe Ala Ser Ile Leu Ile Gly Ala Leu Leu Gly
1 5 10 15

Ile Gly Ala Pro Pro Ser Ala His Ala Gly Ala Asp Asp Val Val Asp
20 25 30

Ser Ser Lys Ser Phe Val Met Glu Asn Phe Ser Ser Tyr His Gly Thr
35 40 45

Lys Pro Gly Tyr Val Asp Ser Ile Gln Lys Gly Ile Gln Lys Pro Lys
50 55 60

Ser Gly Thr Gln Gly Asn Tyr Asp Asp Asp Trp Lys Glu Phe Tyr Ser
65 70 75 80

Thr Asp Asn Lys Tyr Asp Ala Ala Gly Tyr Ser Val Asp Asn Glu Asn
85 90 95

Pro Leu Ser Gly Lys Ala Gly Gly Val Val Lys Val Thr Tyr Pro Gly
100 105 110

Leu Thr Lys Val Leu Ala Leu Lys Val Asp Asn Ala Glu Thr Ile Lys
115 120 125

Lys Glu Leu Gly Leu Ser Leu Thr Glu Pro Leu Met Glu Gln Val Gly
130 135 140

Thr Glu Glu Phe Ile Lys Arg Phe Gly Asp Gly Ala Ser Arg Val Val
145 150 155 160

Leu Ser Leu Pro Phe Ala Glu Gly Ser Ser Ser Val Glu Tyr Ile Asn

Fig. 54 continued 165 170 175

Asn Trp Glu Gln Ala Lys Ala Leu Ser Val Glu Leu Glu Ile Asn Phe
180 185 190

Glu Thr Arg Gly Lys Arg Gly Gln Asp Ala Met Tyr Glu Tyr Met Ala
195 200 205

Gln Ala Cys Ala Gly Asn Arg Val Arg Arg Ser Val Gly Ser Ser Leu
210 215 220

Ser Cys Ile Asn Leu Asp Trp Asp Val Ile Arg Asp Lys Thr Lys Thr
225 230 235 240

Lys Ile Glu Ser Leu Lys Glu His Gly Pro Ile Lys Asn Lys Met Ser
245 250 255

Glu Ser Pro Asn Lys Thr Val Ser Glu Glu Lys Ala Lys Gln Tyr Leu
260 265 270

Glu Glu Phe His Gln Thr Ala Leu Glu His Pro Glu Leu Ser Glu Leu
275 280 285

Lys Thr Val Thr Gly Thr Asn Pro Val Phe Ala Gly Ala Asn Tyr Ala
290 295 300

Ala Trp Ala Val Asn Val Ala Gln Val Ile Asp Ser Glu Thr Ala Asp
305 310 315 320

Asn Leu Glu Lys Thr Thr Ala Ala Leu Ser Ile Leu Pro Gly Ile Gly
325 330 335

Ser Val Met Gly Ile Ala Asp Gly Ala Val His His Asn Thr Glu Glu
340 345 350

Ile Val Ala Gln Ser Ile Ala Leu Ser Ser Leu Met Val Ala Gln Ala
355 360 365

Ile Pro Leu Val Gly Glu Leu Val Asp Ile Gly Phe Ala Ala Tyr Asn
370 375 380

Fig. 54 continued

Phe Val Glu Ser Ile Ile Asn Leu Phe Gln Val Val His Asn Ser Tyr
385 390 395 400

Asn Arg Pro Ala Tyr Ser Pro Gly His Lys Thr Gln Pro Phe Leu His
405 410 415

Asp Gly Tyr Ala Val Ser Trp Asn Thr Val Glu Asp Ser Ile Ile Arg
420 425 430

Thr Gly Phe Gln Gly Glu Ser Gly His Asp Ile Lys Ile Thr Ala Glu
435 440 445

Asn Thr Pro Leu Pro Ile Ala Gly Val Leu Leu Pro Thr Ile Pro Gly
450 455 460

Lys Leu Asp Val Asn Lys Ser Lys Thr His Ile Ser Val Asn Gly Arg
465 470 475 480

Lys Ile Arg Met Arg Cys Arg Ala Ile Asp Gly Asp Val Thr Phe Cys
485 490 495

Arg Pro Lys Ser Pro Val Tyr Val Gly Asn Gly Val His Ala Asn Leu
500 505 510

His Val Ala Phe His Arg Ser Ser Ser Glu Lys Ile His Ser Asn Glu
515 520 525

Ile Ser Ser Asp Ser Ile Gly Val Leu Gly Tyr Gln Lys Thr Val Asp
530 535 540

His Thr Lys Val Asn Ser Lys Leu Ser Leu Phe Phe Glu Ile Lys Ser
545 550 555 560

<210> 19
<211> 535
<212> PRT
<213> Artificial Sequence

<220>
<223> Description of Artificial Sequence: Synthetic
polypeptide

Fig. 54 continued

<400> 19
Gly Ala Asp Asp Val Val Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly 210 215 220

Fig. 54 continued

Pro Ile Lys Asn Lys Met Ser Glu Ser Pro Asn Lys Thr Val Ser Glu
225 230 235 240

Glu Lys Ala Lys Gln Tyr Leu Glu Glu Phe His Gln Thr Ala Leu Glu
245 250 255

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

Ile Asp Ser Glu Thr Ala Asp Asn Leu Glu Lys Thr Thr Ala Ala Leu
290 295 300

Ser Ile Leu Pro Gly Ile Gly Ser Val Met Gly Ile Ala Asp Gly Ala
305 310 315 320

Val His His Asn Thr Glu Glu Ile Val Ala Gln Ser Ile Ala Leu Ser
325 330 335

Ser Leu Met Val Ala Gln Ala Ile Pro Leu Val Gly Glu Leu Val Asp
340 345 350

Ile Gly Phe Ala Ala Tyr Asn Phe Val Glu Ser Ile Ile Asn Leu Phe
355 360 365

Gln Val Val His Asn Ser Tyr Asn Arg Pro Ala Tyr Ser Pro Gly His
370 375 380

Lys Thr Gln Pro Phe Phe His Asp Gly Tyr Ala Val Ser Trp Asn Thr
385 390 395 400

Val Glu Asp Ser Ile Ile Arg Thr Gly Phe Gln Gly Glu Ser Gly His
405 410 415

Asp Ile Lys Ile Thr Ala Glu Asn Thr Pro Leu Pro Ile Ala Gly Val
420 425 430

Fig. 54 continued

Leu Leu Pro Thr Ile Pro Gly Lys Leu Asp Val Asn Lys Ser Lys Thr
435 440 445

His Ile Ser Val Asn Gly Arg Lys Ile Arg Met Arg Cys Arg Ala Ile
450 455 460

Asp Gly Asp Val Thr Phe Cys Arg Pro Lys Ser Pro Val Tyr Val Gly
465 470 475 480

Asn Gly Val His Ala Asn Leu His Val Ala Phe His Arg Ser Ser Ser
485 490 495

Glu Lys Ile His Ser Asn Glu Ile Ser Ser Asp Ser Ile Gly Val Leu
500 505 510

Gly Tyr Gln Lys Thr Val Asp His Thr Lys Val Asn Phe Lys Leu Ser
515 520 525

Leu Phe Phe Glu Ile Lys Ser
530 535

<210> 20
<211> 560
<212> PRT
<213> Artificial Sequence

<220>
<223> Description of Artificial Sequence: Synthetic polypeptide

<400> 20
Met Ser Arg Lys Leu Phe Ala Ser Ile Leu Ile Gly Ala Leu Leu Gly
1 5 10 15

Ile Gly Ala Pro Pro Ser Ala His Ala Gly Ala Asp Asp Val Val Asp
20 25 30

Ser Ser Lys Ser Phe Val Met Glu Asn Phe Ser Ser Tyr His Gly Thr
35 40 45

Lys Pro Gly Tyr Val Asp Ser Ile Gln Lys Gly Ile Gln Lys Pro Lys
50 55 60

Fig. 54 continued

Ser Gly Thr Gln Gly Asn Tyr Asp Asp Asp Trp Lys Gly Phe Tyr Ser
65 70 75 80

Thr Asp Asn Lys Tyr Asp Ala Ala Gly Tyr Ser Val Asp Asn Glu Asn
85 90 95

Pro Leu Ser Gly Lys Ala Gly Gly Val Val Lys Val Thr Tyr Pro Gly
100 105 110

Leu Thr Lys Val Leu Ala Leu Lys Val Asp Asn Ala Glu Thr Ile Lys
115 120 125

Lys Glu Leu Gly Leu Ser Leu Thr Glu Pro Leu Met Glu Gln Val Gly
130 135 140

Thr Glu Glu Phe Ile Lys Arg Phe Gly Asp Gly Ala Ser Arg Val Val
145 150 155 160

Leu Ser Leu Pro Phe Ala Glu Gly Ser Ser Ser Val Glu Tyr Ile Asn
165 170 175

Asn Trp Glu Gln Ala Lys Ala Leu Ser Val Glu Leu Glu Ile Asn Phe
180 185 190

Glu Thr Arg Gly Lys Arg Gly Gln Asp Ala Met Tyr Glu Tyr Met Ala
195 200 205

Gln Ala Cys Ala Gly Asn Arg Val Arg Arg Ser Val Gly Ser Ser Leu
210 215 220

Ser Cys Ile Asn Leu Asp Trp Asp Val Ile Arg Asp Lys Thr Lys Thr
225 230 235 240

Lys Ile Glu Ser Leu Lys Glu His Gly Pro Ile Lys Asn Lys Met Ser
245 250 255

Glu Ser Pro Asn Lys Thr Val Ser Glu Glu Lys Ala Lys Gln Tyr Leu
260 265 270

Glu Glu Phe His Gln Thr Ala Leu Glu His Pro Glu Leu Ser Glu Leu

Fig. 54 continued 275 280 285

Lys Thr Val Thr Gly Thr Asn Pro Val Phe Ala Gly Ala Asn Tyr Ala
290 295 300

Ala Trp Ala Val Asn Val Ala Gln Val Ile Asp Ser Glu Thr Ala Asp
305 310 315 320

Asn Leu Glu Lys Thr Thr Ala Ala Leu Ser Ile Leu Pro Gly Ile Gly
325 330 335

Ser Val Met Gly Ile Ala Asp Gly Ala Val His His Asn Thr Glu Glu
340 345 350

Ile Val Ala Gln Ser Ile Ala Leu Ser Ser Leu Met Val Ala Gln Ala
355 360 365

Ile Pro Leu Val Gly Glu Leu Val Asp Ile Gly Phe Ala Ala Tyr Asn
370 375 380

Phe Val Glu Ser Ile Ile Asn Leu Phe Gln Val Val His Asn Ser Tyr
385 390 395 400

Asn Arg Pro Ala Tyr Ser Pro Gly His Lys Thr Gln Pro Phe Phe His
405 410 415

Asp Gly Tyr Ala Val Ser Trp Asn Thr Val Glu Asp Ser Ile Ile Arg
420 425 430

Thr Gly Phe Gln Gly Glu Ser Gly His Asp Ile Lys Ile Thr Ala Glu
435 440 445

Asn Thr Pro Leu Pro Ile Ala Gly Val Leu Leu Pro Thr Ile Pro Gly
450 455 460

Lys Leu Asp Val Asn Lys Ser Lys Thr His Ile Ser Val Asn Gly Arg
465 470 475 480

Lys Ile Arg Met Arg Cys Arg Ala Ile Asp Gly Asp Val Thr Phe Cys
485 490 495

Fig. 54 continued

Arg Pro Lys Ser Pro Val Tyr Val Gly Asn Gly Val His Ala Asn Leu
500 505 510

His Val Ala Phe His Arg Ser Ser Ser Glu Lys Ile His Ser Asn Glu
515 520 525

Ile Ser Ser Asp Ser Ile Gly Val Leu Gly Tyr Gln Lys Thr Val Asp
530 535 540

His Thr Lys Val Asn Phe Lys Leu Ser Leu Phe Phe Glu Ile Lys Ser
545 550 555 560

<210> 21
<211> 6402
<212> DNA
<213> Artificial Sequence

<220>
<223> Description of Artificial Sequence: Synthetic
polynucleotide

<400> 21
ggcgagtgct ttgaatgctt gggcttcttc acggcgggtc ttgaccgcgt tgataagttc 60
gcggccagag ctgaattgct ggcgtggggt ggggttgaac tggtcgtgtc ctgccatatc 120
ccttacctgc tttatcaagt ctccaaggcg catcacccgg ttgtgctgcc tataccaacg 180
ataagcggta ggggctttgc ctgtgtagaa cgggttgcgg ctaaagcggt gggaaaagtg 240
cgggtcatgg tctaaaagct cacccagcac acgcgtggtt gctgcaagaa gcttcatctg 300
cgcagattta ccgttacggt cagcgtagac agggtcaata agccatatga actgggcttt 360
gccgttagtt gggttaatac ccacccaggc tggcccgacg ctatgagtaa tcagtgagcg 420
caccacgtcg cggacgtacg ggtttaagtc tgcggggtca ccgcctgcgg tacctacttg 480
gtcaacgtct acgaccagga cggcggcgta ctgcttggtg gtgagcatgg cgtactcgca 540
ccgtcctaaa gcatcagtct cgaagcgata catacgcggc gagttcgtgc cgtcagcgtt 600
gcgtcgatag gcctttttaa agtctcgtgt gactgaaccg tggagtacat cgcggcctag 660
atgatcgcgt aaaaggtcgc ggtcactggc agatgctggg gtgttgtcca gtccaccacg 720
gtcgcgctcg acgcgggtag gtgttttagt gtgcgcattc tgcgcatgag tctgtaaact 780
catgaccgtg ctttctccca ggtgtgtgct gggtgataag cgaaagtcat cgggttgccg 840

Fig. 54 continued cccggtggct ttcttcgttt ttcattgtct ttccctgact ctaaatgaca ccggtgttat 900
ttactagcca tgacacgcga aaaatatgcc ttttacctgc ggttacgtat ggctagacat 960
atggcaagct atacgtaacc gcgtttcagc tgcacagggc tgtctgcgca gatttaccat 1020
cacgggactt ttcccagttc aggctgcgca tatttacgca tacaacgaaa gcggttgcgc 1080
agatttacca cacactctgc gctgatttac cgatacgcag aaaaagcgtg cgcagattta 1140
cccatacggt ggcgaattat ccagagcaat aggtatacag caatacagta atacaggtgc 1200
cataaacctg tattactgta ttgctgtatg cctgtaaacc tttatttatt gttgtggacg 1260
tattcttcga ggtaggtgct aacaatctcg cggatggtca cgcctttttg ggcggcgatg 1320
actttaagtt ctgcgtgaag gtcgcggtcg atttcaatcg tcatcttctt gacgtagtcg 1380
cggcctgtgg gttggtggaa tgcgcttcgc actgttttct tctcggctgc tggagttagc 1440
ttcgtggctt ttttcattga ggttcgcggg ccttgctgcg ccctggcgcg ttctttactg 1500
gtgctcattt catcatctcc atgagttcgt cggcgacgtg gtcgtagccg tgcatgtcgg 1560
ggcctgggca gtatccaaac gctaggtgca tatcttcgcg tagcgggatt tcggttttaa 1620
agtgcggcat gtgttccgcg tcgagcgctt ctcgtgccgc gtcaagggcg ctggtgcctt 1680
tcctggcgaa cgtcagtaag actgcatgag gtgttccgtt gactgcgtcg cgcagctccc 1740
atactcggga gaggtcggca gcagcagaac gggtcggaag aatgatgaag tcgctgactg 1800
cgattgctgc ttcgatagcg ttctcgtctc ctggcggcac atcgataccg actgggcgat 1860
ggcccactac gtgaaccatc accctaatca agttttttgg ggtcgaggtg ccgtaaagca 1920
ctaaatcgga accctaaagg gagcccccga tttagagctt gacggggaaa gccggcgaac 1980
gtggcgagaa aggaagggaa gaaagcgaaa ggagcgggcg ctagggcgct ggcaagtgta 2040
gcggtcacgc tgcgcgtaac caccacaccc gccgcgctta atgcgccgct acagggcgct 2100
cccattcgcc attcaggctg cgcaactgtt gggaagggcg atcggtgcgg gcctcttcgc 2160
tattacgcca gctggcgaaa gggggatgtg ctgcaaggcg attaagttgg gtaacgccag 2220
ggttttccca gtcacgacgt tgtaaaacga cggccagtga attgtaatac gactcactat 2280
agggcgaatt ggagctccac cgcggtggcg gccgctctag aactagtgga tccagggcat 2340
tgatttcaga gcacccttat aattaggata gctaagtcca ttattttatg agtcctggta 2400
aggggatacg ttgtgagcag aaaactgttt gcgtcaatct taatagggc gctactgggg 2460

Fig. 54 continued ataggggccc caccttcagc ccatgcaggc gctgatgatg ttgttgattc ttctaaatct 2520
tttgtgatgg aaaacttttc ttcgtaccac gggactaaac ctggttatgt agattccatt 2580
caaaaaggta tacaaaagcc aaaatctggt acacaaggaa attatgacga tgattggaaa 2640
gggttttata gtaccgacaa taaatacgac gctgcgggat actctgtaga taatgaaaac 2700
ccgctctctg gaaaagctgg aggcgtggtc aaagtgacgt atccaggact gacgaaggtt 2760
ctcgcactaa aagtggataa tgccgaaact attaagaaag agttaggttt aagtctcact 2820
gaaccgttga tggagcaagt cggaacggaa gagtttatca aaaggttcgg tgatggtgct 2880
tcgcgtgtag tgctcagcct tcccttcgct gaggggagtt ctagcgttga atatattaat 2940
aactgggaac aggcgaaagc gttaagcgta gaacttgaga ttaattttga aacccgtgga 3000
aaacgtggcc aagatgcgat gtatgagtat atggctcaag cctgtgcagg aaatcgtgtc 3060
aggcgatcag taggtagctc attgtcatgc atcaacctgg attgggatgt tatccgtgat 3120
aaaactaaaa ctaagatcga atctctgaaa gaacacggtc cgatcaaaaa caaaatgagc 3180
gaaagcccga acaaaactgt atctgaagaa aaagctaaac agtacctgga agaattccac 3240
cagactgcac tggaacaccc ggaactgtct gaacttaaga ccgttactgg taccaacccg 3300
gtattcgctg gtgctaacta cgctgcttgg gcagtaaacg ttgctcaggt tatcgatagc 3360
gaaactgctg ataacctgga aaaaactacc gcggctctgt ctatcctgcc gggtatcggt 3420
agcgtaatgg gcatcgcaga cggcgccgtt caccacaaca ctgaagaaat cgttgcacag 3480
tctatcgctc tgagctctct gatggttgct caggccatcc cgctggtagg tgaactggtt 3540
gatatcggtt tcgctgcata caacttcgtt gaaagcatca tcaacctgtt ccaggttgtt 3600
cacaactctt acaaccgccc ggcttactct ccgggtcaca agacgcatgc acctacttct 3660
agctctacca agaaaaccca gctgcagctc gagcacctgc tgctggattt gcagatgatc 3720
ctgaacggta tcaacaatta caagaacccg aaactgacgc gtatgctgac cttcaagttc 3780
tacatgccga agaaggccac cgaactgaaa cacctgcagt gtctagaaga agaactgaaa 3840
ccgctggagg aagttctgaa cctggctcag tctaaaaact tccacctgcg gccgcgtgac 3900
ctgatctcta acatcaacgt aatcgttctg gaactgaagg gctctgaaac caccttcatg 3960
tgtgaatacg ctgatgagac cgcaaccatc gtagaattcc tgaaccgttg gatcaccttc 4020
tgtcagtcta tcatctctac cctgacctga ggatcccccg ggctgcagga attcgatatc 4080

Fig. 54 continued aagcttatcg ataccgtcga cctcgagggg gggcccggta ccagcttttg ttccctttag 4140
tgagggttaa tttcgagctt ggcgtaatca tggtcatagc tgtttcctgt gtgaaattgt 4200
tatccgctca caattccaca caacatacga gccggaagca taaagtgtaa agcctggggt 4260
gcctaatgag tgagtccccg atccgtcgag ctcgacctgc aggggggggg gggcgctgag 4320
gtctgcctcg tgaagaaggt gttgctgact cataccaggc ctgaatcgcc ccatcatcca 4380
gccagaaagt gagggagcca cggttgatga gagctttgtt gtaggtggac cagttggtga 4440
ttttgaactt ttgctttgcc acggaacggt ctgcgttgtc gggaagatgc gtgatctgat 4500
ccttcaactc agcaaaagtt cgatttattc aacaaagccg ccgtcccgtc aagtcagcgt 4560
aatgctctgc cagtgttaca accaattaac caattctgat tagaaaaact catcgagcat 4620
caaatgaaac tgcaatttat tcatatcagg attatcaata ccatattttt gaaaaagccg 4680
tttctgtaat gaaggagaaa actcaccgag gcagttccat aggatggcaa gatcctggta 4740
tcggtctgcg attccgactc gtccaacatc aatacaacct attaatttcc cctcgtcaaa 4800
aataaggtta tcaagtgaga aatcaccatg agtgacgact gaatccggtg agaatggcaa 4860
aagcttatgc atttctttcc agacttgttc aacaggccag ccattacgct cgtcatcaaa 4920
atcactcgca tcaaccaaac cgttattcat tcgtgattgc gcctgagcga gacgaaatac 4980
gcgatcgctg ttaaaaggac aattacaaac aggaatcgaa tgcaaccggc gcaggaacac 5040
tgccagcgca tcaacaatat tttcacctga atcaggatat tcttctaata cctggaatgc 5100
tgttttcccg gggatcgcag tggtgagtaa ccatgcatca tcaggagtac ggataaaatg 5160
cttgatggtc ggaagaggca taaattccgt cagccagttt agtctgacca tctcatctgt 5220
aacatcattg gcaacgctac ctttgccatg tttcagaaac aactctggcg catcgggctt 5280
cccatacaat cgatagattg tcgcacctga ttgcccgaca ttatcgcgag cccatttata 5340
cccatataaa tcagcatcca tgttggaatt taatcgcggc ctcgagcaag acgtttcccg 5400
ttgaatatgg ctcataacac cccttgtatt actgtttatg taagcagaca gttttattgt 5460
tcatgatgat atatttttat cttgtgcaat gtaacatcag agattttgag acacaacgtg 5520
gctttccccc cccccctgc aggtcgagct cgacggatcg ggctgcagga attcggtgag 5580
gttatggcgg agggttgcga ggtctaggag aacagaggaa gtcatgcttt gaagcatata 5640
agctgccctg cccctcaagg ttttcttcaa gtgaggtttt atctaactgc ctaacggcag 5700

Fig. 54 continued gggaaccgta tattgcttac ggtatgagac cccttaaacg tccggatagt caccgctctt 5760
ctttagctcc gcgacatgcc tagcaaccgt ggcgcgagag actcctacct ctgcccctat 5820
ttcagcccac gtgggaactg tccctgtctg gaaatactga tcgttcacca tttggctaat 5880
acgggacttc gtagatcgtc cttgagcctt tttcttacgg tgcgtctttt caagcttcga 5940
cctttgtgct tgcgcatatt tgccctcggg gtctgttttc cagcgttgtg cggctttttg 6000
tccgcctctg cgtcccatcg tggccaaggc tttccgctcg ctgctggtgg ctttacctgg 6060
tgcgttagag ccgctgtagg tctcgctctt ggattgggcg acatacccgc gcacgcgcct 6120
tgccatggtt tggcggtcgc gcatgggtgg catctcgttg tcgcggcctg caccgccgtg 6180
ggtgtgtgcg acgttgtagg cgtgctcata ggcgtcgatg attgctgcgt ctgtcaggcg 6240
ttggccttgc tggcgcaagc ggtggccagt cttaagcgca tgtctaaagg ctgtttcgtc 6300
gcgtgctgcg gttccttgga caatccagag cacacgcaca ccgtcgataa gttccgggtc 6360
atactggtcg agaccaccgg cgatttccgc gtctacgtcc tg 6402

<210> 22
<211> 25
<212> PRT
<213> Artificial Sequence

<220>
<223> Description of Artificial Sequence: Synthetic
peptide

<400> 22
Met Ser Arg Lys Leu Phe Ala Ser Ile Leu Ile Gly Ala Leu Leu Gly
1 5 10 15

Ile Gly Ala Pro Pro Ser Ala His Ala
20 25

<210> 23
<211> 6
<212> PRT
<213> Artificial Sequence

<220>
<223> Description of Artificial Sequence: Synthetic
6xHis tag

His His His His His His
1 5

<210> 24
<211> 8
<212> PRT
<213> Artificial Sequence

<220>
<223> Description of Artificial Sequence: Synthetic
peptide

<400> 24
Asp Tyr Lys Asp Asp Asp Asp Lys
1 5

<210> 25
<211> 19
<212> DNA
<213> Unknown

<220>
<223> Description of Unknown:
wild-type toxO sequence

<400> 25
ttaggatagc tttacctaa 19

<210> 26
<211> 32
<212> PRT
<213> Artificial Sequence

<220>
<223> Description of Artificial Sequence: Synthetic
polypeptide

<400> 26
Met Gly Ala Asp Asp Val Val Asp Ser Ser Lys Ser Phe Val Met Glu
1 5 10 15

Asn Phe Ser Ser Tyr His Gly Thr Lys Pro Gly Tyr Val Asp Ser Ile
20 25 30

<210> 27
<211> 31
<212> PRT
<213> Artificial Sequence

Fig. 54 continued

<220>
<223> Description of Artificial Sequence: Synthetic
polypeptide

<400> 27
Met Ser Arg Lys Leu Phe Ala Ser Ile Leu Ile Gly Ala Leu Leu Gly
1 5 10 15

Ile Gly Ala Pro Pro Ser Ala His Ala Gly Ala Asp Asp Val Val
20 25 30

<210> 28
<211> 5
<212> PRT
<213> Artificial Sequence

<220>
<223> Description of Artificial Sequence: Synthetic
peptide

<400> 28
Met Gly Ala Asp Asp
1 5

<210> 29
<211> 4
<212> PRT
<213> Artificial Sequence

<220>
<223> Description of Artificial Sequence: Synthetic
peptide

<400> 29
Gly Ala Asp Asp
1

<210> 30
<211> 526
<212> PRT
<213> Artificial Sequence

<220>
<223> Description of Artificial Sequence: Synthetic
polypeptide

<400> 30
Gly Ala Asp Asp Val Ala Asp Ser Ser Lys Ser Phe Val Met Glu Asn
1 5 10 15

Fig. 54 continued

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly
210 215 220

Pro Ile Lys Asn Lys Met Ser Glu Ser Pro Asn Lys Thr Val Ser Glu 225 230 235 240

Fig. 54 continued

Glu Lys Ala Lys Gln Tyr Leu Glu Glu Phe His Gln Thr Ala Leu Glu
245 250 255

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

Ile Asp Ser Glu Thr Ala Asp Asn Leu Glu Lys Thr Thr Ala Ala Leu
290 295 300

Ser Ile Leu Pro Gly Ile Gly Ser Val Met Gly Ile Ala Asp Gly Ala
305 310 315 320

Val His His Asn Thr Glu Glu Ile Val Ala Gln Ser Ile Ala Leu Ser
325 330 335

Ser Leu Met Val Ala Gln Ala Ile Pro Leu Val Gly Glu Leu Val Asp
340 345 350

Ile Gly Phe Ala Ala Tyr Asn Phe Val Glu Ser Ile Ile Asn Leu Phe
355 360 365

Gln Val Val His Asn Ser Tyr Asn Arg Pro Ala Tyr Ser Pro Gly His
370 375 380

Lys Thr His Ala Pro Thr Ser Ser Ser Thr Lys Lys Thr Gln Leu Gln
385 390 395 400

Leu Glu His Leu Leu Leu Asp Leu Gln Met Ile Leu Asn Gly Ile Asn
405 410 415

Asn Tyr Lys Asn Pro Lys Leu Thr Arg Met Leu Thr Phe Lys Phe Tyr
420 425 430

Met Pro Lys Lys Ala Thr Glu Leu Lys His Leu Gln Cys Leu Glu Glu
435 440 445

Fig. 54 continued

Glu Leu Lys Pro Leu Glu Glu Val Leu Asn Leu Ala Gln Ser Lys Asn
450 455 460

Phe His Leu Arg Pro Arg Asp Leu Ile Ser Asn Ile Asn Val Ile Val
465 470 475 480

Leu Glu Leu Lys Gly Ser Glu Thr Thr Phe Met Cys Glu Tyr Ala Asp
485 490 495

Glu Thr Ala Thr Ile Val Glu Phe Leu Asn Arg Trp Ile Thr Phe Cys
500 505 510

Gln Ser Ile Ile Ser Thr Leu Thr Glu Asn Leu Tyr Phe Gln
515 520 525

<210> 31
<211> 1686
<212> DNA
<213> Artificial Sequence

<220>
<223> Description of Artificial Sequence: Synthetic
polynucleotide

<400> 31
gtgagcagaa aactgtttgc gtcaatctta ataggggcgc tactggggat aggggcccca 60
ccttcagccc atgcaggcgc tgatgatgtt gctgattctt ctaaatcttt tgtgatggaa 120
aacttttctt cgtaccacgg gactaaacct ggttatgtag attccattca aaaaggtata 180
caaaagccaa aatctggtac acaaggaaat tatgacgatg attggaaagg gttttatagt 240
accgacaata aatacgacgc tgcgggatac tctgtagata atgaaaaccc gctctctgga 300
aaagctggag gcgtggtcaa agtgacgtat ccaggactga cgaaggttct cgcactaaaa 360
gtggataatg ccgaaactat taagaaagag ttaggtttaa gtctcactga accgttgatg 420
gagcaagtcg gaacggaaga gtttatcaaa aggttcggtg atggtgcttc gcgtgtagtg 480
ctcagccttc ccttcgctga ggggagttct agcgttgaat atattaataa ctgggaacag 540
gcgaaagcgt taagcgtaga acttgagatt aattttgaaa cccgtggaaa acgtggccaa 600
gatgcgatgt atgagtatat ggctcaagcc tgtgcaggaa atcgtgtcag gcgatcagta 660
ggtagctcat tgtcatgcat caacctggat tgggatgtta tccgtgataa aactaaaact 720

Fig. 54 continued aagatcgaat ctctgaaaga acacggtccg atcaaaaaca aaatgagcga aagcccgaac 780
aaaactgtat ctgaagaaaa agctaaacag tacctggaag aattccacca gactgcactg 840
gaacacccgg aactgtctga acttaagacc gttactggta ccaacccggt attcgctggt 900
gctaactacg ctgcttgggc agtaaacgtt gctcaggtta tcgatagcga aactgctgat 960
aacctggaaa aaactaccgc ggctctgtct atcctgccgg gtatcggtag cgtaatgggc 1020
atcgcagacg gcgccgttca ccacaacact gaagaaatcg ttgcacagtc tatcgctctg 1080
agctctctga tggttgctca ggccatcccg ctggtaggtg aactggttga tatcggtttc 1140
gctgcataca acttcgttga aagcatcatc aacctgttcc aggttgttca caactcttac 1200
aaccgcccgg cttactctcc gggtcacaag acgcatgcac ctacttctag ctctaccaag 1260
aaaacccagc tgcagctcga gcacctgctg ctggatttgc agatgatcct gaacggtatc 1320
aacaattaca agaacccgaa actgacgcgt atgctgacct tcaagttcta catgccgaag 1380
aaggccaccg aactgaaaca cctgcagtgt ctagaagaag aactgaaacc gctggaggaa 1440
gttctgaacc tggctcagtc taaaaacttc cacctgcggc cgcgtgacct gatctctaac 1500
atcaacgtaa tcgttctgga actgaagggc tctgaaacca ccttcatgtg tgaatacgct 1560
gatgagaccg caaccatcgt agaattcctg aaccgttgga tcaccttctg tcagtctatc 1620
atctctaccc tgaccgagaa cctgtacttc cagggccatc accaccacca ccaccatcat 1680
cactag 1686

<210> 32
<211> 250
<212> PRT
<213> Corynebacterium diphtheriae

<400> 32
Met Arg Lys Ile Val Thr Leu Ala Ala Ala Ser Leu Leu Gly Ile Ala
1 5 10 15

Gly Thr Ser Gly Val Leu Gly Ala Ala Thr Ala Thr Ala Leu Thr Asn
20 25 30

Gly Thr Pro Val Ser Pro Glu Asp Asp Thr Ala Ala Glu Gly Val Val
35 40 45

Fig. 54 continued

Gln Val Ala Ser Cys Thr Gly Thr Val Val Ala Ser Gln Trp Val Leu
50 55 60

Thr Ala Gln His Cys Val Glu Val Pro Asn Leu Gln Arg Pro Val Tyr
65 70 75 80

Val Gly Thr Thr Arg Glu Gln Gln Gln Arg Glu Glu Asn Thr Phe Thr
85 90 95

Ser Asp Tyr Ala Val Trp Ala Pro His Gly Asp Val Ala Leu Val His
100 105 110

Val Thr Asp Ala Leu Pro Gln Arg Leu Val Arg Ala Val Arg Arg Ala
115 120 125

Pro Val Ser Phe Gly Glu Gln Gly Arg Val Tyr Gly Trp Gly Ala Gly
130 135 140

Thr Gly Glu Thr Leu Gln Tyr Ala Arg Ala Ala Val Gly Lys Thr Ser
145 150 155 160

Ser Gly Val Arg Pro Gln Gly Asn Gln His Gly Ala Phe Ile Val Gln
165 170 175

Tyr Leu Asp Glu Ala Lys Ala Gly Arg Gly Asp Ser Gly Gly Pro Leu
180 185 190

Phe Val Asn Gly Glu Val Ala Gly Val Thr Ser Phe Lys Ala Pro Gln
195 200 205

Gly Gly Gly Arg Phe Ser Leu Phe Ala Ser Leu His Gly Leu Gly Asp
210 215 220

Trp Ile Ala Gln Thr Thr Ala Ala Lys Pro Glu Asn Pro Asn Ser Lys
225 230 235 240

Asn Gln Gln Ser Gln Gln Pro Arg Arg Pro
245 250

<212> DNA
<213> Corynebacterium diphtheriae

<400> 33
atgcggaaaa ttgttactct tgctgcagca agcttgctgg gtattgcggg taccagcggt 60
gttcttggtg cggcaacagc caccgcactg acaaatggca cgcccgtctc ccctgaggac 120
gataccgctg ccgaaggcgt ggttcaagtg gctagttgta ctggcaccgt ggttgcttct 180
cagtgggtgc tgaccgccca gcattgcgtc gaggtgccca atttgcagcg gccggtctat 240
gttggcacca cccgcgagca gcaacaacgg gaagaaaata cgttcacctc ggattacgca 300
gtgtgggcac cgcacggcga tgtggcgttg gtgcatgtca ccgatgcgct gccgcagcgt 360
ctggtccgcg cggttcgccg cgcaccggtg agctttggtg agcagggacg cgtgtacggc 420
tggggtgctg gcaccggcga gacgctgcag tatgcccgcg ctgcggttgg taaaacttct 480
tccggagttc ggccgcaggg caaccagcat ggtgcattca tcgtgcagta tttggacgag 540
gctaaagccg ggcgtggcga ttccggcggg ccgctttttg tcaacggtga ggttgctggg 600
gtgacctcgt ttaaggctcc tcaaggtggt gggcgtttct cgctgtttgc ttcgctgcat 660
gggctaggcg attggattgc gcagaccacc gccgccaagc ccgagaaccc gaattccaag 720
aatcaacagt cccagcaacc acgtagaccg tag 753

<210> 34
<211> 1012
<212> DNA
<213> Corynebacterium diphtheriae

<400> 34
ggatccgcaa ttgcgggaat cgtcgtgctt tttagccgaa attttcttgc agccagcgct 60
atgcttatcg cctcagggtt agccgctgac atttaccgct tgaggaataa tatgagtgga 120
aatcaacggt aatttcagaa gacttgccta cacctttagc tagcgaccac cattggtggt 180
cgctagcttt ttgatggctt aagggacatt tgggcatccg tgtatcgcac attagtcata 240
caggaaatcc tccaagattt cgtccgcatg cccgaccaga cactacagca cccacatagc 300
ttctcgattg tcttgcggag cgggagtagg tagctcacgt gctaccgcac ggggaaccgt 360
atattgctta tggtgtgccc attacccacc gttggtgcta tgatccgaac ggaaaaagtc 420
agtcgtatta gtgaatcacc gttccgccgc gcgagaacgc agggctccaa caagcgtgtg 480
gttccacaag attgcaagga tgtgtacggt gctggtggcg gtggctccag cctgggtctg 540

Fig. 54 continued tcgtcttctt agcaagtctg cattcacggt tccctaggca atctttgagc aaatccctgt 600
ttaacgcccc tgtacgttcg gcgccgcaga aacctgccgg atcgtgatgt taatcctgcc 660
ttgttccagc ccgcagccgt cgggaagcgt ggcatcattc acgcgcacca ccccgtgata 720
agcaaaacgc ttcggcccac cgaaaaccac caagtcgccg gagcacagag tcacatcgtc 780
ccagggttgg gtgcgtgatt cggtgtgtcc catccgaaac agtgcttcgt cgccaatcga 840
tactgaaatg accggcgccc gcgattcctc aaattcatcg acgtgcatgc ccatcccgga 900
acccggcgga tagtagttga ccagcaccat ctctgtcacg aaggcctcta cccacggggc 960
tagttcttcg gcaacctccg ctgctgcgcg caacgctgcc ggcgccggat cc 1012

<210> 35
<211> 242
<212> PRT
<213> Corynebacterium diphtheriae

<400> 35
Met Lys Lys Leu Arg Thr Leu Ala Val Thr Leu Thr Ala Ile Ala Ala
1 5 10 15

Ser Thr Met Ala Thr Met Pro Ala Gln Ala Val Ile Ser Pro Thr Pro
20 25 30

Ser His Gln Val Ser Leu Ala Tyr Val Ser Phe Asp Asn Met Gln Cys
35 40 45

Thr Gly Thr Leu Val Ser Pro Thr Ala Val Leu Thr Ala Arg His Cys
50 55 60

Leu Asn Gly Gly Leu Gly His Val Arg Leu Gly Ala Asp His Phe Thr
65 70 75 80

Ala Val Arg Ala Val Ala His Pro Gln Ala Asp Leu Ala Val Leu His
85 90 95

Leu Asp Arg Pro Ala Pro Ile Ala Pro Ser Ala Ile Ser Gly Arg His
100 105 110

Thr Gln Pro Gly Asn Arg Phe Gly Val Ala Gly Tyr Gly Ser Thr Phe
115 120 125

Fig. 54 continued

Thr Gly Ile Pro Met Ala Ala Ala Ala Thr Met Gln Arg Arg Val Thr
130 135 140

Asp Val Pro Ser Pro Asp Arg Gln Ala Val Met Ile Glu Asn His Ile
145 150 155 160

Ser Gln Gly Val Leu Arg Pro Gly Asp Ser Gly Gly Pro Leu Leu Glu
165 170 175

Gly Asn His Val Ile Gly Val Leu Ser Met Ser Ser Ala Ser Gly Arg
180 185 190

Val Gly Trp Tyr Ile Pro Thr Ala Glu His Ala Asp Trp Ile Ala Ala
195 200 205

Ala Ala Gly Ile Pro Ala Pro Gly Ser Val Asp Lys Pro Ala Pro Leu
210 215 220

Val Asp Ala Thr Ala Phe Pro Thr Gln Glu Pro Ser Leu Ala Ser Leu
225 230 235 240

Ser Ser

<210> 36
<211> 729
<212> DNA
<213> Corynebacterium diphtheriae

<400> 36
atgaagaaac ttcgtaccct agccgtaacc ctgaccgcaa tcgcagcatc aaccatggcg 60
accatgccag cacaagcagt gattagtccg acaccgtcac atcaagtttc gctagcgtac 120
gtcagttttg acaacatgca gtgcaccggc acactcgtca gccccaccgc cgtgctcaca 180
gcacgacact gcctcaacgg cggcctcggc cacgtccgac tcggcgccga tcacttcacc 240
gccgtacgtg ccgtggcaca cccccaagca gaccttgccg tcctccacct cgatcgccca 300
gcgccaatag cgccatccgc aatctctgga cgtcacaccc aaccaggtaa ccgcttcgga 360
gttgccggct acggaagcac cttcaccggc atccccatgg cagcagctgc aaccatgcaa 420

Fig. 54 continued cgccgcgtca ccgacgtccc cagccccgac cgccaagcag tcatgatcga aaaccacatc 480
agccaaggtg tactacgccc aggcgactct ggcggccccc tcctagaggg caatcacgtc 540
ataggagtac tcagcatgag cagtgcatcc ggccgcgtcg gctggtacat ccccaccgca 600
gaacacgccg actggatcgc ggcggcagcc ggaatccccg caccgggaag cgtcgacaag 660
cccgctccgc tcgtcgacgc cacagccttc ccgacgcaag agccaagcct cgctagccta 720
tcctcctag 729

<210> 37
<211> 1012
<212> DNA
<213> Corynebacterium diphtheriae

<400> 37
ggatccgggc ttatcaccgc agaagacgcc gaaaaagcca tcgatgccac cctcctagcc 60
gtcgacggca tcacacgcca taacgacgac cccatggcat ggctcgccgc tatgggatac 120
ccactaacat gggcaaaaaa catcacgctt aaggaggccg aatgattacc gtctatcaca 180
acccccgctg ctccacctcg cgcaaagcct tggagtacat agaacaacac agcgacgacg 240
aggtgaccat catccgctac ctcgacgccc ctcctagtga acaagagctg cgcactttgc 300
ttgccgacgc ccacctcagc ccgcacgacg caatccgcac caaagaagcc gaatacaaag 360
aactcggact cagctccacc acccccgaat cagagctaat caaggccatg gtcacccacc 420
cacgcctcat tcagcgccca attgtggcaa catgcaaggg aacgcggatc gcccgaccaa 480
ccgaaattct gaaagaaatt ctctagccga atcgccagcg atctcggaag ccaaggaatc 540
cttcggcatg ttaaaaaatg taaaagttta atgcgggcac aaacgcgttg aaagagcaac 600
acaccaccat cgttgaacat acttgattat ttcccacttt ccagaatttt aatgagcatg 660
cccagctcga catcaagaac gcagggaaga tctcactagc aatcgacgat aggcccttct 720
tcgacaaccc ggaacatctt gccacgtacg acggaactac actggcagga tcgtcaatat 780
gtggtgaatt ccctgttaaa gtaggaagaa cagagggtgt cagtccgttt gtgtacgggg 840
actgacaccc tctgttcaaa tgattcatcg aagacggttt cacttttcta gcaaaacagc 900
aagacccgca agatttcata tattggtcaa gcgcagccac aaactatcac tcatagctat 960
gtagccccct attaattcat atctcaaaga gtatccaagc actttgggat cc 1012

Fig. 54 continued

<210> 38
<211> 558
<212> PRT
<213> Artificial Sequence

<220>
<223> Description of Artificial Sequence: Synthetic
polypeptide

<400> 38
Met Ser Arg Lys Leu Phe Ala Ser Ile Leu Ile Gly Ala Leu Leu Gly
1 5 10 15

Ile Gly Ala Pro Pro Ser Ala His Ala Met His His His His His His
20 25 30

Glu Asn Leu Tyr Phe Gln Gly Ala Asp Asp Val Ala Asp Ser Ser Lys
35 40 45

Ser Phe Val Met Glu Asn Phe Ser Ser Tyr His Gly Thr Lys Pro Gly
50 55 60

Tyr Val Asp Ser Ile Gln Lys Gly Ile Gln Lys Pro Lys Ser Gly Thr
65 70 75 80

Gln Gly Asn Tyr Asp Asp Asp Trp Lys Gly Phe Tyr Ser Thr Asp Asn
85 90 95

Lys Tyr Asp Ala Ala Gly Tyr Ser Val Asp Asn Glu Asn Pro Leu Ser
100 105 110

Gly Lys Ala Gly Gly Val Val Lys Val Thr Tyr Pro Gly Leu Thr Lys
115 120 125

Val Leu Ala Leu Lys Val Asp Asn Ala Glu Thr Ile Lys Lys Glu Leu
130 135 140

Gly Leu Ser Leu Thr Glu Pro Leu Met Glu Gln Val Gly Thr Glu Glu
145 150 155 160

Phe Ile Lys Arg Phe Gly Asp Gly Ala Ser Arg Val Val Leu Ser Leu
165 170 175

Fig. 54 continued

Pro Phe Ala Glu Gly Ser Ser Ser Val Glu Tyr Ile Asn Asn Trp Glu
180 185 190

Gln Ala Lys Ala Leu Ser Val Glu Leu Glu Ile Asn Phe Glu Thr Arg
195 200 205

Gly Lys Arg Gly Gln Asp Ala Met Tyr Glu Tyr Met Ala Gln Ala Cys
210 215 220

Ala Gly Asn Arg Val Arg Arg Ser Val Gly Ser Ser Leu Ser Cys Ile
225 230 235 240

Asn Leu Asp Trp Asp Val Ile Arg Asp Lys Thr Lys Thr Lys Ile Glu
245 250 255

Ser Leu Lys Glu His Gly Pro Ile Lys Asn Lys Met Ser Glu Ser Pro
260 265 270

Asn Lys Thr Val Ser Glu Glu Lys Ala Lys Gln Tyr Leu Glu Glu Phe
275 280 285

His Gln Thr Ala Leu Glu His Pro Glu Leu Ser Glu Leu Lys Thr Val
290 295 300

Thr Gly Thr Asn Pro Val Phe Ala Gly Ala Asn Tyr Ala Ala Trp Ala
305 310 315 320

Val Asn Val Ala Gln Val Ile Asp Ser Glu Thr Ala Asp Asn Leu Glu
325 330 335

Lys Thr Thr Ala Ala Leu Ser Ile Leu Pro Gly Ile Gly Ser Val Met
340 345 350

Gly Ile Ala Asp Gly Ala Val His His Asn Thr Glu Glu Ile Val Ala
355 360 365

Gln Ser Ile Ala Leu Ser Ser Leu Met Val Ala Gln Ala Ile Pro Leu
370 375 380

Val Gly Glu Leu Val Asp Ile Gly Phe Ala Ala Tyr Asn Phe Val Glu
385 390 395 400

Fig. 54 continued

Ser Ile Ile Asn Leu Phe Gln Val Val His Asn Ser Tyr Asn Arg Pro
405 410 415

Ala Tyr Ser Pro Gly His Lys Thr His Ala Pro Thr Ser Ser Ser Thr
420 425 430

Lys Lys Thr Gln Leu Gln Leu Glu His Leu Leu Leu Asp Leu Gln Met
435 440 445

Ile Leu Asn Gly Ile Asn Asn Tyr Lys Asn Pro Lys Leu Thr Arg Met
450 455 460

Leu Thr Phe Lys Phe Tyr Met Pro Lys Lys Ala Thr Glu Leu Lys His
465 470 475 480

Leu Gln Cys Leu Glu Glu Glu Leu Lys Pro Leu Glu Glu Val Leu Asn
485 490 495

Leu Ala Gln Ser Lys Asn Phe His Leu Arg Pro Arg Asp Leu Ile Ser
500 505 510

Asn Ile Asn Val Ile Val Leu Glu Leu Lys Gly Ser Glu Thr Thr Phe
515 520 525

Met Cys Glu Tyr Ala Asp Glu Thr Ala Thr Ile Val Glu Phe Leu Asn
530 535 540

Arg Trp Ile Thr Phe Cys Gln Ser Ile Ile Ser Thr Leu Thr
545 550 555

<210> 39
<211> 533
<212> PRT
<213> Artificial Sequence

<220>
<223> Description of Artificial Sequence: Synthetic
polypeptide

<400> 39
Met His His His His His His Glu Asn Leu Tyr Phe Gln Gly Ala Asp
1 5 10 15

Fig. 54 continued

Asp Val Ala Asp Ser Ser Lys Ser Phe Val Met Glu Asn Phe Ser Ser
20 25 30

Tyr His Gly Thr Lys Pro Gly Tyr Val Asp Ser Ile Gln Lys Gly Ile
35 40 45

Gln Lys Pro Lys Ser Gly Thr Gln Gly Asn Tyr Asp Asp Asp Trp Lys
50 55 60

Gly Phe Tyr Ser Thr Asp Asn Lys Tyr Asp Ala Ala Gly Tyr Ser Val
65 70 75 80

Asp Asn Glu Asn Pro Leu Ser Gly Lys Ala Gly Gly Val Val Lys Val
85 90 95

Thr Tyr Pro Gly Leu Thr Lys Val Leu Ala Leu Lys Val Asp Asn Ala
100 105 110

Glu Thr Ile Lys Lys Glu Leu Gly Leu Ser Leu Thr Glu Pro Leu Met
115 120 125

Glu Gln Val Gly Thr Glu Glu Phe Ile Lys Arg Phe Gly Asp Gly Ala
130 135 140

Ser Arg Val Val Leu Ser Leu Pro Phe Ala Glu Gly Ser Ser Ser Val
145 150 155 160

Glu Tyr Ile Asn Asn Trp Glu Gln Ala Lys Ala Leu Ser Val Glu Leu
165 170 175

Glu Ile Asn Phe Glu Thr Arg Gly Lys Arg Gly Gln Asp Ala Met Tyr
180 185 190

Glu Tyr Met Ala Gln Ala Cys Ala Gly Asn Arg Val Arg Arg Ser Val
195 200 205

Gly Ser Ser Leu Ser Cys Ile Asn Leu Asp Trp Asp Val Ile Arg Asp
210 215 220

Fig. 54 continued

Lys Thr Lys Thr Lys Ile Glu Ser Leu Lys Glu His Gly Pro Ile Lys
225 230 235 240

Asn Lys Met Ser Glu Ser Pro Asn Lys Thr Val Ser Glu Glu Lys Ala
245 250 255

Lys Gln Tyr Leu Glu Glu Phe His Gln Thr Ala Leu Glu His Pro Glu
260 265 270

Leu Ser Glu Leu Lys Thr Val Thr Gly Thr Asn Pro Val Phe Ala Gly
275 280 285

Ala Asn Tyr Ala Ala Trp Ala Val Asn Val Ala Gln Val Ile Asp Ser
290 295 300

Glu Thr Ala Asp Asn Leu Glu Lys Thr Thr Ala Ala Leu Ser Ile Leu
305 310 315 320

Pro Gly Ile Gly Ser Val Met Gly Ile Ala Asp Gly Ala Val His His
325 330 335

Asn Thr Glu Glu Ile Val Ala Gln Ser Ile Ala Leu Ser Ser Leu Met
340 345 350

Val Ala Gln Ala Ile Pro Leu Val Gly Glu Leu Val Asp Ile Gly Phe
355 360 365

Ala Ala Tyr Asn Phe Val Glu Ser Ile Ile Asn Leu Phe Gln Val Val
370 375 380

His Asn Ser Tyr Asn Arg Pro Ala Tyr Ser Pro Gly His Lys Thr His
385 390 395 400

Ala Pro Thr Ser Ser Ser Thr Lys Lys Thr Gln Leu Gln Leu Glu His
405 410 415

Leu Leu Leu Asp Leu Gln Met Ile Leu Asn Gly Ile Asn Asn Tyr Lys
420 425 430

Asn Pro Lys Leu Thr Arg Met Leu Thr Phe Lys Phe Tyr Met Pro Lys
435 440 445

Fig. 54 continued

Lys Ala Thr Glu Leu Lys His Leu Gln Cys Leu Glu Glu Glu Leu Lys
450 455 460

Pro Leu Glu Glu Val Leu Asn Leu Ala Gln Ser Lys Asn Phe His Leu
465 470 475 480

Arg Pro Arg Asp Leu Ile Ser Asn Ile Asn Val Ile Val Leu Glu Leu
485 490 495

Lys Gly Ser Glu Thr Thr Phe Met Cys Glu Tyr Ala Asp Glu Thr Ala
500 505 510

Thr Ile Val Glu Phe Leu Asn Arg Trp Ile Thr Phe Cys Gln Ser Ile
515 520 525

Ile Ser Thr Leu Thr
530

<210> 40
<211> 520
<212> PRT
<213> Artificial Sequence

<220>
<223> Description of Artificial Sequence: Synthetic
polypeptide

<400> 40
Gly Ala Asp Asp Val Ala Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Fig. 54 continued

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly
210 215 220

Pro Ile Lys Asn Lys Met Ser Glu Ser Pro Asn Lys Thr Val Ser Glu
225 230 235 240

Glu Lys Ala Lys Gln Tyr Leu Glu Glu Phe His Gln Thr Ala Leu Glu
245 250 255

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

Fig. 54 continued

Ile Asp Ser Glu Thr Ala Asp Asn Leu Glu Lys Thr Thr Ala Ala Leu
290 295 300

Ser Ile Leu Pro Gly Ile Gly Ser Val Met Gly Ile Ala Asp Gly Ala
305 310 315 320

Val His His Asn Thr Glu Glu Ile Val Ala Gln Ser Ile Ala Leu Ser
325 330 335

Ser Leu Met Val Ala Gln Ala Ile Pro Leu Val Gly Glu Leu Val Asp
340 345 350

Ile Gly Phe Ala Ala Tyr Asn Phe Val Glu Ser Ile Ile Asn Leu Phe
355 360 365

Gln Val Val His Asn Ser Tyr Asn Arg Pro Ala Tyr Ser Pro Gly His
370 375 380

Lys Thr His Ala Pro Thr Ser Ser Ser Thr Lys Lys Thr Gln Leu Gln
385 390 395 400

Leu Glu His Leu Leu Leu Asp Leu Gln Met Ile Leu Asn Gly Ile Asn
405 410 415

Asn Tyr Lys Asn Pro Lys Leu Thr Arg Met Leu Thr Phe Lys Phe Tyr
420 425 430

Met Pro Lys Lys Ala Thr Glu Leu Lys His Leu Gln Cys Leu Glu Glu
435 440 445

Glu Leu Lys Pro Leu Glu Glu Val Leu Asn Leu Ala Gln Ser Lys Asn
450 455 460

Phe His Leu Arg Pro Arg Asp Leu Ile Ser Asn Ile Asn Val Ile Val
465 470 475 480

Leu Glu Leu Lys Gly Ser Glu Thr Thr Phe Met Cys Glu Tyr Ala Asp
485 490 495

Glu Thr Ala Thr Ile Val Glu Phe Leu Asn Arg Trp Ile Thr Phe Cys
500 505 510

Fig. 54 continued

Gln Ser Ile Ile Ser Thr Leu Thr
   515             520

<210> 41
<211> 1677
<212> DNA
<213> Artificial Sequence

<220>
<223> Description of Artificial Sequence: Synthetic
polynucleotide

<400> 41

| | |
|---|---|
| gtgagcagaa aactgtttgc gtcaatctta ataggggcgc tactggggat aggggcccca | 60 |
| ccttcagccc atgcaatgca tcaccaccac caccacgaga acctgtactt ccagggcgct | 120 |
| gatgatgttg ctgattcttc taaatctttt gtgatggaaa acttttcttc gtaccacggg | 180 |
| actaaacctg gttatgtaga ttccattcaa aaaggtatac aaaagccaaa atctggtaca | 240 |
| caaggaaatt atgacgatga ttggaaaggg ttttatagta ccgacaataa atacgacgct | 300 |
| gcgggatact ctgtagataa tgaaaacccg ctctctggaa aagctggagg cgtggtcaaa | 360 |
| gtgacgtatc caggactgac gaaggttctc gcactaaaag tggataatgc cgaaactatt | 420 |
| aagaaagagt taggtttaag tctcactgaa ccgttgatgg agcaagtcgg aacggaagag | 480 |
| tttatcaaaa ggttcggtga tggtgcttcg cgtgtagtgc tcagccttcc cttcgctgag | 540 |
| gggagttcta gcgttgaata tattaataac tgggaacagg cgaaagcgtt aagcgtagaa | 600 |
| cttgagatta attttgaaac ccgtggaaaa cgtggccaag atgcgatgta tgagtatatg | 660 |
| gctcaagcct gtgcaggaaa tcgtgtcagg cgatcagtag gtagctcatt gtcatgcatc | 720 |
| aacctggatt gggatgttat ccgtgataaa actaaaacta agatcgaatc tctgaaagaa | 780 |
| cacggtccga tcaaaaacaa aatgagcgaa agcccgaaca aaactgtatc tgaagaaaaa | 840 |
| gctaaacagt acctggaaga attccaccag actgcactgg aacacccgga actgtctgaa | 900 |
| cttaagaccg ttactggtac caacccggta ttcgctggtg ctaactacgc tgcttgggca | 960 |
| gtaaacgttg ctcaggttat cgatagcgaa actgctgata acctggaaaa aactaccgcg | 1020 |
| gctctgtcta tcctgccggg tatcggtagc gtaatgggca tcgcagacgg cgccgttcac | 1080 |
| cacaacactg aagaaatcgt tgcacagtct atcgctctga gctctctgat ggttgctcag | 1140 |

Fig. 54 continued

```
gccatcccgc tggtaggtga actggttgat atcggtttcg ctgcatacaa cttcgttgaa    1200

agcatcatca acctgttcca ggttgttcac aactcttaca accgcccggc ttactctccg    1260

ggtcacaaga cgcatgcacc tacttctagc tctaccaaga aaacccagct gcagctcgag    1320

cacctgctgc tggatttgca gatgatcctg aacggtatca acaattacaa gaacccgaaa    1380

ctgacgcgta tgctgacctt caagttctac atgccgaaga aggccaccga actgaaacac    1440

ctgcagtgtc tagaagaaga actgaaaccg ctggaggaag ttctgaacct ggctcagtct    1500

aaaaacttcc acctgcggcc gcgtgacctg atctctaaca tcaacgtaat cgttctggaa    1560

ctgaagggct ctgaaaccac cttcatgtgt gaatacgctg atgagaccgc aaccatcgta    1620

gaattcctga accgttggat caccttctgt cagtctatca tctctaccct gacctga         1677
```

<210> 42
<211> 551
<212> PRT
<213> Artificial Sequence

<220>
<223> Description of Artificial Sequence: Synthetic
    polypeptide

<400> 42
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Ala Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
            85                  90                  95

Pro Leu Ser Gly Lys Ala Gly Gly Val Val Lys Val Thr Tyr Pro Gly

Fig. 54 continued 100 105 110

Leu Thr Lys Val Leu Ala Leu Lys Val Asp Asn Ala Glu Thr Ile Lys
115 120 125

Lys Glu Leu Gly Leu Ser Leu Thr Glu Pro Leu Met Glu Gln Val Gly
130 135 140

Thr Glu Glu Phe Ile Lys Arg Phe Gly Asp Gly Ala Ser Arg Val Val
145 150 155 160

Leu Ser Leu Pro Phe Ala Glu Gly Ser Ser Ser Val Glu Tyr Ile Asn
165 170 175

Asn Trp Glu Gln Ala Lys Ala Leu Ser Val Glu Leu Glu Ile Asn Phe
180 185 190

Glu Thr Arg Gly Lys Arg Gly Gln Asp Ala Met Tyr Glu Tyr Met Ala
195 200 205

Gln Ala Cys Ala Gly Asn Arg Val Arg Arg Ser Val Gly Ser Ser Leu
210 215 220

Ser Cys Ile Asn Leu Asp Trp Asp Val Ile Arg Asp Lys Thr Lys Thr
225 230 235 240

Lys Ile Glu Ser Leu Lys Glu His Gly Pro Ile Lys Asn Lys Met Ser
245 250 255

Glu Ser Pro Asn Lys Thr Val Ser Glu Glu Lys Ala Lys Gln Tyr Leu
260 265 270

Glu Glu Phe His Gln Thr Ala Leu Glu His Pro Glu Leu Ser Glu Leu
275 280 285

Lys Thr Val Thr Gly Thr Asn Pro Val Phe Ala Gly Ala Asn Tyr Ala
290 295 300

Ala Trp Ala Val Asn Val Ala Gln Val Ile Asp Ser Glu Thr Ala Asp
305 310 315 320

Fig. 54 continued

Asn Leu Glu Lys Thr Thr Ala Ala Leu Ser Ile Leu Pro Gly Ile Gly
325 330 335

Ser Val Met Gly Ile Ala Asp Gly Ala Val His His Asn Thr Glu Glu
340 345 350

Ile Val Ala Gln Ser Ile Ala Leu Ser Ser Leu Met Val Ala Gln Ala
355 360 365

Ile Pro Leu Val Gly Glu Leu Val Asp Ile Gly Phe Ala Ala Tyr Asn
370 375 380

Phe Val Glu Ser Ile Ile Asn Leu Phe Gln Val Val His Asn Ser Tyr
385 390 395 400

Asn Arg Pro Ala Tyr Ser Pro Gly His Lys Thr His Ala Pro Thr Ser
405 410 415

Ser Ser Thr Lys Lys Thr Gln Leu Gln Leu Glu His Leu Leu Leu Asp
420 425 430

Leu Gln Met Ile Leu Asn Gly Ile Asn Asn Tyr Lys Asn Pro Lys Leu
435 440 445

Thr Arg Met Leu Thr Phe Lys Phe Tyr Met Pro Lys Lys Ala Thr Glu
450 455 460

Leu Lys His Leu Gln Cys Leu Glu Glu Glu Leu Lys Pro Leu Glu Glu
465 470 475 480

Val Leu Asn Leu Ala Gln Ser Lys Asn Phe His Leu Arg Pro Arg Asp
485 490 495

Leu Ile Ser Asn Ile Asn Val Ile Val Leu Glu Leu Lys Gly Ser Glu
500 505 510

Thr Thr Phe Met Cys Glu Tyr Ala Asp Glu Thr Ala Thr Ile Val Glu
515 520 525

Phe Leu Asn Arg Trp Ile Thr Phe Cys Gln Ser Ile Ile Ser Thr Leu 530 535 540

Fig. 54 continued

Thr His His His His His His
545 550

<210> 43
<211> 526
<212> PRT
<213> Artificial Sequence

<220>
<223> Description of Artificial Sequence: Synthetic
polypeptide

<400> 43
Gly Ala Asp Asp Val Ala Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser 145 150 155 160

Fig. 54 continued

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly
210 215 220

Pro Ile Lys Asn Lys Met Ser Glu Ser Pro Asn Lys Thr Val Ser Glu
225 230 235 240

Glu Lys Ala Lys Gln Tyr Leu Glu Glu Phe His Gln Thr Ala Leu Glu
245 250 255

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

Ile Asp Ser Glu Thr Ala Asp Asn Leu Glu Lys Thr Thr Ala Ala Leu
290 295 300

Ser Ile Leu Pro Gly Ile Gly Ser Val Met Gly Ile Ala Asp Gly Ala
305 310 315 320

Val His His Asn Thr Glu Glu Ile Val Ala Gln Ser Ile Ala Leu Ser
325 330 335

Ser Leu Met Val Ala Gln Ala Ile Pro Leu Val Gly Glu Leu Val Asp
340 345 350

Ile Gly Phe Ala Ala Tyr Asn Phe Val Glu Ser Ile Ile Asn Leu Phe
355 360 365

Fig. 54 continued

Gln Val Val His Asn Ser Tyr Asn Arg Pro Ala Tyr Ser Pro Gly His
370 375 380

Lys Thr His Ala Pro Thr Ser Ser Ser Thr Lys Lys Thr Gln Leu Gln
385 390 395 400

Leu Glu His Leu Leu Leu Asp Leu Gln Met Ile Leu Asn Gly Ile Asn
405 410 415

Asn Tyr Lys Asn Pro Lys Leu Thr Arg Met Leu Thr Phe Lys Phe Tyr
420 425 430

Met Pro Lys Lys Ala Thr Glu Leu Lys His Leu Gln Cys Leu Glu Glu
435 440 445

Glu Leu Lys Pro Leu Glu Glu Val Leu Asn Leu Ala Gln Ser Lys Asn
450 455 460

Phe His Leu Arg Pro Arg Asp Leu Ile Ser Asn Ile Asn Val Ile Val
465 470 475 480

Leu Glu Leu Lys Gly Ser Glu Thr Thr Phe Met Cys Glu Tyr Ala Asp
485 490 495

Glu Thr Ala Thr Ile Val Glu Phe Leu Asn Arg Trp Ile Thr Phe Cys
500 505 510

Gln Ser Ile Ile Ser Thr Leu Thr His His His His His His
515 520 525

<210> 44
<211> 1656
<212> DNA
<213> Artificial Sequence

<220>
<223> Description of Artificial Sequence: Synthetic polynucleotide

<400> 44
gtgagcagaa aactgtttgc gtcaatctta ataggggcgc tactggggat aggggcccca 60
ccttcagccc atgcaggcgc tgatgatgtt gctgattctt ctaaatcttt tgtgatggaa 120

Fig. 54 continued aacttttctt cgtaccacgg gactaaacct ggttatgtag attccattca aaaaggtata 180
caaaagccaa aatctggtac acaaggaaat tatgacgatg attggaaagg gttttatagt 240
accgacaata aatacgacgc tgcgggatac tctgtagata atgaaaaccc gctctctgga 300
aaagctggag gcgtggtcaa agtgacgtat ccaggactga cgaaggttct cgcactaaaa 360
gtggataatg ccgaaactat taagaaagag ttaggtttaa gtctcactga accgttgatg 420
gagcaagtcg gaacggaaga gtttatcaaa aggttcggtg atggtgcttc gcgtgtagtg 480
ctcagccttc ccttcgctga ggggagttct agcgttgaat atattaataa ctgggaacag 540
gcgaaagcgt taagcgtaga acttgagatt aattttgaaa cccgtggaaa acgtggccaa 600
gatgcgatgt atgagtatat ggctcaagcc tgtgcaggaa atcgtgtcag gcgatcagta 660
ggtagctcat tgtcatgcat caacctggat tgggatgtta tccgtgataa aactaaaact 720
aagatcgaat ctctgaaaga acacggtccg atcaaaaaca aaatgagcga aagcccgaac 780
aaaactgtat ctgaagaaaa agctaaacag tacctggaag aattccacca gactgcactg 840
gaacacccgg aactgtctga acttaagacc gttactggta ccaacccggt attcgctggt 900
gctaactacg ctgcttgggc agtaaacgtt gctcaggtta tcgatagcga aactgctgat 960
aacctggaaa aaactaccgc ggctctgtct atcctgccgg gtatcggtag cgtaatgggc 1020
atcgcagacg gcgccgttca ccacaacact gaagaaatcg ttgcacagtc tatcgctctg 1080
agctctctga tggttgctca ggccatcccg ctggtaggtg aactggttga tatcggtttc 1140
gctgcataca acttcgttga aagcatcatc aacctgttcc aggttgttca caactcttac 1200
aaccgcccgg cttactctcc gggtcacaag acgcatgcac ctacttctag ctctaccaag 1260
aaaacccagc tgcagctcga gcacctgctg ctggatttgc agatgatcct gaacggtatc 1320
aacaattaca agaacccgaa actgacgcgt atgctgacct tcaagttcta catgccgaag 1380
aaggccaccg aactgaaaca cctgcagtgt ctagaagaag aactgaaacc gctggaggaa 1440
gttctgaacc tggctcagtc taaaaacttc cacctgcggc cgcgtgacct gatctctaac 1500
atcaacgtaa tcgttctgga actgaagggc tctgaaacca ccttcatgtg tgaatacgct 1560
gatgagaccg caaccatcgt agaattcctg aaccgttgga tcaccttctg tcagtctatc 1620
atctctaccc tgacccacca tcaccatcat cactga 1656

Fig. 54 continued

<210> 45
<211> 561
<212> PRT
<213> Artificial Sequence

<220>
<223> Description of Artificial Sequence: Synthetic
polypeptide

<400> 45
Met Ser Arg Lys Leu Phe Ala Ser Ile Leu Ile Gly Ala Leu Leu Gly
1 5 10 15

Ile Gly Ala Pro Pro Ser Ala His Ala Gly Ala Asp Asp Val Ala Asp
20 25 30

Ser Ser Lys Ser Phe Val Met Glu Asn Phe Ser Ser Tyr His Gly Thr
35 40 45

Lys Pro Gly Tyr Val Asp Ser Ile Gln Lys Gly Ile Gln Lys Pro Lys
50 55 60

Ser Gly Thr Gln Gly Asn Tyr Asp Asp Asp Trp Lys Gly Phe Tyr Ser
65 70 75 80

Thr Asp Asn Lys Tyr Asp Ala Ala Gly Tyr Ser Val Asp Asn Glu Asn
85 90 95

Pro Leu Ser Gly Lys Ala Gly Gly Val Val Lys Val Thr Tyr Pro Gly
100 105 110

Leu Thr Lys Val Leu Ala Leu Lys Val Asp Asn Ala Glu Thr Ile Lys
115 120 125

Lys Glu Leu Gly Leu Ser Leu Thr Glu Pro Leu Met Glu Gln Val Gly
130 135 140

Thr Glu Glu Phe Ile Lys Arg Phe Gly Asp Gly Ala Ser Arg Val Val
145 150 155 160

Leu Ser Leu Pro Phe Ala Glu Gly Ser Ser Ser Val Glu Tyr Ile Asn
165 170 175

Fig. 54 continued

Asn Trp Glu Gln Ala Lys Ala Leu Ser Val Glu Leu Glu Ile Asn Phe
180 185 190

Glu Thr Arg Gly Lys Arg Gly Gln Asp Ala Met Tyr Glu Tyr Met Ala
195 200 205

Gln Ala Cys Ala Gly Asn Arg Val Arg Arg Ser Val Gly Ser Ser Leu
210 215 220

Ser Cys Ile Asn Leu Asp Trp Asp Val Ile Arg Asp Lys Thr Lys Thr
225 230 235 240

Lys Ile Glu Ser Leu Lys Glu His Gly Pro Ile Lys Asn Lys Met Ser
245 250 255

Glu Ser Pro Asn Lys Thr Val Ser Glu Glu Lys Ala Lys Gln Tyr Leu
260 265 270

Glu Glu Phe His Gln Thr Ala Leu Glu His Pro Glu Leu Ser Glu Leu
275 280 285

Lys Thr Val Thr Gly Thr Asn Pro Val Phe Ala Gly Ala Asn Tyr Ala
290 295 300

Ala Trp Ala Val Asn Val Ala Gln Val Ile Asp Ser Glu Thr Ala Asp
305 310 315 320

Asn Leu Glu Lys Thr Thr Ala Ala Leu Ser Ile Leu Pro Gly Ile Gly
325 330 335

Ser Val Met Gly Ile Ala Asp Gly Ala Val His His Asn Thr Glu Glu
340 345 350

Ile Val Ala Gln Ser Ile Ala Leu Ser Ser Leu Met Val Ala Gln Ala
355 360 365

Ile Pro Leu Val Gly Glu Leu Val Asp Ile Gly Phe Ala Ala Tyr Asn
370 375 380

Phe Val Glu Ser Ile Ile Asn Leu Phe Gln Val Val His Asn Ser Tyr
385 390 395 400

Fig. 54 continued

Asn Arg Pro Ala Tyr Ser Pro Gly His Lys Thr His Ala Pro Thr Ser
405 410 415

Ser Ser Thr Lys Lys Thr Gln Leu Gln Leu Glu His Leu Leu Leu Asp
420 425 430

Leu Gln Met Ile Leu Asn Gly Ile Asn Asn Tyr Lys Asn Pro Lys Leu
435 440 445

Thr Arg Met Leu Thr Phe Lys Phe Tyr Met Pro Lys Lys Ala Thr Glu
450 455 460

Leu Lys His Leu Gln Cys Leu Glu Glu Glu Leu Lys Pro Leu Glu Glu
465 470 475 480

Val Leu Asn Leu Ala Gln Ser Lys Asn Phe His Leu Arg Pro Arg Asp
485 490 495

Leu Ile Ser Asn Ile Asn Val Ile Val Leu Glu Leu Lys Gly Ser Glu
500 505 510

Thr Thr Phe Met Cys Glu Tyr Ala Asp Glu Thr Ala Thr Ile Val Glu
515 520 525

Phe Leu Asn Arg Trp Ile Thr Phe Cys Gln Ser Ile Ile Ser Thr Leu
530 535 540

Thr Glu Asn Leu Tyr Phe Gln Gly His His His His His His His His
545 550 555 560

His

<210> 46
<211> 536
<212> PRT
<213> Artificial Sequence

<220>
<223> Description of Artificial Sequence: Synthetic
polypeptide

Fig. 54 continued

<400> 46
Gly Ala Asp Asp Val Ala Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Fig. 54 continued

Ile Arg Asp Lys Thr Lys Thr Lys Ile Glu Ser Leu Lys Glu His Gly
210 215 220

Pro Ile Lys Asn Lys Met Ser Glu Ser Pro Asn Lys Thr Val Ser Glu
225 230 235 240

Glu Lys Ala Lys Gln Tyr Leu Glu Glu Phe His Gln Thr Ala Leu Glu
245 250 255

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

Ile Asp Ser Glu Thr Ala Asp Asn Leu Glu Lys Thr Thr Ala Ala Leu
290 295 300

Ser Ile Leu Pro Gly Ile Gly Ser Val Met Gly Ile Ala Asp Gly Ala
305 310 315 320

Val His His Asn Thr Glu Glu Ile Val Ala Gln Ser Ile Ala Leu Ser
325 330 335

Ser Leu Met Val Ala Gln Ala Ile Pro Leu Val Gly Glu Leu Val Asp
340 345 350

Ile Gly Phe Ala Ala Tyr Asn Phe Val Glu Ser Ile Ile Asn Leu Phe
355 360 365

Gln Val Val His Asn Ser Tyr Asn Arg Pro Ala Tyr Ser Pro Gly His
370 375 380

Lys Thr His Ala Pro Thr Ser Ser Ser Thr Lys Lys Thr Gln Leu Gln
385 390 395 400

Leu Glu His Leu Leu Leu Asp Leu Gln Met Ile Leu Asn Gly Ile Asn
405 410 415

Asn Tyr Lys Asn Pro Lys Leu Thr Arg Met Leu Thr Phe Lys Phe Tyr
420 425 430

Fig. 54 continued

Met Pro Lys Lys Ala Thr Glu Leu Lys His Leu Gln Cys Leu Glu Glu
435 440 445

Glu Leu Lys Pro Leu Glu Glu Val Leu Asn Leu Ala Gln Ser Lys Asn
450 455 460

Phe His Leu Arg Pro Arg Asp Leu Ile Ser Asn Ile Asn Val Ile Val
465 470 475 480

Leu Glu Leu Lys Gly Ser Glu Thr Thr Phe Met Cys Glu Tyr Ala Asp
485 490 495

Glu Thr Ala Thr Ile Val Glu Phe Leu Asn Arg Trp Ile Thr Phe Cys
500 505 510

Gln Ser Ile Ile Ser Thr Leu Thr Glu Asn Leu Tyr Phe Gln Gly His
515 520 525

His His His His His His His His
530 535

<210> 47
<211> 4679
<212> DNA
<213> Artificial Sequence

<220>
<223> Description of Artificial Sequence: Synthetic
polynucleotide

<400> 47
ggatcccccg ggctgcagga attcgatatc aagcttatcg ataccgtcga cctcgagggg 60
gggcccggta ccagcttttg ttccctttag tgagggttaa tttcgagctt ggcgtaatca 120
tggtcatagc tgtttcctgt gtgaaattgt tatccgctca caattccaca caacatacga 180
gccggaagca taaagtgtaa agcctggggt gcctaatgag tgagtccccg atccgtcgag 240
ctcgacctgc aggggggggg gggcgctgag gtctgcctcg tgaagaaggt gttgctgact 300
cataccaggc ctgaatcgcc ccatcatcca gccagaaagt gagggagcca cggttgatga 360
gagctttgtt gtaggtggac cagttggtga ttttgaactt ttgctttgcc acggaacggt 420

Fig. 54 continued ctgcgttgtc gggaagatgc gtgatctgat ccttcaactc agcaaaagtt cgatttattc 480
aacaaagccg ccgtcccgtc aagtcagcgt aatgctctgc cagtgttaca accaattaac 540
caattctgat tagaaaaact catcgagcat caaatgaaac tgcaatttat tcatatcagg 600
attatcaata ccatattttt gaaaaagccg tttctgtaat gaaggagaaa actcaccgag 660
gcagttccat aggatggcaa gatcctggta tcggtctgcg attccgactc gtccaacatc 720
aatacaacct attaatttcc cctcgtcaaa aataaggtta tcaagtgaga aatcaccatg 780
agtgacgact gaatccggtg agaatggcaa aagcttatgc atttctttcc agacttgttc 840
aacaggccag ccattacgct cgtcatcaaa atcactcgca tcaaccaaac cgttattcat 900
tcgtgattgc gcctgagcga gacgaaatac gcgatcgctg ttaaaaggac aattacaaac 960
aggaatcgaa tgcaaccggc gcaggaacac tgccagcgca tcaacaatat tttcacctga 1020
atcaggatat tcttctaata cctggaatgc tgttttcccg gggatcgcag tggtgagtaa 1080
ccatgcatca tcaggagtac ggataaaatg cttgatggtc ggaagaggca taaattccgt 1140
cagccagttt agtctgacca tctcatctgt aacatcattg gcaacgctac ctttgccatg 1200
tttcagaaac aactctggcg catcgggctt cccatacaat cgatagattg tcgcacctga 1260
ttgcccgaca ttatcgcgag cccatttata cccatataaa tcagcatcca tgttggaatt 1320
taatcgcggc ctcgagcaag acgtttcccg ttgaatatgg ctcataacac cccttgtatt 1380
actgtttatg taagcagaca gttttattgt tcatgatgat atatttttat cttgtgcaat 1440
gtaacatcag agattttgag acacaacgtg gctttccccc cccccccctgc aggtcgagct 1500
cgacggatcg ggctgcagga attcggtgag gttatggcgg agggttgcga ggtctaggag 1560
aacagaggaa gtcatgcttt gaagcatata agctgccctg cccctcaagg ttttcttcaa 1620
gtgaggtttt atctaactgc ctaacggcag ggaaccgta tattgcttac ggtatgagac 1680
cccttaaacg tccggatagt caccgctctt ctttagctcc gcgacatgcc tagcaaccgt 1740
ggcgcgagag actcctacct ctgcccctat ttcagcccac gtgggaactg tccctgtctg 1800
gaaatactga tcgttcacca tttggctaat acgggacttc gtagatcgtc cttgagcctt 1860
tttcttacgg tgcgtctttt caagcttcga cctttgtgct tgcgcatatt tgccctcggg 1920
gtctgttttc cagcgttgtg cggctttttg tccgcctctg cgtcccatcg tggccaaggc 1980
tttccgctcg ctgctggtgg ctttacctgg tgcgttagag ccgctgtagg tctcgctctt 2040

Fig. 54 continued ggattgggcg acatacccgc gcacgcgcct tgccatggtt tggcggtcgc gcatgggtgg 2100
catctcgttg tcgcggcctg caccgccgtg ggtgtgtgcg acgttgtagg cgtgctcata 2160
ggcgtcgatg attgctgcgt ctgtcaggcg ttggccttgc tggcgcaagc ggtggccagt 2220
cttaagcgca tgtctaaagg ctgtttcgtc gcgtgctgcg gttccttgga caatccagag 2280
cacacgcaca ccgtcgataa gttccgggtc atactggtcg agaccaccgg cgatttccgc 2340
gtctacgtcc tgggcgagtg ctttgaatgc ttgggcttct tcacggcggg tcttgaccgc 2400
gttgataagt tcgcggccag agctgaattg ctggcgtggg gtggggttga actggtcgtg 2460
tcctgccata tcccttacct gctttatcaa gtctccaagg cgcatcaccc ggttgtgctg 2520
cctataccaa cgataagcgg taggggcttt gcctgtgtag aacgggttgc ggctaaagcg 2580
gtgggaaaag tgcgggtcat ggtctaaaag ctcacccagc acacgcgtgg ttgctgcaag 2640
aagcttcatc tgcgcagatt taccgttacg gtcagcgtag acagggtcaa taagccatat 2700
gaactgggct ttgccgttag ttgggttaat acccacccag gctggcccga cgctatgagt 2760
aatcagtgag cgcaccacgt cgcggacgta cgggtttaag tctgcggggt caccgcctgc 2820
ggtacctact tggtcaacgt ctacgaccag gacggcggcg tactgcttgg tggtgagcat 2880
ggcgtactcg caccgtccta aagcatcagt ctcgaagcga tacatacgcg gcgagttcgt 2940
gccgtcagcg ttgcgtcgat aggccttttt aaagtctcgt gtgactgaac cgtggagtac 3000
atcgcggcct agatgatcgc gtaaaaggtc gcggtcactg gcagatgctg gggtgttgtc 3060
cagtccacca cggtcgcgct cgacgcgggt aggtgtttta gtgtgcgcat tctgcgcatg 3120
agtctgtaaa ctcatgaccg tgctttctcc caggtgtgtg ctgggtgata agcgaaagtc 3180
atcgggttgc cgccccggtgg ctttcttcgt ttttcattgt ctttccctga ctctaaatga 3240
caccggtgtt atttactagc catgacacgc gaaaaatatg ccttttacct gcggttacgt 3300
atggctagac atatggcaag ctatacgtaa ccgcgtttca gctgcacagg gctgtctgcg 3360
cagatttacc atcacgggac ttttcccagt tcaggctgcg catatttacg catacaacga 3420
aagcggttgc gcagatttac cacacactct gcgctgattt accgatacgc agaaaaagcg 3480
tgcgcagatt tacccatacg gtggcgaatt atccagagca ataggtatac agcaatacag 3540
taatacaggt gccataaacc tgtattactg tattgctgta tgcctgtaaa cctttattta 3600
ttgttgtgga cgtattcttc gaggtaggtg ctaacaatct cgcggatggt cacgcctttt 3660

Fig. 54 continued tgggcggcga tgactttaag ttctgcgtga aggtcgcggt cgatttcaat cgtcatcttc 3720
ttgacgtagt cgcggcctgt gggttggtgg aatgcgcttc gcactgtttt cttctcggct 3780
gctggagtta gcttcgtggc tttttcatt gaggttcgcg ggccttgctg cgccctggcg 3840
cgttctttac tggtgctcat ttcatcatct ccatgagttc gtcggcgacg tggtcgtagc 3900
cgtgcatgtc ggggcctggg cagtatccaa acgctaggtg catatcttcg cgtagcggga 3960
tttcggtttt aaagtgcggc atgtgttccg cgtcgagcgc ttctcgtgcc gcgtcaaggg 4020
cgctggtgcc tttcctggcg aacgtcagta agactgcatg aggtgttccg ttgactgcgt 4080
cgcgcagctc ccatactcgg gagaggtcgg cagcagcaga acgggtcgga agaatgatga 4140
agtcgctgac tgcgattgct gcttcgatag cgttctcgtc tcctggcggc acatcgatac 4200
cgactgggcg atggcccact acgtgaacca tcaccctaat caagtttttt ggggtcgagg 4260
tgccgtaaag cactaaatcg gaaccctaaa gggagccccc gatttagagc ttgacgggga 4320
aagccggcga acgtggcgag aaaggaaggg aagaaagcga aaggagcggg cgctagggcg 4380
ctggcaagtg tagcggtcac gctgcgcgta accaccacac ccgccgcgct taatgcgccg 4440
ctacagggcg ctcccattcg ccattcaggc tgcgcaactg ttgggaaggg cgatcggtgc 4500
gggcctcttc gctattacgc cagctggcga aagggggatg tgctgcaagg cgattaagtt 4560
gggtaacgcc agggttttcc cagtcacgac gttgtaaaac gacggccagt gaattgtaat 4620
acgactcact atagggcgaa ttggagctcc accgcggtgg cggccgctct agaactagt 4679

<210> 48
<211> 9
<212> PRT
<213> Artificial Sequence

<220>
<223> Description of Artificial Sequence: Synthetic
9xHis tag

<400> 48
His His His His His His His His His
1 5

<210> 49
<211> 7
<212> PRT
<213> Unknown

Fig. 54 continued

<220>
<223> Description of Unknown:
TEV cleavage site peptide

<220>
<221> MOD_RES
<222> (7)..(7)
<223> Any small hydrophobic or polar amino acid
<400> 49
Glu Asn Leu Tyr Phe Gln Xaa
1 5

<210> 50
<211> 12
<212> PRT
<213> Artificial Sequence

<220>
<223> Description of Artificial Sequence: Synthetic
peptide

<400> 50
His His His His His His Glu Asn Leu Tyr Phe Gln
1 5 10

<210> 51
<211> 6
<212> PRT
<213> Artificial Sequence

<220>
<223> Description of Artificial Sequence: Synthetic
peptide

<400> 51
Gly Ala Asp Asp Val Ala
1 5

<210> 52
<211> 13
<212> PRT
<213> Artificial Sequence

<220>
<223> Description of Artificial Sequence: Synthetic
peptide

<400> 52
Met His His His His His His Glu Asn Leu Tyr Phe Gln 1 5 10

Fig. 54 continued

<210> 53
<211> 6
<212> PRT
<213> Artificial Sequence

<220>
<223> Description of Artificial Sequence: Synthetic
peptide

<400> 53
Ile Ile Ser Thr Leu Thr
1 5

<210> 54
<211> 16
<212> PRT
<213> Artificial Sequence

<220>
<223> Description of Artificial Sequence: Synthetic
peptide

<400> 54
Glu Asn Leu Tyr Phe Gln Gly His His His His His His His His His
1 5 10 15

<210> 55
<211> 10
<212> PRT
<213> Artificial Sequence

<220>
<223> Description of Artificial Sequence: Synthetic
peptide

<400> 55
Gly His His His His His His His His His
1 5 10

<210> 56
<211> 6
<212> PRT
<213> Artificial Sequence

<220>
<223> Description of Artificial Sequence: Synthetic
peptide

Fig. 54 continued

<400> 56
Glu Asn Leu Tyr Phe Gln
1 5

<210> 57
<211> 12
<212> PRT
<213> Artificial Sequence

<220>
<223> Description of Artificial Sequence: Synthetic
peptide

<400> 57
Ile Ile Ser Thr Leu Thr Glu Asn Leu Tyr Phe Gln
1 5 10

<210> 58
<211> 526
<212> PRT
<213> Artificial Sequence

<220>
<223> Description of Artificial Sequence: Synthetic
polypeptide

<400> 58
Gly Ala Asp Asp Val Val Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu 100 105 110

Fig. 54 continued

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly
210 215 220

Pro Ile Lys Asn Lys Met Ser Glu Ser Pro Asn Lys Thr Val Ser Glu
225 230 235 240

Glu Lys Ala Lys Gln Tyr Leu Glu Glu Phe His Gln Thr Ala Leu Glu
245 250 255

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

Ile Asp Ser Glu Thr Ala Asp Asn Leu Glu Lys Thr Thr Ala Ala Leu
290 295 300

Ser Ile Leu Pro Gly Ile Gly Ser Val Met Gly Ile Ala Asp Gly Ala
305 310 315 320

Fig. 54 continued

Val His His Asn Thr Glu Glu Ile Val Ala Gln Ser Ile Ala Leu Ser
325 330 335

Ser Leu Met Val Ala Gln Ala Ile Pro Leu Val Gly Glu Leu Val Asp
340 345 350

Ile Gly Phe Ala Ala Tyr Asn Phe Val Glu Ser Ile Ile Asn Leu Phe
355 360 365

Gln Val Val His Asn Ser Tyr Asn Arg Pro Ala Tyr Ser Pro Gly His
370 375 380

Lys Thr His Ala Pro Thr Ser Ser Ser Thr Lys Lys Thr Gln Leu Gln
385 390 395 400

Leu Glu His Leu Leu Leu Asp Leu Gln Met Ile Leu Asn Gly Ile Asn
405 410 415

Asn Tyr Lys Asn Pro Lys Leu Thr Arg Met Leu Thr Phe Lys Phe Tyr
420 425 430

Met Pro Lys Lys Ala Thr Glu Leu Lys His Leu Gln Cys Leu Glu Glu
435 440 445

Glu Leu Lys Pro Leu Glu Glu Val Leu Asn Leu Ala Gln Ser Lys Asn
450 455 460

Phe His Leu Arg Pro Arg Asp Leu Ile Ser Asn Ile Asn Val Ile Val
465 470 475 480

Leu Glu Leu Lys Gly Ser Glu Thr Thr Phe Met Cys Glu Tyr Ala Asp
485 490 495

Glu Thr Ala Thr Ile Val Glu Phe Leu Asn Arg Trp Ile Thr Phe Cys
500 505 510

Gln Ser Ile Ile Ser Thr Leu Thr His His His His His His
515 520 525

<211> 1729
<212> DNA
<213> Artificial Sequence

<220>
<223> Description of Artificial Sequence: Synthetic
polynucleotide

<400> 59
ttgatttcag agcaccctta taattaggat agctaagtcc attattttat gagtcctggt 60
aaggggatac gttgtgagca gaaaactgtt tgcgtcaatc ttaatagggg cgctactggg 120
gataggggcc ccaccttcag cccatgcagg cgctgatgat gttgttgatt cttctaaatc 180
ttttgtgatg gaaaactttt cttcgtacca cgggactaaa cctggttatg tagattccat 240
tcaaaaaggt atacaaaagc caaaatctgg tacacaagga aattatgacg atgattggaa 300
agggttttat agtaccgaca ataaatacga cgctgcggga tactctgtag ataatgaaaa 360
cccgctctct ggaaaagctg gaggcgtggt caaagtgacg tatccaggac tgacgaaggt 420
tctcgcacta aaagtggata atgccgaaac tattaagaaa gagttaggtt taagtctcac 480
tgaaccgttg atggagcaag tcggaacgga agagtttatc aaaaggttcg gtgatggtgc 540
ttcgcgtgta gtgctcagcc ttcccttcgc tgaggggagt tctagcgttg aatatattaa 600
taactgggaa caggcgaaag cgttaagcgt agaacttgag attaattttg aaacccgtgg 660
aaaacgtggc caagatgcga tgtatgagta tatggctcaa gcctgtgcag gaaatcgtgt 720
caggcgatca gtaggtagct cattgtcatg catcaacctg gattgggatg ttatccgtga 780
taaaactaaa actaagatcg aatctctgaa agaacacggt ccgatcaaaa acaaaatgag 840
cgaaagcccg aacaaaactg tatctgaaga aaaagctaaa cagtacctgg aagaattcca 900
ccagactgca ctggaacacc cggaactgtc tgaacttaag accgttactg gtaccaaccc 960
ggtattcgct ggtgctaact acgctgcttg ggcagtaaac gttgctcagg ttatcgatag 1020
cgaaactgct gataacctgg aaaaaactac cgcggctctg tctatcctgc cgggtatcgg 1080
tagcgtaatg ggcatcgcag acggcgccgt tcaccacaac actgaagaaa tcgttgcaca 1140
gtctatcgct ctgagctctc tgatggttgc tcaggccatc ccgctggtag gtgaactggt 1200
tgatatcggt ttcgctgcat acaacttcgt tgaaagcatc atcaacctgt tccaggttgt 1260
tcacaactct tacaaccgcc cggcttactc tccgggtcac aagacgcatg cacctacttc 1320
tagctctacc aagaaaaccc agctgcagct cgagcacctg ctgctggatt tgcagatgat 1380

Fig. 54 continued cctgaacggt atcaacaatt acaagaaccc gaaactgacg cgtatgctga ccttcaagtt 1440
ctacatgccg aagaaggcca ccgaactgaa acacctgcag tgtctagaag aagaactgaa 1500
accgctggag gaagttctga acctggctca gtctaaaaac ttccacctgc ggccgcgtga 1560
cctgatctct aacatcaacg taatcgttct ggaactgaag ggctctgaaa ccaccttcat 1620
gtgtgaatac gctgatgaga ccgcaaccat cgtagaattc ctgaaccgtt ggatcacctt 1680
ctgtcagtct atcatctcta ccctgaccca ccatcaccat catcactga 1729

Fig. 55

SEQ ID NO: 60 (D3E s-Ontak or D3E Ontak®)

```
1     GAEDVVDSSKSFVMENFSSYHGTKP
26    GYVDSIQKGIQKPKSGTQGNYDDDWKGFYSTDNKYDAAGYSVDNENPLSG
76    KAGGVVKVTYPGLTKVLALKVDNAETIKKELGLSLTEPLMEQVGTEEFIK
126   RFGDGASRVVLSLPFAEGSSSVEYINNWEQAKALSVELEINFETRGKRGQ
176   DAMYEYMAQACAGNRVRRSVGSSLSCINLDWDVIRDKTKTKIESLKEHGP
226   IKNKMSESPNKTVSEEKAKQYLEEFHQTALEHPELSELKTVTGTNPVFAG
276   ANYAAWAVNVAQVIDSETADNLEKTTAALSILPGIGSVMGIADGAVHHNT
326   EEIVAQSIALSSLMVAQAIPLVGELVDIGFAAYNFVESIINLFQVVHNSY
376   NRPAYSPGHKTHAPTSSSTKKTQLQLEHLLLDLQMILNGINNYKNPKLTR
426   MLTFKFYMPKKATELKHLQCLEEELKPLEEVLNLAQSKNFHLRPRDLISN
476   INVIVLELKGSETTFMCEYADETATIVEFLNRWITFCQSIISTLT <520
```

Fig. 55 continued

SEQ ID NO: 61 (DNA sequence encoding secreted D3E Ontak®, or D3E s-Ontak. Sequence includes *toxP*, mutant *tox*O, signal sequence, and D3E Ontak®. Bold font and asterisks indicate the changes introduces to create the mutant *toxO*.

```
                                                 ****  *  *
1     TTGATTTCAGAGCACCCTTATAATTAGGATAGCTAAGTCCATTATTTTAT
51    GAGTCCTGGTAAGGGGATACGTTGTGAGCAGAAAACTGTTTGCGTCAATC
101   TTAATAGGGGCGCTACTGGGGATAGGGGCCCCACCTTCAGCCCATGCAGG
151   CGCTGAAGATGTTGTTGATTCTTCTAAATCTTTTGTGATGGAAAACTTTT
201   CTTCGTACCACGGGACTAAACCTGGTTATGTAGATTCCATTCAAAAAGGT
251   ATACAAAAGCCAAAATCTGGTACACAAGGAAATTATGACGATGATTGGAA
301   AGGGTTTTATAGTACCGACAATAAATACGACGCTGCGGGATACTCTGTAG
351   ATAATGAAAACCCGCTCTCTGGAAAAGCTGGAGGCGTGGTCAAAGTGACG
401   TATCCAGGACTGACGAAGGTTCTCGCACTAAAAGTGGATAATGCCGAAAC
451   TATTAAGAAAGAGTTAGGTTTAAGTCTCACTGAACCGTTGATGGAGCAAG
501   TCGGAACGGAAGAGTTTATCAAAAGGTTCGGTGATGGTGCTTCGCGTGTA
551   GTGCTCAGCCTTCCCTTCGCTGAGGGGAGTTCTAGCGTTGAATATATTAA
601   TAACTGGGAACAGGCGAAAGCGTTAAGCGTAGAACTTGAGATTAATTTTG
651   AAACCCGTGGAAAACGTGGCCAAGATGCGATGTATGAGTATATGGCTCAA
701   GCCTGTGCAGGAAATCGTGTCAGGCGATCAGTAGGTAGCTCATTGTCATG
751   CATCAACCTGGATTGGGATGTTATCCGTGATAAAACTAAAACTAAGATCG
801   AATCTCTGAAAGAACACGGTCCGATCAAAAACAAAATGAGCGAAAGCCCG
851   AACAAAACTGTATCTGAAGAAAAAGCTAAACAGTACCTGGAAGAATTCCA
901   CCAGACTGCACTGGAACACCCGGAACTGTCTGAACTTAAGACCGTTACTG
951   GTACCAACCCGGTATTCGCTGGTGCTAACTACGCTGCTTGGGCAGTAAAC
1001  GTTGCTCAGGTTATCGATAGCGAAACTGCTGATAACCTGGAAAAAACTAC
1051  CGCGGCTCTGTCTATCCTGCCGGGTATCGGTAGCGTAATGGGCATCGCAG
1101  ACGGCGCCGTTCACCACAACACTGAAGAAATCGTTGCACAGTCTATCGCT
1151  CTGAGCTCTCTGATGGTTGCTCAGGCCATCCCGCTGGTAGGTGAACTGGT
1201  TGATATCGGTTTCGCTGCATACAACTTCGTTGAAAGCATCATCAACCTGT
1251  TCCAGGTTGTTCACAACTCTTACAACCGCCCGGCTTACTCTCCGGGTCAC
1301  AAGACGCATGCACCTACTTCTAGCTCTACCAAGAAAACCCAGCTGCAGCT
1351  CGAGCACCTGCTGCTGGATTTGCAGATGATCCTGAACGGTATCAACAATT
1401  ACAAGAACCCGAAACTGACGCGTATGCTGACCTTCAAGTTCTACATGCCG
1451  AAGAAGGCCACCGAACTGAAACACCTGCAGTGTCTAGAAGAAGAACTGAA
1501  ACCGCTGGAGGAAGTTCTGAACCTGGCTCAGTCTAAAAACTTCCACCTGC
```

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA< 1711

Fig. 55 continued

SEQ ID NO: 62 (D3E-His6 s-Ontak or D3E-His6 Ontak®)

1 GAEDVVDSSKSFVMENFSSYHGTKP
26 GYVDSIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLTHHHHH
H <526

Fig. 55 continued

SEQ ID NO: 63 (DNA sequence encoding secreted D3E-His6 Ontak®, or D3E-His6 s-Ontak. Sequence includes *toxP*, mutant *tox*O, signal sequence, and D3E-His6 Ontak®. Bold font and asterisks indicate the changes introduces to create the mutant *toxO*).

**** * *

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGAAGATGTTGTTGATTCTTCTAAATCTTTTGTGATGGAAAACTTTT
201 CTTCGTACCACGGGACTAAACCTGGTTATGTAGATTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCCACCATCACCATCATCACTGA< 1729

Fig. 55 continued

SEQ ID NO: 64 (D7E s-Ontak or D7E Ontak®)

1 GAEDVVESSKSFVMENFSSYHGTKP
26 GYVDSIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLT <520

Fig. 55 continued

SEQ ID NO: 65 (DNA sequence encoding secreted D7E Ontak®, or D7E s-Ontak. Sequence includes *toxP*, mutant *tox*O, signal sequence, and D7E Ontak®. Bold font and asterisks indicate the changes introduces to create the mutant *toxO*).

**** * *

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGATGATGTTGTTGAATCTTCTAAATCTTTTGTGATGGAAAACTTTT
201 CTTCGTACCACGGGACTAAACCTGGTTATGTAGATTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA< 1711

Fig. 55 continued

SEQ ID NO: 66 (D7E-$His_6$ s-Ontak or D7E-$His_6$ Ontak®)

1 GAEDVVESSKSFVMENFSSYHGTKP
26 GYVDSIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLTHHHHH
H <526

Fig. 55 continued

SEQ ID NO: 67 (DNA sequence encoding secreted D7E-His$_6$ Ontak®, or D7E-His$_6$ s-Ontak. Sequence includes *toxP*, mutant *tox*O, signal sequence, and D7E Ontak®. Bold font and asterisks indicate the changes introduces to create the mutant *toxO*).

**** * *

1 TTGATTTCAGAGCACCCTTATAATTAGGATAGCTAAGTCCATTATTTTAT

51 GAGTCCTGGTAAGGGGATACGTTGTGAGCAGAAAACTGTTTGCGTCAATC

101 TTAATAGGGGCGCTACTGGGGATAGGGGCCCCACCTTCAGCCCATGCAGG

151 CGCTGATGATGTTGTTGAATCTTCTAAATCTTTTGTGATGGAAAACTTTT

201 CTTCGTACCACGGGACTAAACCTGGTTATGTAGATTCCATTCAAAAAGGT

251 ATACAAAAGCCAAAATCTGGTACACAAGGAAATTATGACGATGATTGGAA

301 AGGGTTTTATAGTACCGACAATAAATACGACGCTGCGGGATACTCTGTAG

351 ATAATGAAAACCCGCTCTCTGGAAAAGCTGGAGGCGTGGTCAAAGTGACG

401 TATCCAGGACTGACGAAGGTTCTCGCACTAAAAGTGGATAATGCCGAAAC

451 TATTAAGAAAGAGTTAGGTTTAAGTCTCACTGAACCGTTGATGGAGCAAG

501 TCGGAACGGAAGAGTTTATCAAAAGGTTCGGTGATGGTGCTTCGCGTGTA

551 GTGCTCAGCCTTCCCTTCGCTGAGGGGAGTTCTAGCGTTGAATATATTAA

601 TAACTGGGAACAGGCGAAAGCGTTAAGCGTAGAACTTGAGATTAATTTTG

651 AAACCCGTGGAAAACGTGGCCAAGATGCGATGTATGAGTATATGGCTCAA

701 GCCTGTGCAGGAAATCGTGTCAGGCGATCAGTAGGTAGCTCATTGTCATG

751 CATCAACCTGGATTGGGATGTTATCCGTGATAAAACTAAAACTAAGATCG

801 AATCTCTGAAAGAACACGGTCCGATCAAAAACAAAATGAGCGAAAGCCCG

851 AACAAAACTGTATCTGAAGAAAAAGCTAAACAGTACCTGGAAGAATTCCA

901 CCAGACTGCACTGGAACACCCGGAACTGTCTGAACTTAAGACCGTTACTG

951 GTACCAACCCGGTATTCGCTGGTGCTAACTACGCTGCTTGGGCAGTAAAC

1001 GTTGCTCAGGTTATCGATAGCGAAACTGCTGATAACCTGGAAAAAACTAC

1051 CGCGGCTCTGTCTATCCTGCCGGGTATCGGTAGCGTAATGGGCATCGCAG

1101 ACGGCGCCGTTCACCACAACACTGAAGAAATCGTTGCACAGTCTATCGCT

1151 CTGAGCTCTCTGATGGTTGCTCAGGCCATCCCGCTGGTAGGTGAACTGGT

1201 TGATATCGGTTTCGCTGCATACAACTTCGTTGAAAGCATCATCAACCTGT

1251 TCCAGGTTGTTCACAACTCTTACAACCGCCCGGCTTACTCTCCGGGTCAC

1301 AAGACGCATGCACCTACTTCTAGCTCTACCAAGAAAACCCAGCTGCAGCT

1351 CGAGCACCTGCTGCTGGATTTGCAGATGATCCTGAACGGTATCAACAATT

1401 ACAAGAACCCGAAACTGACGCGTATGCTGACCTTCAAGTTCTACATGCCG

1451 AAGAAGGCCACCGAACTGAAACACCTGCAGTGTCTAGAAGAAGAACTGAA

1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG

1601 GGCTCTGAAACCACCTTCATGTGTGAATACGCTGATGAGACCGCAACCAT

1651 CGTAGAATTCCTGAACCGTTGGATCACCTTCTGTCAGTCTATCATCTCTA

1701 CCCTGACCCACCATCACCATCATCACTGA< 1729

Fig. 55 continued

SEQ ID NO: 68 (S8T s-Ontak or S8T Ontak®)

1 GAEDVVDTSKSFVMENFSSYHGTKP
26 GYVDSIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLT <520

Fig. 55 continued

SEQ ID NO: 69 (DNA sequence encoding secreted S8T Ontak®, or S8T s-Ontak. Sequence includes *toxP*, mutant *tox*O, signal sequence, and S8T Ontak®. Bold font and asterisks indicate the changes introduces to create the mutant *toxO*).

**** * *

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGATGATGTTGTTGATACTTCTAAATCTTTTGTGATGGAAAACTTTT
201 CTTCGTACCACGGGACTAAACCTGGTTATGTAGATTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA < 1711

Fig. 55 continued

SEQ ID NO: 70 (S8T-$His_6$ s-Ontak or S8T-$His_6$ Ontak®)

1 GAEDVVDTSKSFVMENFSSYHGTKP
26 GYVDSIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLTHHHHH
H <526

Fig. 55 continued

SEQ ID NO: 71 (DNA sequence encoding secreted S8T-$His_6$ Ontak®, or S8T-$His_6$ s-Ontak. Sequence includes *toxP*, mutant *tox*O, signal sequence, and S8T Ontak®. Bold font and asterisks indicate the changes introduces to create the mutant *toxO*).

**** * *

1 TTGATTTCAGAGCACCCTTATAATTAGGATAGCTAAGTCCATTATTTTAT

51 GAGTCCTGGTAAGGGGATACGTTGTGAGCAGAAAACTGTTTGCGTCAATC

101 TTAATAGGGGCGCTACTGGGGATAGGGGCCCCACCTTCAGCCCATGCAGG

151 CGCTGATGATGTTGTTGATACTTCTAAATCTTTTGTGATGGAAAACTTTT

201 CTTCGTACCACGGGACTAAACCTGGTTATGTAGATTCCATTCAAAAAGGT

251 ATACAAAAGCCAAAATCTGGTACACAAGGAAATTATGACGATGATTGGAA

301 AGGGTTTTATAGTACCGACAATAAATACGACGCTGCGGGATACTCTGTAG

351 ATAATGAAAACCCGCTCTCTGGAAAAGCTGGAGGCGTGGTCAAAGTGACG

401 TATCCAGGACTGACGAAGGTTCTCGCACTAAAAGTGGATAATGCCGAAAC

451 TATTAAGAAAGAGTTAGGTTTAAGTCTCACTGAACCGTTGATGGAGCAAG

501 TCGGAACGGAAGAGTTTATCAAAAGGTTCGGTGATGGTGCTTCGCGTGTA

551 GTGCTCAGCCTTCCCTTCGCTGAGGGGAGTTCTAGCGTTGAATATATTAA

601 TAACTGGGAACAGGCGAAAGCGTTAAGCGTAGAACTTGAGATTAATTTTG

651 AAACCCGTGGAAAACGTGGCCAAGATGCGATGTATGAGTATATGGCTCAA

701 GCCTGTGCAGGAAATCGTGTCAGGCGATCAGTAGGTAGCTCATTGTCATG

751 CATCAACCTGGATTGGGATGTTATCCGTGATAAAACTAAAACTAAGATCG

801 AATCTCTGAAAGAACACGGTCCGATCAAAAACAAAATGAGCGAAAGCCCG

851 AACAAAACTGTATCTGAAGAAAAAGCTAAACAGTACCTGGAAGAATTCCA

901 CCAGACTGCACTGGAACACCCGGAACTGTCTGAACTTAAGACCGTTACTG

951 GTACCAACCCGGTATTCGCTGGTGCTAACTACGCTGCTTGGGCAGTAAAC

1001 GTTGCTCAGGTTATCGATAGCGAAACTGCTGATAACCTGGAAAAAACTAC

1051 CGCGGCTCTGTCTATCCTGCCGGGTATCGGTAGCGTAATGGGCATCGCAG

1101 ACGGCGCCGTTCACCACAACACTGAAGAAATCGTTGCACAGTCTATCGCT

1151 CTGAGCTCTCTGATGGTTGCTCAGGCCATCCCGCTGGTAGGTGAACTGGT

1201 TGATATCGGTTTCGCTGCATACAACTTCGTTGAAAGCATCATCAACCTGT

1251 TCCAGGTTGTTCACAACTCTTACAACCGCCCGGCTTACTCTCCGGGTCAC

1301 AAGACGCATGCACCTACTTCTAGCTCTACCAAGAAAACCCAGCTGCAGCT

1351 CGAGCACCTGCTGCTGGATTTGCAGATGATCCTGAACGGTATCAACAATT

1401 ACAAGAACCCGAAACTGACGCGTATGCTGACCTTCAAGTTCTACATGCCG

1451 AAGAAGGCCACCGAACTGAAACACCTGCAGTGTCTAGAAGAAGAACTGAA

1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGACACCATCACCATCATCACTGA< 1729

Fig. 55 continued

SEQ ID NO: 72 (D3E/V6A s-Ontak or D3E/V6A Ontak®)

1 GAEDVADSSKSFVMENFSSYHGTKP
26 GYVDSIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLT <520

Fig. 55 continued

SEQ ID NO: 73 (DNA sequence encoding secreted D3E/V6A Ontak®, or D3E/V6A s-Ontak. Sequence includes *toxP*, mutant *tox*O, signal sequence, and D3E/V6A Ontak®. Bold font and asterisks indicate the changes introduces to create the mutant *toxO*.

**** * *

1 TTGATTTCAGAGCACCCTTATAATTAGGATAGCTAAGTCCATTATTTTAT

51 GAGTCCTGGTAAGGGGATACGTTGTGAGCAGAAAACTGTTTGCGTCAATC

101 TTAATAGGGGCGCTACTGGGGATAGGGGCCCCACCTTCAGCCCATGCAGG

151 CGCTGAAGATGTTGCTGATTCTTCTAAATCTTTTGTGATGGAAAACTTTT

201 CTTCGTACCACGGGACTAAACCTGGTTATGTAGATTCCATTCAAAAAGGT

251 ATACAAAAGCCAAAATCTGGTACACAAGGAAATTATGACGATGATTGGAA

301 AGGGTTTTATAGTACCGACAATAAATACGACGCTGCGGGATACTCTGTAG

351 ATAATGAAAACCCGCTCTCTGGAAAAGCTGGAGGCGTGGTCAAAGTGACG

401 TATCCAGGACTGACGAAGGTTCTCGCACTAAAAGTGGATAATGCCGAAAC

451 TATTAAGAAAGAGTTAGGTTTAAGTCTCACTGAACCGTTGATGGAGCAAG

501 TCGGAACGGAAGAGTTTATCAAAAGGTTCGGTGATGGTGCTTCGCGTGTA

551 GTGCTCAGCCTTCCCTTCGCTGAGGGGAGTTCTAGCGTTGAATATATTAA

601 TAACTGGGAACAGGCGAAAGCGTTAAGCGTAGAACTTGAGATTAATTTTG

651 AAACCCGTGGAAAACGTGGCCAAGATGCGATGTATGAGTATATGGCTCAA

701 GCCTGTGCAGGAAATCGTGTCAGGCGATCAGTAGGTAGCTCATTGTCATG

751 CATCAACCTGGATTGGGATGTTATCCGTGATAAAACTAAAACTAAGATCG

801 AATCTCTGAAAGAACACGGTCCGATCAAAAACAAAATGAGCGAAAGCCCG

851 AACAAAACTGTATCTGAAGAAAAAGCTAAACAGTACCTGGAAGAATTCCA

901 CCAGACTGCACTGGAACACCCGGAACTGTCTGAACTTAAGACCGTTACTG

951 GTACCAACCCGGTATTCGCTGGTGCTAACTACGCTGCTTGGGCAGTAAAC

1001 GTTGCTCAGGTTATCGATAGCGAAACTGCTGATAACCTGGAAAAAACTAC

1051 CGCGGCTCTGTCTATCCTGCCGGGTATCGGTAGCGTAATGGGCATCGCAG

1101 ACGGCGCCGTTCACCACAACACTGAAGAAATCGTTGCACAGTCTATCGCT

1151 CTGAGCTCTCTGATGGTTGCTCAGGCCATCCCGCTGGTAGGTGAACTGGT

1201 TGATATCGGTTTCGCTGCATACAACTTCGTTGAAAGCATCATCAACCTGT

1251 TCCAGGTTGTTCACAACTCTTACAACCGCCCGGCTTACTCTCCGGGTCAC

1301 AAGACGCATGCACCTACTTCTAGCTCTACCAAGAAAACCCAGCTGCAGCT

1351 CGAGCACCTGCTGCTGGATTTGCAGATGATCCTGAACGGTATCAACAATT

1401 ACAAGAACCCGAAACTGACGCGTATGCTGACCTTCAAGTTCTACATGCCG

1451 AAGAAGGCCACCGAACTGAAACACCTGCAGTGTCTAGAAGAAGAACTGAA

1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA< 1711

Fig. 55 continued

SEQ ID NO: 74 (D3E/V6A-$His_6$ s-Ontak or D3E/V6A-$His_6$ Ontak®)

```
1     GAEDVADSSKSFVMENFSSYHGTKP
26    GYVDSIQKGIQKPKSGTQGNYDDDWKGFYSTDNKYDAAGYSVDNENPLSG
76    KAGGVVKVTYPGLTKVLALKVDNAETIKKELGLSLTEPLMEQVGTEEFIK
126   RFGDGASRVVLSLPFAEGSSSVEYINNWEQAKALSVELEINFETRGKRGQ
176   DAMYEYMAQACAGNRVRRSVGSSLSCINLDWDVIRDKTKTKIESLKEHGP
226   IKNKMSESPNKTVSEEKAKQYLEEFHQTALEHPELSELKTVTGTNPVFAG
276   ANYAAWAVNVAQVIDSETADNLEKTTAALSILPGIGSVMGIADGAVHHNT
326   EEIVAQSIALSSLMVAQAIPLVGELVDIGFAAYNFVESIINLFQVVHNSY
376   NRPAYSPGHKTHAPTSSSTKKTQLQLEHLLLDLQMILNGINNYKNPKLTR
426   MLTFKFYMPKKATELKHLQCLEEELKPLEEVLNLAQSKNFHLRPRDLISN
476   INVIVLELKGSETTFMCEYADETATIVEFLNRWITFCQSIISTLTHHHHH
      H <526
```

Fig. 55 continued

SEQ ID NO: 75 (DNA sequence encoding secreted D3E/V6A-His6 Ontak®, or D3E/V6A-His6 s-Ontak. Sequence includes *toxP*, mutant *tox*O, signal sequence, and D3E/V6A Ontak®. Bold font and asterisks indicate the changes introduces to create the mutant *toxO*.

**** * *

1 TTGATTTCAGAGCACCCTTATAATTAGGATAGCTAAGTCCATTATTTTAT

51 GAGTCCTGGTAAGGGGATACGTTGTGAGCAGAAAACTGTTTGCGTCAATC

101 TTAATAGGGGCGCTACTGGGGATAGGGGCCCCACCTTCAGCCCATGCAGG

151 CGCTGAAGATGTTGCTGATTCTTCTAAATCTTTTGTGATGGAAAACTTTT

201 CTTCGTACCACGGGACTAAACCTGGTTATGTAGATTCCATTCAAAAAGGT

251 ATACAAAAGCCAAAATCTGGTACACAAGGAAATTATGACGATGATTGGAA

301 AGGGTTTTATAGTACCGACAATAAATACGACGCTGCGGGATACTCTGTAG

351 ATAATGAAAACCCGCTCTCTGGAAAAGCTGGAGGCGTGGTCAAAGTGACG

401 TATCCAGGACTGACGAAGGTTCTCGCACTAAAAGTGGATAATGCCGAAAC

451 TATTAAGAAAGAGTTAGGTTTAAGTCTCACTGAACCGTTGATGGAGCAAG

501 TCGGAACGGAAGAGTTTATCAAAAGGTTCGGTGATGGTGCTTCGCGTGTA

551 GTGCTCAGCCTTCCCTTCGCTGAGGGGAGTTCTAGCGTTGAATATATTAA

601 TAACTGGGAACAGGCGAAAGCGTTAAGCGTAGAACTTGAGATTAATTTTG

651 AAACCCGTGGAAAACGTGGCCAAGATGCGATGTATGAGTATATGGCTCAA

701 GCCTGTGCAGGAAATCGTGTCAGGCGATCAGTAGGTAGCTCATTGTCATG

751 CATCAACCTGGATTGGGATGTTATCCGTGATAAAACTAAAACTAAGATCG

801 AATCTCTGAAAGAACACGGTCCGATCAAAAACAAAATGAGCGAAAGCCCG

851 AACAAAACTGTATCTGAAGAAAAAGCTAAACAGTACCTGGAAGAATTCCA

901 CCAGACTGCACTGGAACACCCGGAACTGTCTGAACTTAAGACCGTTACTG

951 GTACCAACCCGGTATTCGCTGGTGCTAACTACGCTGCTTGGGCAGTAAAC

1001 GTTGCTCAGGTTATCGATAGCGAAACTGCTGATAACCTGGAAAAAACTAC

1051 CGCGGCTCTGTCTATCCTGCCGGGTATCGGTAGCGTAATGGGCATCGCAG

1101 ACGGCGCCGTTCACCACAACACTGAAGAAATCGTTGCACAGTCTATCGCT

1151 CTGAGCTCTCTGATGGTTGCTCAGGCCATCCCGCTGGTAGGTGAACTGGT

1201 TGATATCGGTTTCGCTGCATACAACTTCGTTGAAAGCATCATCAACCTGT

1251 TCCAGGTTGTTCACAACTCTTACAACCGCCCGGCTTACTCTCCGGGTCAC

1301 AAGACGCATGCACCTACTTCTAGCTCTACCAAGAAAACCCAGCTGCAGCT

1351 CGAGCACCTGCTGCTGGATTTGCAGATGATCCTGAACGGTATCAACAATT

1401 ACAAGAACCCGAAACTGACGCGTATGCTGACCTTCAAGTTCTACATGCCG

1451 AAGAAGGCCACCGAACTGAAACACCTGCAGTGTCTAGAAGAAGAACTGAA

1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCCACCATCACCATCATCACTGA< 1729

Fig. 55 continued

SEQ ID NO: 76 (D3E/D7E s-Ontak or D3E/D7E Ontak®)

| | |
|---|---|
| 1 | GAEDVVESSKSFVMENFSSYHGTKP |
| 26 | GYVDSIQKGIQKPKSGTQGNYDDDWKGFYSTDNKYDAAGYSVDNENPLSG |
| 76 | KAGGVVKVTYPGLTKVLALKVDNAETIKKELGLSLTEPLMEQVGTEEFIK |
| 126 | RFGDGASRVVLSLPFAEGSSSVEYINNWEQAKALSVELEINFETRGKRGQ |
| 176 | DAMYEYMAQACAGNRVRRSVGSSLSCINLDWDVIRDKTKTKIESLKEHGP |
| 226 | IKNKMSESPNKTVSEEKAKQYLEEFHQTALEHPELSELKTVTGTNPVFAG |
| 276 | ANYAAWAVNVAQVIDSETADNLEKTTAALSILPGIGSVMGIADGAVHHNT |
| 326 | EEIVAQSIALSSLMVAQAIPLVGELVDIGFAAYNFVESIINLFQVVHNSY |
| 376 | NRPAYSPGHKTHAPTSSSTKKTQLQLEHLLLDLQMILNGINNYKNPKLTR |
| 426 | MLTFKFYMPKKATELKHLQCLEEELKPLEEVLNLAQSKNFHLRPRDLISN |
| 476 | INVIVLELKGSETTFMCEYADETATIVEFLNRWITFCQSIISTLT <520 |

Fig. 55 continued

SEQ ID NO: 77 (DNA sequence encoding secreted D3E/D7E Ontak®, or D3E/D7E s-Ontak. Sequence includes *toxP*, mutant *tox*O, signal sequence, and D3E/D7E Ontak®. Bold font and asterisks indicate the changes introduces to create the mutant *toxO*).

```
                                         ****  *  *
1     TTGATTTCAGAGCACCCTTATAATTAGGATAGCTAAGTCCATTATTTTAT
51    GAGTCCTGGTAAGGGGATACGTTGTGAGCAGAAAACTGTTTGCGTCAATC
101   TTAATAGGGGCGCTACTGGGGATAGGGGCCCCACCTTCAGCCCATGCAGG
151   CGCTGAAGATGTTGTTGAATCTTCTAAATCTTTTGTGATGGAAAACTTTT
201   CTTCGTACCACGGGACTAAACCTGGTTATGTAGATTCCATTCAAAAAGGT
251   ATACAAAAGCCAAAATCTGGTACACAAGGAAATTATGACGATGATTGGAA
301   AGGGTTTTATAGTACCGACAATAAATACGACGCTGCGGGATACTCTGTAG
351   ATAATGAAAACCCGCTCTCTGGAAAAGCTGGAGGCGTGGTCAAAGTGACG
401   TATCCAGGACTGACGAAGGTTCTCGCACTAAAAGTGGATAATGCCGAAAC
451   TATTAAGAAAGAGTTAGGTTTAAGTCTCACTGAACCGTTGATGGAGCAAG
501   TCGGAACGGAAGAGTTTATCAAAAGGTTCGGTGATGGTGCTTCGCGTGTA
551   GTGCTCAGCCTTCCCTTCGCTGAGGGGAGTTCTAGCGTTGAATATATTAA
601   TAACTGGGAACAGGCGAAAGCGTTAAGCGTAGAACTTGAGATTAATTTTG
651   AAACCCGTGGAAAACGTGGCCAAGATGCGATGTATGAGTATATGGCTCAA
701   GCCTGTGCAGGAAATCGTGTCAGGCGATCAGTAGGTAGCTCATTGTCATG
751   CATCAACCTGGATTGGGATGTTATCCGTGATAAAACTAAAACTAAGATCG
801   AATCTCTGAAAGAACACGGTCCGATCAAAAACAAAATGAGCGAAAGCCCG
851   AACAAAACTGTATCTGAAGAAAAAGCTAAACAGTACCTGGAAGAATTCCA
901   CCAGACTGCACTGGAACACCCGGAACTGTCTGAACTTAAGACCGTTACTG
951   GTACCAACCCGGTATTCGCTGGTGCTAACTACGCTGCTTGGGCAGTAAAC
1001  GTTGCTCAGGTTATCGATAGCGAAACTGCTGATAACCTGGAAAAAACTAC
1051  CGCGGCTCTGTCTATCCTGCCGGGTATCGGTAGCGTAATGGGCATCGCAG
1101  ACGGCGCCGTTCACCACAACACTGAAGAAATCGTTGCACAGTCTATCGCT
1151  CTGAGCTCTCTGATGGTTGCTCAGGCCATCCCGCTGGTAGGTGAACTGGT
1201  TGATATCGGTTTCGCTGCATACAACTTCGTTGAAAGCATCATCAACCTGT
1251  TCCAGGTTGTTCACAACTCTTACAACCGCCCGGCTTACTCTCCGGGTCAC
1301  AAGACGCATGCACCTACTTCTAGCTCTACCAAGAAAACCCAGCTGCAGCT
1351  CGAGCACCTGCTGCTGGATTTGCAGATGATCCTGAACGGTATCAACAATT
1401  ACAAGAACCCGAAACTGACGCGTATGCTGACCTTCAAGTTCTACATGCCG
1451  AAGAAGGCCACCGAACTGAAACACCTGCAGTGTCTAGAAGAAGAACTGAA
1501  ACCGCTGGAGGAAGTTCTGAACCTGGCTCAGTCTAAAAACTTCCACCTGC
```

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA< 1711

Fig. 55 continued

SEQ ID NO: 78 (D3E/D7E-$His_6$ s-Ontak or D3E/D7E-$His_6$ Ontak®)

```
1     GAEDVVESSKSFVMENFSSYHGTKP
26    GYVDSIQKGIQKPKSGTQGNYDDDWKGFYSTDNKYDAAGYSVDNENPLSG
76    KAGGVVKVTYPGLTKVLALKVDNAETIKKELGLSLTEPLMEQVGTEEFIK
126   RFGDGASRVVLSLPFAEGSSSVEYINNWEQAKALSVELEINFETRGKRGQ
176   DAMYEYMAQACAGNRVRRSVGSSLSCINLDWDVIRDKTKTKIESLKEHGP
226   IKNKMSESPNKTVSEEKAKQYLEEFHQTALEHPELSELKTVTGTNPVFAG
276   ANYAAWAVNVAQVIDSETADNLEKTTAALSILPGIGSVMGIADGAVHHNT
326   EEIVAQSIALSSLMVAQAIPLVGELVDIGFAAYNFVESIINLFQVVHNSY
376   NRPAYSPGHKTHAPTSSSTKKTQLQLEHLLLDLQMILNGINNYKNPKLTR
426   MLTFKFYMPKKATELKHLQCLEEELKPLEEVLNLAQSKNFHLRPRDLISN
476   INVIVLELKGSETTFMCEYADETATIVEFLNRWITFCQSIISTLTHHHHH
      H <526
```

Fig. 55 continued

SEQ ID NO: 79 (DNA sequence encoding secreted D3E/D7E-His$_6$ Ontak®, or D3E/D7E-His$_6$ s-Ontak. Sequence includes *toxP*, mutant *tox*O, signal sequence, and D3E/D7E Ontak®. Bold font and asterisks indicate the changes introduces to create the mutant *toxO*).

```
                                           ****  *  *
1     TTGATTTCAGAGCACCCTTATAATTAGGATAGCTAAGTCCATTATTTTAT
51    GAGTCCTGGTAAGGGGATACGTTGTGAGCAGAAAACTGTTTGCGTCAATC
101   TTAATAGGGGCGCTACTGGGGATAGGGGCCCCACCTTCAGCCCATGCAGG
151   CGCTGAAGATGTTGTTGAATCTTCTAAATCTTTTGTGATGGAAAACTTTT
201   CTTCGTACCACGGGACTAAACCTGGTTATGTAGATTCCATTCAAAAAGGT
251   ATACAAAAGCCAAAATCTGGTACACAAGGAAATTATGACGATGATTGGAA
301   AGGGTTTTATAGTACCGACAATAAATACGACGCTGCGGGATACTCTGTAG
351   ATAATGAAAACCCGCTCTCTGGAAAAGCTGGAGGCGTGGTCAAAGTGACG
401   TATCCAGGACTGACGAAGGTTCTCGCACTAAAAGTGGATAATGCCGAAAC
451   TATTAAGAAAGAGTTAGGTTTAAGTCTCACTGAACCGTTGATGGAGCAAG
501   TCGGAACGGAAGAGTTTATCAAAAGGTTCGGTGATGGTGCTTCGCGTGTA
551   GTGCTCAGCCTTCCCTTCGCTGAGGGGAGTTCTAGCGTTGAATATATTAA
601   TAACTGGGAACAGGCGAAAGCGTTAAGCGTAGAACTTGAGATTAATTTTG
651   AAACCCGTGGAAAACGTGGCCAAGATGCGATGTATGAGTATATGGCTCAA
701   GCCTGTGCAGGAAATCGTGTCAGGCGATCAGTAGGTAGCTCATTGTCATG
751   CATCAACCTGGATTGGGATGTTATCCGTGATAAAACTAAAACTAAGATCG
801   AATCTCTGAAAGAACACGGTCCGATCAAAAACAAAATGAGCGAAAGCCCG
851   AACAAAACTGTATCTGAAGAAAAAGCTAAACAGTACCTGGAAGAATTCCA
901   CCAGACTGCACTGGAACACCCGGAACTGTCTGAACTTAAGACCGTTACTG
951   GTACCAACCCGGTATTCGCTGGTGCTAACTACGCTGCTTGGGCAGTAAAC
1001  GTTGCTCAGGTTATCGATAGCGAAACTGCTGATAACCTGGAAAAAACTAC
1051  CGCGGCTCTGTCTATCCTGCCGGGTATCGGTAGCGTAATGGGCATCGCAG
1101  ACGGCGCCGTTCACCACAACACTGAAGAAATCGTTGCACAGTCTATCGCT
1151  CTGAGCTCTCTGATGGTTGCTCAGGCCATCCCGCTGGTAGGTGAACTGGT
1201  TGATATCGGTTTCGCTGCATACAACTTCGTTGAAAGCATCATCAACCTGT
1251  TCCAGGTTGTTCACAACTCTTACAACCGCCCGGCTTACTCTCCGGGTCAC
1301  AAGACGCATGCACCTACTTCTAGCTCTACCAAGAAAACCCAGCTGCAGCT
1351  CGAGCACCTGCTGCTGGATTTGCAGATGATCCTGAACGGTATCAACAATT
1401  ACAAGAACCCGAAACTGACGCGTATGCTGACCTTCAAGTTCTACATGCCG
1451  AAGAAGGCCACCGAACTGAAACACCTGCAGTGTCTAGAAGAAGAACTGAA
1501  ACCGCTGGAGGAAGTTCTGAACCTGGCTCAGTCTAAAAACTTCCACCTGC
```

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCCACCATCACCATCATCACTGA< 1729

Fig. 55 continued

SEQ ID NO: 80 (D3E/S8T s-Ontak or D3E/S8T Ontak®)

1 GAEDVVDTSKSFVMENFSSYHGTKP
26 GYVDSIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLT <520

Fig. 55 continued

SEQ ID NO: 81 (DNA sequence encoding secreted D3E/S8T Ontak®, or D3E/S8T s-Ontak. Sequence includes *toxP*, mutant *tox*O, signal sequence, and D3E/S8T Ontak®. Bold font and asterisks indicate the changes introduces to create the mutant *toxO*).

**** * *

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGAAGATGTTGTTGATACTTCTAAATCTTTTGTGATGGAAAACTTTT
201 CTTCGTACCACGGGACTAAACCTGGTTATGTAGATTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA < 1711

Fig. 55 continued

SEQ ID NO: 82 (D3E/S8T-$His_6$ s-Ontak or D3E/S8T-$His_6$ Ontak®)

```
1      GAEDVVDTSKSFVMENFSSYHGTKP
26     GYVDSIQKGIQKPKSGTQGNYDDDWKGFYSTDNKYDAAGYSVDNENPLSG
76     KAGGVVKVTYPGLTKVLALKVDNAETIKKELGLSLTEPLMEQVGTEEFIK
126    RFGDGASRVVLSLPFAEGSSSVEYINNWEQAKALSVELEINFETRGKRGQ
176    DAMYEYMAQACAGNRVRRSVGSSLSCINLDWDVIRDKTKTKIESLKEHGP
226    IKNKMSESPNKTVSEEKAKQYLEEFHQTALEHPELSELKTVTGTNPVFAG
276    ANYAAWAVNVAQVIDSETADNLEKTTAALSILPGIGSVMGIADGAVHHNT
326    EEIVAQSIALSSLMVAQAIPLVGELVDIGFAAYNFVESIINLFQVVHNSY
376    NRPAYSPGHKTHAPTSSSTKKTQLQLEHLLLDLQMILNGINNYKNPKLTR
426    MLTFKFYMPKKATELKHLQCLEEELKPLEEVLNLAQSKNFHLRPRDLISN
476    INVIVLELKGSETTFMCEYADETATIVEFLNRWITFCQSIISTLTHHHHH
       H <526
```

Fig. 55 continued

SEQ ID NO: 83 (DNA sequence encoding secreted D3E/S8T-His$_6$ Ontak®, or D3E/S8T-His$_6$ s-Ontak. Sequence includes *toxP*, mutant *tox*O, signal sequence, and D3E/S8T Ontak®. Bold font and asterisks indicate the changes introduces to create the mutant *toxO*).

**** * *

1 TTGATTTCAGAGCACCCTTATAATTAGGATAGCTAAGTCCATTATTTTAT

51 GAGTCCTGGTAAGGGGATACGTTGTGAGCAGAAAACTGTTTGCGTCAATC

101 TTAATAGGGGCGCTACTGGGGATAGGGGCCCCACCTTCAGCCCATGCAGG

151 CGCTGAAGATGTTGTTGATACTTCTAAATCTTTTGTGATGGAAAACTTTT

201 CTTCGTACCACGGGACTAAACCTGGTTATGTAGATTCCATTCAAAAAGGT

251 ATACAAAAGCCAAAATCTGGTACACAAGGAAATTATGACGATGATTGGAA

301 AGGGTTTTATAGTACCGACAATAAATACGACGCTGCGGGATACTCTGTAG

351 ATAATGAAAACCCGCTCTCTGGAAAAGCTGGAGGCGTGGTCAAAGTGACG

401 TATCCAGGACTGACGAAGGTTCTCGCACTAAAAGTGGATAATGCCGAAAC

451 TATTAAGAAAGAGTTAGGTTTAAGTCTCACTGAACCGTTGATGGAGCAAG

501 TCGGAACGGAAGAGTTTATCAAAAGGTTCGGTGATGGTGCTTCGCGTGTA

551 GTGCTCAGCCTTCCCTTCGCTGAGGGGAGTTCTAGCGTTGAATATATTAA

601 TAACTGGGAACAGGCGAAAGCGTTAAGCGTAGAACTTGAGATTAATTTTG

651 AAACCCGTGGAAAACGTGGCCAAGATGCGATGTATGAGTATATGGCTCAA

701 GCCTGTGCAGGAAATCGTGTCAGGCGATCAGTAGGTAGCTCATTGTCATG

751 CATCAACCTGGATTGGGATGTTATCCGTGATAAAACTAAAACTAAGATCG

801 AATCTCTGAAAGAACACGGTCCGATCAAAAACAAAATGAGCGAAAGCCCG

851 AACAAAACTGTATCTGAAGAAAAAGCTAAACAGTACCTGGAAGAATTCCA

901 CCAGACTGCACTGGAACACCCGGAACTGTCTGAACTTAAGACCGTTACTG

951 GTACCAACCCGGTATTCGCTGGTGCTAACTACGCTGCTTGGGCAGTAAAC

1001 GTTGCTCAGGTTATCGATAGCGAAACTGCTGATAACCTGGAAAAAACTAC

1051 CGCGGCTCTGTCTATCCTGCCGGGTATCGGTAGCGTAATGGGCATCGCAG

1101 ACGGCGCCGTTCACCACAACACTGAAGAAATCGTTGCACAGTCTATCGCT

1151 CTGAGCTCTCTGATGGTTGCTCAGGCCATCCCGCTGGTAGGTGAACTGGT

1201 TGATATCGGTTTCGCTGCATACAACTTCGTTGAAAGCATCATCAACCTGT

1251 TCCAGGTTGTTCACAACTCTTACAACCGCCCGGCTTACTCTCCGGGTCAC

1301 AAGACGCATGCACCTACTTCTAGCTCTACCAAGAAAACCCAGCTGCAGCT

1351 CGAGCACCTGCTGCTGGATTTGCAGATGATCCTGAACGGTATCAACAATT

1401 ACAAGAACCCGAAACTGACGCGTATGCTGACCTTCAAGTTCTACATGCCG

1451 AAGAAGGCCACCGAACTGAAACACCTGCAGTGTCTAGAAGAAGAACTGAA

1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGACACCATCACCATCATCACTGA< 1729

Fig. 55 continued

SEQ ID NO: 84 (V6A/D7E s-Ontak or V6A/D7E Ontak®)

1 GADDVAESSKSFVMENFSSYHGTKP
26 GYVDSIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLT <520

Fig. 55 continued

SEQ ID NO: 85 (DNA sequence encoding secreted V6A/D7E Ontak®, or V6A/D7E s-Ontak. Sequence includes *toxP*, mutant *tox*O, signal sequence, and V6A/D7E Ontak®. Bold font and asterisks indicate the changes introduces to create the mutant *toxO*).

**** * *

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGATGATGTTGCTGAATCTTCTAAATCTTTTGTGATGGAAAACTTTT
201 CTTCGTACCACGGGACTAAACCTGGTTATGTAGATTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA< 1711

Fig. 55 continued

SEQ ID NO: 86 (V6A/D7E-His$_6$ s-Ontak or V6A/D7E-His$_6$ Ontak®)

```
1     GAEDVAESSKSFVMENFSSYHGTKP
26    GYVDSIQKGIQKPKSGTQGNYDDDWKGFYSTDNKYDAAGYSVDNENPLSG
76    KAGGVVKVTYPGLTKVLALKVDNAETIKKELGLSLTEPLMEQVGTEEFIK
126   RFGDGASRVVLSLPFAEGSSSVEYINNWEQAKALSVELEINFETRGKRGQ
176   DAMYEYMAQACAGNRVRRSVGSSLSCINLDWDVIRDKTKTKIESLKEHGP
226   IKNKMSESPNKTVSEEKAKQYLEEFHQTALEHPELSELKTVTGTNPVFAG
276   ANYAAWAVNVAQVIDSETADNLEKTTAALSILPGIGSVMGIADGAVHHNT
326   EEIVAQSIALSSLMVAQAIPLVGELVDIGFAAYNFVESIINLFQVVHNSY
376   NRPAYSPGHKTHAPTSSSTKKTQLQLEHLLLDLQMILNGINNYKNPKLTR
426   MLTFKFYMPKKATELKHLQCLEEELKPLEEVLNLAQSKNFHLRPRDLISN
476   INVIVLELKGSETTFMCEYADETATIVEFLNRWITFCQSIISTLTHHHHH
      H <526
```

Fig. 55 continued

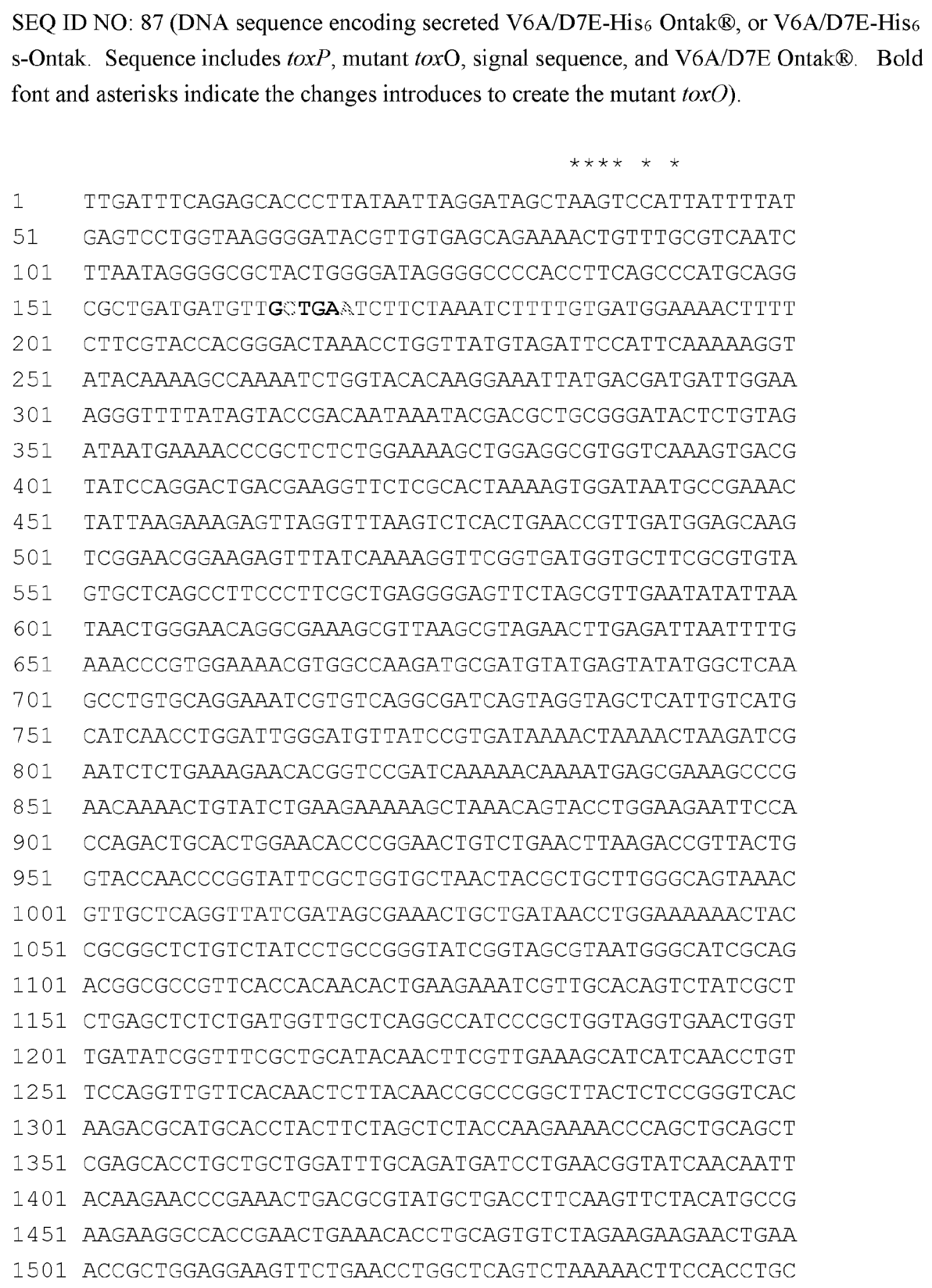

SEQ ID NO: 87 (DNA sequence encoding secreted V6A/D7E-His$_6$ Ontak®, or V6A/D7E-His$_6$ s-Ontak. Sequence includes *toxP*, mutant *tox*O, signal sequence, and V6A/D7E Ontak®. Bold font and asterisks indicate the changes introduces to create the mutant *toxO*).

```
                                                 ****  *  *
1     TTGATTTCAGAGCACCCTTATAATTAGGATAGCTAAGTCCATTATTTTAT
51    GAGTCCTGGTAAGGGGATACGTTGTGAGCAGAAAACTGTTTGCGTCAATC
101   TTAATAGGGGCGCTACTGGGGATAGGGGCCCCACCTTCAGCCCATGCAGG
151   CGCTGATGATGTTGCTGAATCTTCTAAATCTTTTGTGATGGAAAACTTTT
201   CTTCGTACCACGGGACTAAACCTGGTTATGTAGATTCCATTCAAAAAGGT
251   ATACAAAAGCCAAAATCTGGTACACAAGGAAATTATGACGATGATTGGAA
301   AGGGTTTTATAGTACCGACAATAAATACGACGCTGCGGGATACTCTGTAG
351   ATAATGAAAACCCGCTCTCTGGAAAAGCTGGAGGCGTGGTCAAAGTGACG
401   TATCCAGGACTGACGAAGGTTCTCGCACTAAAAGTGGATAATGCCGAAAC
451   TATTAAGAAAGAGTTAGGTTTAAGTCTCACTGAACCGTTGATGGAGCAAG
501   TCGGAACGGAAGAGTTTATCAAAAGGTTCGGTGATGGTGCTTCGCGTGTA
551   GTGCTCAGCCTTCCCTTCGCTGAGGGGAGTTCTAGCGTTGAATATATTAA
601   TAACTGGGAACAGGCGAAAGCGTTAAGCGTAGAACTTGAGATTAATTTTG
651   AAACCCGTGGAAAACGTGGCCAAGATGCGATGTATGAGTATATGGCTCAA
701   GCCTGTGCAGGAAATCGTGTCAGGCGATCAGTAGGTAGCTCATTGTCATG
751   CATCAACCTGGATTGGGATGTTATCCGTGATAAAACTAAAACTAAGATCG
801   AATCTCTGAAAGAACACGGTCCGATCAAAAACAAAATGAGCGAAAGCCCG
851   AACAAAACTGTATCTGAAGAAAAAGCTAAACAGTACCTGGAAGAATTCCA
901   CCAGACTGCACTGGAACACCCGGAACTGTCTGAACTTAAGACCGTTACTG
951   GTACCAACCCGGTATTCGCTGGTGCTAACTACGCTGCTTGGGCAGTAAAC
1001  GTTGCTCAGGTTATCGATAGCGAAACTGCTGATAACCTGGAAAAAACTAC
1051  CGCGGCTCTGTCTATCCTGCCGGGTATCGGTAGCGTAATGGGCATCGCAG
1101  ACGGCGCCGTTCACCACAACACTGAAGAAATCGTTGCACAGTCTATCGCT
1151  CTGAGCTCTCTGATGGTTGCTCAGGCCATCCCGCTGGTAGGTGAACTGGT
1201  TGATATCGGTTTCGCTGCATACAACTTCGTTGAAAGCATCATCAACCTGT
1251  TCCAGGTTGTTCACAACTCTTACAACCGCCCGGCTTACTCTCCGGGTCAC
1301  AAGACGCATGCACCTACTTCTAGCTCTACCAAGAAAACCCAGCTGCAGCT
1351  CGAGCACCTGCTGCTGGATTTGCAGATGATCCTGAACGGTATCAACAATT
1401  ACAAGAACCCGAAACTGACGCGTATGCTGACCTTCAAGTTCTACATGCCG
1451  AAGAAGGCCACCGAACTGAAACACCTGCAGTGTCTAGAAGAAGAACTGAA
1501  ACCGCTGGAGGAAGTTCTGAACCTGGCTCAGTCTAAAAACTTCCACCTGC
```

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCCACCATCACCATCATCACTGA< 1729

Fig. 55 continued

SEQ ID NO: 88 (V6A/S8T s-Ontak or V6A/S8T Ontak®)

```
1     GAEDVADTSKSFVMENFSSYHGTKP
26    GYVDSIQKGIQKPKSGTQGNYDDDWKGFYSTDNKYDAAGYSVDNENPLSG
76    KAGGVVKVTYPGLTKVLALKVDNAETIKKELGLSLTEPLMEQVGTEEFIK
126   RFGDGASRVVLSLPFAEGSSSVEYINNWEQAKALSVELEINFETRGKRGQ
176   DAMYEYMAQACAGNRVRRSVGSSLSCINLDWDVIRDKTKTKIESLKEHGP
226   IKNKMSESPNKTVSEEKAKQYLEEFHQTALEHPELSELKTVTGTNPVFAG
276   ANYAAWAVNVAQVIDSETADNLEKTTAALSILPGIGSVMGIADGAVHHNT
326   EEIVAQSIALSSLMVAQAIPLVGELVDIGFAAYNFVESIINLFQVVHNSY
376   NRPAYSPGHKTHAPTSSSTKKTQLQLEHLLLDLQMILNGINNYKNPKLTR
426   MLTFKFYMPKKATELKHLQCLEEELKPLEEVLNLAQSKNFHLRPRDLISN
476   INVIVLELKGSETTFMCEYADETATIVEFLNRWITFCQSIISTLT <520
```

Fig. 55 continued

SEQ ID NO: 89 (DNA sequence encoding secreted V6A/S8T Ontak®, or V6A/S8T s-Ontak. Sequence includes *toxP*, mutant *tox*O, signal sequence, and V6A/S8T Ontak®. Bold font and asterisks indicate the changes introduces to create the mutant *toxO*).

****  *  *

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGATGATGTTGCTGATACTTCTAAATCTTTTGTGATGGAAAACTTTT
201 CTTCGTACCACGGGACTAAACCTGGTTATGTAGATTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA < 1711

Fig. 55 continued

SEQ ID NO: 90 (V6A/S8T-$His_6$ s-Ontak or V6A/S8T-$His_6$ Ontak®)

```
1     GAEDVADTSKSFVMENFSSYHGTKP
26    GYVDSIQKGIQKPKSGTQGNYDDDWKGFYSTDNKYDAAGYSVDNENPLSG
76    KAGGVVKVTYPGLTKVLALKVDNAETIKKELGLSLTEPLMEQVGTEEFIK
126   RFGDGASRVVLSLPFAEGSSSVEYINNWEQAKALSVELEINFETRGKRGQ
176   DAMYEYMAQACAGNRVRRSVGSSLSCINLDWDVIRDKTKTKIESLKEHGP
226   IKNKMSESPNKTVSEEKAKQYLEEFHQTALEHPELSELKTVTGTNPVFAG
276   ANYAAWAVNVAQVIDSETADNLEKTTAALSILPGIGSVMGIADGAVHHNT
326   EEIVAQSIALSSLMVAQAIPLVGELVDIGFAAYNFVESIINLFQVVHNSY
376   NRPAYSPGHKTHAPTSSSTKKTQLQLEHLLLDLQMILNGINNYKNPKLTR
426   MLTFKFYMPKKATELKHLQCLEEELKPLEEVLNLAQSKNFHLRPRDLISN
476   INVIVLELKGSETTFMCEYADETATIVEFLNRWITFCQSIISTLTHHHHH
      H <526
```

Fig. 55 continued

SEQ ID NO: 91 (DNA sequence encoding secreted V6A/S8T-$His_6$ Ontak®, or V6A/S8T-$His_6$ s-Ontak. Sequence includes *toxP*, mutant *tox*O, signal sequence, and V6A/S8T Ontak®. Bold font and asterisks indicate the changes introduces to create the mutant *toxO*).

```
                                         ****  *  *
1     TTGATTTCAGAGCACCCTTATAATTAGGATAGCTAAGTCCATTATTTTAT
51    GAGTCCTGGTAAGGGGATACGTTGTGAGCAGAAAACTGTTTGCGTCAATC
101   TTAATAGGGGCGCTACTGGGGATAGGGGCCCCACCTTCAGCCCATGCAGG
151   CGCTGATGATGTTGCTGATACTTCTAAATCTTTTGTGATGGAAAACTTTT
201   CTTCGTACCACGGGACTAAACCTGGTTATGTAGATTCCATTCAAAAAGGT
251   ATACAAAAGCCAAAATCTGGTACACAAGGAAATTATGACGATGATTGGAA
301   AGGGTTTTATAGTACCGACAATAAATACGACGCTGCGGGATACTCTGTAG
351   ATAATGAAAACCCGCTCTCTGGAAAAGCTGGAGGCGTGGTCAAAGTGACG
401   TATCCAGGACTGACGAAGGTTCTCGCACTAAAAGTGGATAATGCCGAAAC
451   TATTAAGAAAGAGTTAGGTTTAAGTCTCACTGAACCGTTGATGGAGCAAG
501   TCGGAACGGAAGAGTTTATCAAAAGGTTCGGTGATGGTGCTTCGCGTGTA
551   GTGCTCAGCCTTCCCTTCGCTGAGGGGAGTTCTAGCGTTGAATATATTAA
601   TAACTGGGAACAGGCGAAAGCGTTAAGCGTAGAACTTGAGATTAATTTTG
651   AAACCCGTGGAAAACGTGGCCAAGATGCGATGTATGAGTATATGGCTCAA
701   GCCTGTGCAGGAAATCGTGTCAGGCGATCAGTAGGTAGCTCATTGTCATG
751   CATCAACCTGGATTGGGATGTTATCCGTGATAAAACTAAAACTAAGATCG
801   AATCTCTGAAAGAACACGGTCCGATCAAAAACAAAATGAGCGAAAGCCCG
851   AACAAAACTGTATCTGAAGAAAAAGCTAAACAGTACCTGGAAGAATTCCA
901   CCAGACTGCACTGGAACACCCGGAACTGTCTGAACTTAAGACCGTTACTG
951   GTACCAACCCGGTATTCGCTGGTGCTAACTACGCTGCTTGGGCAGTAAAC
1001  GTTGCTCAGGTTATCGATAGCGAAACTGCTGATAACCTGGAAAAAACTAC
1051  CGCGGCTCTGTCTATCCTGCCGGGTATCGGTAGCGTAATGGGCATCGCAG
1101  ACGGCGCCGTTCACCACAACACTGAAGAAATCGTTGCACAGTCTATCGCT
1151  CTGAGCTCTCTGATGGTTGCTCAGGCCATCCCGCTGGTAGGTGAACTGGT
1201  TGATATCGGTTTCGCTGCATACAACTTCGTTGAAAGCATCATCAACCTGT
1251  TCCAGGTTGTTCACAACTCTTACAACCGCCCGGCTTACTCTCCGGGTCAC
1301  AAGACGCATGCACCTACTTCTAGCTCTACCAAGAAAACCCAGCTGCAGCT
1351  CGAGCACCTGCTGCTGGATTTGCAGATGATCCTGAACGGTATCAACAATT
1401  ACAAGAACCCGAAACTGACGCGTATGCTGACCTTCAAGTTCTACATGCCG
1451  AAGAAGGCCACCGAACTGAAACACCTGCAGTGTCTAGAAGAAGAACTGAA
1501  ACCGCTGGAGGAAGTTCTGAACCTGGCTCAGTCTAAAAACTTCCACCTGC
```

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGACACCATCACCATCATCACTGA< 1729

Fig. 55 continued

SEQ ID NO: 92 (D7E/S8T s-Ontak or D7E/S8T Ontak®)

| | |
|---|---|
| 1 | GAEDVVETSKSFVMENFSSYHGTKP |
| 26 | GYVDSIQKGIQKPKSGTQGNYDDDWKGFYSTDNKYDAAGYSVDNENPLSG |
| 76 | KAGGVVKVTYPGLTKVLALKVDNAETIKKELGLSLTEPLMEQVGTEEFIK |
| 126 | RFGDGASRVVLSLPFAEGSSSVEYINNWEQAKALSVELEINFETRGKRGQ |
| 176 | DAMYEYMAQACAGNRVRRSVGSSLSCINLDWDVIRDKTKTKIESLKEHGP |
| 226 | IKNKMSESPNKTVSEEKAKQYLEEFHQTALEHPELSELKTVTGTNPVFAG |
| 276 | ANYAAWAVNVAQVIDSETADNLEKTTAALSILPGIGSVMGIADGAVHHNT |
| 326 | EEIVAQSIALSSLMVAQAIPLVGELVDIGFAAYNFVESIINLFQVVHNSY |
| 376 | NRPAYSPGHKTHAPTSSSTKKTQLQLEHLLLDLQMILNGINNYKNPKLTR |
| 426 | MLTFKFYMPKKATELKHLQCLEEELKPLEEVLNLAQSKNFHLRPRDLISN |
| 476 | INVIVLELKGSETTFMCEYADETATIVEFLNRWITFCQSIISTLT <520 |

Fig. 55 continued

SEQ ID NO: 93 (DNA sequence encoding secreted D7E/S8T Ontak®, or D7E/S8T s-Ontak. Sequence includes *toxP*, mutant *tox*O, signal sequence, and D7E/S8T Ontak®. Bold font and asterisks indicate the changes introduces to create the mutant *toxO*).

**** * *

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGATGATGTTGTTGAAACTTCTAAATCTTTTGTGATGGAAAACTTTT
201 CTTCGTACCACGGGACTAAACCTGGTTATGTAGATTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA< 1711

Fig. 55 continued

SEQ ID NO: 94 (D7E/S8T-His$_6$ s-Ontak or D7E/S8T-His$_6$ Ontak®)

1 GAEDVVETSKSFVMENFSSYHGTKP
26 GYVDSIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLTHHHHH
H <526

Fig. 55 continued

SEQ ID NO: 95 (DNA sequence encoding secreted D7E/S8T-$His_6$ Ontak®, or D7E/S8T-$His_6$ s-Ontak. Sequence includes *toxP*, mutant *tox*O, signal sequence, and D7E/S8T Ontak®. Bold font and asterisks indicate the changes introduces to create the mutant *toxO*).

```
                                          ****  *  *
1     TTGATTTCAGAGCACCCTTATAATTAGGATAGCTAAGTCCATTATTTTAT
51    GAGTCCTGGTAAGGGGATACGTTGTGAGCAGAAAACTGTTTGCGTCAATC
101   TTAATAGGGGCGCTACTGGGGATAGGGGCCCCACCTTCAGCCCATGCAGG
151   CGCTGATGATGTTGTTGAAACTTCTAAATCTTTTGTGATGGAAAACTTTT
201   CTTCGTACCACGGGACTAAACCTGGTTATGTAGATTCCATTCAAAAAGGT
251   ATACAAAAGCCAAAATCTGGTACACAAGGAAATTATGACGATGATTGGAA
301   AGGGTTTTATAGTACCGACAATAAATACGACGCTGCGGGATACTCTGTAG
351   ATAATGAAAACCCGCTCTCTGGAAAAGCTGGAGGCGTGGTCAAAGTGACG
401   TATCCAGGACTGACGAAGGTTCTCGCACTAAAAGTGGATAATGCCGAAAC
451   TATTAAGAAAGAGTTAGGTTTAAGTCTCACTGAACCGTTGATGGAGCAAG
501   TCGGAACGGAAGAGTTTATCAAAAGGTTCGGTGATGGTGCTTCGCGTGTA
551   GTGCTCAGCCTTCCCTTCGCTGAGGGGAGTTCTAGCGTTGAATATATTAA
601   TAACTGGGAACAGGCGAAAGCGTTAAGCGTAGAACTTGAGATTAATTTTG
651   AAACCCGTGGAAAACGTGGCCAAGATGCGATGTATGAGTATATGGCTCAA
701   GCCTGTGCAGGAAATCGTGTCAGGCGATCAGTAGGTAGCTCATTGTCATG
751   CATCAACCTGGATTGGGATGTTATCCGTGATAAAACTAAAACTAAGATCG
801   AATCTCTGAAAGAACACGGTCCGATCAAAAACAAAATGAGCGAAAGCCCG
851   AACAAAACTGTATCTGAAGAAAAAGCTAAACAGTACCTGGAAGAATTCCA
901   CCAGACTGCACTGGAACACCCGGAACTGTCTGAACTTAAGACCGTTACTG
951   GTACCAACCCGGTATTCGCTGGTGCTAACTACGCTGCTTGGGCAGTAAAC
1001  GTTGCTCAGGTTATCGATAGCGAAACTGCTGATAACCTGGAAAAAACTAC
1051  CGCGGCTCTGTCTATCCTGCCGGGTATCGGTAGCGTAATGGGCATCGCAG
1101  ACGGCGCCGTTCACCACAACACTGAAGAAATCGTTGCACAGTCTATCGCT
1151  CTGAGCTCTCTGATGGTTGCTCAGGCCATCCCGCTGGTAGGTGAACTGGT
1201  TGATATCGGTTTCGCTGCATACAACTTCGTTGAAAGCATCATCAACCTGT
1251  TCCAGGTTGTTCACAACTCTTACAACCGCCCGGCTTACTCTCCGGGTCAC
1301  AAGACGCATGCACCTACTTCTAGCTCTACCAAGAAAACCCAGCTGCAGCT
1351  CGAGCACCTGCTGCTGGATTTGCAGATGATCCTGAACGGTATCAACAATT
1401  ACAAGAACCCGAAACTGACGCGTATGCTGACCTTCAAGTTCTACATGCCG
1451  AAGAAGGCCACCGAACTGAAACACCTGCAGTGTCTAGAAGAAGAACTGAA
```

Fig. 55 continued

1501 ACCGCTGGAGGAAGTTCTGAACCTGGCTCAGTCTAAAAACTTCCACCTGC
1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCCACCATCACCATCATCACTGA< 1729

Fig. 55 continued

SEQ ID NO: 96 (DT$_{1-389}$-mIL4[mouse IL4]-V6A. Sequence corresponds to the mature protein devoid of signal sequence and with valine to alanine mutation. The mutated residue is highlighted in red)

```
  1 GADDVADSSKSFVMENFSSYHGTKPGYVDSIQKGIQKPKSGTQGNYDDDW
 51 KGFYSTDNKYDAAGYSVDNENPLSGKAGGVVKVTYPGLTKVLALKVDNAE
101 TIKKELGLSLTEPLMEQVGTEEFIKRFGDGASRVVLSLPFAEGSSSVEYI
151 NNWEQAKALSVELEINFETRGKRGQDAMYEYMAQACAGNRVRRSVGSSLS
201 CINLDWDVIRDKTKTKIESLKEHGPIKNKMSESPNKTVSEEKAKQYLEEF
251 HQTALEHPELSELKTVTGTNPVFAGANYAAWAVNVAQVIDSETADNLEKT
301 TAALSILPGIGSVMGIADGAVHHNTEEIVAQSIALSSLMVAQAIPLVGEL
351 VDIGFAAYNFVESIINLFQVVHNSYNRPAYSPGHKTHIHGCDKNHLREII
401 GILNEVTGEGTPCTEMDVPNVLTATKNTTESELVCRASKVLRIFYLKHGK
451 TPCLKKNSSVLMELQRLFRAFRCLDSSISCTMNESKSTSLKDFLESLKSI
501 MQMDYS        <506
```

SEQ ID NO: 97 (DNA sequence encoding secreted DT$_{1-389}$-mIL4-[mouse IL4]-V6A. The sequence starts with the first codon of the polypeptide's signal sequence. This DNA sequence encodes the signal sequence, DT$_{1-389}$ and its fusion to mouse IL-4. The mutated codon for the V6A mutation is boldfaced and the sequence change is highlighted in red)

```
  1 GTGAGCAGAAAACTGTTTGCGTCAATCTTAATAGGGGCGCTACTGGGGAT
 51 AGGGGCCCCACCTTCAGCCCATGCAGGCGCTGATGATGTTGCTGATTCTT
101 CTAAATCTTTTGTGATGGAAAACTTTTCTTCGTACCACGGGACTAAACCT
151 GGTTATGTAGATTCCATTCAAAAAGGTATACAAAAGCCAAAATCTGGTAC
201 ACAAGGAAATTATGACGATGATTGGAAAGGGTTTTATAGTACCGACAATA
251 AATACGACGCTGCGGGATACTCTGTAGATAATGAAAACCCGCTCTCTGGA
301 AAAGCTGGAGGCGTGGTCAAAGTGACGTATCCAGGACTGACGAAGGTTCT
351 CGCACTAAAAGTGGATAATGCCGAAACTATTAAGAAAGAGTTAGGTTTAA
401 GTCTCACTGAACCGTTGATGGAGCAAGTCGGAACGGAAGAGTTTATCAAA
451 AGGTTCGGTGATGGTGCTTCGCGTGTAGTGCTCAGCCTTCCCTTCGCTGA
501 GGGGAGTTCTAGCGTTGAATATATTAATAACTGGGAACAGGCGAAAGCGT
551 TAAGCGTAGAACTTGAGATTAATTTTGAAACCCGTGGAAAACGTGGCCAA
```

Fig. 55 continued

```
 601 GATGCGATGTATGAGTATATGGCTCAAGCCTGTGCAGGAAATCGTGTCAG
 651 GCGATCAGTAGGTAGCTCATTGTCATGCATCAACCTGGATTGGGATGTTA
 701 TCCGTGATAAAACTAAAACTAAGATCGAATCTCTGAAAGAACACGGTCCG
 751 ATCAAAAACAAAATGAGCGAAAGCCCGAACAAAACTGTATCTGAAGAAAA
 801 AGCTAAACAGTACCTGGAAGAATTCCACCAGACTGCACTGGAACACCCGG
 851 AACTGTCTGAACTTAAGACCGTTACTGGTACCAACCCGGTATTCGCTGGT
 901 GCTAACTACGCTGCTTGGGCAGTAAACGTTGCTCAGGTTATCGATAGCGA
 951 AACTGCTGATAACCTGGAAAAAACTACCGCGGCTCTGTCTATCCTGCCGG
1001 GTATCGGTAGCGTAATGGGCATCGCAGACGGCGCCGTTCACCACAACACT
1051 GAAGAAATCGTTGCACAGTCTATCGCTCTGAGCTCTCTGATGGTTGCTCA
1101 GGCCATCCCGCTGGTAGGTGAACTGGTTGATATCGGTTTCGCTGCATACA
1151 ACTTCGTTGAAAGCATCATCAACCTGTTCCAGGTTGTTCACAACTCTTAC
1201 AACCGCCCGGCTTACTCTCCGGGTCACAAGACGCATATTCATGGCTGCGA
1251 TAAAAACCATCTGCGCGAAATTATTGGCATTCTGAACGAAGTGACCGGCG
1301 AAGGCACCCCGTGCACCGAAATGGATGTGCCGAACGTGCTGACCGCGACC
1351 AAAAACACCACCGAAAGCGAACTGGTGTGCCGCGCGAGCAAAGTGCTGCG
1401 CATTTTTTATCTGAAACATGGCAAAACCCCGTGCCTGAAAAAAAACAGCA
1451 GCGTGCTGATGGAACTGCAGCGCCTGTTTCGCGCGTTTCGCTGCCTGGAT
1501 AGCAGCATTAGCTGCACCATGAACGAAAGCAAAAGCACCAGCCTGAAAGA
1551 TTTTCTGGAAAGCCTGAAAAGCATTATGCAGATGGATTATAGCTAG <1596
```

SEQ ID NO: 98 (Protein sequence for $DT_{1-389}$-mIL4-V6A-$His_6$). The sequence corresponds to the mature protein devoid of signal sequence and with valine to alanine mutation at position 6. The mutated residue is highlighted in red)

```
  1 GADDVADSSKSFVMENFSSYHGTKPGYVDSIQKGIQKPKSGTQGNYDDDW
 51 KGFYSTDNKYDAAGYSVDNENPLSGKAGGVVKVTYPGLTKVLALKVDNAE
101 TIKKELGLSLTEPLMEQVGTEEFIKRFGDGASRVVLSLPFAEGSSSVEYI
151 NNWEQAKALSVELEINFETRGKRGQDAMYEYMAQACAGNRVRRSVGSSLS
201 CINLDWDVIRDKTKTKIESLKEHGPIKNKMSESPNKTVSEEKAKQYLEEF
251 HQTALEHPELSELKTVTGTNPVFAGANYAAWAVNVAQVIDSETADNLEKT
301 TAALSILPGIGSVMGIADGAVHHNTEEIVAQSIALSSLMVAQAIPLVGEL
351 VDIGFAAYNFVESIINLFQVVHNSYNRPAYSPGHKTHIHGCDKNHLREII
401 GILNEVTGEGTPCTEMDVPNVLTATKNTTESELVCRASKVLRIFYLKHGK
451 TPCLKKNSSVLMELQRLFRAFRCLDSSISCTMNESKSTSLKDFLESLKSI
501 MQMDYSENLYFQGHHHHHH        <519
```

Fig. 55 continued

SEQ ID NO: 99 (DNA sequence encoding secreted $DT_{1-389}$-mIL4-V6A-$His_6$. The sequence starts with the first codon of the polypeptide's signal sequence. This DNA sequences encodes the signal sequence, $DT_{1-389}$ and its fusion to mouse IL-4 followed by the TEV protease site and His-6 sequence (underlined). The mutated codon for the V6A mutation is boldfaced and the sequence change is highlighted in red. Boldfaced nucleotides at the 3' end of the sequence indicate the coding sequences for the TEV protease site.

1 GTGAGCAGAAAACTGTTTGCGTCAATCTTAATAGGGGCGCTACTGGGGAT
51 AGGGGCCCCACCTTCAGCCCATGCAGGCGCTGATGATGTTGCTGATTCTT
101 CTAAATCTTTTGTGATGGAAAACTTTTCTTCGTACCACGGGACTAAACCT
151 GGTTATGTAGATTCCATTCAAAAAGGTATACAAAAGCCAAAATCTGGTAC
201 ACAAGGAAATTATGACGATGATTGGAAAGGGTTTTATAGTACCGACAATA
251 AATACGACGCTGCGGGATACTCTGTAGATAATGAAAACCCGCTCTCTGGA
301 AAAGCTGGAGGCGTGGTCAAAGTGACGTATCCAGGACTGACGAAGGTTCT
351 CGCACTAAAAGTGGATAATGCCGAAACTATTAAGAAAGAGTTAGGTTTAA
401 GTCTCACTGAACCGTTGATGGAGCAAGTCGGAACGGAAGAGTTTATCAAA
451 AGGTTCGGTGATGGTGCTTCGCGTGTAGTGCTCAGCCTTCCCTTCGCTGA
501 GGGGAGTTCTAGCGTTGAATATATTAATAACTGGGAACAGGCGAAAGCGT
551 TAAGCGTAGAACTTGAGATTAATTTTGAAACCCGTGGAAAACGTGGCCAA
601 GATGCGATGTATGAGTATATGGCTCAAGCCTGTGCAGGAAATCGTGTCAG
651 GCGATCAGTAGGTAGCTCATTGTCATGCATCAACCTGGATTGGGATGTTA
701 TCCGTGATAAAACTAAAACTAAGATCGAATCTCTGAAAGAACACGGTCCG
751 ATCAAAAACAAAATGAGCGAAAGCCCGAACAAAACTGTATCTGAAGAAAA
801 AGCTAAACAGTACCTGGAAGAATTCCACCAGACTGCACTGGAACACCCGG
851 AACTGTCTGAACTTAAGACCGTTACTGGTACCAACCCGGTATTCGCTGGT
901 GCTAACTACGCTGCTTGGGCAGTAAACGTTGCTCAGGTTATCGATAGCGA
951 AACTGCTGATAACCTGGAAAAAACTACCGCGGCTCTGTCTATCCTGCCGG
1001 GTATCGGTAGCGTAATGGGCATCGCAGACGGCGCCGTTCACCACAACACT
1051 GAAGAAATCGTTGCACAGTCTATCGCTCTGAGCTCTCTGATGGTTGCTCA
1101 GGCCATCCCGCTGGTAGGTGAACTGGTTGATATCGGTTTCGCTGCATACA
1151 ACTTCGTTGAAAGCATCATCAACCTGTTCCAGGTTGTTCACAACTCTTAC
1201 AACCGCCCGGCTTACTCTCCGGGTCACAAGACGCATATTCATGGCTGCGA
1251 TAAAAACCATCTGCGCGAAATTATTGGCATTCTGAACGAAGTGACCGGCG
1301 AAGGCACCCCGTGCACCGAAATGGATGTGCCGAACGTGCTGACCGCGACC
1351 AAAAACACCACCGAAAGCGAACTGGTGTGCCGCGCGAGCAAAGTGCTGCG

Fig. 55 continued

1401 CATTTTTTATCTGAAACATGGCAAAACCCCGTGCCTGAAAAAAAACAGCA
1451 GCGTGCTGATGGAACTGCAGCGCCTGTTTCGCGCGTTTCGCTGCCTGGAT
1501 AGCAGCATTAGCTGCACCATGAACGAAAGCAAAAGCACCAGCCTGAAAGA
1551 TTTTCTGGAAAGCCTGAAAAGCATTATGCAGATGGATTATAGCGAGAACC
1601 TGTACTTCCAGGGCCATCACCACCACCACCACTAG <1635

SEQ ID NO: 100 (DT1-389-hIL4-[human IL4]-V6A. The sequence corresponds to the mature protein devoid of its signal sequence with a valine to alanine mutation at position 6. The mutated residue is highlighted in red)

1 GADDVADSSKSFVMENFSSYHGTKPGYVDSIQKGIQKPKSGTQGNYDDDW
51 KGFYSTDNKYDAAGYSVDNENPLSGKAGGVVKVTYPGLTKVLALKVDNAE
101 TIKKELGLSLTEPLMEQVGTEEFIKRFGDGASRVVLSLPFAEGSSSVEYI
151 NNWEQAKALSVELEINFETRGKRGQDAMYEYMAQACAGNRVRRSVGSSLS
201 CINLDWDVIRDKTKTKIESLKEHGPIKNKMSESPNKTVSEEKAKQYLEEF
251 HQTALEHPELSELKTVTGTNPVFAGANYAAWAVNVAQVIDSETADNLEKT
301 TAALSILPGIGSVMGIADGAVHHNTEEIVAQSIALSSLMVAQAIPLVGEL
351 VDIGFAAYNFVESIINLFQVVHNSYNRPAYSPGHKTHHKCDITLQEIIKT
401 LNSLTEQKTLCTELTVTDIFAASKNTTEKETFCRAATVLRQFYSHHEKDT
451 RCLGATAQQFHRHKQLIRFLKRLDRNLWGLAGLNSCPVKEANQSTLENFL
501 ERLKTIMREKYSKCSS <516

SEQ ID NO: 101 (DNA sequence encoding secreted DT1-389-hIL4-[human IL4]-V6A. The sequence starts with the first codon of the polypeptide's signal sequence. The sequence encodes the signal sequence, DT1-389 and human IL-4. The mutated codon for the V6A mutation is boldfaced and the sequence change is highlighted in red)

1 GTGAGCAGAAAACTGTTTGCGTCAATCTTAATAGGGGCGCTACTGGGGAT
51 AGGGGCCCCACCTTCAGCCCATGCAGGCGCTGATGATGTTGCTGATTCTT
101 CTAAATCTTTTGTGATGGAAAACTTTTCTTCGTACCACGGGACTAAACCT
151 GGTTATGTAGATTCCATTCAAAAAGGTATACAAAAGCCAAAATCTGGTAC
201 ACAAGGAAATTATGACGATGATTGGAAAGGGTTTTATAGTACCGACAATA
251 AATACGACGCTGCGGGATACTCTGTAGATAATGAAAACCCGCTCTCTGGA

Fig. 55 continued

```
 301 AAAGCTGGAGGCGTGGTCAAAGTGACGTATCCAGGACTGACGAAGGTTCT
 351 CGCACTAAAAGTGGATAATGCCGAAACTATTAAGAAAGAGTTAGGTTTAA
 401 GTCTCACTGAACCGTTGATGGAGCAAGTCGGAACGGAAGAGTTTATCAAA
 451 AGGTTCGGTGATGGTGCTTCGCGTGTAGTGCTCAGCCTTCCCTTCGCTGA
 501 GGGGAGTTCTAGCGTTGAATATATTAATAACTGGGAACAGGCGAAAGCGT
 551 TAAGCGTAGAACTTGAGATTAATTTTGAAACCCGTGGAAAACGTGGCCAA
 601 GATGCGATGTATGAGTATATGGCTCAAGCCTGTGCAGGAAATCGTGTCAG
 651 GCGATCAGTAGGTAGCTCATTGTCATGCATCAACCTGGATTGGGATGTTA
 701 TCCGTGATAAAACTAAAACTAAGATCGAATCTCTGAAAGAACACGGTCCG
 751 ATCAAAAACAAAATGAGCGAAAGCCCGAACAAAACTGTATCTGAAGAAAA
 801 AGCTAAACAGTACCTGGAAGAATTCCACCAGACTGCACTGGAACACCCGG
 851 AACTGTCTGAACTTAAGACCGTTACTGGTACCAACCCGGTATTCGCTGGT
 901 GCTAACTACGCTGCTTGGGCAGTAAACGTTGCTCAGGTTATCGATAGCGA
 951 AACTGCTGATAACCTGGAAAAAACTACCGCGGCTCTGTCTATCCTGCCGG
1001 GTATCGGTAGCGTAATGGGCATCGCAGACGGCGCCGTTCACCACAACACT
1051 GAAGAAATCGTTGCACAGTCTATCGCTCTGAGCTCTCTGATGGTTGCTCA
1101 GGCCATCCCGCTGGTAGGTGAACTGGTTGATATCGGTTTCGCTGCATACA
1151 ACTTCGTTGAAAGCATCATCAACCTGTTCCAGGTTGTTCACAACTCTTAC
1201 AACCGCCCGGCTTACTCTCCGGGTCACAAGACGCATCACAAGTGCGATAT
1251 CACCTTGCAGGAAATCATCAAGACCCTCAACTCGTTGACCGAACAAAAAA
1301 CCTTGTGCACCGAGCTGACCGTGACCGACATCTTCGCAGCCTCTAAGAAC
1351 ACCACCGAAAAAGAGACCTTCTGCCGCGCTGCGACCGTTCTGCGTCAGTT
1401 TTACTCCCACCACGAGAAAGATACCCGCTGCCTTGGCGCAACCGCCCAGC
1451 AATTCCACCGCCACAAGCAACTCATCCGTTTTCTGAAACGCCTTGACCGT
1501 AACCTCTGGGGCTTGGCTGGTCTGAACTCTTGCCCAGTGAAGGAAGCGAA
1551 CCAGTCCACCCTCGAAAACTTTCTTGAGCGCCTCAAAACCATCATGCGTG
1601 AGAAGTACTCGAAATGCTCCTCGTAA         <1626
```

SEQ ID NO: 102 ($DT_{1-389}$-hIL4-V6A-$His_6$. This sequence corresponds to the mature protein devoid of its signal sequence and carrying a valine to alanine substitution at position 6 highlighted in red)

```
  1 GADDVADSSKSFVMENFSSYHGTKPGYVDSIQKGIQKPKSGTQGNYDDDW
 51 KGFYSTDNKYDAAGYSVDNENPLSGKAGGVVKVTYPGLTKVLALKVDNAE
101 TIKKELGLSLTEPLMEQVGTEEFIKRFGDGASRVVLSLPFAEGSSSVEYI
```

Fig. 55 continued

```
151 NNWEQAKALSVELEINFETRGKRGQDAMYEYMAQACAGNRVRRSVGSSLS
201 CINLDWDVIRDKTKTKIESLKEHGPIKNKMSESPNKTVSEEKAKQYLEEF
251 HQTALEHPELSELKTVTGTNPVFAGANYAAWAVNVAQVIDSETADNLEKT
301 TAALSILPGIGSVMGIADGAVHHNTEEIVAQSIALSSLMVAQAIPLVGEL
351 VDIGFAAYNFVESIINLFQVVHNSYNRPAYSPGHKTHHKCDITLQEIIKT
401 LNSLTEQKTLCTELTVTDIFAASKNTTEKETFCRAATVLRQFYSHHEKDT
451 RCLGATAQQFHRHKQLIRFLKRLDRNLWGLAGLNSCPVKEANQSTLENFL
501 ERLKTIMREKYSKCSSENLYFQGHHHHHH           <529
```

SEQ ID NO: 103 (DNA sequence encoding secreted $DT_{1\text{-}389}$-hIL4-V6A-$His_6$ V6A. The sequence starts with the first codon of the polypeptide's signal sequence. The sequence encodes the signal sequence, $DT_{1\text{-}389}$ and its fusion to human IL-4 followed by the TEV protease site and $His_6$ sequences (underlined). The mutated codon for the V6A mutation is boldfaced and the sequence change is highlighted in red. Boldfaced nucleotides at the 3' end of the sequence indicate the coding sequences for the TEV protease site.

1 GTGAGCAGAAAACTGTTTGCGTCAATCTTAATAGGGGCGCTACTGGGGAT
51 AGGGGCCCCACCTTCAGCCCATGCAGGCGCTGATGATGTTGCTGATTCTT
101 CTAAATCTTTTGTGATGGAAAACTTTTCTTCGTACCACGGGACTAAACCT
151 GGTTATGTAGATTCCATTCAAAAAGGTATACAAAAGCCAAAATCTGGTAC
201 ACAAGGAAATTATGACGATGATTGGAAAGGGTTTTATAGTACCGACAATA
251 AATACGACGCTGCGGGATACTCTGTAGATAATGAAAACCCGCTCTCTGGA
301 AAAGCTGGAGGCGTGGTCAAAGTGACGTATCCAGGACTGACGAAGGTTCT
351 CGCACTAAAAGTGGATAATGCCGAAACTATTAAGAAAGAGTTAGGTTTAA
401 GTCTCACTGAACCGTTGATGGAGCAAGTCGGAACGGAAGAGTTTATCAAA
451 AGGTTCGGTGATGGTGCTTCGCGTGTAGTGCTCAGCCTTCCCTTCGCTGA
501 GGGGAGTTCTAGCGTTGAATATATTAATAACTGGGAACAGGCGAAAGCGT
551 TAAGCGTAGAACTTGAGATTAATTTTGAAACCCGTGGAAAACGTGGCCAA
601 GATGCGATGTATGAGTATATGGCTCAAGCCTGTGCAGGAAATCGTGTCAG
651 GCGATCAGTAGGTAGCTCATTGTCATGCATCAACCTGGATTGGGATGTTA
701 TCCGTGATAAAACTAAAACTAAGATCGAATCTCTGAAAGAACACGGTCCG
751 ATCAAAAACAAAATGAGCGAAAGCCCGAACAAAACTGTATCTGAAGAAAA
801 AGCTAAACAGTACCTGGAAGAATTCCACCAGACTGCACTGGAACACCCGG
851 AACTGTCTGAACTTAAGACCGTTACTGGTACCAACCCGGTATTCGCTGGT
901 GCTAACTACGCTGCTTGGGCAGTAAACGTTGCTCAGGTTATCGATAGCGA

Fig. 55 continued

```
 951 AACTGCTGATAACCTGGAAAAAACTACCGCGGCTCTGTCTATCCTGCCGG
1001 GTATCGGTAGCGTAATGGGCATCGCAGACGGCGCCGTTCACCACAACACT
1051 GAAGAAATCGTTGCACAGTCTATCGCTCTGAGCTCTCTGATGGTTGCTCA
1101 GGCCATCCCGCTGGTAGGTGAACTGGTTGATATCGGTTTCGCTGCATACA
1151 ACTTCGTTGAAAGCATCATCAACCTGTTCCAGGTTGTTCACAACTCTTAC
1201 AACCGCCCGGCTTACTCTCCGGGTCACAAGACGCATCACAAGTGCGATAT
1251 CACCTTGCAGGAAATCATCAAGACCCTCAACTCGTTGACCGAACAAAAAA
1301 CCTTGTGCACCGAGCTGACCGTGACCGACATCTTCGCAGCCTCTAAGAAC
1351 ACCACCGAAAAAGAGACCTTCTGCCGCGCTGCGACCGTTCTGCGTCAGTT
1401 TTACTCCCACCACGAGAAAGATACCCGCTGCCTTGGCGCAACCGCCCAGC
1451 AATTCCACCGCCACAAGCAACTCATCCGTTTTCTGAAACGCCTTGACCGT
1501 AACCTCTGGGGCTTGGCTGGTCTGAACTCTTGCCCAGTGAAGGAAGCGAA
1551 CCAGTCCACCCTCGAAAACTTTCTTGAGCGCCTCAAAACCATCATGCGTG
1601 AGAAGTACTCGAAATGCTCCTCGGAAAACCTCTACTTCCAGGGCCACCAC
1651 CACCACCACCACTAA      <1665
```

Fig. 55 continued

SEQ ID NO: 104. $DT_{1-389}$-EGF-V6A (Protein sequence)

```
  1 GADDVADSSKSFVMENFSSYHGTKPGYVDSIQKGIQKPKSGTQGNYDDDW
 51 KGFYSTDNKYDAAGYSVDNENPLSGKAGGVVKVTYPGLTKVLALKVDNAE
101 TIKKELGLSLTEPLMEQVGTEEFIKRFGDGASRVVLSLPFAEGSSSVEYI
151 NNWEQAKALSVELEINFETRGKRGQDAMYEYMAQACAGNRVRRSVGSSLS
201 CINLDWDVIRDKTKTKIESLKEHGPIKNKMSESPNKTVSEEKAKQYLEEF
251 HQTALEHPELSELKTVTGTNPVFAGANYAAWAVNVAQVIDSETADNLEKT
301 TAALSILPGIGSVMGIADGAVHHNTEEIVAQSIALSSLMVAQAIPLVGEL
351 VDIGFAAYNFVESIINLFQVVHNSYNRPAYSPGHKTHAMNSDSECPLSHD
401 GYCLHDGVCMYIEALDKYACNCVVGYIGERCQYRDLKWWELR <442
```

SEQ ID NO: 105. $DT_{1-389}$-EGF-V6A (This DNA sequence encodes the mature polypeptide beginning with first codon of the mature protein. The signal sequence-encoding DNA is not shown. The boldfaced codon encodes the 6th residue of the mature polypeptide. The red base indicates the change from a Val-encoding GTT to an Ala-encoding GCT)

1 GGCGCTGATGATGTTGCTGATTCTTCTAAATCTTTTGTGATGGAAAACTT

```
  51 TTCTTCGTACCACGGGACTAAACCTGGTTATGTAGATTCCATTCAAAAAG
 101 GTATACAAAAGCCAAAATCTGGTACACAAGGAAATTATGACGATGATTGG
 151 AAAGGGTTTTATAGTACCGACAATAAATACGACGCTGCGGGATACTCTGT
 201 AGATAATGAAAACCCGCTCTCTGGAAAAGCTGGAGGCGTGGTCAAAGTGA
 251 CGTATCCAGGACTGACGAAGGTTCTCGCACTAAAAGTGGATAATGCCGAA
 301 ACTATTAAGAAAGAGTTAGGTTTAAGTCTCACTGAACCGTTGATGGAGCA
 351 AGTCGGAACGGAAGAGTTTATCAAAAGGTTCGGTGATGGTGCTTCGCGTG
 401 TAGTGCTCAGCCTTCCCTTCGCTGAGGGGAGTTCTAGCGTTGAATATATT
 451 AATAACTGGGAACAGGCGAAAGCGTTAAGCGTAGAACTTGAGATTAATTT
 501 TGAAACCCGTGGAAAACGTGGCCAAGATGCGATGTATGAGTATATGGCTC
 551 AAGCCTGTGCAGGAAATCGTGTCAGGCGATCAGTAGGTAGCTCATTGTCA
 601 TGCATCAACCTGGATTGGGATGTTATCCGTGATAAAACTAAAACTAAGAT
 651 CGAATCTCTGAAAGAACACGGTCCGATCAAAAACAAAATGAGCGAAAGCC
 701 CGAACAAAACTGTATCTGAAGAAAAAGCTAAACAGTACCTGGAAGAATTC
 751 CACCAGACTGCACTGGAACACCCGGAACTGTCTGAACTTAAGACCGTTAC
 801 TGGTACCAACCCGGTATTCGCTGGTGCTAACTACGCTGCTTGGGCAGTAA
 851 ACGTTGCTCAGGTTATCGATAGCGAAACTGCTGATAACCTGGAAAAAACT
 901 ACCGCGGCTCTGTCTATCCTGCCGGGTATCGGTAGCGTAATGGGCATCGC
 951 AGACGGCGCCGTTCACCACAACACTGAAGAAATCGTTGCACAGTCTATCG
1001 CTCTGAGCTCTCTGATGGTTGCTCAGGCCATCCCGCTGGTAGGTGAACTG
1051 GTTGATATCGGTTTCGCTGCATACAACTTCGTTGAAAGCATCATCAACCT
1101 GTTCCAGGTTGTTCACAACTCTTACAACCGCCCGGCTTACTCTCCGGGTC
1151 ACAAGACGCATGCAATGAACTCCGACTCCGAGTGCCCGCTCTCCCACGAC
1201 GGTTACTGCCTCCACGACGGTGTCTGCATGTACATCGAGGCCCTCGACAA
1251 GTACGCCTGCAACTGCGTCGTCGGTTACATCGGTGAGCGCTGCCAGTACC
1301 GCGACCTGAAGTGGTGGGAGCTCCGCTGATGA <1332
```

Fig. 55 continued

SEQ ID NO: 106. DT$_{1-389}$-EGF-V6A-His$_6$ (Protein sequence)

```
  1 GADDVADSSKSFVMENFSSYHGTKPGYVDSIQKGIQKPKSGTQGNYDDDW
 51 KGFYSTDNKYDAAGYSVDNENPLSGKAGGVVKVTYPGLTKVLALKVDNAE
101 TIKKELGLSLTEPLMEQVGTEEFIKRFGDGASRVVLSLPFAEGSSSVEYI
151 NNWEQAKALSVELEINFETRGKRGQDAMYEYMAQACAGNRVRRSVGSSLS
201 CINLDWDVIRDKTKTKIESLKEHGPIKNKMSESPNKTVSEEKAKQYLEEF
251 HQTALEHPELSELKTVTGTNPVFAGANYAAWAVNVAQVIDSETADNLEKT
301 TAALSILPGIGSVMGIADGAVHHNTEEIVAQSIALSSLMVAQAIPLVGEL
351 VDIGFAAYNFVESIINLFQVVHNSYNRPAYSPGHKTHAMNSDSECPLSHD
401 GYCLHDGVCMYIEALDKYACNCVVGYIGERCQYRDLKWWELRHHHHHH
     <448
```

SEQ ID NO: 107. DT$_{1-389}$-EGF-V6A-His$_6$ (This DNA sequence encodes the mature polypeptide beginning with first codon of the mature protein. The signal sequence-encoding DNA is not shown. The boldfaced codon encodes the 6$^{th}$ residue of the mature polypeptide. The red base indicates the change from a Val-encoding GTT to an Ala-encoding GCT)

```
   1 GGCGCTGATGATGTTGCTGATTCTTCTAAATCTTTTGTGATGGAAAACTT
  51 TTCTTCGTACCACGGGACTAAACCTGGTTATGTAGATTCCATTCAAAAAG
 101 GTATACAAAAGCCAAAATCTGGTACACAAGGAAATTATGACGATGATTGG
 151 AAAGGGTTTTATAGTACCGACAATAAATACGACGCTGCGGGATACTCTGT
 201 AGATAATGAAAACCCGCTCTCTGGAAAAGCTGGAGGCGTGGTCAAAGTGA
 251 CGTATCCAGGACTGACGAAGGTTCTCGCACTAAAAGTGGATAATGCCGAA
 301 ACTATTAAGAAAGAGTTAGGTTTAAGTCTCACTGAACCGTTGATGGAGCA
 351 AGTCGGAACGGAAGAGTTTATCAAAAGGTTCGGTGATGGTGCTTCGCGTG
 401 TAGTGCTCAGCCTTCCCTTCGCTGAGGGGAGTTCTAGCGTTGAATATATT
 451 AATAACTGGGAACAGGCGAAAGCGTTAAGCGTAGAACTTGAGATTAATTT
 501 TGAAACCCGTGGAAAACGTGGCCAAGATGCGATGTATGAGTATATGGCTC
 551 AAGCCTGTGCAGGAAATCGTGTCAGGCGATCAGTAGGTAGCTCATTGTCA
 601 TGCATCAACCTGGATTGGGATGTTATCCGTGATAAAACTAAAACTAAGAT
 651 CGAATCTCTGAAAGAACACGGTCCGATCAAAAACAAAATGAGCGAAAGCC
 701 CGAACAAAACTGTATCTGAAGAAAAAGCTAAACAGTACCTGGAAGAATTC
 751 CACCAGACTGCACTGGAACACCCGGAACTGTCTGAACTTAAGACCGTTAC
 801 TGGTACCAACCCGGTATTCGCTGGTGCTAACTACGCTGCTTGGGCAGTAA
 851 ACGTTGCTCAGGTTATCGATAGCGAAACTGCTGATAACCTGGAAAAAACT
 901 ACCGCGGCTCTGTCTATCCTGCCGGGTATCGGTAGCGTAATGGGCATCGC
 951 AGACGGCGCCGTTCACCACAACACTGAAGAAATCGTTGCACAGTCTATCG
1001 CTCTGAGCTCTCTGATGGTTGCTCAGGCCATCCCGCTGGTAGGTGAACTG
1051 GTTGATATCGGTTTCGCTGCATACAACTTCGTTGAAAGCATCATCAACCT
1101 GTTCCAGGTTGTTCACAACTCTTACAACCGCCCGGCTTACTCTCCGGGTC
1151 ACAAGACGCATGCAATGAACTCCGACTCCGAGTGCCCGCTCTCCCACGAC
1201 GGTTACTGCCTCCACGACGGTGTCTGCATGTACATCGAGGCCCTCGACAA
1251 GTACGCCTGCAACTGCGTCGTCGGTTACATCGGTGAGCGCTGCCAGTACC
1301 GCGACCTGAAGTGGTGGGAGCTCCGCCACCATCACCATCATCACTGATGA
  <1350
```

Fig. 55 continued

SEQ ID NO. 108 $P_{tox}$ (WT)-*tox* operator (WT). The sequence includes *tox* promoter, *tox* operator and 5'UTR nucleotides up to the first codon of the diphtheria fragment. The operator sequence is underlined. The GTG at the 3' end corresponds to the start site of translation. This sequence when used as the 5'UTR for sequences encoding diphtheria toxin fusion proteins gives high levels of expression from the Δ*dtxR* mutant of *Corynebacterium diphtheriae* C7(-).

```
 1 GGATCCAGGGCATTGATTTCAGAGCACCCTTATAATTAGGATAGCTTTAC
51 CTAATTATTTTATGAGTCCTGGTAAGGGGATACGTTGTG   <89
```

SEQ ID NO: 109 (5' untranslated sequences corresponding to $P_{hsp65}$ from *Mycobacterium leprae* to be fused to DNA sequences encoding various diphtheria toxin fusion proteins. This 5'UTR sequence is known to serve as a strong promoter for expressing polypeptides in members of the Actinomycetales order of bacteria which includes all species of the Corynebacterium genus). The promoter-containing sequences are underlined. The ATG at the 3' end corresponds to the start site of translation. Convenient restriction sites (BamHI, GGATCC and NdeI, CATATG) are shown in boldface.

1 GGATCCTTCTAGAATTCCGGAATTGCACTCGCCTTAGGGGAGTGCTAAAA
51 ATGATCCTGGCACTCGCGATCAGCGAGTGCCAGGTCGGGACGGTGAGACC
101 CAGCCAGCAAGCTGTGGTCGTCCGTCGCGGGCACTGCACCCGGCCAGCGT
151 AAGTAATGGGGGTTGTCGGCACCCGGTGACCTAGACACATGCATGCATGC
201 TTAATTAATTAAGCGATATCCGGAGGAATCACTTCCATATGATG

Fig. 55 continued

SEQ ID NO. 110 $P_{tac}$ promoter and 5'UTR. The sequence includes *tac* promoter, *lac* operator and nucleotides encoding the first codon of the diphtheria fragment. The promoter sequence is underlined, and the *lac* operator is boldfaced. This 5'UTR sequence is known to serve as a strong promoter in many bacterial species and to allow inducible expression in Lac-repressor containing bacteria by addition of lactose or lactose-mimetics such as IPTG 1 TTGACAATTAATCATCGGCTCGTATAATGTGTGGAATTGTGAGCGGATAA
51 CAATTTCACACAGGAAACAGCCAGTCCGTTTAGGTGTTTTCACGAGCACT
101 TCACCAACAAGGACCATAGATTGTG <125

SEQ ID NO: 111 (D29E s-Ontak or D29E Ontak®)

1 GADDVVDSSKSFVMENFSSYHGTKP
26 GYVESIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLT <520

Fig. 55 continued

SEQ ID NO: 112 (DNA sequence encoding secreted D29E Ontak®, or D29E s-Ontak. Sequence includes *toxP*, mutant *tox*O, signal sequence, and D3E Ontak®. Bold font and asterisks indicate the changes introduces to create the mutant *toxO*.

**** * *

1 TTGATTTCAGAGCACCCTTATAATTAGGATAGCTAAGTCCATTATTTTAT

51 GAGTCCTGGTAAGGGGATACGTTGTGAGCAGAAAACTGTTTGCGTCAATC

101 TTAATAGGGGCGCTACTGGGGATAGGGGCCCCACCTTCAGCCCATGCAGG

151 CGCTGATGATGTTGTTGATTCTTCTAAATCTTTTGTGATGGAAAACTTTT

201 CTTCGTACCACGGACTAAACCTGGTTATGTAGAGTCCATTCAAAAAGGT

251 ATACAAAAGCCAAAATCTGGTACACAAGGAAATTATGACGATGATTGGAA

301 AGGGTTTTATAGTACCGACAATAAATACGACGCTGCGGGATACTCTGTAG

351 ATAATGAAAACCCGCTCTCTGGAAAAGCTGGAGGCGTGGTCAAAGTGACG

401 TATCCAGGACTGACGAAGGTTCTCGCACTAAAAGTGGATAATGCCGAAAC

451 TATTAAGAAAGAGTTAGGTTTAAGTCTCACTGAACCGTTGATGGAGCAAG

501 TCGGAACGGAAGAGTTTATCAAAAGGTTCGGTGATGGTGCTTCGCGTGTA

551 GTGCTCAGCCTTCCCTTCGCTGAGGGGAGTTCTAGCGTTGAATATATTAA

601 TAACTGGGAACAGGCGAAAGCGTTAAGCGTAGAACTTGAGATTAATTTTG

651 AAACCCGTGGAAAACGTGGCCAAGATGCGATGTATGAGTATATGGCTCAA

701 GCCTGTGCAGGAAATCGTGTCAGGCGATCAGTAGGTAGCTCATTGTCATG

751 CATCAACCTGGATTGGGATGTTATCCGTGATAAAACTAAAACTAAGATCG

801 AATCTCTGAAAGAACACGGTCCGATCAAAAACAAAATGAGCGAAAGCCCG

851 AACAAAACTGTATCTGAAGAAAAAGCTAAACAGTACCTGGAAGAATTCCA

901 CCAGACTGCACTGGAACACCCGGAACTGTCTGAACTTAAGACCGTTACTG

951 GTACCAACCCGGTATTCGCTGGTGCTAACTACGCTGCTTGGGCAGTAAAC

1001 GTTGCTCAGGTTATCGATAGCGAAACTGCTGATAACCTGGAAAAAACTAC

Fig. 55 continued

1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC
1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA< 1711

Fig. 55 continued

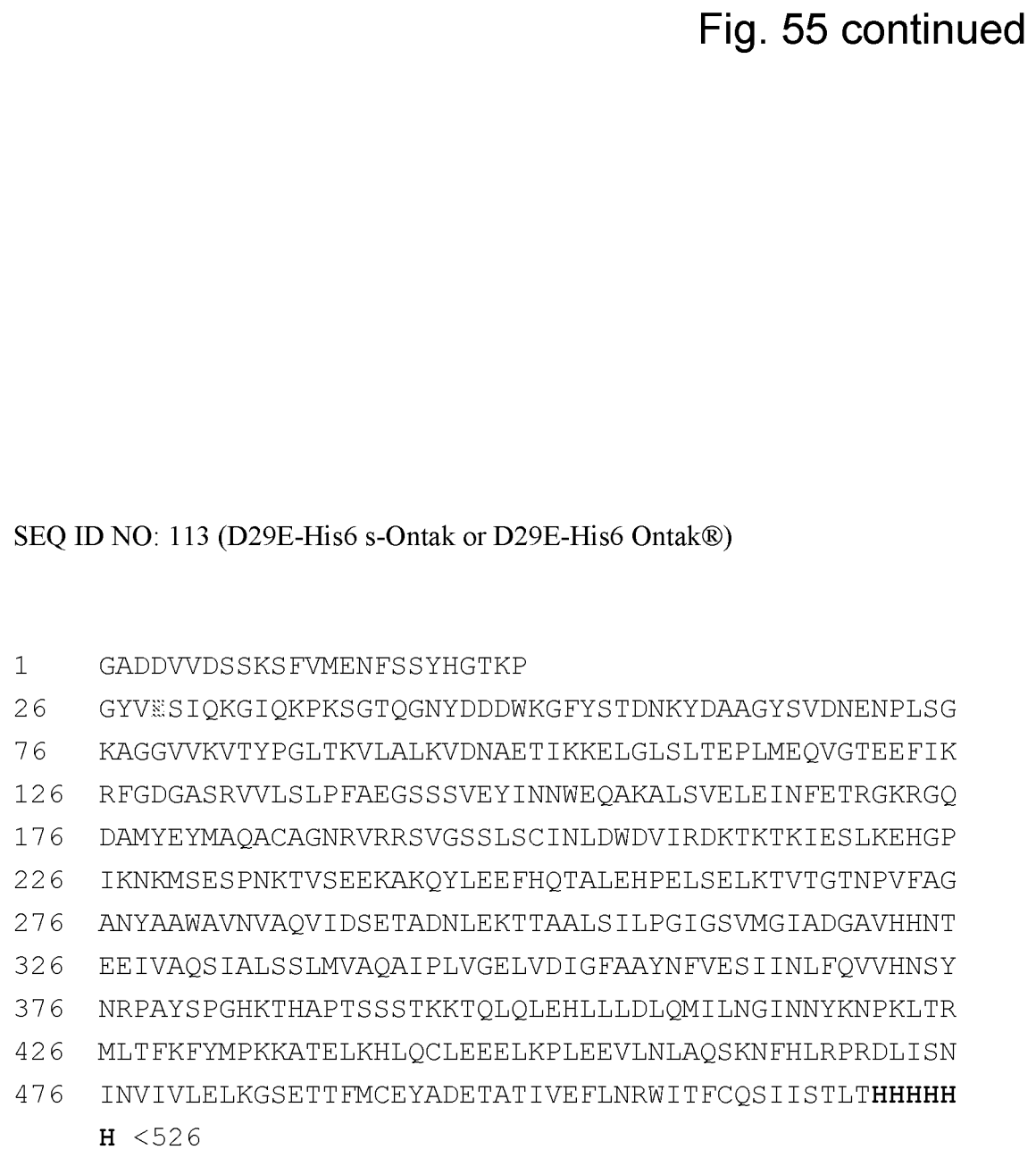

SEQ ID NO: 113 (D29E-His6 s-Ontak or D29E-His6 Ontak®)

```
1    GADDVVDSSKSFVMENFSSYHGTKP
26   GYVESIQKGIQKPKSGTQGNYDDDWKGFYSTDNKYDAAGYSVDNENPLSG
76   KAGGVVKVTYPGLTKVLALKVDNAETIKKELGLSLTEPLMEQVGTEEFIK
126  RFGDGASRVVLSLPFAEGSSSVEYINNWEQAKALSVELEINFETRGKRGQ
176  DAMYEYMAQACAGNRVRRSVGSSLSCINLDWDVIRDKTKTKIESLKEHGP
226  IKNKMSESPNKTVSEEKAKQYLEEFHQTALEHPELSELKTVTGTNPVFAG
276  ANYAAWAVNVAQVIDSETADNLEKTTAALSILPGIGSVMGIADGAVHHNT
326  EEIVAQSIALSSLMVAQAIPLVGELVDIGFAAYNFVESIINLFQVVHNSY
376  NRPAYSPGHKTHAPTSSSTKKTQLQLEHLLLDLQMILNGINNYKNPKLTR
426  MLTFKFYMPKKATELKHLQCLEEELKPLEEVLNLAQSKNFHLRPRDLISN
476  INVIVLELKGSETTFMCEYADETATIVEFLNRWITFCQSIISTLT**HHHHH
     H** <526
```

Fig. 55 continued

SEQ ID NO:114 (DNA sequence encoding secreted D29E-His6 Ontak®, or D29E-His6 s-Ontak. Sequence includes *toxP*, mutant *tox*O, signal sequence, and D29E-His6 Ontak®. Bold font and asterisks indicate the changes introduces to create the mutant *toxO*).

```
                                                ****  *  *
1     TTGATTTCAGAGCACCCTTATAATTAGGATAGCTAAGTCCATTATTTTAT
51    GAGTCCTGGTAAGGGGATACGTTGTGAGCAGAAAACTGTTTGCGTCAATC
101   TTAATAGGGGCGCTACTGGGGATAGGGGCCCCACCTTCAGCCCATGCAGG
151   CGCTGATGATGTTGTTGATTCTTCTAAATCTTTTGTGATGGAAAACTTTT
201   CTTCGTACCACGGGACTAAACCTGGTTATGTAGAGTCCATTCAAAAAGGT
251   ATACAAAAGCCAAAATCTGGTACACAAGGAAATTATGACGATGATTGGAA
301   AGGGTTTTATAGTACCGACAATAAATACGACGCTGCGGGATACTCTGTAG
351   ATAATGAAAACCCGCTCTCTGGAAAAGCTGGAGGCGTGGTCAAAGTGACG
401   TATCCAGGACTGACGAAGGTTCTCGCACTAAAAGTGGATAATGCCGAAAC
451   TATTAAGAAAGAGTTAGGTTTAAGTCTCACTGAACCGTTGATGGAGCAAG
501   TCGGAACGGAAGAGTTTATCAAAAGGTTCGGTGATGGTGCTTCGCGTGTA
551   GTGCTCAGCCTTCCCTTCGCTGAGGGGAGTTCTAGCGTTGAATATATTAA
601   TAACTGGGAACAGGCGAAAGCGTTAAGCGTAGAACTTGAGATTAATTTTG
651   AAACCCGTGGAAAACGTGGCCAAGATGCGATGTATGAGTATATGGCTCAA
701   GCCTGTGCAGGAAATCGTGTCAGGCGATCAGTAGGTAGCTCATTGTCATG
751   CATCAACCTGGATTGGGATGTTATCCGTGATAAAACTAAAACTAAGATCG
801   AATCTCTGAAAGAACACGGTCCGATCAAAAACAAAATGAGCGAAAGCCCG
851   AACAAAACTGTATCTGAAGAAAAAGCTAAACAGTACCTGGAAGAATTCCA
901   CCAGACTGCACTGGAACACCCGGAACTGTCTGAACTTAAGACCGTTACTG
951   GTACCAACCCGGTATTCGCTGGTGCTAACTACGCTGCTTGGGCAGTAAAC
1001  GTTGCTCAGGTTATCGATAGCGAAACTGCTGATAACCTGGAAAAAACTAC
1051  CGCGGCTCTGTCTATCCTGCCGGGTATCGGTAGCGTAATGGGCATCGCAG
1101  ACGGCGCCGTTCACCACAACACTGAAGAAATCGTTGCACAGTCTATCGCT
```

Fig. 55 continued

1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC
1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCCACCATCACCATCATCACTGA< 1729

Fig. 55 continued

SEQ ID NO: 115 (D3E/D29E s-Ontak or D3E/D29E Ontak®)

1 GAEDVVDSSKSFVMENFSSYHGTKP
26 GYVESIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLT <520

Fig. 55 continued

SEQ ID NO: 116 (DNA sequence encoding secreted D3E/D29E Ontak®, or D3E/D29E s-Ontak. Sequence includes *toxP*, mutant *tox*O, signal sequence, and D3E/D29E Ontak®. Bold font and asterisks indicate the changes introduces to create the mutant *toxO*.

**** * *

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGAAGATGTTGTTGATTCTTCTAAATCTTTTGTGATGGAAAACTTTT
201 CTTCGTACCACGGGACTAAACCTGGTTATGTAGAGTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT

Fig. 55 continued

1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC
1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA< 1711

Fig. 55 continued

SEQ ID NO: 117 (D3E/D29E-His6 s-Ontak or D3E/D29E-His6 Ontak®)

```
1     GAEDVVDSSKSFVMENFSSYHGTKP
26    GYVESIQKGIQKPKSGTQGNYDDDWKGFYSTDNKYDAAGYSVDNENPLSG
76    KAGGVVKVTYPGLTKVLALKVDNAETIKKELGLSLTEPLMEQVGTEEFIK
126   RFGDGASRVVLSLPFAEGSSSVEYINNWEQAKALSVELEINFETRGKRGQ
176   DAMYEYMAQACAGNRVRRSVGSSLSCINLDWDVIRDKTKTKIESLKEHGP
226   IKNKMSESPNKTVSEEKAKQYLEEFHQTALEHPELSELKTVTGTNPVFAG
276   ANYAAWAVNVAQVIDSETADNLEKTTAALSILPGIGSVMGIADGAVHHNT
326   EEIVAQSIALSSLMVAQAIPLVGELVDIGFAAYNFVESIINLFQVVHNSY
376   NRPAYSPGHKTHAPTSSSTKKTQLQLEHLLLDLQMILNGINNYKNPKLTR
426   MLTFKFYMPKKATELKHLQCLEEELKPLEEVLNLAQSKNFHLRPRDLISN
476   INVIVLELKGSETTFMCEYADETATIVEFLNRWITFCQSIISTLTHHHHH
      H <526
```

Fig. 55 continued

SEQ ID NO:118 (DNA sequence encoding secreted D3E/D29E-His6 Ontak®, or D3E/D29E-His6 s-Ontak. Sequence includes *toxP*, mutant *tox*O, signal sequence, and D3E/D29E-His6 Ontak®. Bold font and asterisks indicate the changes introduces to create the mutant *toxO*).

```
                                                  **** * *
1     TTGATTTCAGAGCACCCTTATAATTAGGATAGCTAAGTCCATTATTTTAT
51    GAGTCCTGGTAAGGGGATACGTTGTGAGCAGAAAACTGTTTGCGTCAATC
101   TTAATAGGGGCGCTACTGGGGATAGGGGCCCCACCTTCAGCCCATGCAGG
151   CGCTGAAGATGTTGTTGATTCTTCTAAATCTTTTGTGATGGAAAACTTTT
201   CTTCGTACCACGGGACTAAACCTGGTTATGTAGAGTCCATTCAAAAAGGT
251   ATACAAAAGCCAAAATCTGGTACACAAGGAAATTATGACGATGATTGGAA
301   AGGGTTTTATAGTACCGACAATAAATACGACGCTGCGGGATACTCTGTAG
351   ATAATGAAAACCCGCTCTCTGGAAAAGCTGGAGGCGTGGTCAAAGTGACG
401   TATCCAGGACTGACGAAGGTTCTCGCACTAAAAGTGGATAATGCCGAAAC
451   TATTAAGAAAGAGTTAGGTTTAAGTCTCACTGAACCGTTGATGGAGCAAG
501   TCGGAACGGAAGAGTTTATCAAAAGGTTCGGTGATGGTGCTTCGCGTGTA
551   GTGCTCAGCCTTCCCTTCGCTGAGGGGAGTTCTAGCGTTGAATATATTAA
601   TAACTGGGAACAGGCGAAAGCGTTAAGCGTAGAACTTGAGATTAATTTTG
651   AAACCCGTGGAAAACGTGGCCAAGATGCGATGTATGAGTATATGGCTCAA
701   GCCTGTGCAGGAAATCGTGTCAGGCGATCAGTAGGTAGCTCATTGTCATG
751   CATCAACCTGGATTGGGATGTTATCCGTGATAAAACTAAAACTAAGATCG
801   AATCTCTGAAAGAACACGGTCCGATCAAAAACAAAATGAGCGAAAGCCCG
851   AACAAAACTGTATCTGAAGAAAAAGCTAAACAGTACCTGGAAGAATTCCA
901   CCAGACTGCACTGGAACACCCGGAACTGTCTGAACTTAAGACCGTTACTG
951   GTACCAACCCGGTATTCGCTGGTGCTAACTACGCTGCTTGGGCAGTAAAC
1001  GTTGCTCAGGTTATCGATAGCGAAACTGCTGATAACCTGGAAAAAACTAC
1051  CGCGGCTCTGTCTATCCTGCCGGGTATCGGTAGCGTAATGGGCATCGCAG
1101  ACGGCGCCGTTCACCACAACACTGAAGAAATCGTTGCACAGTCTATCGCT
1151  CTGAGCTCTCTGATGGTTGCTCAGGCCATCCCGCTGGTAGGTGAACTGGT
1201  TGATATCGGTTTCGCTGCATACAACTTCGTTGAAAGCATCATCAACCTGT
1251  TCCAGGTTGTTCACAACTCTTACAACCGCCCGGCTTACTCTCCGGGTCAC
```

Fig. 55 continued

1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC
1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCCACCATCACCATCATCACTGA< 1729

Fig. 55 continued

SEQ ID NO: 119 (D7E/D29E s-Ontak or D7E/D29E Ontak®)

1 GAEDVV[illegible]SSKSFVMENFSSYHGTKP
26 GYV[illegible]SIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLT <520

Fig. 55 continued

SEQ ID NO: 120 (DNA sequence encoding secreted D7E/D29E Ontak®, or D7E/D29E s-Ontak. Sequence includes *toxP*, mutant *tox*O, signal sequence, and D7E/D29E Ontak®. Bold font and asterisks indicate the changes introduces to create the mutant *toxO*).

**** * *

1 TTGATTTCAGAGCACCCTTATAATTAGGATAGCTAAGTCCATTATTTTAT

51 GAGTCCTGGTAAGGGGATACGTTGTGAGCAGAAAACTGTTTGCGTCAATC

101 TTAATAGGGGCGCTACTGGGGATAGGGGCCCCACCTTCAGCCCATGCAGG

151 CGCTGATGATGTTGTTGAATCTTCTAAATCTTTTGTGATGGAAAACTTTT

201 CTTCGTACCACGGGACTAAACCTGGTTATGTAGAGTCCATTCAAAAAGGT

251 ATACAAAAGCCAAAATCTGGTACACAAGGAAATTATGACGATGATTGGAA

301 AGGGTTTTATAGTACCGACAATAAATACGACGCTGCGGGATACTCTGTAG

351 ATAATGAAAACCCGCTCTCTGGAAAAGCTGGAGGCGTGGTCAAAGTGACG

401 TATCCAGGACTGACGAAGGTTCTCGCACTAAAAGTGGATAATGCCGAAAC

451 TATTAAGAAAGAGTTAGGTTTAAGTCTCACTGAACCGTTGATGGAGCAAG

501 TCGGAACGGAAGAGTTTATCAAAAGGTTCGGTGATGGTGCTTCGCGTGTA

551 GTGCTCAGCCTTCCCTTCGCTGAGGGGAGTTCTAGCGTTGAATATATTAA

601 TAACTGGGAACAGGCGAAAGCGTTAAGCGTAGAACTTGAGATTAATTTTG

651 AAACCCGTGGAAAACGTGGCCAAGATGCGATGTATGAGTATATGGCTCAA

701 GCCTGTGCAGGAAATCGTGTCAGGCGATCAGTAGGTAGCTCATTGTCATG

751 CATCAACCTGGATTGGGATGTTATCCGTGATAAAACTAAAACTAAGATCG

801 AATCTCTGAAAGAACACGGTCCGATCAAAAACAAAATGAGCGAAAGCCCG

851 AACAAAACTGTATCTGAAGAAAAAGCTAAACAGTACCTGGAAGAATTCCA

901 CCAGACTGCACTGGAACACCCGGAACTGTCTGAACTTAAGACCGTTACTG

951 GTACCAACCCGGTATTCGCTGGTGCTAACTACGCTGCTTGGGCAGTAAAC

1001 GTTGCTCAGGTTATCGATAGCGAAACTGCTGATAACCTGGAAAAAACTAC

1051 CGCGGCTCTGTCTATCCTGCCGGGTATCGGTAGCGTAATGGGCATCGCAG

1101 ACGGCGCCGTTCACCACAACACTGAAGAAATCGTTGCACAGTCTATCGCT

1151 CTGAGCTCTCTGATGGTTGCTCAGGCCATCCCGCTGGTAGGTGAACTGGT

1201 TGATATCGGTTTCGCTGCATACAACTTCGTTGAAAGCATCATCAACCTGT

1251 TCCAGGTTGTTCACAACTCTTACAACCGCCCGGCTTACTCTCCGGGTCAC

1301 AAGACGCATGCACCTACTTCTAGCTCTACCAAGAAAACCCAGCTGCAGCT

Fig. 55 continued

1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC
1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA< 1711

Fig. 55 continued

SEQ ID NO: 121 (D7E/D29E-His$_6$ s-Ontak or D7E/D29E-His$_6$ Ontak®)

1 GAEDVVESSKSFVMENFSSYHGTKP
26 GYVESIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLTHHHHH
H <526

Fig. 55 continued

SEQ ID NO: 122 (DNA sequence encoding secreted D7E/D29E-$His_6$ Ontak®, or D7E/D29E-$His_6$ s-Ontak. Sequence includes *toxP*, mutant *tox*O, signal sequence, and D7E/D29E Ontak®. Bold font and asterisks indicate the changes introduces to create the mutant *toxO*).

**** * *

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGATGATGTTGTTGAATCTTCTAAATCTTTTGTGATGGAAAACTTTT
201 CTTCGTACCACGGGACTAAACCTGGTTATGTAGAGTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT

Fig. 55 continued

1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC
1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCCACCATCACCATCATCACTGA< 1729

Fig. 55 continued

SEQ ID NO: 123 (V6A/D29E s-Ontak or V6A/D29E Ontak®)

1 GADDVADSSKSFVMENFSSYHGTKP
26 GYVESIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLT <520

Fig. 55 continued

SEQ ID NO: 124 (DNA sequence encoding secreted V6A/D29E Ontak®, or V6A/D29E s-Ontak. Sequence includes *toxP*, mutant *tox*O, signal sequence, and V6A/D29E Ontak®. Bold font and asterisks indicate the changes introduces to create the mutant *toxO*.

**** * *

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGATGATGTTGCTGATTCTTCTAAATCTTTTGTGATGGAAAACTTTT
201 CTTCGTACCACGGGACTAAACCTGGTTATGTAGAGTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT

Fig. 55 continued

1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC
1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA< 1711

Fig. 55 continued

SEQ ID NO: 125 (V6A/D29E-His$_6$ s-Ontak or V6A/D29E-His$_6$ Ontak®)

1 GAEDVADSSKSFVMENFSSYHGTKP
26 GYVESIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLTHHHHH
H <526

Fig. 55 continued

SEQ ID NO: 126 (DNA sequence encoding secreted V6A/D29E-$His_6$ Ontak®, or V6A/D29E-$His_6$ s-Ontak. Sequence includes *toxP*, mutant *tox*O, signal sequence, and V6A/D29E Ontak®. Bold font and asterisks indicate the changes introduces to create the mutant *toxO*.

**** * *

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGATGATGTTGCTGATTCTTCTAAATCTTTTGTGATGGAAAACTTTT
201 CTTCGTACCACGGGACTAAACCTGGTTATGTAGACTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA

Fig. 55 continued

1501 ACCGCTGGAGGAAGTTCTGAACCTGGCTCAGTCTAAAAACTTCCACCTGC
1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCCACCATCACCATCATCACTGA< 1729

Fig. 55 continued

SEQ ID NO: 127 (S8T/D29E s-Ontak or S8T/D29E Ontak®)

```
1     GAEDVVDTSKSFVMENFSSYHGTKP
26    GYVESIQKGIQKPKSGTQGNYDDDWKGFYSTDNKYDAAGYSVDNENPLSG
76    KAGGVVKVTYPGLTKVLALKVDNAETIKKELGLSLTEPLMEQVGTEEFIK
126   RFGDGASRVVLSLPFAEGSSSVEYINNWEQAKALSVELEINFETRGKRGQ
176   DAMYEYMAQACAGNRVRRSVGSSLSCINLDWDVIRDKTKTKIESLKEHGP
226   IKNKMSESPNKTVSEEKAKQYLEEFHQTALEHPELSELKTVTGTNPVFAG
276   ANYAAWAVNVAQVIDSETADNLEKTTAALSILPGIGSVMGIADGAVHHNT
326   EEIVAQSIALSSLMVAQAIPLVGELVDIGFAAYNFVESIINLFQVVHNSY
376   NRPAYSPGHKTHAPTSSSTKKTQLQLEHLLLDLQMILNGINNYKNPKLTR
426   MLTFKFYMPKKATELKHLQCLEEELKPLEEVLNLAQSKNFHLRPRDLISN
476   INVIVLELKGSETTFMCEYADETATIVEFLNRWITFCQSIISTLT <520
```

Fig. 55 continued

SEQ ID NO: 128 (DNA sequence encoding secreted S8T/D29E Ontak®, or S8T/D29E s-Ontak. Sequence includes *toxP*, mutant *tox*O, signal sequence, and S8T/D29E Ontak®. Bold font and asterisks indicate the changes introduces to create the mutant *toxO*).

```
                                                 ****  *  *
1    TTGATTTCAGAGCACCCTTATAATTAGGATAGCTAAGTCCATTATTTTAT
```

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGATGATGTTGTTGATACTTCTAAATCTTTTGTGATGGAAAACTTTT
201 CTTCGTACCACGGACTAAACCTGGTTATGTAGACTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGA < 1711

Fig. 55 continued

SEQ ID NO: 129 (S8T/D29E-$His_6$ s-Ontak or S8T/D29E-$His_6$ Ontak®)

1 GAEDVVDTSKSFVMENFSSYHGTKP
26 GYVESIQKGIQKPKSGTQGNYDDDWKGFYSTDNKYDAAGYSVDNENPLSG
76 KAGGVVKVTYPGLTKVLALKVDNAETIKKELGLSLTEPLMEQVGTEEFIK
126 RFGDGASRVVLSLPFAEGSSSVEYINNWEQAKALSVELEINFETRGKRGQ
176 DAMYEYMAQACAGNRVRRSVGSSLSCINLDWDVIRDKTKTKIESLKEHGP
226 IKNKMSESPNKTVSEEKAKQYLEEFHQTALEHPELSELKTVTGTNPVFAG
276 ANYAAWAVNVAQVIDSETADNLEKTTAALSILPGIGSVMGIADGAVHHNT
326 EEIVAQSIALSSLMVAQAIPLVGELVDIGFAAYNFVESIINLFQVVHNSY
376 NRPAYSPGHKTHAPTSSSTKKTQLQLEHLLLDLQMILNGINNYKNPKLTR
426 MLTFKFYMPKKATELKHLQCLEEELKPLEEVLNLAQSKNFHLRPRDLISN
476 INVIVLELKGSETTFMCEYADETATIVEFLNRWITFCQSIISTLTHHHHH
H <526

Fig. 55 continued

SEQ ID NO: 130 (DNA sequence encoding secreted S8T/D29E-His6 Ontak®, or S8T/D29E-His6 s-Ontak. Sequence includes *toxP*, mutant *tox*O, signal sequence, and S8T/D29E Ontak®. Bold font and asterisks indicate the changes introduces to create the mutant *toxO*).

```
                                                 ****  *  *
```

1 TTGATTTCAGAGCACCCTTATAATTAGGATAGCTAAGTCCATTATTTTAT
51 GAGTCCTGGTAAGGGGATACGTTGTGAGCAGAAAACTGTTTGCGTCAATC
101 TTAATAGGGGCGCTACTGGGGATAGGGGCCCCACCTTCAGCCCATGCAGG
151 CGCTGATGATGTTGTTGATACTTCTAAATCTTTTGTGATGGAAAACTTTT
201 CTTCGTACCACGGGACTAAACCTGGTTATGTAGAGTCCATTCAAAAAGGT
251 ATACAAAAGCCAAAATCTGGTACACAAGGAAATTATGACGATGATTGGAA
301 AGGGTTTTATAGTACCGACAATAAATACGACGCTGCGGGATACTCTGTAG
351 ATAATGAAAACCCGCTCTCTGGAAAAGCTGGAGGCGTGGTCAAAGTGACG
401 TATCCAGGACTGACGAAGGTTCTCGCACTAAAAGTGGATAATGCCGAAAC
451 TATTAAGAAAGAGTTAGGTTTAAGTCTCACTGAACCGTTGATGGAGCAAG
501 TCGGAACGGAAGAGTTTATCAAAAGGTTCGGTGATGGTGCTTCGCGTGTA
551 GTGCTCAGCCTTCCCTTCGCTGAGGGGAGTTCTAGCGTTGAATATATTAA
601 TAACTGGGAACAGGCGAAAGCGTTAAGCGTAGAACTTGAGATTAATTTTG
651 AAACCCGTGGAAAACGTGGCCAAGATGCGATGTATGAGTATATGGCTCAA
701 GCCTGTGCAGGAAATCGTGTCAGGCGATCAGTAGGTAGCTCATTGTCATG
751 CATCAACCTGGATTGGGATGTTATCCGTGATAAAACTAAAACTAAGATCG
801 AATCTCTGAAAGAACACGGTCCGATCAAAAACAAAATGAGCGAAAGCCCG
851 AACAAAACTGTATCTGAAGAAAAAGCTAAACAGTACCTGGAAGAATTCCA
901 CCAGACTGCACTGGAACACCCGGAACTGTCTGAACTTAAGACCGTTACTG
951 GTACCAACCCGGTATTCGCTGGTGCTAACTACGCTGCTTGGGCAGTAAAC
1001 GTTGCTCAGGTTATCGATAGCGAAACTGCTGATAACCTGGAAAAAACTAC
1051 CGCGGCTCTGTCTATCCTGCCGGGTATCGGTAGCGTAATGGGCATCGCAG
1101 ACGGCGCCGTTCACCACAACACTGAAGAAATCGTTGCACAGTCTATCGCT
1151 CTGAGCTCTCTGATGGTTGCTCAGGCCATCCCGCTGGTAGGTGAACTGGT
1201 TGATATCGGTTTCGCTGCATACAACTTCGTTGAAAGCATCATCAACCTGT
1251 TCCAGGTTGTTCACAACTCTTACAACCGCCCGGCTTACTCTCCGGGTCAC
1301 AAGACGCATGCACCTACTTCTAGCTCTACCAAGAAAACCCAGCTGCAGCT
1351 CGAGCACCTGCTGCTGGATTTGCAGATGATCCTGAACGGTATCAACAATT
1401 ACAAGAACCCGAAACTGACGCGTATGCTGACCTTCAAGTTCTACATGCCG
1451 AAGAAGGCCACCGAACTGAAACACCTGCAGTGTCTAGAAGAAGAACTGAA
1501 ACCGCTGGAGGAAGTTCTGAACCTGGCTCAGTCTAAAAACTTCCACCTGC

Fig. 55 continued

1551 GGCCGCGTGACCTGATCTCTAACATCAACGTAATCGTTCTGGAACTGAAG
1601 GGCTCTGAAACCACCTTCATGTGTGAATACGCTGATGAGACCGCAACCAT
1651 CGTAGAATTCCTGAACCGTTGGATCACCTTCTGTCAGTCTATCATCTCTA
1701 CCCTGACCTGACACCATCACCATCATCACTGA< 1729

SEQ ID NO. 131 $P_{tac}$ promoter and 5'UTR without *lac* operator sequences. The sequence includes *tac* promoter, *lac* operator and nucleotides encoding the first codon of the diphtheria fragment. The promoter sequence is underlined. This 5'UTR sequence is known to serve as a strong promoter in many bacterial species. The removal of the *lac* operator sequences is expected to give strong constitutive expression.

1 TTGACAATTAATCATCGGCTCGTATAATGTGTGGAATTTCACACAGGAAA
51 CAGCCAGTCCGTTTAGGTGTTTTCACGAGCACTTCACCAACAAGGACCAT
101 AGATTGTG <109

Fig. 55 continued

SEQ ID NO: 132 ($DT_{1-389}$-mIL4 (mouse IL4) protein sequence. Sequence corresponds to mature protein devoid of signal sequence.)

```
  1 GADDVVDSSKSFVMENFSSYHGTKPGYVDSIQKGIQKPKSGTQGNYDDDW
 51 KGFYSTDNKYDAAGYSVDNENPLSGKAGGVVKVTYPGLTKVLALKVDNAE
101 TIKKELGLSLTEPLMEQVGTEEFIKRFGDGASRVVLSLPFAEGSSSVEYI
151 NNWEQAKALSVELEINFETRGKRGQDAMYEYMAQACAGNRVRRSVGSSLS
201 CINLDWDVIRDKTKTKIESLKEHGPIKNKMSESPNKTVSEEKAKQYLEEF
251 HQTALEHPELSELKTVTGTNPVFAGANYAAWAVNVAQVIDSETADNLEKT
301 TAALSILPGIGSVMGIADGAVHHNTEEIVAQSIALSSLMVAQAIPLVGEL
351 VDIGFAAYNFVESIINLFQVVHNSYNRPAYSPGHKTHIHGCDKNHLREII
401 GILNEVTGEGTPCTEMDVPNVLTATKNTTESELVCRASKVLRIFYLKHGK
451 TPCLKKNSSVLMELQRLFRAFRCLDSSISCTMNESKSTSLKDFLESLKSI
501 MQMDYS         <506
```

SEQ ID NO: 133 (DNA sequence encoding secreted $DT_{1-389}$-mIL4 (mouse IL4). The sequence begins with the first codon of the immature polypeptide, and it encodes the signal sequence, $DT_{1-389}$ and mouse IL-4.)

```
  1 GTGAGCAGAAAACTGTTTGCGTCAATCTTAATAGGGGCGCTACTGGGGAT
 51 AGGGGCCCCACCTTCAGCCCATGCAGGCGCTGATGATGTTGTTGATTCTT
101 CTAAATCTTTTGTGATGGAAAACTTTTCTTCGTACCACGGGACTAAACCT
151 GGTTATGTAGATTCCATTCAAAAAGGTATACAAAAGCCAAAATCTGGTAC
201 ACAAGGAAATTATGACGATGATTGGAAAGGGTTTTATAGTACCGACAATA
251 AATACGACGCTGCGGGATACTCTGTAGATAATGAAAACCCGCTCTCTGGA
301 AAAGCTGGAGGCGTGGTCAAAGTGACGTATCCAGGACTGACGAAGGTTCT
351 CGCACTAAAAGTGGATAATGCCGAAACTATTAAGAAAGAGTTAGGTTTAA
401 GTCTCACTGAACCGTTGATGGAGCAAGTCGGAACGGAAGAGTTTATCAAA
451 AGGTTCGGTGATGGTGCTTCGCGTGTAGTGCTCAGCCTTCCCTTCGCTGA
501 GGGGAGTTCTAGCGTTGAATATATTAATAACTGGGAACAGGCGAAAGCGT
551 TAAGCGTAGAACTTGAGATTAATTTTGAAACCCGTGGAAAACGTGGCCAA
601 GATGCGATGTATGAGTATATGGCTCAAGCCTGTGCAGGAAATCGTGTCAG
651 GCGATCAGTAGGTAGCTCATTGTCATGCATCAACCTGGATTGGGATGTTA
701 TCCGTGATAAAACTAAAACTAAGATCGAATCTCTGAAAGAACACGGTCCG
```

Fig. 55 continued

751 ATCAAAAACAAAATGAGCGAAAGCCCGAACAAAACTGTATCTGAAGAAAA
801 AGCTAAACAGTACCTGGAAGAATTCCACCAGACTGCACTGGAACACCCGG
851 AACTGTCTGAACTTAAGACCGTTACTGGTACCAACCCGGTATTCGCTGGT
901 GCTAACTACGCTGCTTGGGCAGTAAACGTTGCTCAGGTTATCGATAGCGA
951 AACTGCTGATAACCTGGAAAAAACTACCGCGGCTCTGTCTATCCTGCCGG
1001 GTATCGGTAGCGTAATGGGCATCGCAGACGGCGCCGTTCACCACAACACT
1051 GAAGAAATCGTTGCACAGTCTATCGCTCTGAGCTCTCTGATGGTTGCTCA
1101 GGCCATCCCGCTGGTAGGTGAACTGGTTGATATCGGTTTCGCTGCATACA
1151 ACTTCGTTGAAAGCATCATCAACCTGTTCCAGGTTGTTCACAACTCTTAC
1201 AACCGCCCGGCTTACTCTCCGGGTCACAAGACGCATATTCATGGCTGCGA
1251 TAAAAACCATCTGCGCGAAATTATTGGCATTCTGAACGAAGTGACCGGCG
1301 AAGGCACCCCGTGCACCGAAATGGATGTGCCGAACGTGCTGACCGCGACC
1351 AAAAACACCACCGAAAGCGAACTGGTGTGCCGCGCGAGCAAAGTGCTGCG
1401 CATTTTTTATCTGAAACATGGCAAAACCCCGTGCCTGAAAAAAAACAGCA
1451 GCGTGCTGATGGAACTGCAGCGCCTGTTTCGCGCGTTTCGCTGCCTGGAT
1501 AGCAGCATTAGCTGCACCATGAACGAAAGCAAAAGCACCAGCCTGAAAGA
1551 TTTTCTGGAAAGCCTGAAAAGCATTATGCAGATGGATTATAGCTAG <1596

SEQ ID NO: 134 ($DT_{1-389}$-mIL4-$His_6$ protein sequence. Sequence corresponds to mature protein devoid of signal sequence.)

1 GADDVVDSSKSFVMENFSSYHGTKPGYVDSIQKGIQKPKSGTQGNYDDDW
51 KGFYSTDNKYDAAGYSVDNENPLSGKAGGVVKVTYPGLTKVLALKVDNAE
101 TIKKELGLSLTEPLMEQVGTEEFIKRFGDGASRVVLSLPFAEGSSSVEYI
151 NNWEQAKALSVELEINFETRGKRGQDAMYEYMAQACAGNRVRRSVGSSLS
201 CINLDWDVIRDKTKTKIESLKEHGPIKNKMSESPNKTVSEEKAKQYLEEF
251 HQTALEHPELSELKTVTGTNPVFAGANYAAWAVNVAQVIDSETADNLEKT
301 TAALSILPGIGSVMGIADGAVHHNTEEIVAQSIALSSLMVAQAIPLVGEL
351 VDIGFAAYNFVESIINLFQVVHNSYNRPAYSPGHKTHIHGCDKNHLREII
401 GILNEVTGEGTPCTEMDVPNVLTATKNTTESELVCRASKVLRIFYLKHGK
451 TPCLKKNSSVLMELQRLFRAFRCLDSSISCTMNESKSTSLKDFLESLKSI
501 MQMDYSENLYFQGHHHHHH <519

SEQ ID NO: 135 (DNA sequence encoding secreted $DT_{1-389}$-mIL4-$His_6$. The sequence begins with the first codon of the immature polypeptide, and it encodes the signal sequence, $DT_{1-389}$,

Fig. 55 continued mouse IL-4, TEV protease site and His-6 sequence (underlined). Bold font indicates the TEV protease site.)

```
   1 GTGAGCAGAAAACTGTTTGCGTCAATCTTAATAGGGGCGCTACTGGGGAT
  51 AGGGGCCCCACCTTCAGCCCATGCAGGCGCTGATGATGTTGTTGATTCTT
 101 CTAAATCTTTTGTGATGGAAAACTTTTCTTCGTACCACGGGACTAAACCT
 151 GGTTATGTAGATTCCATTCAAAAAGGTATACAAAAGCCAAAATCTGGTAC
 201 ACAAGGAAATTATGACGATGATTGGAAAGGGTTTTATAGTACCGACAATA
 251 AATACGACGCTGCGGGATACTCTGTAGATAATGAAAACCCGCTCTCTGGA
 301 AAAGCTGGAGGCGTGGTCAAAGTGACGTATCCAGGACTGACGAAGGTTCT
 351 CGCACTAAAAGTGGATAATGCCGAAACTATTAAGAAAGAGTTAGGTTTAA
 401 GTCTCACTGAACCGTTGATGGAGCAAGTCGGAACGGAAGAGTTTATCAAA
 451 AGGTTCGGTGATGGTGCTTCGCGTGTAGTGCTCAGCCTTCCCTTCGCTGA
 501 GGGGAGTTCTAGCGTTGAATATATTAATAACTGGGAACAGGCGAAAGCGT
 551 TAAGCGTAGAACTTGAGATTAATTTTGAAACCCGTGGAAAACGTGGCCAA
 601 GATGCGATGTATGAGTATATGGCTCAAGCCTGTGCAGGAAATCGTGTCAG
 651 GCGATCAGTAGGTAGCTCATTGTCATGCATCAACCTGGATTGGGATGTTA
 701 TCCGTGATAAAACTAAAACTAAGATCGAATCTCTGAAAGAACACGGTCCG
 751 ATCAAAAACAAAATGAGCGAAAGCCCGAACAAAACTGTATCTGAAGAAAA
 801 AGCTAAACAGTACCTGGAAGAATTCCACCAGACTGCACTGGAACACCCGG
 851 AACTGTCTGAACTTAAGACCGTTACTGGTACCAACCCGGTATTCGCTGGT
 901 GCTAACTACGCTGCTTGGGCAGTAAACGTTGCTCAGGTTATCGATAGCGA
 951 AACTGCTGATAACCTGGAAAAAACTACCGCGGCTCTGTCTATCCTGCCGG
1001 GTATCGGTAGCGTAATGGGCATCGCAGACGGCGCCGTTCACCACAACACT
1051 GAAGAAATCGTTGCACAGTCTATCGCTCTGAGCTCTCTGATGGTTGCTCA
1101 GGCCATCCCGCTGGTAGGTGAACTGGTTGATATCGGTTTCGCTGCATACA
1151 ACTTCGTTGAAAGCATCATCAACCTGTTCCAGGTTGTTCACAACTCTTAC
1201 AACCGCCCGGCTTACTCTCCGGGTCACAAGACGCATATTCATGGCTGCGA
1251 TAAAAACCATCTGCGCGAAATTATTGGCATTCTGAACGAAGTGACCGGCG
1301 AAGGCACCCCGTGCACCGAAATGGATGTGCCGAACGTGCTGACCGCGACC
1351 AAAAACACCACCGAAAGCGAACTGGTGTGCCGCGCGAGCAAAGTGCTGCG
1401 CATTTTTTATCTGAAACATGGCAAAACCCCGTGCCTGAAAAAAAACAGCA
1451 GCGTGCTGATGGAACTGCAGCGCCTGTTTCGCGCGTTTCGCTGCCTGGAT
1501 AGCAGCATTAGCTGCACCATGAACGAAAGCAAAAGCACCAGCCTGAAAGA
1551 TTTTCTGGAAAGCCTGAAAAGCATTATGCAGATGGATTATAGCGAGAACC
1601 TGTACTTCCAGGGCCATCACCACCACCACCACTAG          <1635
```

Fig. 56

| Vascular leak reduction | | |
|---|---|---|
| SEQ ID NO: 10 | E. coli-derived classic Ontak | Protein |
| SEQ ID NO: 15 | V6A protein (previously disclosed), VLM s-Ontak | Protein |
| SEQ ID NO: 43 | V6A-$His_6$ protein (previously disclosed), VLM s-Ontak-$His_6$ | Protein |
| SEQ ID NO: 13 | s-Ontak | Protein |
| SEQ ID NO: 58 | s-Ontak-$His_6$ | Protein |
| | | |
| SEQ ID NO: 60 | D3E | Protein |
| SEQ ID NO: 61 | D3E | DNA |
| SEQ ID NO: 62 | D3E-$His_6$ protein | protein |
| SEQ ID NO: 63 | D3E-$His_6$ | DNA |
| SEQ ID NO: 64 | D7E protein | protein |
| SEQ ID NO: 65 | D7E | DNA |
| SEQ ID NO: 66 | D7E-$His_6$ protein | protein |
| SEQ ID NO: 67 | D7E-$His_6$ | DNA |
| SEQ ID NO: 68 | S8T protein | protein |
| SEQ ID NO: 69 | S8T | DNA |
| SEQ ID NO: 70 | S8T-$His_6$ protein | protein |
| SEQ ID NO: 71 | S8T-$His_6$ | DNA |
| SEQ ID NO: 72 | D3E-V6A double mutant | protein |
| SEQ ID NO: 73 | D3E-V6A double mutant | DNA |
| SEQ ID NO: 74 | D3E-V6A-$His_6$ | protein |
| SEQ ID NO: 75 | D3E-V6A-$His_6$ | DNA |
| SEQ ID NO: 76 | D3E-D7E double mutant | protein |
| SEQ ID NO: 77 | D3E-D7E double mutant | DNA |
| SEQ ID NO: 78 | D3E-D7E-$His_6$ | protein |
| SEQ ID NO: 79 | D3E-D7E-$His_6$ | DNA |
| SEQ ID NO: 80 | D3E-S8T double mutant | protein |
| SEQ ID NO: 81 | D3E-S8T double mutant | DNA |

Fig. 56 continued

| | | |
|---|---|---|
| SEQ ID NO: 82 | D3E-S8T-$His_6$ | protein |
| SEQ ID NO: 83 | D3E-S8T-$His_6$ | DNA |
| SEQ ID NO: 84 | V6A-D7E double mutant | protein |
| SEQ ID NO: 85 | V6A-D7E double mutant | DNA |
| SEQ ID NO: 86 | V6A-D7E-$His_6$ | protein |
| SEQ ID NO: 87 | V6A-D7E-$His_6$ | DNA |
| SEQ ID NO: 88 | V6A-S8T double mutant | protein |
| SEQ ID NO: 89 | V6A-S8T double mutant | DNA |
| SEQ ID NO: 90 | V6A-S8T-$His_6$ | protein |
| SEQ ID NO: 91 | V6A-S8T-$His_6$ | DNA |
| SEQ ID NO: 92 | D7E-S8T double mutant | protein |
| SEQ ID NO: 93 | D7E-S8T double mutant | DNA |
| SEQ ID NO: 94 | D7E-S8T-$His_6$ | protein |
| SEQ ID NO: 95 | D7E-S8T-$His_6$ | DNA |
| | | |
| **New targeting domains** | | |
| SEQ ID NO: 96 | $DT_{1-389}$-mIL4 (mouse IL4)-V6A | protein |
| SEQ ID NO: 97 | $DT_{1-389}$-mIL4 (mouse IL4)-V6A | DNA |
| SEQ ID NO: 98 | $DT_{1-389}$-mIL4-V6A-$His_6$ | protein |
| SEQ ID NO: 99 | $DT_{1-389}$-mIL4-V6A-$His_6$ | DNA |
| SEQ ID NO: 100 | $DT_{1-389}$-hIL4 (human IL4)-V6A | protein |
| SEQ ID NO: 101 | $DT_{1-389}$-hIL4 (human IL4)-V6A | DNA |
| SEQ ID NO: 102 | $DT_{1-389}$-hIL4-V6A-$His_6$ | protein |
| SEQ ID NO: 103 | DT1-389-hIL4-V6A-$His_6$ | DNA |
| SEQ ID NO: 104 | $DT_{1-389}$-EGF-V6A | protein |
| SEQ ID NO: 105 | $DT_{1-389}$-EGF-V6A | DNA |
| SEQ ID NO: 106 | $DT_{1-389}$-EGF-V6A-$His_6$ | protein |
| SEQ ID NO: 107 | $DT_{1-389}$-EGF-V6A-$His_6$ | DNA |
| | | |
| | | |
| **Overexpression** | | |

Fig. 56 continued

| | | |
|---|---|---|
| SEQ ID NO: 2 | Ptox (WT)- mutant operator | |
| SEQ ID NO: 108 | Ptox (WT)-operator (WT) | DNA |
| SEQ ID NO: 109 | $P_{hsp65}$ 5'UTR to replace the Ptox and tox operator | DNA |
| SEQ ID NO: 110 | $P_{tac}$ 5'UTR to replace the Ptox and tox operator | DNA |
| | | |
| **Additional Vascular Leak Reduction Mutants and Double Mutants** | | |
| SEQ ID NO: 111 | D29E s-Ontak | protein |
| SEQ ID NO: 112 | D29E s-Ontak | DNA |
| SEQ ID NO: 113 | D29E s-Ontak-$His_6$ | protein |
| SEQ ID NO: 114 | D29E s-Ontak-$His_6$ | DNA |
| SEQ ID NO: 115 | D3E/D29E s-Ontak | protein |
| SEQ ID NO: 116 | D3E/D29E s-Ontak | DNA |
| SEQ ID NO: 117 | D3E/D29E s-Ontak-$His_6$ | protein |
| SEQ ID NO: 118 | D3E/D29E s-Ontak-$His_6$ | DNA |
| SEQ ID NO: 119 | D7E/D29E s-Ontak | protein |
| SEQ ID NO: 120 | D7E/D29E s-Ontak | DNA |
| SEQ ID NO: 121 | D7E/D29E s-Ontak-$His_6$ | protein |
| SEQ ID NO: 122 | D7E/D29E s-Ontak-$His_6$ | DNA |
| SEQ ID NO: 123 | V6A/D29E s-Ontak | protein |
| SEQ ID NO: 124 | V6A/D29E s-Ontak | DNA |
| SEQ ID NO: 125 | V6A/D29E s-Ontak-$His_6$ | protein |
| SEQ ID NO: 126 | V6A/D29E s-Ontak-$His_6$ | DNA |
| SEQ ID NO: 127 | S8T/D29E s-Ontak | protein |
| SEQ ID NO: 128 | S8T/D29E s-Ontak | DNA |
| SEQ ID NO: 129 | S8T/D29E s-Ontak-$His_6$ | protein |
| SEQ ID NO: 130 | S8T/D29E s-Ontak-$His_6$ | DNA |

Fig. 56 continued

| Overexpression (continued) | | |
|---|---|---|
| SEQ ID NO: 131 | Ptac lacking the lac operator to replace Ptox and the tox operator | DNA |

| New targeting domains (continued) | | |
|---|---|---|
| SEQ ID NO: 132 | $DT_{1-389}$-mIL4 (mouse IL4) | protein |
| SEQ ID NO: 133 | $DT_{1-389}$-mIL4 (mouse IL4) | DNA |
| SEQ ID NO: 134 | $DT_{1-389}$-mIL4-$His_6$ | protein |
| SEQ ID NO: 135 | $DT_{1-389}$-mIL4-$His_6$ | DNA |

Notes on nomenclature:

s-DAB stands for secreted diphtheria toxin fragment A and part of fragment B

DT stands for diphtheria toxin throughout the application s-DAB and DT refer to secreted forms of diphtheria toxin fragment A and part of fragment throughout the application s-DAB and DT are used interchangeably

METHODS OF TREATING OR PREVENTING CANCER WITH AN AGENT THAT DEPLETES TREGS AND A CHECKPOINT INHIBITOR

CROSS-REFERENCE TO RELATED APPLICATIONS

This application is a 35 U.S.C. § 371 U.S. national entry of International Application PCT/US2019/020959, having an international filing date of Mar. 6, 2019, which claims the benefit of U.S. Provisional Application No. 62/639,199, filed Mar. 6, 2018, the content of each of the aforementioned applications is herein incorporated by reference in their entirety.

STATEMENT OF GOVERNMENTAL INTEREST

This invention was made with government support under grant nos. AI37856, HL133190, 10 AI130595, and CA006973 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 1, 2021, is named JHU4290-1_SL.txt and is 396,513 bytes in size.

BACKGROUND OF THE INVENTION

Ontak® (denileukin diftitox), is a 521 amino acid, recombinant, DNA-derived cytotoxic protein composed of the sequences for diphtheria toxin fragments A and a portion of fragment B ($Met_1$-$His_{388}$) and the sequences for human interleukin-2 (IL-2; $Ala_1$-$Thr_{133}$). It is currently produced in an *E. coli* expression system and has a molecular weight of 58 kD. Neomycin is used in the fermentation process but is undetectable in the final product. Ontak®, which is supplied in single use vials as a sterile, frozen solution intended for intravenous (IV) administration, was approved by the FDA in 1999 for the treatment of cutaneous T cell lymphoma (CTCL). The FDA placed Ontak® on clinical hold in June 2011 because of concerns regarding the presence of protein aggregates of heterogeneous molecular weight, excess residual DNA, and excess residual detergent in the final formulation. The production of Ontak® was achieved by expressing the recombinant protein in the *E. coli* cytoplasm, and this expression system resulted in the recombinant protein forming large insoluble aggregates or so-called inclusion bodies comprised of the Ontak® polypeptide. In the current process of production, which includes denaturation and refolding of the inclusion body forms, protein aggregates of heterogeneous molecular weight were still present in the final formulation. The presence of these aggregates in the purified form is a consequence of using *E. coli*-derived cytoplasmic inclusion bodies as the source of the polypeptide and because of the intrinsic hydrophobic nature of the toxin's transmembrane domain even in the presence of Tween 20. Ontak® produced using this method will hereafter be referred to as classic-Ontak® or c-Ontak®.

In addition, like all of the bacterial and plant toxins, c-Ontak® carries amino acid motifs that induce vascular leak syndrome (VLS). Approximately 30% of patients treated with c-Ontak® develop VLS symptoms ranging from peripheral edema with rapid weight gain to hypoalbuminemia to pulmonary edema.

The molecular mechanism of VLS is not well understood. Several mechanisms have been proposed to cause disruption of cell junctions between vascular endothelial cells and different triggers may induce one or more pathways that lead to vascular leak. NK cells can target endothelial cells for lysis and depletion of these cells has been shown to protect against IL-2 induced vascular leakage in mice (Kotasek D, Vercellotti G M, Ochoa A C, Bach F H, White J G, Jacob H S. Mechanism of cultured endothelial injury induced by lymphokine-activated killer cells. Cancer Res. 1988; 48:5528-32. PMID: 3262010). Inflammatory cytokines have also been implicated in causing VLS. TNFα, IL-1, and IL-2 have all been shown to increase permeability of endothelial cell layers in vitro. Baluna and colleagues suggested that specific amino acid motifs in ricin toxin and diphtheria toxin bind to endothelial cells and disrupt cell-cell or cell-extracellular matrix interactions. They found that mutations in the amino acid motif of the A chain of ricin toxin led to decreased disruption endothelial cell monolayers in vitro, and decreased induction of vascular leak in mice; however, the effects of the mutations on enzymatic activity were not assessed (Baluna R, Rizo J, Gordon B E, Ghetie V, Vitetta E S. Evidence for a structural motif in toxins and interleukin-2 that may be responsible for binding to endothelial cells and initiating vascular leak syndrome. Proc Natl Acad Sci USA. 1999; 96:3957-62. PMID: 10097145). *E. coli*-derived classic Ontak (SEQ ID NO: 10) and *C. diphtheriae*-derived secreted-Ontak (s-Ontak, SEQ ID NO: 13) have polypeptide sequences that differ by one amino acid (the *E. coli*-derived protein has an N-terminal methionine residue which is absent in the *C. diphtheriae* protein). However, these two proteins are otherwise identical from a primary amino acid perspective, and they share at least five vascular leak inducing motifs.

Unlike infectious diseases, where drugs such as antibiotics can specifically inhibit essential bacterial proteins while avoiding collateral damage to human cells, cancer drugs often target normal cells as well, leading to serious side effects such as immunosuppression and neuropathy. As cancer cells are very similar to self, the immune system encounters a similar problem in distinguishing tumor from non-tumor, and the same mechanisms that prevent autoimmunity can also inhibit effective anti-tumor immune responses. Cancer immunotherapy seeks to harness the patient's immune response to fight their cancer, and recent successes in clinical trials with immune checkpoint inhibitors such as PD-1 blockade have made evident that enhancing anti-tumor responses can produce durable clinical responses in some patients, with overall response rates of 20-40%. For patients who do not respond to current immunotherapies, further work must be done to discover additional targets and combination regimens that will provide clinical benefit.

Regulatory T cells (Tregs) are inhibitory immune cells that are essential for preventing autoimmunity. While Tregs can protect against detrimental inflammatory responses, their suppressive function also contributes to inhibiting protective immune responses in cancers and infectious disease. In fact, tumor cells can directly promote Treg activity, leading to a decreased anti-tumor immune response. Tumor infiltrating Tregs mediate their immune suppression through various mechanisms, including inhibition of cytotoxic CD8+ T cell and dendritic cell function (Chen M-L, Pittet M, Gorelik L, Flavell R A, Weissleder R, Boehmer H von, et al. Regulatory T cells suppress tumor-specific CD8 T cell cytotoxicity through TGF-B signals in vivo. Proc Natl Acad Sci USA. 2005; 102:419-424. PMID: 15623559 and Jang J, Hajdu C H, Liot C, Miller G, Dustin M L, Bar-Sagi D. Crosstalk between Regulatory T Cells and Tumor-Associated Dendritic Cells Negates Anti-tumor Immunity in Pancreatic Cancer. Cell Rep. 2017; 20:558-71. PMID: 28723561).

What is needed are modified Ontak-like proteins with minimal VLS side-effects and the use of these proteins to create safer cancer treatments that are more effective at eliminating cancer in subjects.

SUMMARY OF THE INVENTION

One embodiment of the present invention is a DNA expression vector comprising: a toxP; a mutant toxO that blocks Fe-mediated regulation of gene expression; and a DNA sequence encoding a protein, wherein the toxP and the mutant toxO regulate expression of the DNA segment encoding the protein. It is preferred that DNA expression vectors of the present invention include DNA sequences encoding a signal peptide so that a protein expressed off a DNA expression vector is attached to the signal peptide that is typically cleaved off to form a mature protein. The preferred mutant toxO is SEQ ID NO: 1 and the preferred signal peptide is SEQ ID NO: 5. The DNA expression vectors of the present invention may be used to produce many kinds of proteins such as CRM 197 and CRM 107, or a combination thereof. CRM protein sequences are illustrated in SEQ ID NOs: 18-21. It is preferred that the DNA expression vectors of the present invention encode a diphtheria toxin, or functional part thereof, attached to a receptor binding protein, or a functional part thereof to form a diphtheria toxin receptor fusion protein. The receptor binding protein portion of such fusion proteins may be selected from the group comprising IL-2, IL-3, IL-4, IL-6, IL-7, IL-15, EGF, FGF, substance P, CD4, αMSH, GRP, TT fragment C, GCSF, heregulin β1, a functional part thereof, or a combination thereof. Examples of diphtheria toxin fusion proteins include the proteins illustrated in any one of SEQ ID NOs: 11-15, 30, 38-40, 42-43, 45-46, and 58, and proteins encoded by a nucleic acid of any one of SEQ ID NOs: 31, 41, 44, and 59.

Another embodiment of the present invention is a DNA expression vector comprising: a toxP; a mutant toxO that blocks Fe-mediated regulation of gene expression; a DNA sequence encoding a protein comprising a signal sequence; a diphtheria toxin, or a functional part thereof, that is free of a diphtheria receptor binding domain or has a non-functional diphtheria toxin receptor binding domain, and a target receptor binding domain selected from the group comprising IL-2, IL-3, IL-4, IL-6, IL-7, IL-15, EGF, FGF, substance P, CD4, αMSH, GRP, TT fragment C, GCSF, heregulin β1, a functional part thereof, or a combination thereof, wherein the toxP and the mutant toxO regulate expression of the DNA sequence encoding the protein. Typically, a bacteria transformed with a DNA expression vector of the present invention produces a diphtheria toxin receptor binding fusion protein attached to a signal peptide that is directed to a periplasm, a culture medium, or both locations by the signal peptide. If the bacteria is *E. coli* then the signal peptide typically directs the diphtheria toxin receptor binding fusion protein to the periplasm. If the bacteria is *Corynebacterium diphtheria* then signal peptide directs the diphtheria toxin receptor binding fusion protein to the culture medium. It is preferred that a DNA expression vector of the present invention comprises SEQ ID NO: 3 and may comprise a DNA encoding a cleavable protein tag wherein the cleavable protein tag is attached to the diphtheria toxin receptor binding fusion protein. Example of diphtheria toxin receptor binding fusion proteins produced from the DNA expression vectors of the present invention include any one of SEQ ID NOs: 11-15, 30, 38-40, 42-43, 45-46, and 58, and proteins encoded by a nucleic acid of any one of SEQ ID NOs: 31, 41, 44, and 59.

Another embodiment of the present invention includes a method for producing aggregate-free monomeric diphtheria toxin fusion proteins comprising the following steps: transforming bacteria with a DNA expression vectors of the present invention; forming a transformant; incubating the transformant in a culture medium to allow expression of a protein that is secreted into the culture medium; and purifying the protein from the culture medium. The preferred bacteria used in this method is *Corynebacterium diphtheria.*

Another embodiment of the present invention includes a method for producing aggregate-free monomeric diphtheria toxin fusion proteins comprising the following steps: 1) transforming *Corynebacterium diphtheriae* strain with a DNA vector comprising: a toxP; a mutant toxO that blocks Fe-mediated regulation of gene expression; a DNA sequence encoding a protein comprising: signal peptide; a diphtheria toxin, or a functional part thereof, that is free of a diphtheria receptor binding domain or has a non-functional diphtheria toxin receptor binding domain; and a target receptor binding domain selected from the group comprising IL-2, IL-3, IL-4, IL-6, IL-7, IL-15, EGF, FGF, substance P, CD4, αMSH, GRP, TT fragment C, GCSF, heregulin β1, TNFα, TGFβ, a functional part thereof, or a combination thereof, wherein the toxP and the mutant toxO regulate expression of the DNA sequence encoding the protein; 2) forming a transformant; 3) incubating the transformant in a culture medium to allow expression of the protein and that is secreted into the culture medium; and 4) purifying the diphtheria toxin fusion protein from the culture medium. Examples of diphtheria toxin receptor fusion proteins produced by methods of the present invention include any one of SEQ ID NOs: 11-15, 30, 38-40, 42-43, 45-46, and 58, and proteins encoded by a nucleic acid of any one of SEQ ID NOs: 31, 41, 44, and 59. The preferred *Corynebacterium diphtheriae* strain used in the methods of the present invention is *Corynebacterium* C7 beta (−), tox (−).

Another embodiment of the present invention includes a method of treating a patient with tuberculosis comprising the following steps: preparing a diphtheria toxin fusion protein as provided in this application; administering the diphtheria toxin fusion protein to a patient with tuberculosis.

Another embodiment of the present invention includes a DNA expression vector comprising a mutant toxO promoter.

Another embodiment of the present invention includes a *Corynebacterium diphtheriae* strain containing a DNA expression vector of the present invention.

Another embodiment of the present invention is method of making a protein comprising the following steps: providing a DNA expression vector comprising a toxP, a mutant toxO that blocks Fe-mediated regulation of gene expression, a signal sequence, and a DNA sequence encoding a protein; transforming a bacteria strain with the DNA vector to form a transformant; incubating the transformant in a culture medium for a period of time to allow expression of a protein that is secreted into the culture medium; and purifying the protein from the culture medium.

Another embodiment of the present invention is a fusion protein selected from any one of SEQ ID NOs: 11-15, 30, 38-40, 42-43, 45-46, and 58, or encoded by a nucleic acid of any one of SEQ ID NOs: 31, 41, 44, and 59.

Another embodiment of the present invention is a pharmaceutical composition comprising a fusion protein described above.

Another embodiment of the present invention is a pharmaceutical composition comprising a fusion protein describe above, and at least one or more other chemotherapy agents. Examples of chemotherapy agents include isoniazid, rifampin, rifabutin, rifapentine, pyrazinamide, ethambutol, streptomycin, amikacin, kanamycin, ethionamide, protionamide, terizidone, thiacetazone, cycloserine, capreomycin, para-amino salicylic acid (PAS), viomycin, ofloxacin, ciprofloxacin, levofloxacin, moxifloxacin, bedaquiline, delamanid, linezolid, tedezolid, amoxicillin-clavulanic acid, meropenem, imipenem, clarithromycin or clofazimine.

A pharmaceutical composition of comprising a fusion protein described above, and at least one or more other antimicrobial agents. Examples of antimicrobial agents include isoniazid, rifampin, rifabutin, rifapentine, pyrazinamide, ethambutol, streptomycin, amikacin, kanamycin, ethionamide, protionamide, terizidone, thiacetazone, cycloserine, capreomycin, para-amino salicylic acid (PAS), viomycin, ofloxacin, ciprofloxacin, levofloxacin, moxifloxacin, bedaquiline, or delamanid, linezolid, tedezolid, amoxicillin-clavulanic acid, meropenem, imipenem, clarithromycin, or clofazimine.

Another embodiment of the present invention is a method of treating or preventing cancer in a subject comprising administering to the subject an effective amount of a pharmaceutical composition comprising a fusion protein selected from any one of SEQ ID NOs: 11-15, 30, 38-40, 42-43, 45-46, and 58, or encoded by a nucleic acid selected from any one of SEQ ID NOs: 31, 41, 44, and 59.

Another embodiment of the present invention is a method of treating or preventing tuberculosis in a subject comprising administering to the subject an effective amount of a pharmaceutical composition comprising a fusion protein selected from any one of SEQ ID NOs: 11-15, 30, 38-40, 42-43, 45-46, and 58, or encoded by a nucleic acid selected from any one of SEQ ID NOs: 31, 41, 44, and 59.

Another embodiment of the present invention is a prokaryotic cell line comprising a DNA expression vector of the present invention.

Another embodiment of the present invention is kit comprising the DNA expression vector of the present invention.

Another embodiment of the present invention is a toxP comprising SEQ ID NO: 2.

Another embodiment of the present invention is a protein of any one of SEQ ID NOs: 11-15, 30, 38-40, 42-43, 45-46, and 58, or a protein encoded by a nucleic acid selected from any one or SEQ ID NOs: 31, 41, 44, and 59.

Another embodiment of the present invention is a method of treating or preventing cancer in a subject comprising administering to a subject having cancer or prone of getting cancer a first agent that depletes the subject's regulatory T cells (Tregs), followed by administering to the subject a second agent comprising a checkpoint inhibitor. The methods treat or prevent the cancers including colon cancer, renal cell cancer, melanoma, glioblastoma multiforme, lung cancer, solid tumors, renal carcinoma, breast cancer, epidermoid carcinoma, or a combination thereof, as examples. Suitable first agents used in the present invention include one or more diphtheria toxin fusion protein of the present invention described in the specification or FIGS. 54, 55, and 56. In some embodiments of the present invention diphtheria toxin fusion protein comprise diphtheria toxin fragment A or a functional part thereof; diphtheria toxin fragment B or a functional part thereof; or a combination thereof. In some embodiments of the present invention, the diphtheria toxin fusion protein comprises human interleukin sequences. In some embodiments of the present invention, the human interleukin sequences consist of an IL-2 protein or functional parts thereof, IL-4 protein or functional parts thereof, or a combination thereof. In some embodiments, the diphtheria toxin fusion protein has reduced vascular leakage when compared to a reference subject administered denileukin diftitox. Examples of suitable diphtheria toxin fusion proteins having reduced vascular leakage used in the methods of the present invention are listed in the specification and FIG. 56, such as SEQ ID NOs: 10, 15, 43, 13, 58, 60, 62, 64, 66, 68, 70, 72, 74, 76, 78, 80, 82, 84, 86, 88, 90, 92, 94, 111, 113, 115, 117, 119, 121, 123, 125, 127, 129, functional parts thereof, or a combination thereof. Other examples of a first agent include SEQ ID NO:13 or a functional part thereof, SEQ ID NO: 58 or a functional part thereof; SEQ ID NO: 15 or a functional part thereof, SEQ ID NO: 43 or a functional part thereof; or a combination thereof. SEQ ID NOs: 13, 58, 15, and 43, or functional parts thereof, may be combined with other sequences describe above or in the specification. Examples of suitable checkpoint inhibitors used in the methods of the present invention include an anti-CTLA-4 antibody or functional part thereof, an anti-PD-1 antibody or functional part thereof, an anti-PD-L1 antibody or functional part thereof, or a combination thereof. In other embodiments of the present invention, the checkpoint inhibitor is selected from the group consisting of ipilimumab (anti-CTLA-4), nivolumab (anti-PD-1), pembrolizumab (anti-PD-1), atezolizumab (anti-PD-L1), avelumab (anti-PD-L1), durvalumab (anti-PD-L1), or a combination thereof. The method of claim 1 wherein the first agent comprises an expression vector encoding a protein sequence comprising SEQ ID NOs: 10, 13, 15, 43, 13, 58, 60, 62, 64, 66, 68, 70, 72, 74, 76, 78, 80, 82, 84, 86, 88, 90, 92, 94, 111, 113, 115, 117, 119, 121, 123, 125, 127, 129, functional parts thereof, or a combination thereof. The expression vectors may comprise the DNA sequence of the present invention provided in FIGS. 54, 55, 56, the specification, functional parts thereof, or combinations thereof.

Another embodiment of the present invention are diphtheria toxin fusion proteins having reduced vascular leakage consisting of SEQ ID Nos: 10, 15, 43, 13, 58, 60, 62, 64, 66, 68, 70, 72, 74, 76, 78, 80, 82, 84, 86, 88, 90, 92, 94, 111, 113, 115, 117, 119, 121, 123, 125, 127, 129, functional parts thereof, or a combination thereof.

Another embodiment of the present invention are nucleic acid sequences that encode diphtheria toxin fusion protein having reduced vascular leakage illustrated in FIG. 56 including SEQ ID NOs 61, 63, 65, 67, 69, 71, 73, 75, 77, 79, 81, 83, 85, 87, 89, 91, 93, 95, 112, 114, 116, 118, 120, 122, 124, 126, 128, 130, functional parts, or combinations thereof. These DNA sequences are typically included in an expression vector.

Another embodiment of the present invention is a method of treating or preventing vascular leak syndrome by administering s-DAB1-389-IL2-V6A, s-DAB1-389-IL2-D3E, other single or double mutant protein described in FIG. 56, functional parts thereof, or a combination thereof to a subject having or prone of getting vascular leak syndrome. Treating or preventing vascular leak syndrome in the patient compared to a reference subject who was not administered s-DAB1-389-IL2-V6A, s-DAB1-389-IL2-D3E, other single or double mutant protein described in FIG. 56, functional parts thereof, or a combination thereof.

Another embodiment of the present invention is a method of treating or preventing colon, renal, and/or breast cancer in subject by administering s-DAB1-389-IL2-V6A, s-DAB1-389-IL2-D3E, other single or double mutant proteins provided described in FIG. 56, functional parts thereof, or a combination thereof to a subject having or prone of getting colon, renal, and/or breast cancer. Treating or preventing the cancer in the subject compared to a reference subject who was not administered s-DAB1-389-IL2-V6A, s-DAB1-389-IL2-D3E, other single or double mutant proteins provided described in FIG. 56, functional parts thereof, or a combination thereof.

Another embodiment of the present invention is a method of depleting myeloid derived suppressor cells in a subject by administering s-DAB1-389-IL2-V6A, s-DAB1-389-IL2-D3E, DAB1-389-hIL4-V6A, s-DAB1-389-hIL4-D3E, or a combination thereof to a subject and depleting myeloid derived suppressor cells in the subject compared to a reference subject who was not administered s-DAB1-389-IL2-V6A, s-DAB1-389-IL2-D3E, DAB1-389-hIL4-V6A, s-DAB1-389-hIL4-D3E or a combination thereof.

Another embodiment of the present invention is a method of depleting a tumor that is CD124+ by administering s-DAB1-389-IL4-V6A, s-DAB1-389-IL4-D3E, or a combination thereof to a subject having or prone of getting a CD124+ tumor, and depleting the tumor compared to a reference subject who was not administered s-DAB1-389-IL4-V6A, s-DAB1-389-IL4-D3E, or a combination thereof. An example of a CD124+ tumor is triple negative breast cancer.

Another embodiment of the present invention is a method of depleting a tumor expressing a EGFR comprising the steps of administering s-DAB1-389-EGF-V6A, s-DAB1-389-EGF-D3E or a combination thereof to a subject having or prone of getting a tumor expressing a EGFR. Depleting the tumor in the subject compared to a reference subject who has not been administered s-DAB1-389-EGF-V6A, s-DAB1-389-EGF-D3E or a combination. An example of a tumor carrying EGFR is glioblastoma multiforme.

BRIEF DESCRIPTION OF THE DRAWINGS

FIG. 1*a*-1*b* illustrates: a) a mutant toxO of the present invention (SEQ ID NO: 1), b) a wild type toxO (SEQ ID NO: 25), and c) a DtxR consensus binding sequence.

FIG. 2*a*-2*b* illustrates: a) illustrates the classic denileukin diftitox (c-denileukin diftitox) expression vector used to manufacture Ontak® and b) illustrates the secreted denileukin diftitox (s-denileukin diftitox) expression vector including the tox promoter (toxP), and mutant toxO of the present invention. FIG. 2*a* discloses SEQ ID NO: 26 and FIG. 2*b* discloses SEQ ID NO: 27.

FIG. 5 illustrates that c-denileukin diftitox-VLM has significantly less acute toxicity in vivo than c-Ontak® using a mouse survival model.

FIG. 6 illustrates a diphtheria toxin-based fusion protein toxin platform technology of the present invention.

FIG. 7 illustrates plasmid pKN2.6Z-LC127 with the tox promoter (toxP of SEQ ID NO: 2) and a mutant tox operator (toxO) (DNA SEQ ID NO: 1), a signal peptide (DNA SEQ ID NO: 4) attached to c-denileukin diftitox DNA sequences (DNA SEQ ID NO: 6).

FIG. 8*a*-8*b* illustrates: a) the problems of the conventional process of manufacturing Ontak® as cytoplasmic inclusion bodies in *E. coli* and *b*) illustrates easy and clean manufacturing process of producing a secreted-denileukin diftitox having one less amino acid than the Ontak® protein. FIG. 8*a* discloses "fMGADD" as SEQ ID NO: 28 and FIG. 8*b* discloses "GADD" as SEQ ID NO: 29.

FIG. 9 illustrates an immunoblot of s-denileukin diftitox prepared by the process of the present invention where s-denileukin diftitox is expressed within a *Corynebacterium diphtheriae* strain C7 beta (−), tox (−) and is secreted into the culture medium.

FIG. 10 illustrates how a denileukin diftitox of the present invention, is expected to deplete IL-2R (CD25+) bearing T cells ($T_{regs}$) within a tuberculosis granuloma. $T_{regs}$ are immunosuppressive by their inhibition of $T_{eff}$ cells.

FIG. 11 illustrates diphtheria fusion proteins used in the in vivo treatment of subjects (mice) with *M. tuberculosis.*

FIG. 12 illustrates the results of treating subjects (mice) infected with *M. tuberculosis* with diphtheria toxin-based fusion proteins.

FIG. 13 illustrates a diphtheria toxin-based fusion protein regimen for treating subjects (mice) infected with *M. tuberculosis.*

FIG. 14 illustrates the use of a diphtheria toxin-based fusion protein to treat subjects (humans) with malignant melanoma.

FIG. 15 illustrates the three constructs for rapid production of VLM s-Ontak and related proteins using His (histidine tags) ("$His_6$/6×His" and "$His_9$/9×His" disclosed as SEQ ID NOs: 23 and 48, respectively).

FIG. 16 illustrates purified VLM s-Ontak-$His_6$ SEQ ID NO: 43 ("$His_6$" disclosed as DNA SEQ ID NO: 23) at greater than 97% purity produced using the C-terminal $His_6$ VLM s-Ontak construct ("$His_6$" disclosed as SEQ ID NO: 23). Specifically, a recombinant *C. diphtheriae* harboring a gene construct encoding VLM s-Ontak-$His_6$ ("$His_6$" disclosed as SEQ ID NO: 23) was grown to an optical density (OD) of ~12. The culture supernatant was harvested, concentrated by tangential flow filtration using a 30 kDa molecular weight cut-off membrane, and diafiltered for buffer exchange using tangential flow filtration as above. The protein mixture was partially purified by Ni-affinity chromatography and then purified to greater than 97% by gel permeation chromatography using S-100 resin. The resulting VLM s-Ontak-$His_6$ SEQ ID NO: 43 ("$His_6$" disclosed as SEQ ID NO: 23) was >97% pure.

FIG. 21 left shows the weights of groups of 5 mice treated with *C. diphtheriae*-derived SEQ ID NO: 43 or with *C. diphtheriae*-derived SEQ ID NO: 58 daily for 17 days or until death at the doses shown. FIG. 21 right shows the Kaplan-Meier survival curve for groups of 5 mice treated with *C. diphtheriae*-derived SEQ ID NO: 43 or with *C. diphtheriae*-derived SEQ ID NO: 58 daily for 17 days or until death at the doses shown.

FIG. 22 illustrates that *C. diphtheriae*-derived SEQ ID NO: 43 is equivalent to *E. coli*-derived SEQ ID NO: 10 in in vitro cell killing and is equivalent to *C. diphtheriae*-derived SEQ ID NO: 58 in melanoma tumor growth inhibition in vivo. FIG. 22 right: the mouse B16F10 melanoma allograft model was performed as described using groups of 5 mice. PBS or the fusion toxins shown were given on day 7 and day 10 post-tumor cell injection at doses of 5 μg per mouse per treatment. The day 22 tumor volumes of *C. diphtheriae*-derived SEQ ID NO: 43-treated and *C. diphtheriae*-derived SEQ ID NO: 58-treated mice were not statistically different from each other. However, tumor volumes of PBS-treated mice were statistically larger ($p<0.05$) than those mice receiving *C. diphtheriae*-derived SEQ ID NO: 43 or *C. diphtheriae*-derived SEQ ID NO: 58. FIG. 22, left: the $IC_{50}$ of *C. diphtheriae*-derived SEQ ID NO: 43 against HUT-102 cells (human T cell lymphoma cells strongly CD25-positive) in vitro compared with the $IC_{50}$ of *E. coli*-derived SEQ ID NO: 10 against the same cells.

FIG. 23 illustrates that *C. diphtheriae*-derived SEQ ID NO: 43 and *C. diphtheriae*-derived SEQ ID NO: 58 deplete Treg cells in vivo in mice. FIG. 23 left: results showing the percent of CD25-positive, FoxP3-positive CD4 cells for mouse splenocytes prepared from treated mice. FIG. 23 right: results showing the percent of CD25-positive, FoxP3-negative CD4 cells for mouse splenocytes prepared from treated mice. Data shown are for *C. diphtheriae*-derived SEQ ID NO: 58. Similar results were observed for *C. diphtheriae*-derived SEQ ID NO: 43.

FIG. 24 illustrates that dual sequential therapy with *C. diphtheriae*-derived SEQ ID NO: 43+anti-PD1 gives improved melanoma tumor growth inhibition compared with either drug used as monotherapy alone. The experiment was performed using the B16F10 melanoma allograft model in C57BL/6 mice with drugs given as indicated at the doses shown. Anti-PD-1 was given at 100 μg per dose per mouse. The tumor volumes of anti-PD-1 plus *C. diphtheriae*-derived SEQ ID NO: 43-treated mice at day 25 were significantly smaller than those of anti-PD-1 isotype-control-treated mice with $p<0.05$.

FIG. 25 illustrates that *C. diphtheriae*-derived SEQ ID NO: 58 treatment inhibits melanoma tumor growth and sequential combination therapy with *C. diphtheriae*-derived SEQ ID NO: 58 given first adds to the effectiveness of anti-PD1 when treatment is started on day 7 post tumor cell challenge.

FIG. 26 illustrates that treatment with anti-PD-1 and *C. diphtheriae*-derived SEQ ID NO: 58 leads to increased frequency of CD8+ IFNγ+ lymphocytes in B16F10 tumors than does anti-PD-1 treatment alone or *C. diphtheriae*-derived SEQ ID NO: 58 alone.

FIG. 27 illustrates that *C. diphtheriae*-derived SEQ ID NO: 58 treatment inhibits melanoma tumor growth and sequential combination therapy with *C. diphtheriae*-derived SEQ ID NO: 58 given first adds to the effectiveness of anti-PD1 when treatment is started on day 10 post tumor cell challenge. This later initiation of treatment leads to larger tumor volumes than that shown in FIG. 25 (treatment initiated on day 7). Nevertheless, sequential combination therapy showed potent activity against these large tumors despite the minimal effectiveness of the monotherapies given alone.

FIG. 28 illustrates a cartoon model demonstrating the rationale for sequential, dual immunotherapy with SEQ ID NO: 15 or SEQ ID NO: 43 (or SEQ ID NO: 13 or SEQ ID NO: 58) first followed by checkpoint-inhibitor therapy. As shown, upon checkpoint blockade, Teff cells express the high-affinity IL-2 receptor and are susceptible to SEQ ID NO: 15 or SEQ ID NO: 43 (or SEQ ID NO: 13 or SEQ ID NO: 58). Hence, depletion of Treg cells with SEQ ID NO: 15 or SEQ ID NO: 43 (or SEQ ID NO: 13 or SEQ ID NO: 58) first, followed by subsequent checkpoint blockade enables Teff cell activation in the absence of inhibitory Treg cells leading to improved antitumor effectiveness.

FIG. 29 is an anti-IL2 Western blot of partially purified and concentrated recombinant *C. diphtheriae* culture supernatants harboring construct that express s-Ontak-$His_6$ (SEQ ID NO: 58). Either 10 or 50 microliters of identically prepared culture supernatants were loaded as shown. The blots were developed with short (5 seconds), intermediate (15 seconds) or long (30 seconds) exposure times. The figure illustrates the comparative level of protein yield from two different promoter-operator sequences (SEQ ID NO: 2 and SEQ ID NO: 83) being expressed in two different strains of

Figure 3:
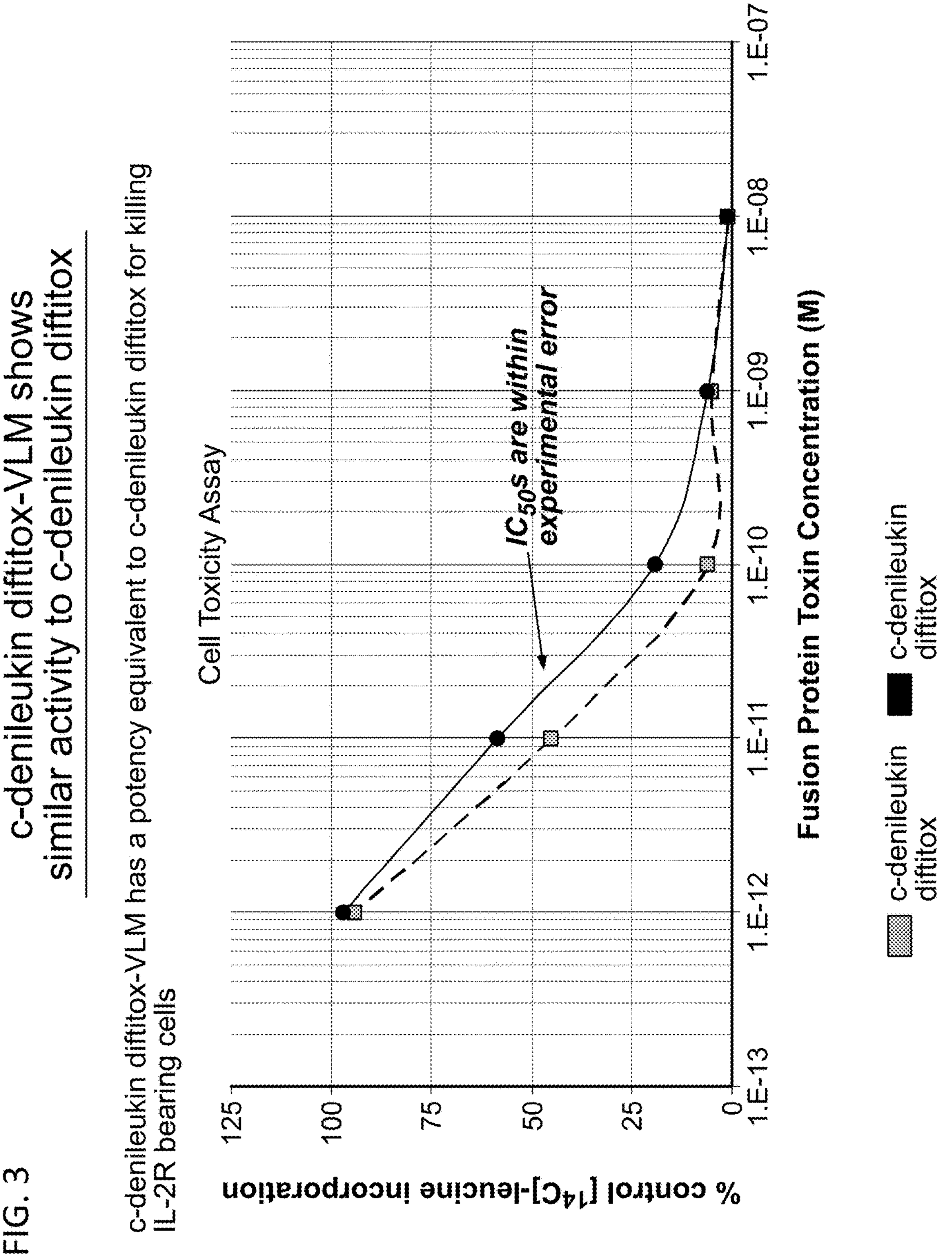
FIG. 3 illustrates a vascular leak mutant (VLM) called c-denileukin diftitox-VLM has equivalent potency to c-denileukin diftitox in killing IL2-receptor-bearing cells.

*C. diphtheriae* C7(−) (wild type and the DdtxR mutant). As may be seen there is a significantly improved level of expression of the desired full length 58 kDa s-Ontak-$His_6$ protein (SEQ ID NO: 58) with the wild type (WT) promoter-operator sequence (SEQ ID NO: 83) being expressed in the DdtxR mutant (red arrow).

FIG. 30 illustrates the use of hydrophobic interaction chromatography to partially purify SEQ ID NO 15 and related proteins.

FIG. 31 illustrates the depletion of Tregs ($CD3^+$ $CD4^+$ $CD25^+$ $FoxP3^+$) and activated Tregs ($CD3^+$ $CD4^+$ $CD25^+$ $FoxP3^+$ $CD39^+$) by SEQ ID NO: 43 within tumors in the murine 4T1 cell model of triple negative breast cancer. Groups of mice received 20,000 4T1 cells implanted in their mammary tissue orthotopically on day 0. Mice were treated intraperitoneally on days 10, 12, and 14 with either PBS (Group 1) or 10 μg of SEQ ID NO 43 (s-Ontak-V6A-$His_6$, Group 2). Mice were sacrificed on day 17 post-tumor implantation, and tumors were removed. The tumors were dispersed into single cell preparations and then subjected to flow cytometry.

FIG. 32 shows the anti-tumor effects of SEQ ID NO: 43 when used as monotherapy or sequentially as dual therapy with an anti-PD1 antibody in the mouse B16 melanoma syngeneic tumor model. As may be seen, SEQ ID NO: 43 is a potent monotherapy. Moreover, when used as initial therapy followed by anti-PD1 (with no overlapping of doses) as dual sequential therapy, SEQ ID NO: 43 adds substantially to the efficacy of anti-PD1

FIG. 33 shows that shows the anti-tumor effects of SEQ ID NO: 43 are retained even when used late in the course of tumor progression (day 10). The data show SEQ ID NO: 43 is active as monotherapy or sequentially as dual therapy with an anti-PD1 antibody in the mouse B16 melanoma syngeneic tumor model when therapy is started at day 10 post-tumor implantation (as opposed to day 7). As may be seen, SEQ ID NO: 43 is a potent monotherapy. Moreover when used as dual sequential therapy, SEQ ID NO: 43 adds substantially to the efficacy of anti-PD1. This figure demonstrates that the activity of SEQ ID NO: 43 (as monotherapy or dual sequential therapy) is demonstrable even when starting therapy late during tumor progression.

Figure 34:
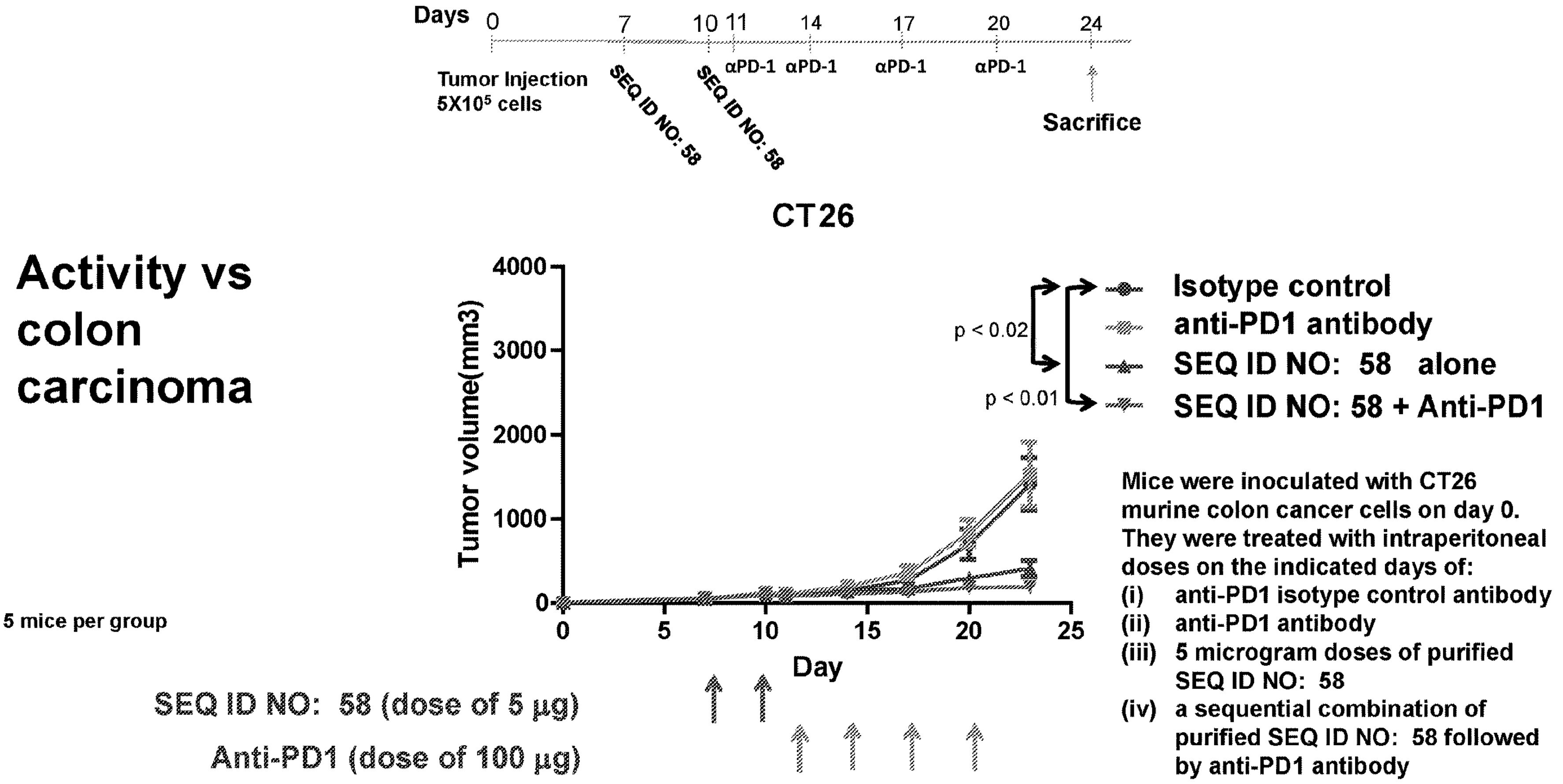

FIG. 34 shows the anti-tumor effects of SEQ ID NO: 58 in the CT26 syngeneic colon carcinoma murine model. As shown, groups of 5 mice were used, and $5\times10^5$ tumor cells were implanted on day 0. Treatment was then given with either anti-PD1 isotype control antibody, anti-PD1 monotherapy, SEQ ID NO: 58 (s-Ontak-$His_6$) monotherapy, or SEQ ID NO: 58 plus anti-PD1 antibody by IP injection on the indicated days. The graph shows the serial tumor volumes over time. As may be seen monotherapy with SEQ ID NO: 58 and dual sequential therapy with SEQ ID NO: 58 followed by anti-PD1 provided good control of tumor growth.

FIG. 35 shows the anti-tumor effects of SEQ ID NO: 58 in the RENCA cell syngeneic renal cell carcinoma murine model. As shown, groups of 7 mice were used, and $5\times10^5$ tumor cells were implanted on day 0. Treatment was then given with either anti-PD1 isotype control antibody, anti-PD1 monotherapy, SEQ ID NO: 58 (s-Ontak-$His_6$) monotherapy, or SEQ ID NO: 58 plus anti-PD1 antibody by IP injection on the indicated days. The graph shows the serial tumor volumes over time. As may be seen monotherapy with SEQ ID NO: 58 and dual sequential therapy with SEQ ID NO: 58 followed by anti-PD1 provided good control of tumor growth. Indeed with SEQ ID NO: 58 monotherapy, 5 of 7 mice had no palpable tumor present at sacrifice on day 20 (the point shown represents the tumor volume of the 2 of 7 mice that had palpable tumors).

FIG. 36 shows that by energy minimization structural analysis, D3E mutation will narrow the distance to VDS motif residue Serine 8 from 4.0 Å to 3.2 Å. By narrowing this inter-residue distance, D3E mutation allows a stronger hydrogen bond between residue 3 and residue 8. This stronger hydrogen bond may have a protein stabilizing effect and limit the exposure of the VDS motif present in residues 6, 7, and 8 in s-Ontak (a known vascular leak inducing tripeptide sequence) to mammalian endothelial cells. Panel A shows a protein structure simulation of SEQ ID NO: 13 (s-Ontak) derived using the Amber ff99SB method described by Hornak et al. (PMID: 16981200). The full protein structure is shown at the bottom and a magnified view of the loop between alpha helix 1 (containing residue D3) and alpha helix 2 (containing residues $V_6D_7S_8$) is shown. Potential hydrogen bonds are shown as dotted lines. Panel B shows that in SEQ ID NO: 13 (s-Ontak), the D3-S8 hydrogen bond distance is 4.0 Å. Panel C shows that by making a D3E substitution, the E3-S8 hydrogen bond distance is reduced to 3.2 Å allowing for a stronger hydrogen bond to form. Panel D shows three new mutations disclosed: D3E (SEQ ID NO: 60), D7E (SEQ ID NO: 64), and S8T (SEQ ID NO: 68). The V6A substitution was previously disclosed (SEQ ID NO: 15).

Figure 37:
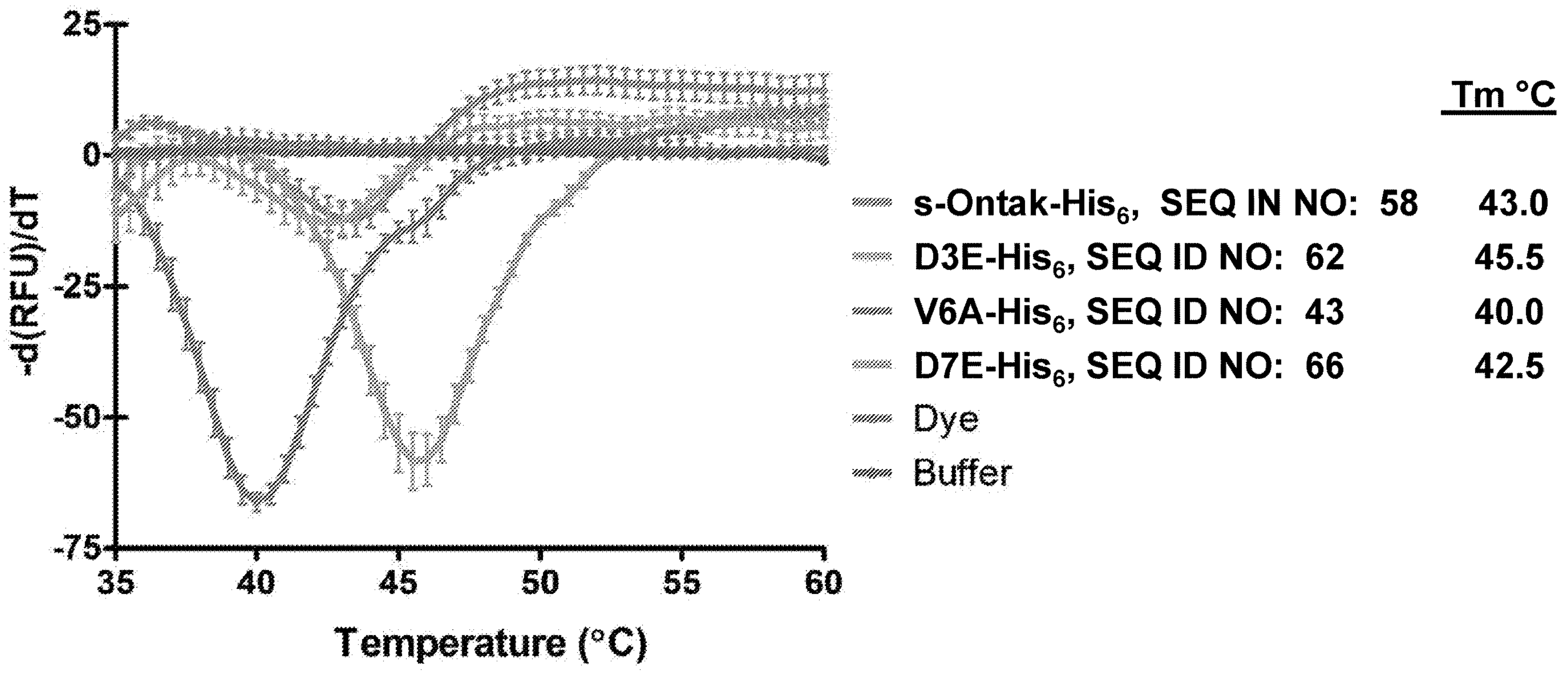

FIG. 37 shows a thermal shift analysis using SYPRO Orange release fluorimetry reveals enhanced thermal stability of the D3E-$His_6$ mutant protein (SEQ ID NO: 62) over s-Ontak-$His_6$ (SEQ ID NO: 58) and other mutant proteins V6A-$His_6$ (SEQ ID NO: 43) and D7E-$His_6$ (SEQ ID NO: 66). As may be seen, the melting temperatures ($T_m$) for the polypeptides in order of highest $T_m$ are: 45.5° C., 43.0° C., 42.5° C., and 40.0° C. for D3E-$His_6$ (SEQ ID NO: 62), s-Ontak-$His_6$ (SEQ ID NO: 58), D7E-$His_6$ (SEQ ID NO: 66), and V6A-$His_6$ (SEQ ID NO: 43), respectively.

Figure 38:
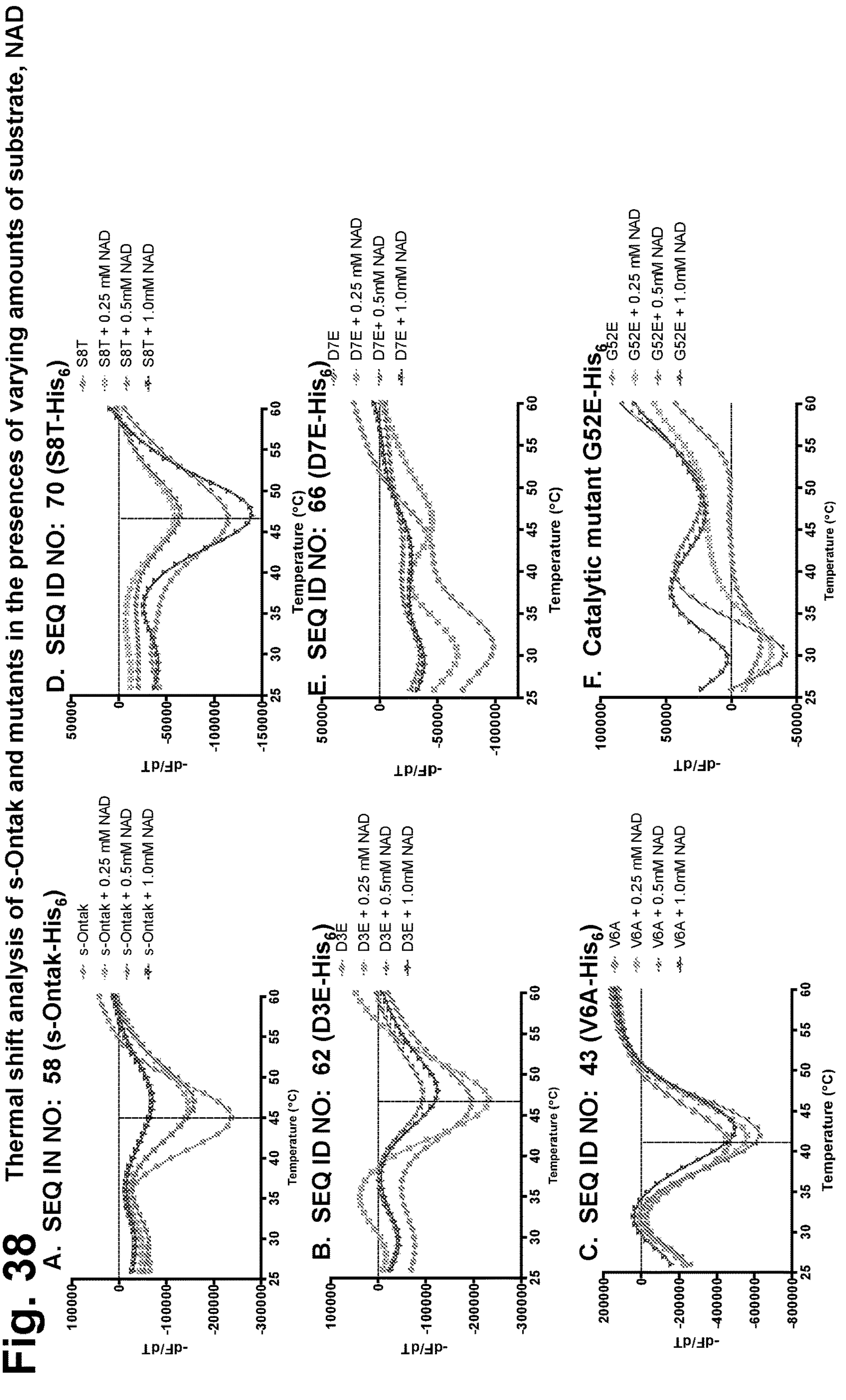

FIG. 38 shows a thermal shift analysis using SYPRO Orange release fluorimetry in the presence of varying amounts of the substrate NAD. As may be seen, increasing amounts of NAD increase the thermal stability (increase the Tm) for SEQ ID NO: 58 (s-Ontak-$His_6$) and SEQ ID NO: 62 (D3E-$His_6$). In contrast, the addition of substrate has little effect on the less stable proteins SEQ ID NO: 43 (V6A-$His_6$), SEQ ID NO: 70 (S8T-$His_6$), or SEQ ID NO: 66 (D7E-$His_6$). Also, the catalytically inactive G52E-$His_6$ mutant form of s-Ontak shows little to no thermal shift with the addition of NAD.

Figure 39:
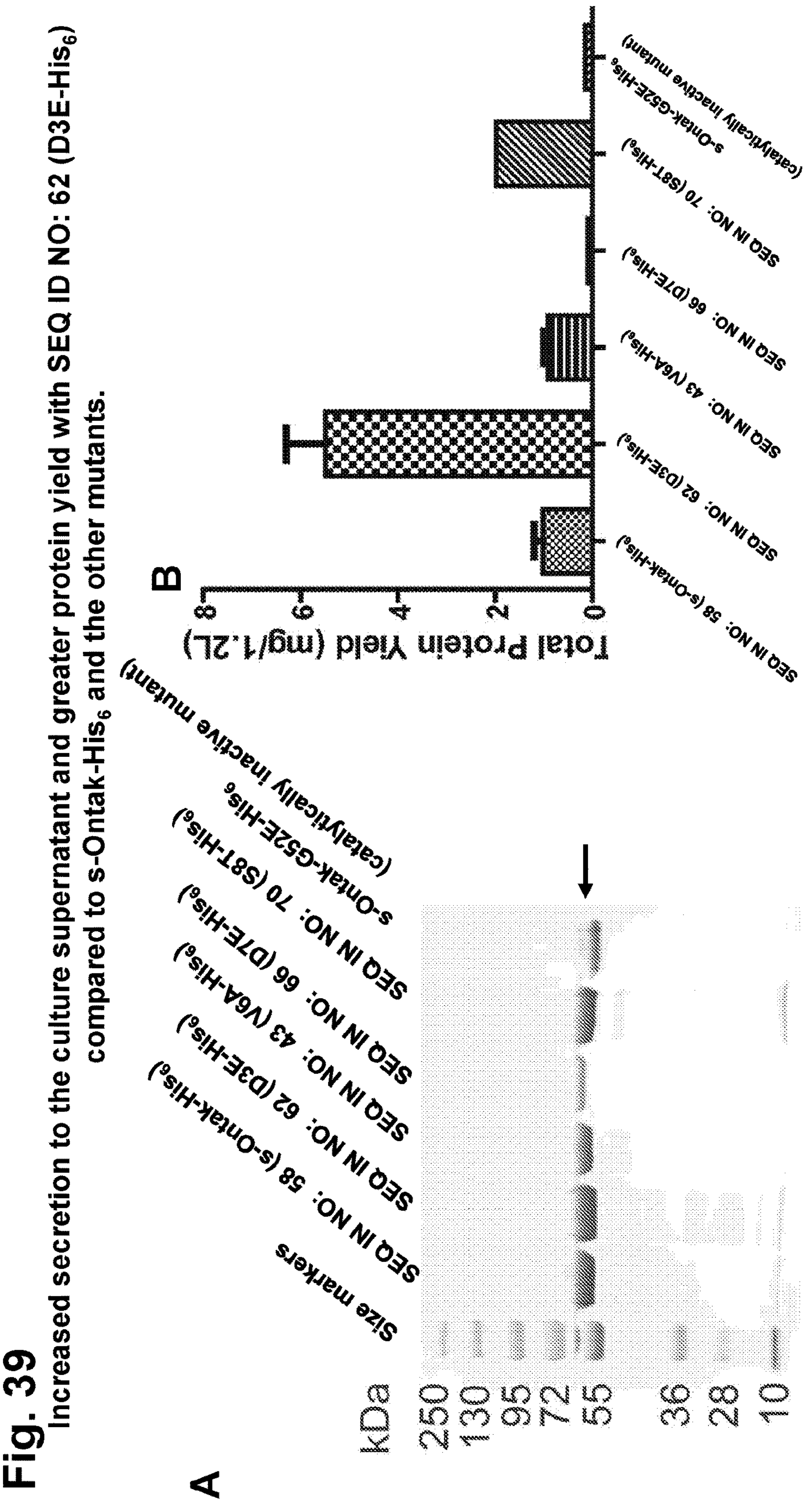

FIG. 39 reveals that the overall protein yield of SEQ ID NO: 62 (D3E-$His_6$) is 4-fold higher than that of SEQ ID NO: 58 (s-Ontak-$His_6$) in the *Corynebacterium diphtheriae* strain C7(−) expression system. Panel A shows an SDS-PAGE gel stained with Coomassie blue corresponding to equal amounts of purified, concentrated protein from wild type *C. diphtheriae* C7(−) strains harboring plasmids that carry DNA sequences encoding s-Ontak-$His_6$, D3E-$His_6$, V6A-$His_6$, and S8T-$His_6$, respectively) as well as an analogous plasmid construct encoding for the catalytically inactive version of s-Ontak, G52E. Each plasmid was under the control the $P_{tox}$ (WT)-mutant operator sequence disclosed as SEQ ID NO: 2. Purified protein corresponding to SEQ ID NO: 58, 62, 43, 66, 70 and G52E (s-Ontak-$His_6$, D3E-$His_6$, V6A-$His_6$, and S8T-$His_6$ proteins, respectively) was prepared in each case from 1.2 liter fermenter runs with identical media and growth parameters. The proteins indicated were then purified in identical fashion from the culture supernatant as described by Cheung et al (PMID 30718426) with concentration by tangential flow filtration and diafiltration followed by initial purification by Ni-affinity chromatography, re-concentration with Amicon centrifugal units, and a final purification on Sephacryl S100HR gel permeation chromatography. The arrow shows 58 kDa, the anticipated molecular mass of the fusion proteins. Panel B shows the yield of pure protein in milligrams per liter of fermenter culture.

FIG. 40 shows that SEQ ID NO: 62 (D3E-$His_6$) retains nearly full activity in killing $CD25^+$ cells compared with SEQ ID NO: 58 (s-Ontak-His). However, as previously disclosed SEQ ID NO: 43 (V6A-$His_6$) is 3-5-fold less active. Shown are cytotoxic activity of s-Ontak-$His_6$ and related mutant proteins for the $CD25^+$ MT-2 cell line (adult T-cell leukemia, NIH AIDS Reagent Program Catalog number 237). MT-2 cells were prepared and treated with the diphtheria toxin fusion proteins indicated as described in Cheung et al. (PMID: 30718426). MTS reagent (Promega) was used to measure cell proliferation capacity. Panels A-D and panel F show the killing curves with $IC_{50}$ values for SEQ ID NO: 62, 43, 66, 70 and 58 (D3E-$His_6$, V6A-$His_6$, D7E-$His_6$, S8T-$His_6$ proteins, and s-Ontak-$His_6$), respectively. Panel E shows the same data for s-Ontak-G52E-$His_6$ (catalytically inactive). Panel H shows the IC50 values as well as the potencies of the proteins relative to s-Ontak. As may be seen the relative potency of SEQ ID NO: 62 (D3E-$His_6$) is 0.84, while that of SEQ ID NO: 43 (V6A-$His_6$) is 0.20. It is important to note that the $IC_{50}$ values determined by MT-2 cell assay can be somewhat variable (probably due to cell line passage number and the abundance of CD25 receptors), so the values shown vary somewhat from those disclosed in earlier figures However the relative potency values are generally consistent with this assay. Please note that in earlier disclosed data SEQ ID NO: 58 (s-Ontak-$His_6$) had an MT-2 cell $IC_{50}$ of 0.12 pM and SEQ ID NO: 43 (V6A-$His_6$) had an IC50 of 0.33 pM. The relative potency of V6A to s-Ontak in that instance was 0.36, which is comparable to the value in FIG. 40 of 0.20.

FIG. 41 shows the results of HUVEC monolayer permeation assays that quantify the level of vascular leak induced by s-Ontak and related proteins. As may be seen, SEQ ID NO: 62 (D3E-$His_6$) and SEQ ID NO: 43 (V6A-$His_6$) give significantly lower levels of vascular leak than SEQ ID NO: 58 (s-Ontak-$His_6$).

FIG. 42 shows the results of HUVEC monolayer permeation assays that quantify the level of vascular leak induced by peptides related to s-Ontak. Peptides 15 amino acids in length were synthesized and purified. The 15-mers span residues 1-15 and residues 23-37 of s-Ontak which contain the vascular leak-associated tripeptide motif (x) D(y) where x is valine, isoleucine, leucine, or glycine and y is serine, leucine, or valine. The drawing shows that peptide 15-mers with D3E, V6A, and D29E substitutions give lower levels of vascular leak than the corresponding wild type 15-mers. FIG. 42 discloses SEQ ID NOS 136-140, respectively, in order of appearance.

FIG. 43 shows that D3E-$His_6$ has a significantly longer half-life than s-Ontak-$His_6$ in mice. Similarly, the half-life of s-Ontak-$His_6$ is significantly longer than that of V6A-$His_6$. The estimated half-lives were s-Ontak-$His_6$ 150 min, D3E-$His_6$ 240 min, and V6A-$His_6$ 60 min, respectively. These half-lives correspond to the protein stability of the respective proteins by thermal shift as shown in FIG. 37 and FIG. 38. The levels of the proteins in mouse serum were determined by biological activity of MT-2 cell ($CD25^+$ adult T-cell leukemia cells) inhibition in serum of mice treated with the various proteins and monitored over time.

FIG. 44 shows that D3E-$His_6$ and s-Ontak-$His_6$ induce similar toxicity in mice. The figure shows weights and lethality curves in mice receiving a range of doses of the two agents. Both s-Ontak-$His_6$, and D3E-$His_6$ lead to weight loss in mice when given at doses of 3.2 mg daily or greater. The minimal lethal dose for s-Ontak-$His_6$ and D3E-$His_6$ is between 3.2 and 10 mg daily.

FIG. 45 shows the anti-tumor effects of SEQ ID NO: 62 (D3E-$His_6$) in the B16 syngeneic melanoma murine model. As shown, groups of 7 mice were used, and $5\times10^5$ tumor cells were implanted on day 0. Treatment was then given with either anti-PD1 isotype control antibody, anti-PD1 monotherapy, SEQ ID NO: 62 (D3E-$His_6$) monotherapy, or SEQ ID NO: 62 plus anti-PD1 antibody by IP injection on the indicated days. The graph shows the serial tumor volumes over time. As may be seen monotherapy with SEQ ID NO: 62 and dual sequential therapy with SEQ ID NO: 62 followed by anti-PD1 provided good control of tumor growth.

FIG. 46 shows that SEQ ID NO: 98 (s-$DAB_{1-389}$-mIL4-V6A-$His_6$) is expressed from *C. diphtheriae* C7(−) and is readily purified from the culture supernatant. Purified protein corresponding to SEQ ID NO: 98 was prepared in a 3 liter fermenter run. The expression construct was a fusion of SEQ ID NO: 2 ($P_{tox}$ with a mutant operator) driving SEQ ID NO: 101 (DNA encoding s-$DAB_{1-389}$-mIL4-V6A-$His_6$). The protein was purified from the culture supernatant as described by Cheung et al (PMID 30718426) with concentration by tangential flow filtration and diafiltration followed by initial purification by Ni-affinity chromatography, re-concentration with Amicon centrifugal units, and a final purification on Sephacryl S100HR gel permeation chromatography. The arrow shows 57.2 kDa, the anticipated molecular mass of the fusion protein.

FIG. 47 shows that SEQ ID NO: 134 (s-$DAB_{1-389}$-mIL4-$His_6$) is active in killing 4T1 triple-negative breast cancer cells in vitro and that it inhibits 4T1 cell migration in vitro. Panel A shows the results of an $IC_{50}$ determination for the potency of SEQ ID NO: 134 to kill 4T1 cells using Trypan blue to score cell viability. As may be seen the $IC_{50}$ of SEQ ID NO: 134-mediated growth inhibition was 10 pM. Panel B shows the results of an assay scoring 4T1 cell migration in a clonogenic assay using Giemsa staining to visualize cell migration from the midpoint of the well where cells were initially inoculated. As may be seen the $IC_{50}$ of SEQ ID NO: 134-mediated migration inhibition was 800 pM. The concentrations (nM) of SEQ ID NO: 134 are shown on the left edge of the panel.

FIG. 48 shows that SEQ ID NO: 134 (s-$DAB_{1-389}$-mIL4-$His_6$) is active in killing 4T1 triple-negative breast tumors in mice, depletes myeloid derived suppressor cells (MDSCs) in mice, and reduces lung metastases in mice. Groups of mice received 20,000 4T1 cells implanted in their mammary tissue orthotopically on day 0. Mice were treated intraperitoneally on days 8, 11, 13, 15, 18, 20, 22, and 25 with either PBS (Group 1), 5 μg of SEQ ID NO 134 (s-$DAB_{1-389}$-mIL4-$His_6$, Group 2), or 10 □g of SEQ ID NO 134 (s-$DAB_{1-389}$-mIL4-$His_6$, Group 3) as shown by the scheme in Panel A. Panel A shows the tumor volumes for the three groups over time and reveals a dose-dependent inhibition of tumor growth by SEQ ID NO: 134. Panel B shows that treatment with SEQ ID NO: 134 significantly reduced the percentage of $CD124^+$ MDSCs in the mouse spleens with MDSCs defined as being CD45+ CD11b+ Gr1+ cells. Panel C shows the abundance of lung metastases in mice in this model when sacrificed at day 27, and it reveals a dose-dependent inhibition of tumor metastases by SEQ ID NO: 134.

Figure 49:
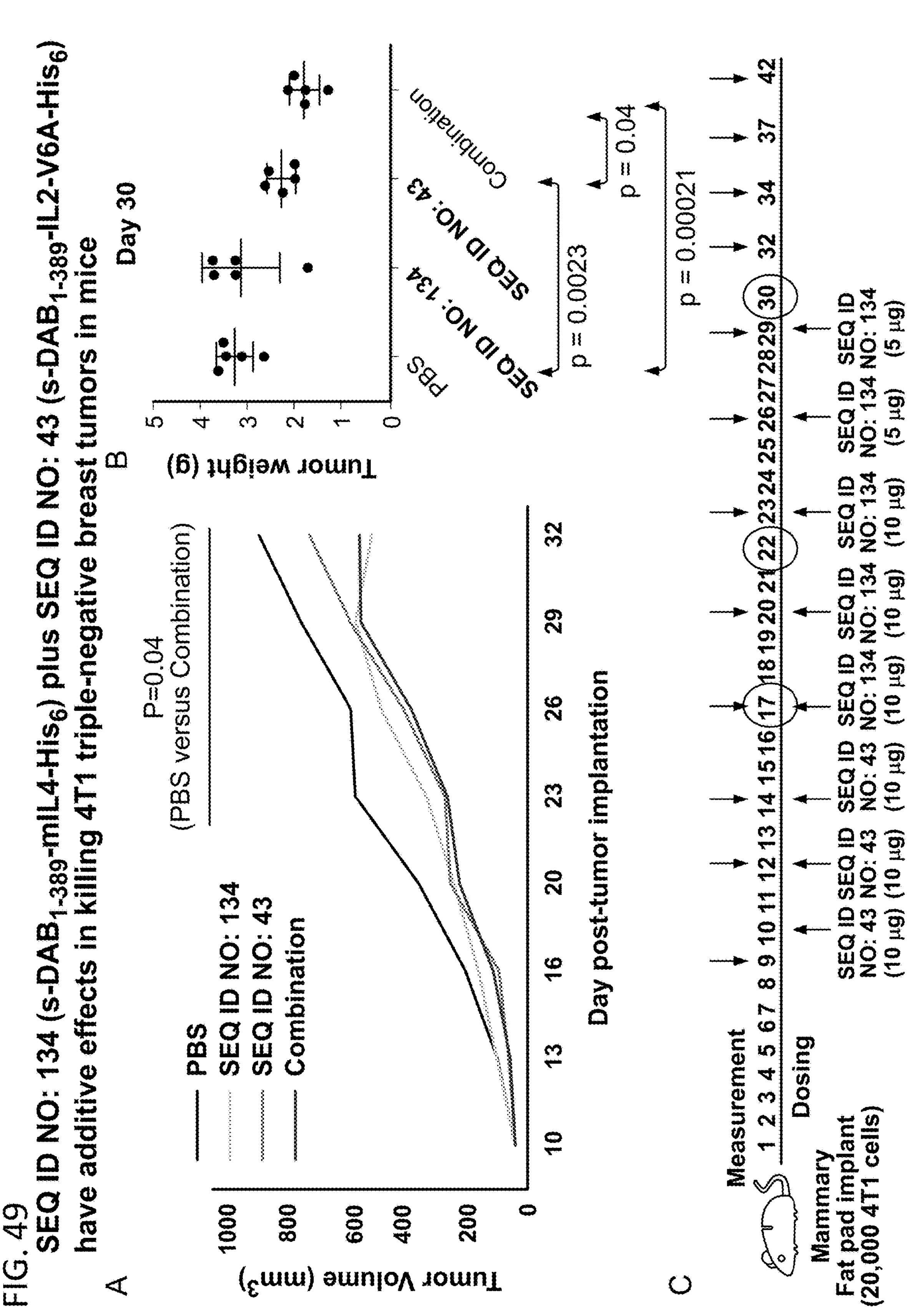

FIG. 49 shows that SEQ ID NO: 134 (s-DAB$_{1-389}$-mIL4-His$_6$) plus SEQ ID NO: 43 (s-DAB$_{1-389}$-IL2-V6A-His$_6$) have additive effects in killing 4T1 triple-negative breast tumors in mice. Groups of mice received 20,000 4T1 cells implanted in their mammary tissue orthotopically on day 0. Group 1 mice received PBS on days 10, 12, 14, 17, 20, 23, 26 and 29 intraperitoneally. Group 2 mice received 10 pg of SEQ ID NO: 43 (s-DAB$_{1-389}$-IL2-V6A-His$_6$) on days 10, 12, and 14 intraperitoneally. Group 3 mice received 10 pg of SEQ ID NO 134 (s-DAB$_{1-389}$-mIL4-His$_6$) on days 17, 20, and 23 intraperitoneally and 5 pg of SEQ ID NO 134 (s-DAB$_{1-389}$-mIL4-His$_6$) on days 26 and 29 intraperitoneally. Group 4 mice received both SEQ ID NO: 134 (s-DAB$_{1-389}$-mIL4-His$_6$) plus SEQ ID NO: 43 (s-DAB$_{1-389}$-IL2-V6A-His$_6$) with 3 doses of SEQ ID NO: 43 as were given to Group 2 mice and 5 doses of SEQ ID NO: 134 as were given to Group 3 mice. Panel A shows the tumor volumes for the four groups as measured over the course of the experiment. Panel B shows the tumor weights at necropsy on day 30. Panel C shows the experimental scheme: green arrows indicate tumor volume assessments, yellow circles indicate sacrifice dates, blue arrows indicate dosing of SEQ ID NO: 43, and red arrows indicate dosing of SEQ ID NO: 134. “Combination” refers to Group 4 mice, which received a combination of 3 doses of SEQ ID NO: 43 and 5 doses of SEQ ID NO: 134.

Figure 50:
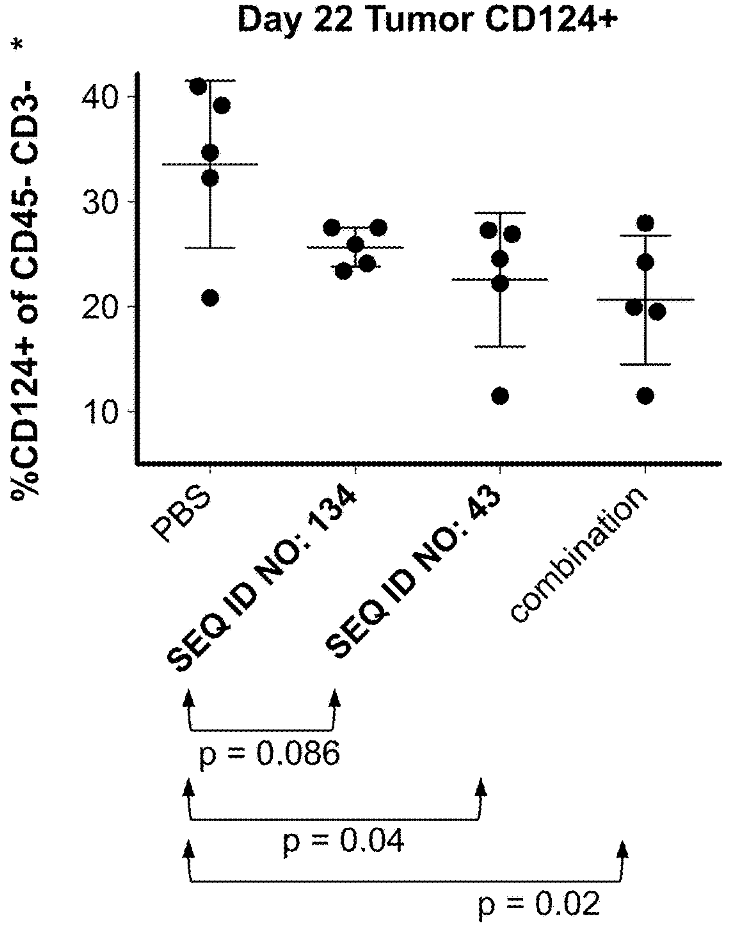

FIG. 50 shows that SEQ ID NO: 134 (s-DAB$_{1-389}$-mIL4-His$_6$), SEQ ID NO: 43 (s-DAB$_{1-389}$-IL2-V6A-His$_6$), and combination therapy with both agents deplete CD124$^+$ tumor cells in the mouse 4T1 model of triple negative breast cancer. Mice were injected with 4T1 breast cancer tumor cells in mammary tissue orthotopically on day 0 and treated with SEQ ID NO: 134 (s-DAB$_{1-389}$-mIL4-His$_6$), SEQ ID NO: 43 (s-DAB$_{1-389}$-IL2-V6A-His$_6$), and combination therapy according the schedule shown in FIG. 49. Tumors were removed from mice sacrificed on day 22 post-tumor implantation. The tumors were dispersed into single cell preparations and then subjected to flow cytometry. Tumor cells were CD45$^-$ CD3$^-$, and the percent of CD124$^+$ cells among CD45$^-$ CD3$^-$ cells was determined (CD124=IL4-receptor).

FIG. 51 shows that SEQ ID NO: 134 (s-DAB$_{1-389}$-mIL4-His$_6$), SEQ ID NO: 43 (s-DAB$_{1-389}$-IL2-V6A-His$_6$), and combination therapy with both agents deplete CD124$^+$ myeloid derived suppressor cells (MDSCs) in the mouse 4T1 model of triple negative breast cancer. Mice were injected with 4T1 breast cancer tumor cells in mammary tissue orthotopically on day 0, and mice were treated with SEQ ID NO: 134 (s-DAB$_{1-389}$-mIL4-His$_6$), SEQ ID NO: 43 (s-DAB$_{1-389}$-IL2-V6A-His$_6$), and combination therapy according the schedule shown in FIG. 49. Splenocytes were prepared from mice sacrificed on day 22 and day 30 post-tumor implantation. MDSCs are defined as being CD45$^+$ CD11b$^+$ Gr1$^+$ cells, and the percent of CD124$^+$ cells among CD45$^+$ CD11b$^+$ Gr1$^+$ cells was determined (CD124=IL4-receptor).

FIG. 52 shows that SEQ ID NO: 106 (s-DAB$_{1-389}$-EGF-V6A-His$_6$) is expressed from *C. diphtheriae* C7 (–) and is readily purified from the culture supernant. Purified protein corresponding to SEQ ID NO: 106 was prepared in a 3 liter fermenter run. The expression construct was a fusion of SEQ ID NO: 2 ($P_{tox}$ with a mutant operator) driving SEQ ID NO: 107 (DNA encoding s-DAB$_{1-389}$-EGF-V6A-His$_6$). The protein was purified from the culture supernatant as described by Cheung et al (PMID 30718426) with concentration by tangential flow filtration and diafiltration followed by initial purification by Ni-affinity chromatography, re-concentration with Amicon centrifugal units, and a final purification on Sephacryl S100HR gel permeation chromatography. Panel A is a Coomassie-blue-stained SDS-PAGE gel with the purified protein run in the absence and presence of beta-mercaptoethanol (βME). The arrow shows 48 kDa, the anticipated molecular mass of the fusion protein. Panel B shows immunoblots prepared from SDS-PAGE gels with the purified protein run in the absence and presence of beta-mercaptoethanol (βME) as shown. The blots were developed with antibodies against EGF (α-EGF), diphtheria toxin (α-Diph. Toxin), and His$_6$ (a-His$_6$) as shown (“His$_6$” disclosed as SEQ ID NO: 23).

FIG. 53 shows that SEQ ID NO: 106 (s-DAB$_{1-389}$-EGF-V6A-His$_6$) is active in killing EGF-receptor (EGFR) positive cells. Shown is the cytotoxic activity of SEQ ID NO: 106 for the A431 epidermoid carcinoma cell line which expresses high levels of the EGFR. A431 cells were prepared and treated with SEQ ID NO: 106 for 42 hours and 72 hours as described in Cheung et al. (PMID: 30718426). MTS reagent (Promega) was used to measure cell proliferation capacity. The IC50 of SEQ ID NO: 106 for A431 cells was found to be 300 pM (42 hour time point).

FIG. 54 shows biological sequences of SEQ ID NOs: 1-59.

FIG. 55 shows biological sequences of SEQ ID NOs: 60-135.

FIG. 56 shows groupings of SEQ ID Nos based on characteristics such as vascular leak reduction, new targeting domains, overexpression, and mutants.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term “activity” refers to the ability of a gene to perform its function such as Indoleamine 2,3-dioxygenase (an oxidoreductase) catalyzing the degradation of the essential amino acid tryptophan (trp) to N-formyl-kynurenine.

By “agent” is meant any small molecule chemical compound, antibody, nucleic acid molecule, or polypeptide, or fragments thereof.

By “ameliorate” is meant decrease, suppress, attenuate, diminish, arrest, or stabilize the development or progression of a disease.

By “alteration” is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.”

By “analog” is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

c- means "classic" when attached to a term such as c-denileukin diftitox means Ontak® or that commercially available protein.

By "disease" is meant any condition or disorder that damages or interferes with the normal function of a cell, tissue, or organ. Examples of diseases include cancer and tuberculosis.

The term "DT" refers to diphtheria toxin.

The terms "DT" and "s-DAB" are used interchangeably and refers to secreted forms of diphtheria toxin fragment A and part of fragment B.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "EGF" is meant epidermal growth factor.

By "EGFR" is meant epidermal growth factor receptor.

The term "express" refers to the ability of a gene to express the gene product including for example its corresponding mRNA or protein sequence (s).

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids is- means "immature secreted" when attached to a term such as is-denileukin diftitox means immature secreted denileukin diftitox that contains a signal peptide.

ms- means "mature secreted" when attached to a term such as ms-denileukin diftitox means mature secreted denileukin diftitox that has been processed and no longer contains a signal peptide.

n- means "new" when attached to a term such as n-denileukin diftitox means new denileukin diftitox.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

The term "purity" refers to the amount of polypeptide of the invention present in a pharmaceutical composition free of other polypeptides. For example, a polypeptide of the invention present in a pharmaceutical composition having a purity of about 80% means that greater than about 80% of polypeptide is full-length and contaminated by less than about 20% of either product-related or unrelated polypeptides. Purity can be determined, for example, by SDS polyacrylamide gel electrophoresis and staining with Coomassie blue, methods which are described in this application or by other methods known to those skilled in the art.

The term "aggregate-free, full-length, monomeric polypeptide" refers to the amount of polypeptide of the invention present in a pharmaceutical composition in monomeric form. For example, a pharmaceutical composition of the invention comprising greater than about 80% aggregate-free, full-length, monomeric polypeptide means that greater than about 80% of the full-length polypeptide is in monomeric form. The amount of aggregate-free, full-length, monomeric polypeptide can be determined, for example, by gel permeation chromatography using known monomeric polypeptides as size standards or by non-reducing, SDS-free native polyacrylamide gel electrophoresis, methods which are described in this application or by other methods known to those skilled in the art.

By "reduces" is meant a negative alteration of at least 10%, 25%, 50%, 75%, or 100%.

A "reference" refers to a standard or control conditions such as a sample (human cells) or a subject that is a free, or substantially free, of an agent such as one or more compositions of the present invention comprising a nucleic acid or protein sequence such as anyone of SEQ ID NOs: 11-15, or fusion proteins thereof.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

s- means "secreted" when attached to a term such as s-denileukin diftitox means secreted denileukin diftitox. Secreted denileukin diftitox includes is- and m-forms.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

VLM- means "vascular leakage mutant" when attached to a tem such as denileukin diftitox-VLM means denileukin diftitox vascular leakage mutant.

w- means "wild type" when attached to a term such as w-diphtheria toxin means wild type-diphtheria toxin.

DETAILED DESCRIPTION OF THE INVENTION

One embodiment of the present invention is the discovery of a process that produces aggregate-free, monomeric, diphtheria toxin fusion proteins having enhanced purity and quality. This process includes transforming bacteria including preferably, strains of *Corynebacterium diphtheria* with DNA expression vectors of the present invention. DNA expression vectors of the present invention are designed to include specific genetic elements comprising a tox promoter (toxP) and an overlapping novel, mutated tox operator (toxO), preferably a signal sequence, and a DNA sequence encoding a protein. The protein is preferably a fusion protein including a diphtheria toxin, or functional part thereof, and a target receptor binding domain or a functional part thereof. The term "functional part thereof" means a part of a diphtheria toxin protein that acts as a toxin or the part of a target receptor binding domain that binds to its receptor. DNA expression vectors of the present invention are designed so proteins are expressed from a tox promoter (toxP) and a mutant tox operator (toxO).

Mutant toxO toxO, is a 19-bp operator region that is composed of two 9 bp imperfect palindromic arms interrupted by a central cytosine (C) base. The wild type toxO (FIG. 1*b*) and a mutant toxO (FIG. 1*a*) operator discovered by inventors are shown in FIG. 1. SEQ ID NO: 1 illustrates one embodiment of the DNA sequence of a mutant toxO this invention. toxP is a promoter having a DNA sequence of SEQ ID NO: 2. SEQ ID NO: 2 illustrates the toxP DNA sequences include the toxO DNA sequences. SEQ ID NO: 3 is a DNA sequence including a toxP, a toxO, a signal peptide, and a DNA sequence encoding a protein. The asterisks in SEQ ID NO: 3 indicate the changes introduced to create the mutant toxO.

SEQ ID NO: 1 (Mutant toxO DNA sequence)
TTAGGATAGCTAAGTCCAT

SEQ ID NO: 2 (toxP including the mutant toxO DNA sequence where the mutant toxO sequence is underlined)

TTGATTTCAGAGCACCCTTATAATTAGGATAGCTAAGTCCAT

The toxO DNA operator sequence is bound by a protein known as the diphtheria toxin repressor, DtxR. DtxR is a global iron-activated regulatory protein that is able to control gene expression. In iron-replete conditions, $Fe^{2+}$ and $Fe^{3+}$ ions bind to apo-DtxR causing a conformational change that allows the formation of homodimers of the DtxR repressor, which bind to the tox operator (toxO) DNA sequence and repress tox gene expression. In low iron environments, $Fe^{2+}$ and $Fe^{3+}$ ions disassociate from DtxR causing it to lose its DNA binding capability and disassociate from the operator; this event thereby allows expression of tox gene products. FIG. 1*b* illustrates the wild type toxO DNA sequence.

To overcome the inhibitory effect of $Fe^{2+}$ and $Fe^{3+}$ ions on tox expression, a DNA expression vector was created replacing the wild type (WT) toxO with a mutant toxO DNA sequence. This change blocks Fe ion-mediated regulation of tox gene expression. FIG. 1*a*, SEQ ID NO: 1, and SEQ ID NO: 3 illustrate the mutant toxO DNA sequence of the present invention. Under this invention, bacteria such as *E. coli* and *C. diphtheriae* harboring a recombinant plasmid encoding a diphtheria toxin fusion protein under the control of toxP and the mutant toxO may be grown in Fe-replete media, allowed to grow to high densities, and will not require a shift to Fe-free media to induce expression. The constitutive expression of tox gene products in iron replete medium represents a significant advance in the field. *C. diphtheriae*, specifically the C7 beta (−), tox (−) strain is the preferred host bacteria for the production of all diphtheria-toxin related recombinant proteins using the DNA expression vectors of the present invention. The DNA expression vectors of the present invention may be used in other bacteria such as *E. coli.*

DNA Expression Vectors

The DNA expression vectors of the present invention includes a toxP, mutant toxO, a DNA sequence encoding a protein, and preferably a signal sequence. SEQ ID NO: 3 is one example of a DNA sequence containing these genetic elements that may be part of a DNA expression vector of the present invention. As mentioned, the asterisks observed in SEQ ID NO: 3 are placed above the base pair changes between the mutant and wild type toxO. SEQ ID NO: 3 is numbered such that the toxP extends from base 1 to 30, and toxO begins at base 24 and ends at base 42 (prior to the underlined DNA sequence). The underlined DNA sequence represents base 74 to base 148 and is a region of DNA encoding a 25 amino acid signal sequence (also observe in SEQ ID NO:4, SEQ ID NO: 5, and FIG. 2). The DNA expression vectors of the present invention are preferably constructed so one or more proteins are expressed from toxP, mutant toxO, and are translated with an N-terminal signal sequence. The N-terminal signal sequence targets the one or more proteins (expressed from the vector) for secretion, and the N-terminal signal peptide is later cleaved to make mature active proteins. SEQ ID NO: 3 includes DNA sequences encoding proteins such as a novel denileukin diftitox called secreted-denileukin diftitox, or s-denileukin diftitox. The s-denileukin diftitox has two forms called immature secreted-denileukin diftitox (is-denileukin diftitox) and mature secreted-denileukin diftitox (ms-denileukin diftitox). SEQ ID NO: 12 is of is-denileukin diftitox of the present invention and SEQ ID NO: 13 is of ms-denileukin diftitox of the present invention. The is-denileukin diftitox contains a signal sequence that during processing is cleaved off to form ms-denileukin diftitox. In addition, SEQ ID NO:3 includes a DNA sequence beginning at base 149 to 1711 that encodes a protein, specifically a fusion protein containing the functional parts of a diphtheria toxin and the functional parts of IL 2. A new denileukin diftitox fusion protein sequence is formed called ms-denileukin diftitox that is a 520 amino acid polypeptide and is composed of the amino acid sequences for diphtheria toxin fragments A and a portion of fragment B ($Gly_1$-$His_{387}$) and the sequences for human interleukin-2 As a result of cleavage of the signal sequence, ms-denileukin diftitox of the present invention lacks the first methionine present in classic-denileukin diftitox (c-denileukin diftitox) and is thereby one amino acid shorter than the amino acid sequence of the classic-denileukin diftitox protein known as Ontak®. SEQ ID NO: 13 is the protein sequence of the new diftitox protein sequence ms-denileukin diftitox which may be compared to SEQ ID NO: 10 containing the protein sequence of the classis-denileukin diftitox (c-denileukin diftitox) known as Ontak®.

DNA expression vectors of the present invention include DNA sequences encoding one or more protein(s). A preferred protein of the present invention is a fusion protein comprising a diphtheria toxin (or a functional part thereof) and a target receptor binding protein (or a functional part thereof). An example of a diphtheria toxin that may be produced from a DNA expression is any functional part of a diphtheria toxin or any functional part of a diphtheria toxin vascular leakage mutant. Examples of proteins of target receptor binding domains produced from a DNA expression vector of the present invention include, IL-2, IL-3, IL-4, IL-6, IL-7, IL-15, EGF, FGF, substance P, CD4, αMSH, GRP, TT fragment C, GCSF, heregulin β1, TNFα, TGFβ, or a combination thereof. Other target receptor binding domains may be used depending upon the therapeutic application; however, SEQ. ID NO. 9 is a preferred DNA sequence encoding a functional part of IL2 receptor binding domain. For the purposes of the present invention, some of the DNA plasmids and the genetic elements thereof are illustrated in FIG. 1, FIG. 2, FIG. 6, and FIG. 7. Examples of fusion proteins encoded by DNA expression vectors of the present invention include SEQ ID NOs: 11, 12, 13, 14, 15, 19, and 21.

(DNA sequence encoding secreted-denileukin diftitox or s-denileukin diftitox. Sequence includes toxP, mutant toxO, signal sequence, a functional part of diphtheria toxin and a functional part of IL2. Bold font and asterisks indicate the changes introduces to create the mutant toxO)

SEQ ID NO: 3

```
                                            **** * *
  1 TTGATTTCAGAGCACCCTTATAATTAGGATAGCTAAGTCCATTATTTTAT

 51 GAGTCCTGGTAAGGGGATACGTTGTGAGCAGAAAACTGTTTGCGTCAATC

101 TTAATAGGGGCGCTACTGGGGATAGGGGCCCCACCTTCAGCCCATGCAGG

151 CGCTGATGATGTTGTTGATTCTTCTAAATCTTTTGTGATGGAAAACTTTT

201 CTTCGTACCACGGGACTAAACCTGGTTATGTAGATTCCATTCAAAAAGGT

251 ATACAAAAGCCAAAATCTGGTACACAAGGAAATTATGACGATGATTGGAA

301 AGGGTTTTATAGTACCGACAATAAATACGACGCTGCGGGATACTCTGTAG

351 ATAATGAAAACCCGCTCTCTGGAAAAGCTGGAGGCGTGGTCAAAGTGACG

401 TATCCAGGACTGACGAAGGTTCTCGCACTAAAAGTGGATAATGCCGAAAC

451 TATTAAGAAAGAGTTAGGTTTAAGTCTCACTGAACCGTTGATGGAGCAAG

501 TCGGAACGGAAGAGTTTATCAAAAGGTTCGGTGATGGTGCTTCGCGTGTA

551 GTGCTCAGCCTTCCCTTCGCTGAGGGGAGTTCTAGCGTTGAATATATTAA

601 TAACTGGGAACAGGCGAAAGCGTTAAGCGTAGAACTTGAGATTAATTTTG
```

-continued

```
 651 AAACCCGTGGAAAACGTGGCCAAGATGCGATGTATGAGTATATGGCTCAA

 701 GCCTGTGCAGGAAATCGTGTCAGGCGATCAGTAGGTAGCTCATTGTCATG

 751 CATCAACCTGGATTGGGATGTTATCCGTGATAAAACTAAAACTAAGATCG

 801 AATCTCTGAAAGAACACGGTCCGATCAAAAACAAAATGAGCGAAAGCCCG

 851 AACAAAACTGTATCTGAAGAAAAAGCTAAACAGTACCTGGAAGAATTCCA

 901 CCAGACTGCACTGGAACACCCGGAACTGTCTGAACTTAAGACCGTTACTG

 951 GTACCAACCCGGTATTCGCTGGTGCTAACTACGCTGCTTGGGCAGTAAAC

1001 GTTGCTCAGGTTATCGATAGCGAAACTGCTGATAACCTGGAAAAAACTAC

1051 CGCGGCTCTGTCTATCCTGCCGGGTATCGGTAGCGTAATGGGCATCGCAG

1101 ACGGCGCCGTTCACCACAACACTGAAGAAATCGTTGCACAGTCTATCGCT

1151 CTGAGCTCTCTGATGGTTGCTCAGGCCATCCCGCTGGTAGGTGAACTGGT

1201 TGATATCGGTTTCGCTGCATACAACTTCGTTGAAAGCATCATCAACCTGT

1251 TCCAGGTTGTTCACAACTCTTACAACCGCCCGGCTTACTCTCCGGGTCAC

1301 AAGACGCATGCACCTACTTCTAGCTCTACCAAGAAAACCCAGCTGCAGCT

1351 CGAGCACCTGCTGCTGGATTTGCAGATGATCCTGAACGGTATCAACAATT

1401 ACAAGAACCCGAAACTGACGCGTATGCTGACCTTCAAGTTCTACATGCCG

1451 AAGAAGGCCACCGAACTGAAACACCTGCAGTGTCTAGAAGAAGAACTGAA

1501 ACCGCTGGAGGAAGTTCTGAACCTGGCTCAGTCTAAAAACTTCCACCTGC

1551 GGCCGCGTGACCTGATCTCTAACATCAACGTAATCGTTCTGGAACTGAAG

1601 GGCTCTGAAACCACCTTCATGTGTGAATACGCTGATGAGACCGCAACCAT

1651 CGTAGAATTCCTGAACCGTTGGATCACCTTCTGTCAGTCTATCATCTCTA

1701 CCCTGACCTGA <1711
```

(Signal DNA Sequence)

SEQ ID NO: 4

```
  74 GTGAGCAGAAAACTGTTTGCGTCAATCTTAATAGGGGCGCTACTGGGGAT

 124 AGGGGCCCCACCTTCAGCCCATGCA <148
```

(Signal Protein Sequence)

SEQ ID NO: 5

```
 -25 MSRKLFASILIGALLGIGAPPSAHA <-1
```

(classic-denileukin diftitox DNA sequence)

SEQ ID NO: 6

```
   1 ATG

   4 GGCGCTGATGATGTTGTTGATTCTTCTAAATCTTTTGTGATGGAAAACTT

  54 TTCTTCGTACCACGGGACTAAACCTGGTTATGTAGATTCCATTCAAAAAG

 104 GTATACAAAAGCCAAAATCTGGTACACAAGGAAATTATGACGATGATTGG

 154 AAAGGGTTTTATAGTACCGACAATAAATACGACGCTGCGGGATACTCTGT

 204 AGATAATGAAAACCCGCTCTCTGGAAAAGCTGGAGGCGTGGTCAAAGTGA

 254 CGTATCCAGGACTGACGAAGGTTCTCGCACTAAAAGTGGATAATGCCGAA

 304 ACTATTAAGAAAGAGTTAGGTTTAAGTCTCACTGAACCGTTGATGGAGCA

 354 AGTCGGAACGGAAGAGTTTATCAAAAGGTTCGGTGATGGTGCTTCGCGTG

 404 TAGTGCTCAGCCTTCCCTTCGCTGAGGGGAGTTCTAGCGTTGAATATATT

 454 AATAACTGGGAACAGGCGAAAGCGTTAAGCGTAGAACTTGAGATTAATTT

 504 TGAAACCCGTGGAAAACGTGGCCAAGATGCGATGTATGAGTATATGGCTC

 554 AAGCCTGTGCAGGAAATCGTGTCAGGCGATCAGTAGGTAGCTCATTGTCA
```

-continued

604 TGCATCAACCTGGATTGGGATGTTATCCGTGATAAAACTAAAACTAAGAT

654 CGAATCTCTGAAAGAACACGGTCCGATCAAAAACAAAATGAGCGAAAGCC

704 CGAACAAAACTGTATCTGAAGAAAAAGCTAAACAGTACCTGGAAGAATTC

754 CACCAGACTGCACTGGAACACCCGGAACTGTCTGAACTTAAGACCGTTAC

804 TGGTACCAACCCGGTATTCGCTGGTGCTAACTACGCTGCTTGGGCAGTAA

854 ACGTTGCTCAGGTTATCGATAGCGAAACTGCTGATAACCTGGAAAAAACT

904 ACCGCGGCTCTGTCTATCCTGCCGGGTATCGGTAGCGTAATGGGCATCGC

954 AGACGGCGCCGTTCACCACAACACTGAAGAAATCGTTGCACAGTCTATCG

1004 CTCTGAGCTCTCTGATGGTTGCTCAGGCCATCCCGCTGGTAGGTGAACTG

1054 GTTGATATCGGTTTCGCTGCATACAACTTCGTTGAAAGCATCATCAACCT

1104 GTTCCAGGTTGTTCACAACTCTTACAACCGCCCGGCTTACTCTCCGGGTC

1154 ACAAGACGCATGCACCTACTTCTAGCTCTACCAAGAAAACCCAGCTGCAG

1204 CTCGAGCACCTGCTGCTGGATTTGCAGATGATCCTGAACGGTATCAACAA

1254 TTACAAGAACCCGAAACTGACGCGTATGCTGACCTTCAAGTTCTACATGC

1304 CGAAGAAGGCCACCGAACTGAAACACCTGCAGTGTCTAGAAGAAGAACTG

1354 AAACCGCTGGAGGAAGTTCTGAACCTGGCTCAGTCTAAAAACTTCCACCT

1404 GCGGCCGCGTGACCTGATCTCTAACATCAACGTAATCGTTCTGGAACTGA

1454 AGGGCTCTGAAACCACCTTCATGTGTGAATACGCTGATGAGACCGCAACC

1504 ATCGTAGAATTCCTGAACCGTTGGATCACCTTCTGTCAGTCTATCATCTC

1554 TACCCTGACCTGA <1566

Formation of Diphtheria Toxin Fusion Proteins Having Minimal, or No, Vascular Leakage (Denileukin Diftitox-VLMs)

Figure 4:
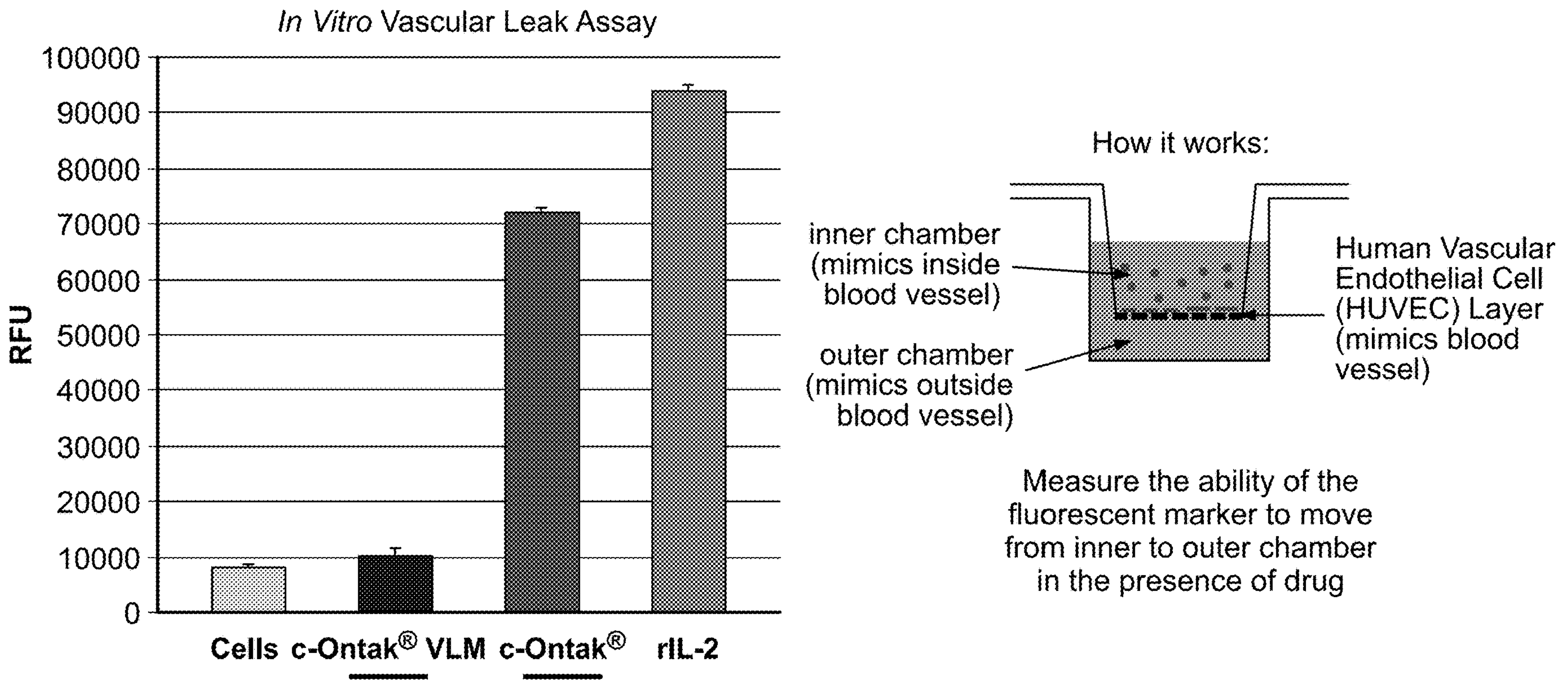
FIG. 4 illustrates c-denileukin diftitox-VLM does not cause vascular leak in vitro.
Figure 17:
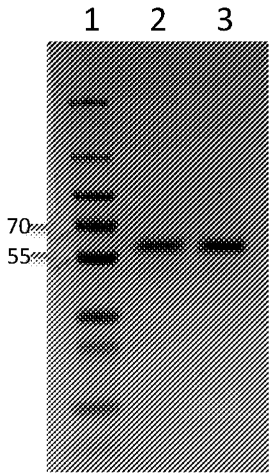
FIG. 17 illustrates purified s-Ontak at greater than 97% purity produced using the C-terminal $His_6$ s-Ontak construct (SEQ ID NOs: 58-59; "$His_6$" disclosed as SEQ ID NO: 23). Specifically, a recombinant *C. diphtheriae* harboring a gene construct encoding s-Ontak-$His_6$ ("$His_6$" disclosed as SEQ ID NO: 23) was grown to OD~12. The culture supernatant was harvested, concentrated by tangential flow filtration using a 30 kDa molecular weight cut-off membrane, and diafiltered for buffer exchange using tangential flow filtration as above. The protein mixture was partially purified by Ni-affinity chromatography and then purified to greater than 97% by gel permeation chromatography using S-100 resin. The resulting s-Ontak-$His_6$ ("$His_6$" disclosed as SEQ ID NO: 23) was >97% pure and stable at 4° C.
Figure 18:
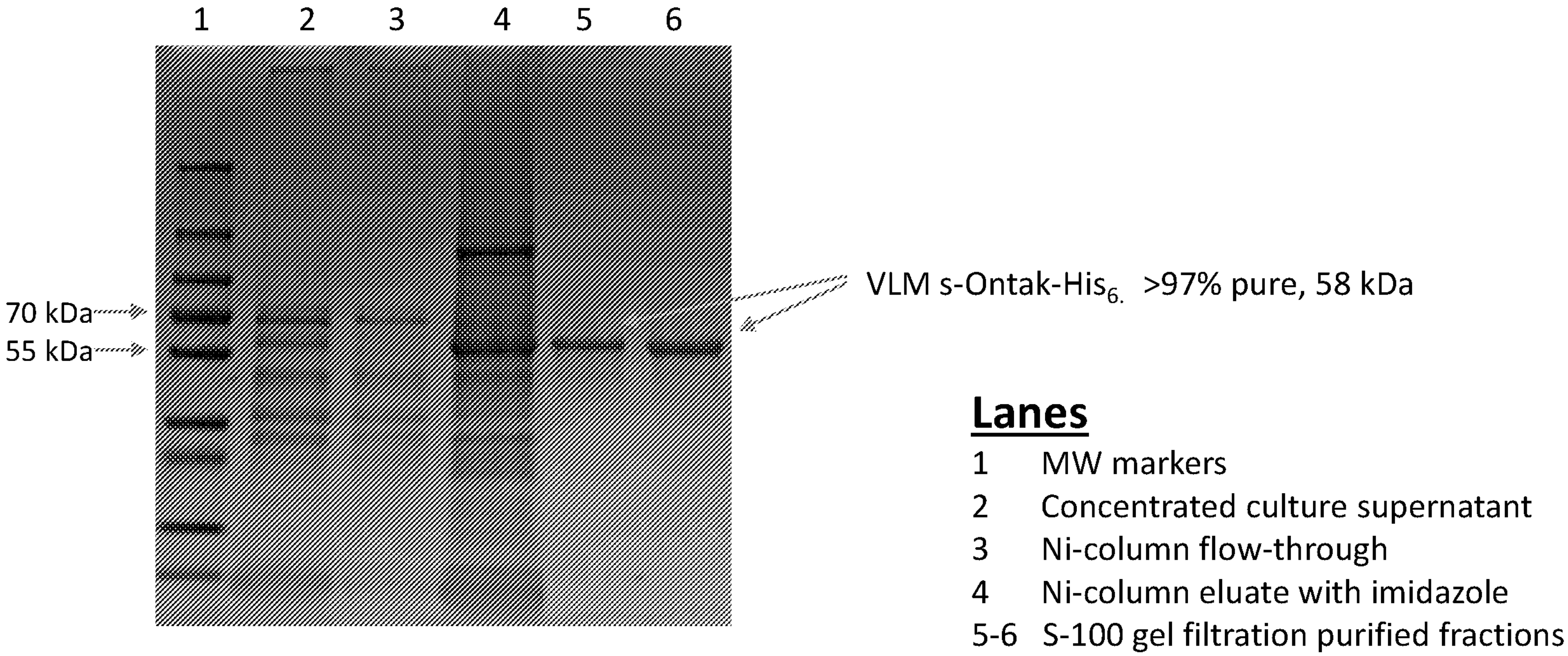
FIG. 18 illustrates purified VLM s-Ontak-$His_6$ ("$His_6$" disclosed as SEQ ID NO: 23) at greater than 97% purity produced using the C-terminal $His_6$ VLM s-Ontak construct (SEQ ID NO: 23). Specifically, a recombinant *C. diphtheriae* harboring a gene construct encoding VLM s-Ontak-$His_6$ ("$His_6$" disclosed as SEQ ID NO: 23) was grown to OD~12. The culture supernatant was harvested, concentrated by tangential flow filtration using a 30 kDa molecular weight cut-off membrane, and diafiltered for buffer exchange using tangential flow filtration as above. The protein mixture was partially purified by Ni-affinity chromatography and then purified to greater than 97% by gel permeation chromatography using S-100 resin. The resulting VLM s-Ontak-$His_6$ ("$His_6$" disclosed as SEQ ID NO: 23) was >97% pure.
Figure 19:
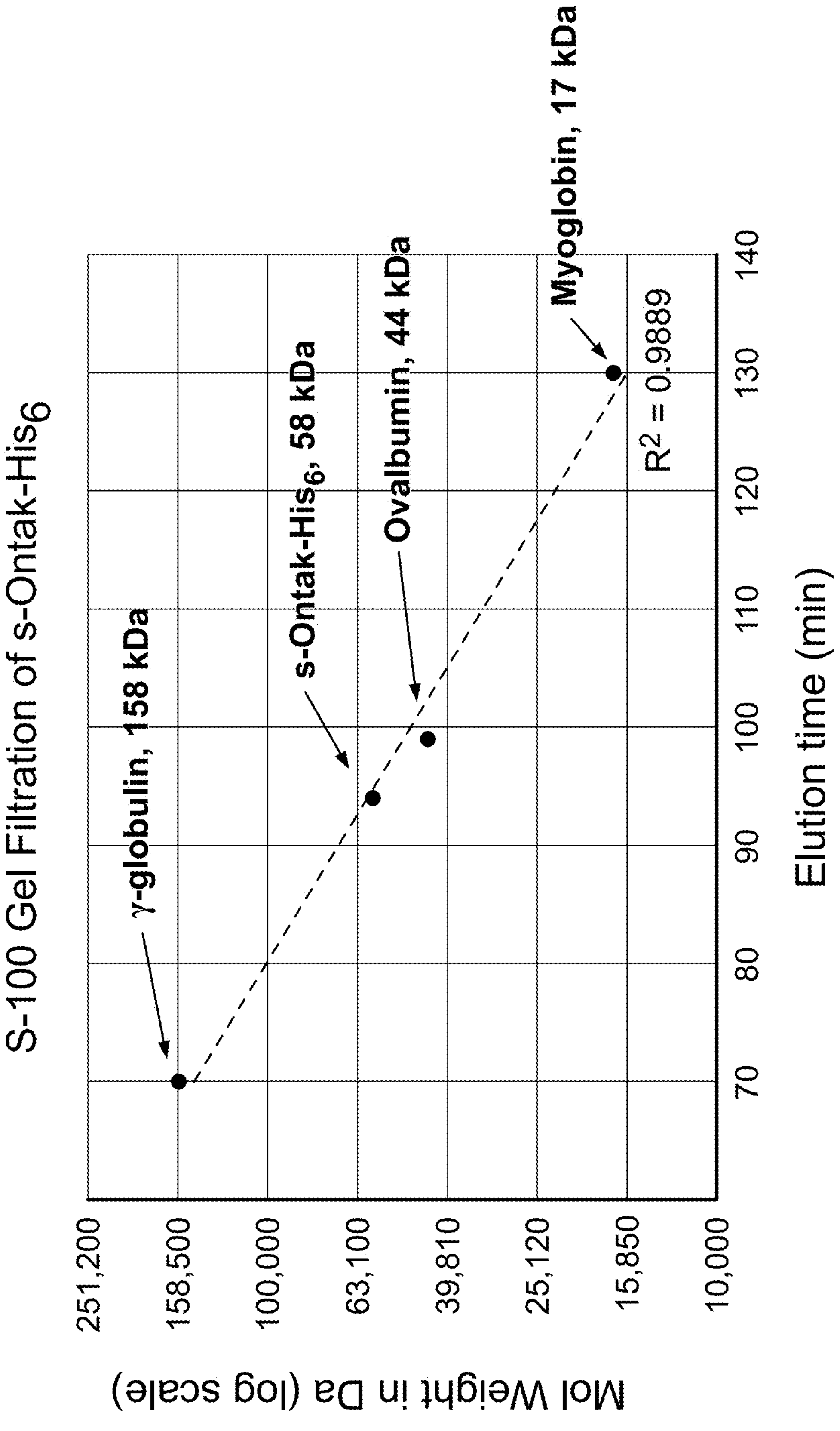
FIG. 19 illustrates the S-100 gel filtration column used to purify s-Ontak-$His_6$ ("$His_6$" disclosed as SEQ ID NO: 23) and VLM s-Ontak-$His_6$ ("$His_6$" disclosed as SEQ ID NO: 23) was calibrated for retention of proteins of known molecular weight: g-globulin (158 kDa), ovalbumin (43.5 kDa), and myoglobin (17 kDa). The retention time for s-Ontak-$His_6$ ("Hiss" disclosed as SEQ ID NO: 23) was 94 minutes, confirming that the s-Ontak-$His_6$ polypeptide is a >97% aggregate-free, full-length, monomeric diphtheria toxin fusion protein with an apparent molecular weight of 58 kDa and neither dimers nor higher order aggregates were detected by immunoblot probed with monoclonal anti-IL-2 antibody.

Like all of the bacterial and plant toxins, denileukin diftitox carries amino acid motifs that may induce vascular leak syndrome (VLS). Approximately 30% of patients treated with Ontak® develop VLS ranging from rapid weight gain with peripheral edema to hypoalbuminemia to pulmonary edema. Mutations were made to the DNA sequence of Ontak® as described in U.S. Pat. No. 8,865,866. It was discovered that DNA mutations made to the DNA sequence such that the valine (GTT) at the $7^{th}$ residue of SEQ ID NO: 10 is replaced with an alanine as shown in SEQ ID NO: 16, resulted in the fusion toxin having little, or no, vascular leak syndrome side effects. These mutants are referred to as "vascular leak mutants" (VLM). The vascular leak mutants, or denileukin diftitox-VLMS are shown to have the same potency as c-denileukin diftitox in FIG. 3, not to cause vascular leak in FIG. 4, and to have significantly less acute toxicity in vivo than c-denileukin diftitox in FIG. 5. s-denileukin diftitox-VLM, has an alanine replacing the valine at the $6^{th}$ residue shown in in SEQ ID NOs: 14 and 15. s-denileukin diftitox-VLM protein should have a similar decrease in toxicity as that found with the c-denileukin diftitox-VLM protein.

Also, the sequences $V_{29}D_{30}S_{31}$ and $I_{290}D_{291}S_{292}$ shown in SEQ ID NO: 10 (amino acid sequence of c-denileukin diftitox), when mutated also will reduce VLS. A claim in this discovery is that introduction of substitutions in $V_{29}D_{30}S_{31}$ and/or $I_{290}D_{291}S_{292}$ such as V29A or I290A may be introduced into the corresponding positions of diphtheria toxin fusion proteins and that these substitutions will also have value in further reducing vascular leakage syndrome.

Demonstration of Reduced Vascular Leak, Reduced Mouse Lethality and Increased Mouse Tolerability with *C. diphtheriae*-Derived SEQ ID NO: 43 Compared to *C. diphtheriae*-Derived SEQ ID NO: 58

| Equivalent polypeptides in this document | | | |
|---|---|---|---|
| *E. coli*-derived classic Ontak | denileukin diftitox | classic-Ontak ® (c-Ontak ®) | SEQ ID NO: 10 |
| *C. diphtheriae*-derived SEQ ID NO: 15 | ms-denileukin diftitox-VLM | VLM s-Ontak | SEQ ID NO: 15 |
| *C. diphtheriae*-derived SEQ ID NO: 43 | ms-denileukin diftitox-VLM-$His_6$ | VLM s-Ontak-$His_6$ | SEQ ID NO: 43 |
| *C. diphtheriae*-derived s-Ontak | ms-denileukin diftitox | s-Ontak | SEQ ID NO: 13 |
| *C. diphtheriae*-derived s-Ontak-$His_6$ | ms-denileukin diftitox-$His_6$ | s-Ontak-$His_6$ | SEQ ID NO: 58 |

Classic Ontak (*E. coli*-derived) and s-Ontak (soluble, monomeric, secreted; derived from *C. diphtheriae*) is a diphtheria fusion toxin that targets high affinity IL-2 receptor bearing cells and is approved for the treatment of cutaneous T cell lymphoma (CTCL). Additionally, *E. coli*-derived classic Ontak has been found to transiently deplete regulatory T cells (Tregs) in patients, and previous studies suggest the drug may have utility as a cancer immunotherapy. A serious side effect of *E. coli*-derived classic Ontak treatment is the induction of vascular leak syndrome (VLS). VLS can cause hypotension, hypoalbuminemia, and peripheral edema and is a major cause of treatment cessation. The inventors have made a *C. diphtheriae*-derived analogue of *E. coli*-derived classic Ontak in which the protein is secreted in fully soluble form and is monomeric. Further the inventors made *C. diphtheriae*-derived SEQ ID NO: 15 which is *C. diphtheriae*-derived s-Ontak with a V6A amino acid substitution and *C. diphtheriae*-derived SEQ ID NO: 43 which is *C. diphtheriae*-derived s-Ontak-$His_6$ with a V6A amino acid substitution. The inventors show that *C. diphtheriae*-derived SEQ ID NO: 43 decreases vascular leak in vitro, is less toxic in mice, and is better tolerated by surviving mice than *C. diphtheriae*-derived s-Ontak-$His_6$ (SEQ ID NO: 58. Taken together, these data reveal that *C. diphtheriae*-derived SEQ ID NO: 43 is less toxic than *C. diphtheriae*-derived SEQ ID NO: 58 and has promise as a cancer immunotherapy. *C. diphtheriae*-derived SEQ ID NO: 15 (V6A not his-tagged) is therefore anticipated to be less toxic than *C. diphtheriae*-derived SEQ ID NO: 13 s-Ontak (not his tagged) and also has promise as a cancer immunotherapy The inventors hypothesized that mutating one or more of these motifs would decrease toxicity of the drug due to VLS. The inventors made a single amino acid substitution, V6A, in *C. diphtheriae*-derived s-Ontak in a predicted motif and assessed the affect of the mutation on vascular leak, toxicity, and activity.

*C. diphtheriae*-Derived SEQ ID NO: 43 Induces Less HUVEC Permeability In Vitro than *C. diphtheriae*-Derived SEQ ID NO: 58.

Figure 20:
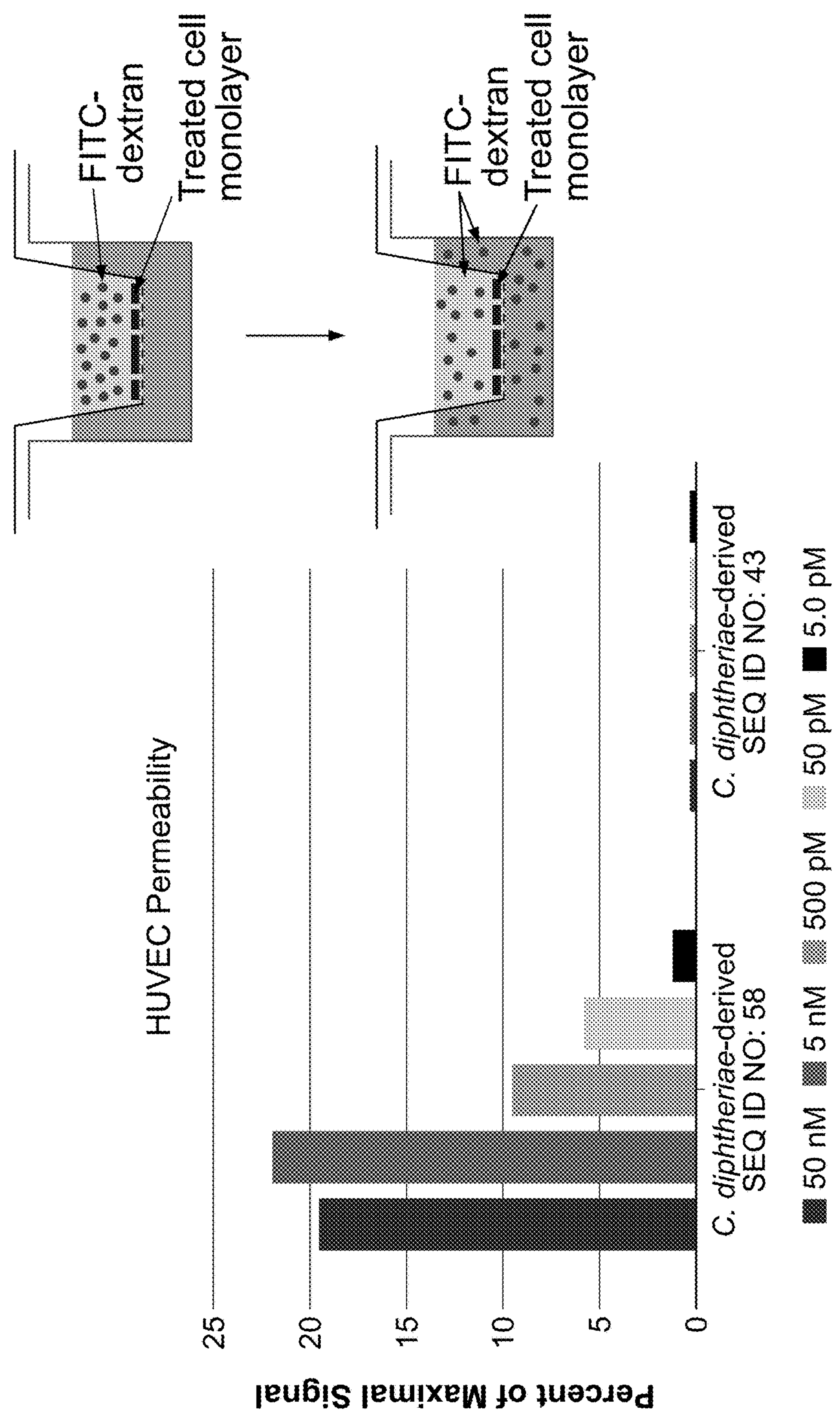
FIG. 20 illustrates the reduction in vascular leak of *C. diphtheriae*-derived SEQ ID NO: 43 compared with *C. diphtheriae*-derived SEQ ID NO: 58 using a HUVEC cell monolayer permeation test. Early passage HUVEC cells (passage 2-4, purchased from Lonza, Walkersville, MD, catalog number CC-2517) were grown on the insert well of dual chamber 24 well-plants in EndoGRO™-LS media until a complete monolayer was formed. Test polypeptides at the concentrations shown were added for 19 h. FITC-conjugated dextran beads (10,000 dalton size) were added for 30 min. to the upper well. The fluorescence intensity of the lower chamber was then measured. The fluorescent intensity was measured at 490 $nm_{excitation}$ and 520 $nm_{emission}$. Maximal signal was that observed for LPS at 10 μg/ml.

The catalytic domain of diphtheria toxin has 4 predicted vascular leak inducing motifs, while IL-2 has a single predicted motif. The N-terminal predicted motif of *E. coli*-derived classic Ontak (residues 7-9) and *C. diphtheriae*-derived s-Ontak (residues 6-8) are not part of the ADP-ribosyl transferase active site, and the inventors chose to mutate this motif to avoid affecting catalytic activity. The inventors made a single amino acid substitution in *C. diphtheriae*-derived s-Ontak-$His_6$ of Val to Ala at position 6, denoted as *C. diphtheriae*-derived SEQ ID NO: 43. The inventors then compared the effect of *C. diphtheriae*-derived SEQ ID NO: 43 compared to *C. diphtheriae*-derived s-Ontak-$His_6$ (SEQ ID NO: 58) in a HUVEC permeability assay that is used to model vascular leakage in vitro. HUVEC cells are grown on tissue culture inserts and when the monolayer is intact, FITC-dextran beads added to the upper chamber are unable to diffuse through the cell layer to the lower chamber. Increased permeability with a dose-response relationship was observed when cells were treated 5 pM, 50 pM, 500 pM, 5 nM, and 50 nM of *C. diphtheriae*-derived SEQ ID NO: 58. In contrast, no detectable vascular leak was detected with *C. diphtheriae*-derived SEQ ID NO: 43 over the same concentrations (FIG. 20).

*C. diphtheriae*-Derived SEQ ID NO: 43 Shows Reduced Lethality in Mice and is Better Tolerated in Surviving Mice than *C. diphtheriae*-Derived SEQ ID NO: 58.

Figure 21:
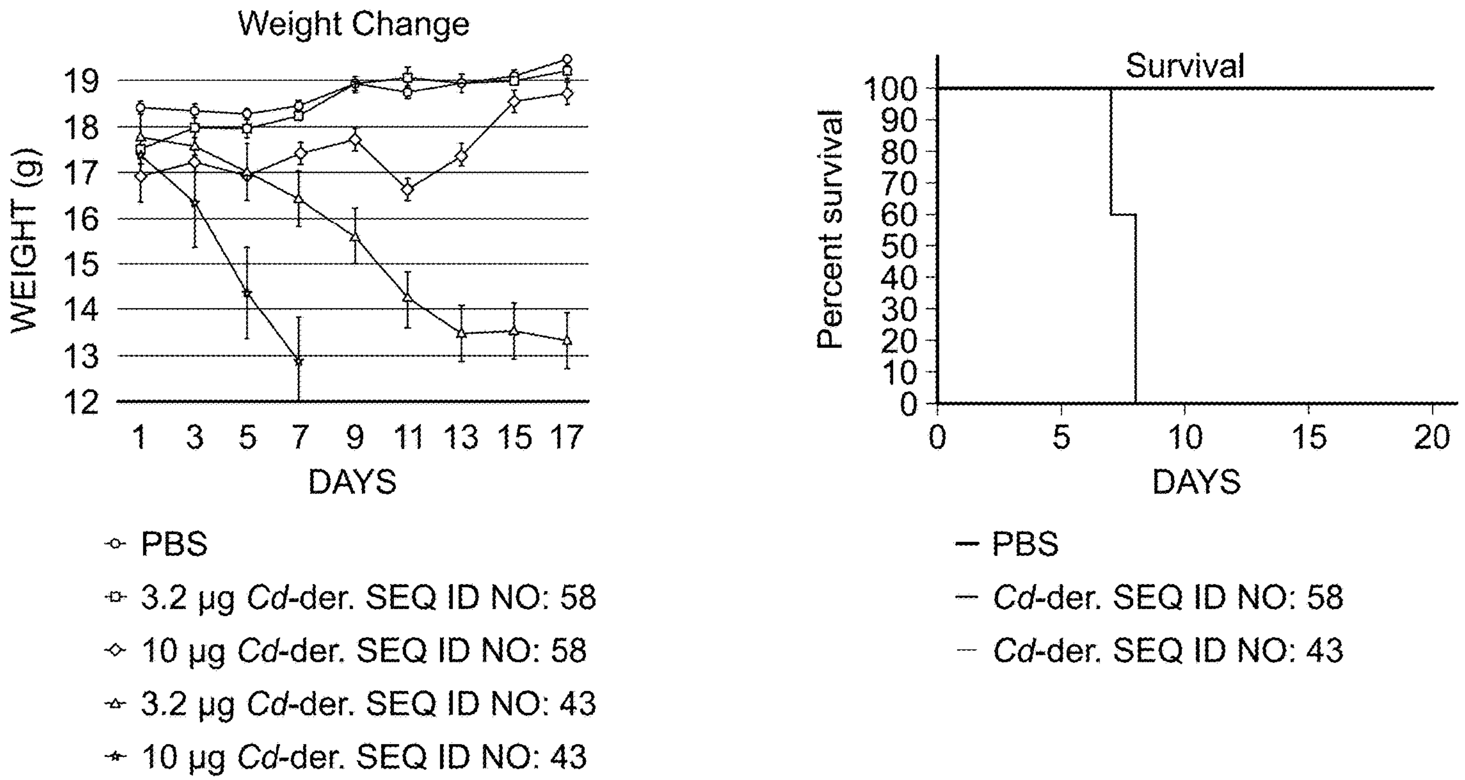
FIG. 21 illustrates the increased mouse tolerability with *C. diphtheriae*-derived SEQ ID NO: 43 compared with *C. diphtheriae*-derived SEQ ID NO: 58 daily as assessed by daily weights and the reduced mouse lethality with *C. diphtheriae*-derived SEQ ID NO: 43 or with *C. diphtheriae*-derived SEQ ID NO: 58 as assessed by time-to-death.

To assess toxicity in vivo, mice were treated daily with *C. diphtheriae*-derived SEQ ID NO: 58 or *C. diphtheriae*-derived SEQ ID NO: 43. All mice treated with 32 μg of *C. diphtheriae*-derived SEQ ID NO: 58 died on day 3 of treatment after receiving 2 doses of drug. When 32 μg of *C. diphtheriae*-derived SEQ ID NO: 43 was given to mice daily, 3 mice died on day 3, but 2 mice survived 1-2 additional doses. At a daily dose 3.2-fold lower, all mice receiving 10 μg of *C. diphtheriae*-derived SEQ ID NO: 58 lost weight and died, but no mortality or weight loss was observed in mice receiving 10 μg of *C. diphtheriae*-derived SEQ ID NO: 43 (FIG. 21). Additionally, mice dosed with 3.2 μg per day of *C. diphtheriae*-derived SEQ ID NO: 58 lost weight for the 17-day duration of the experiment, while mice given 3.2 μg *C. diphtheriae*-derived SEQ ID NO: 43 were indistinguishable from control mice which received PBS daily. (FIG. 21). When the inventors applied Reed-Muensch statistics, the $LD_{50}$ of *C. diphtheriae*-derived SEQ ID NO: 58 was 4.9 μg per day, and the $LD_{50}$ of *C. diphtheriae*-derived SEQ ID NO: 43 was 18.2 μg per day (3.7-fold lower). Taken together, these data demonstrate that the V6A mutation decreases toxicity in mice and shows that *C. diphtheriae*-derived SEQ ID NO: 43 is better tolerated at higher doses than *C. diphtheriae*-derived SEQ ID NO: 43.

V6A Mutation does not Affect In Vitro Killing Activity of CD25+ Cells or Anti-Tumor Activity of *C. diphtheriae*-Derived SEQ ID NO: 43 in B16F10 In Vivo in a Murine Melanoma Model.

The inventors evaluated the $IC_{50}$ of *C. diphtheriae*-derived SEQ ID NO: 43 against HUT-102 T cell lymphoma cells which are CD25 receptor-positive and found the $IC_{50}$ to be 3.5 pM (mean of three determinations). The inventors also tested an aliquot of *E. coli*-derived classic Ontak and found that its $IC_{50}$ for the same cell line is 1.8 pM (mean of two determinations, FIG. 22). These $IC_{50}$ values are comparable, and both are dramatically lower than those for potent other biologics or small molecules which typically have $IC_{50}$ values in the nM or μM range. Next the inventors tested whether the V6A mutation alters the activity *C. diphtheriae*-derived SEQ ID NO: 43 in vivo in a mouse allograft model of anti-tumor activity against melanoma B16F10 tumors implanted in C57BL/6 mice. Mice with established B16F10 tumors were treated on day 7 and day 10 post-implantation with either 5 μg of *C. diphtheriae*-derived SEQ ID NO: 43 or *C. diphtheriae*-derived SEQ ID NO: 58, and tumor growth was measured over time. Both drugs significantly inhibited tumor growth with similar efficacy (FIG. 22). Additionally, both drugs depleted Tregs in the lymph nodes and spleens of mice and their effects were equivalent (FIG. 23). These data demonstrate that the V6A mutation has no significant effect on CD25+ cell killing in vitro, no effect on Treg depletion and anti-tumor activity in vivo.

```
(denileukin diftitox-VLM underlined codon
encodes for alanine, here shown as GCT,
described in U.S. Pat. No. 8,865,866.)
                                        SEQ ID NO: 7
  1 ATG

  4 GGCGCTGATGATGTTGCTGATTCTT

    CTAAATCTTTTGTGATGGAAAACTT

 54 TTCTTCGTACCACGGGACTAAACCT

    GGTTATGTAGATTCCATTCAAAAAG

104 GTATACAAAAGCCAAAATCTGGTAC

    ACAAGGAAATTATGACGATGATTGG

154 AAAGGGTTTTATAGTACCGACAATA

    AATACGACGCTGCGGGATACTCTGT

204 AGATAATGAAAACCCGCTCTCTGGA

    AAAGCTGGAGGCGTGGTCAAAGTGA

254 CGTATCCAGGACTGACGAAGGTTCT

    CGCACTAAAAGTGGATAATGCCGAA
```

-continued

```
304 ACTATTAAGAAAGAGTTAGGTTTAA

    GTCTCACTGAACCGTTGATGGAGCA

354 AGTCGGAACGGAAGAGTTTATCAAA

    AGGTTCGGTGATGGTGCTTCGCGTG

404 TAGTGCTCAGCCTTCCCTTCGCTGA

    GGGGAGTTCTAGCGTTGAATATATT

454 AATAACTGGGAACAGGCGAAAGCGT

    TAAGCGTAGAACTTGAGATTAATTT

504 TGAAACCCGTGGAAAACGTGGCCAA

    GATGCGATGTATGAGTATATGGCTC

554 AAGCCTGTGCAGGAAATCGTGTCAG

    GCGATCAGTAGGTAGCTCATTGTCA

604 TGCATCAACCTGGATTGGGATGTTA

    TCCGTGATAAAACTAAAACTAAGAT

654 CGAATCTCTGAAAGAACACGGTCCG

    ATCAAAAACAAAATGAGCGAAAGCC

704 CGAACAAAACTGTATCTGAAGAAAA

    AGCTAAACAGTACCTGGAAGAATTC

754 CACCAGACTGCACTGGAACACCCGG

    AACTGTCTGAACTTAAGACCGTTAC

804 TGGTACCAACCCGGTATTCGCTGGT

    GCTAACTACGCTGCTTGGGCAGTAA

854 ACGTTGCTCAGGTTATCGATAGCGA

    AACTGCTGATAACCTGGAAAAAACT

904 ACCGCGGCTCTGTCTATCCTGCCGG

    GTATCGGTAGCGTAATGGGCATCGC
```

-continued

```
954 AGACGGCGCCGTTCACCACAACACT

    GAAGAAATCGTTGCACAGTCTATCG

1004 CTCTGAGCTCTCTGATGGTTGCTCA

     GGCCATCCCGCTGGTAGGTGAACTG

1054 GTTGATATCGGTTTCGCTGCATACA

     ACTTCGTTGAAAGCATCATCAACCT

1104 GTTCCAGGTTGTTCACAACTCTTAC

     AACCGCCCGGCTTACTCTCCGGGTC

1154 ACAAGACGCATGCACCTACTTCTAG

     CTCTACCAAGAAAACCCAGCTGCAG

1204 CTCGAGCACCTGCTGCTGGATTTGC

     AGATGATCCTGAACGGTATCAACAA

1254 TTACAAGAACCCGAAACTGACGCGT

     ATGCTGACCTTCAAGTTCTACATGC

1304 CGAAGAAGGCCACCGAACTGAAACA

     CCTGCTGCAGTGTCTAGAAGAAGAA

1354 CTGAAACCGCTGGAGGAAGTTCTGA

     ACCTGGCTCAGTCTAAAAACTTCCA

1404 CCTGCGGCCGCGTGACCTGATCTCT

     AACATCAACGTAATCGTTCTGGAAC

1454 TGAAGGGCTCTGAAACCACCTTCAT

     GTGTGAATACGCTGATGAGACCGCA

1504 ACCATCGTAGAATTCCTGAACCGTT

     GGATCACCTTCTGTCAGTCTATCAT

1554 CTCTACCCTGACC <1566
```

Alignment of DNA sequences comparing SEQ ID NO: 7 [denileukin diftitox-VLM described in U.S. Pat. No. 8,865,866] with SEQ ID NO: 8 [is-denileukin diftitox-VLM of the present invention] demonstrates SEQ ID NO: 8 is missing a codon (three bases) in line 1381-1437.

```
Similarity: 1563/1638 (95.42%)
NO: 7      1  ------------------------------------------------------------    0
              ############################################################
NO: 8      1  GTGAGCAGAAAACTGTTTGCGTCAATCTTAATAGGGGCGCTACTGGGGATAGGGGCCCCA   60

NO: 7      1  ----------ATG--GGCGCTGATGATGTTGCTGATTCTTCTAAATCTTTTGTGATGGAA   48
              ##########|||##|||||||||||||||||||||||||||||||||||||||||||||
NO: 8     61  CCTTCAGCCCATGCAGGCGCTGATGATGTTGCTGATTCTTCTAAATCTTTTGTGATGGAA  120

NO: 7     45  AACTTTTCTTCGTACCACGGGACTAAACCTGGTTATGTAGATTCCATTCAAAAAGGTATA  108
              ||||||||||||||||||||||||||||||||||||||||||||||||||||||||||||
NO: 8    121  AACTTTTCTTCGTACCACGGGACTAAACCTGGTTATGTAGATTCCATTCAAAAAGGTATA  180

NO: 7    109  CAAAAGCCAAAATCTGGTACACAAGGAAATTATGACGATGATTGGAAAGGGTTTTATAGT  168
              ||||||||||||||||||||||||||||||||||||||||||||||||||||||||||||
NO: 8    181  CAAAAGCCAAAATCTGGTACACAAGGAAATTATGACGATGATTGGAAAGGGTTTTATAGT  240

NO: 7    169  ACCGACAATAAATACGACGCTGCGGGATACTCTGTAGATAATGAAAACCCGCTCTCTGGA  228
              ||||||||||||||||||||||||||||||||||||||||||||||||||||||||||||
NO: 8    241  ACCGACAATAAATACGACGCTGCGGGATACTCTGTAGATAATGAAAACCCGCTCTCTGGA  300
```

-continued

```
NO: 7    229  AAAGCTGGAGGCGTGGTCAAAGTGACGTATCCAGGACTGACGAAGGTTCTCGCACTAAAA  288
              ||||||||||||||||||||||||||||||||||||||||||||||||||||||||||||
NO: 8    301  AAAGCTGGAGGCGTGGTCAAAGTGACGTATCCAGGACTGACGAAGGTTCTCGCACTAAAA  360

NO: 7    289  GTGGATAATGCCGAAACTATTAAGAAAGAGTTAGGTTTAAGTCTCACTGAACCGTTGATG  348
              ||||||||||||||||||||||||||||||||||||||||||||||||||||||||||||
NO: 8    361  GTGGATAATGCCGAAACTATTAAGAAAGAGTTAGGTTTAAGTCTCACTGAACCGTTGATG  420

NO: 7    349  GAGCAAGTCGGAACGGAAGAGTTTATCAAAAGGTTCGGTGATGGTGCTTCGCGTGTAGTG  408
              ||||||||||||||||||||||||||||||||||||||||||||||||||||||||||||
NO: 8    421  GAGCAAGTCGGAACGGAAGAGTTTATCAAAAGGTTCGGTGATGGTGCTTCGCGTGTAGTG  480

NO: 7    409  CTCAGCCTTCCCTTCGCTGAGGGGAGTTCTAGCGTTGAATATATTAATAACTGGGAACAG  468
              ||||||||||||||||||||||||||||||||||||||||||||||||||||||||||||
NO: 8    481  CTCAGCCTTCCCTTCGCTGAGGGGAGTTCTAGCGTTGAATATATTAATAACTGGGAACAG  540

NO: 7    469  GCGAAAGCGTTAAGCGTAGAACTTGAGATTAATTTTGAAACCCGTGGAAAACGTGGCCAA  528
              ||||||||||||||||||||||||||||||||||||||||||||||||||||||||||||
NO: 8    541  GCGAAAGCGTTAAGCGTAGAACTTGAGATTAATTTTGAAACCCGTGGAAAACGTGGCCAA  600

NO: 7    529  GATGCGATGTATGAGTATATGGCTCAAGCCTGTGCAGGAAATCGTGTCAGGCGATCAGTA  588
              ||||||||||||||||||||||||||||||||||||||||||||||||||||||||||||
NO: 8    601  GATGCGATGTATGAGTATATGGCTCAAGCCTGTGCAGGAAATCGTGTCAGGCGATCAGTA  660

NO: 7    589  GGTAGCTCATTGTCATGCATCAACCTGGATTGGGATGTTATCCGTGATAAAACTAAAACT  648
              ||||||||||||||||||||||||||||||||||||||||||||||||||||||||||||
NO: 8    661  GGTAGCTCATTGTCATGCATCAACCTGGATTGGGATGTTATCCGTGATAAAACTAAAACT  720

NO: 7    649  AAGATCGAATCTCTGAAAGAACACGGTCCGATCAAAAACAAAATGAGCGAAAGCCCGAAC  708
              ||||||||||||||||||||||||||||||||||||||||||||||||||||||||||||
NO: 8    721  AAGATCGAATCTCTGAAAGAACACGGTCCGATCAAAAACAAAATGAGCGAAAGCCCGAAC  780

NO: 7    709  AAAACTGTATCTGAAGAAAAAGCTAAACAGTACCTGGAAGAATTCCACCAGACTGCACTG  768
              ||||||||||||||||||||||||||||||||||||||||||||||||||||||||||||
NO: 8    781  AAAACTGTATCTGAAGAAAAAGCTAAACAGTACCTGGAAGAATTCCACCAGACTGCACTG  840

NO: 7    769  GAACACCCGGAACTGTCTGAACTTAAGACCGTTACTGGTACCAACCCGGTATTCGCTGGT  828
              ||||||||||||||||||||||||||||||||||||||||||||||||||||||||||||
NO: 8    841  GAACACCCGGAACTGTCTGAACTTAAGACCGTTACTGGTACCAACCCGGTATTCGCTGGT  900

NO: 7    829  GCTAACTACGCTGCTTGGGCAGTAAACGTTGCTCAGGTTATCGATAGCGAAACTGCTGAT  888
              ||||||||||||||||||||||||||||||||||||||||||||||||||||||||||||
NO: 8    901  GCTAACTACGCTGCTTGGGCAGTAAACGTTGCTCAGGTTATCGATAGCGAAACTGCTGAT  960

NO: 7    889  AACCTGGAAAAAACTACCGCGGCTCTGTCTATCCTGCCGGGTATCGGTAGCGTAATGGGC  948
              ||||||||||||||||||||||||||||||||||||||||||||||||||||||||||||
NO: 8    961  AACCTGGAAAAAACTACCGCGGCTCTGTCTATCCTGCCGGGTATCGGTAGCGTAATGGGC 1020

NO: 7    949  ATCGCAGACGGCGCCGTTCACCACAACACTGAAGAAATCGTTGCACAGTCTATCGCTCTG 1008
              ||||||||||||||||||||||||||||||||||||||||||||||||||||||||||||
NO: 8   1021  ATCGCAGACGGCGCCGTTCACCACAACACTGAAGAAATCGTTGCACAGTCTATCGCTCTG 1080

NO: 7   1009  AGCTCTCTGATGGTTGCTCAGGCCATCCCGCTGGTAGGTGAACTGGTTGATATCGGTTTC 1068
              ||||||||||||||||||||||||||||||||||||||||||||||||||||||||||||
NO: 8   1081  AGCTCTCTGATGGTTGCTCAGGCCATCCCGCTGGTAGGTGAACTGGTTGATATCGGTTTC 1140

NO: 7   1069  GCTGCATACAACTTCGTTGAAAGCATCATCAACCTGTTCCAGGTTGTTCACAACTCTTAC 1128
              ||||||||||||||||||||||||||||||||||||||||||||||||||||||||||||
NO: 8   1141  GCTGCATACAACTTCGTTGAAAGCATCATCAACCTGTTCCAGGTTGTTCACAACTCTTAC 1200

NO: 7   1129  AACCGCCCGGCTTACTCTCCGGGTCACAAGACGCATGCACCTACTTCTAGCTCTACCAAG 1188
              ||||||||||||||||||||||||||||||||||||||||||||||||||||||||||||
NO: 7   1201  AACCGCCCGGCTTACTCTCCGGGTCACAAGACGCATGCACCTACTTCTAGCTCTACCAAG 1260

NO: 7   1189  AAAACCCAGCTGCAGCTCGAGCACCTGCTGCTGGATTTGCAGATGATCCTGAACGGTATC 1248
              ||||||||||||||||||||||||||||||||||||||||||||||||||||||||||||
NO: 8   1261  AAAACCCAGCTGCAGCTCGAGCACCTGCTGCTGGATTTGCAGATGATCCTGAACGGTATC 1320

NO: 7   1249  AACAATTACAAGAACCCGAAACTGACGCGTATGCTGACCTTCAAGTTCTACATGCCGAAG 1308
              ||||||||||||||||||||||||||||||||||||||||||||||||||||||||||||
NO: 8   1321  AACAATTACAAGAACCCGAAACTGACGCGTATGCTGACCTTCAAGTTCTACATGCCGAAG 1380

NO: 7   1309  AAGGCCACCGAACTGAAACACCTGCTGCAGTGTCTAGAAGAAGAACTGAAACCGCTGGAG 1368
              |||||||||||||||||||||||||###||||||||||||||||||||||||||||||||
NO: 8   1381  AAGGCCACCGAACTGAAACACCTGC---AGTGTCTAGAAGAAGAACTGAAACCGCTGGAG 1437

NO: 7   1369  GAAGTTCTGAACCTGGCTCAGTCTAAAAACTTCCACCTGCGGCCGCGTGACCTGATCTCT 1428
              ||||||||||||||||||||||||||||||||||||||||||||||||||||||||||||
NO: 8   1438  GAAGTTCTGAACCTGGCTCAGTCTAAAAACTTCCACCTGCGGCCGCGTGACCTGATCTCT 1497
```

-continued

```
NO: 7   1429  AACATCAACGTAATCGTTCTGGAACTGAAGGGCTCTGAAACCACCTTCATGTGTGAATAC 1488
              ||||||||||||||||||||||||||||||||||||||||||||||||||||||||||||
NO: 8   1498  AACATCAACGTAATCGTTCTGGAACTGAAGGGCTCTGAAACCACCTTCATGTGTGAATAC 1557

NO: 7   1489  GCTGATGAGACCGCAACCATCGTAGAATTCCTGAACCGTTGGATCACCTTCTGTCAGTCT 1548
NO: 7         ||||||||||||||||||||||||||||||||||||||||||||||||||||||||||||
NO: 8   1558  GCTGATGAGACCGCAACCATCGTAGAATTCCTGAACCGTTGGATCACCTTCTGTCAGTCT 1617

NO: 7   1549  ATCATCTCTACCCTGACC---                                        1566
              ||||||||||||||||||###
NO: 8  1618   ATCATCTCTACCCTGACCTGA                                        1638
```

(DNA sequence IL-2 portion of denileukin diftitox)

SEQ ID NO: 9

```
  1 GCACCTACTTCTAGCTCTACCAAGAAAACCCAGCTGCAGCTCGAGCACCT

 51 GCTGCTGGATTTGCAGATGATCCTGAACGGTATCAACAATTACAAGAACC

101 CGAAACTGACGCGTATGCTGACCTTCAAGTTCTACATGCCGAAGAAGGCC

151 ACCGAACTGAAACACCTGCAGTGTCTAGAAGAAGAACTGAAACCGCTGGA

201 GGAAGTTCTGAACCTGGCTCAGTCTAAAAACTTCCACCTGCGGCCGCGTG

251 ACCTGATCTCTAACATCAACGTAATCGTTCTGGAACTGAAGGGCTCTGAA

301 ACCACCTTCATGTGTGAATACGCTGATGAGACCGCAACCATCGTAGAATT

351 CCTGAACCGTTGGATCACCTTCTGTCAGTCTATCATCTCTACCCTGACCT

401 GA <402
```

Proteins Produced Using DNA Expression Vectors of the Present Invention

The first amino acid of a mature active diphtheria toxin related fusion protein of the present invention is a glycine as shown in bold (amino acid 1) in SEQ ID NOs: 13 and 15. The signal sequence within SEQ ID NO: 4 is labeled with negative numbers, counting back from the first glycine of the mature fusion protein and has the following amino acid sequence MSRKLFASILIGALLGIGAPPSAHA (SEQ ID NO: 22). The signal sequence is shown in SEQ ID NOs: 11 and 12 and is underlined. The mature secreted diphtheria toxin fusion protein includes a diphtheria toxin portion, such as $Gly_1$-$His_{387}$, and a target receptor binding domain, such as an IL-2 protein from $Ala_{388}$-$Thr_{520}$ in SEQ ID NO: 3. Other target receptor binding domains used in the present invention that may be fused to a diphtheria toxin protein (or functional part thereof) include IL-3, IL-4, IL-6, IL-7, IL-15, EGF, FGF, substance P, CD4, αMSH, GRP, TT fragment C, GCSF, heregulin β1, TNFα, TGFβ, among others, or a combination thereof. SEQ ID NO: 10 describes c-denileukin diftitox that is not secreted and is requires purification from inclusion bodies in *E. coli*. SEQ ID NO: 12 describes immature secreted is-denileukin diftitox with a signal sequence. SEQ ID NO: 13 describes MS-denileukin diftitox wherein the signal sequence has been cleaved off during the process of secretion to the extracellular space.

(Protein Sequence of c-denileukin diftitox known as Ontak®)

SEQ ID NO: 10

```
  1 MGADDVVDSSKSFVMENFSSYHGTKP

 27 GYVDSIQKGIQKPKSGTQGNYDDDWKGFYSIDNKYDAAGYSVDNENPLSG

 77 KAGGVVKVTYPGLIKVLALKVDNAETIKKELGLSLTEPLMEQVGTEEFIK

127 RFGDGASRVVLSLPFAEGSSSVEYINNWEQAKALSVELEINFETRGKRGQ

177 DAMYEYMAQACAGNRVRRSVGSSLSCINLDWDVIRDKIKTKIESLKEHGP

227 IKNKMSESPNKTVSEEKAKQYLEEFHQTALEHPELSELKTVIGINPVFAG

277 ANYAAWAVNVAQVIDSETADNLEKTTAALSILPGIGSVMGIADGAVHHNT

327 EEIVAQSIALSSLMVAQAIPLVGELVDIGFAAYNFVESIINLFQVVHNSY

377 NRPAYSPGHKTHAPTSSSIKKTQLQLEHLLLDLQMILNGINNYKNPKLIR

427 MLIFKFYMPKKATELKHLQCLEEELKPLEEVLNLAQSKNFHLRPRDLISN

477 INVIVLELKGSETTFMCEYADETATIVEFLNRWITFCQSIISTLT <521
```

(w-diphtheria toxin)

SEQ ID NO: 11

```
  1 MSRKLFASILIGALLGIGAPPSAHAGADDVVDSSKSFVMENFSSYHGTKP

 51 GYVDSIQKGIQKPKSGTQGNYDDDWKGFYSIDNKYDAAGYSVDNENPLSG
```

-continued

101 KAGGVVKVTYPGLIKVLALKVDNAETIKKELGLSLTEPLMEQVGTEEFIK

151 RFGDGASRVVLSLPFAEGSSSVEYINNWEQAKALSVELEINFETRGKRGQ

201 DAMYEYMAQACAGNRVRRSVGSSLSCINLDWDVIRDKIKTKIESLKEHGP

251 IKNKMSESPNKTVSEEKAKQYLEEFHQTALEHPELSELKTVIGINPVFAG

301 ANYAAWAVNVAQVIDSETADNLEKTTAALSILPGIGSVMGIADGAVHHNT

351 EEIVAQSIALSSLMVAQAIPLVGELVDIGFAAYNFVESIINLFQVVHNSY

401 NRPAYSPGHKTQPFLHDGYAVSWNIVEDSIIRTGFQGESGHDIKITAENT

451 PLPIAGVLLPTIPGKLDVNKSKTHISVNGRKIRMRCRAIDGDVTFCRPKS

501 PVYVGNGVHANLHVAFHRSSSEKIHSNEISSDSIGVLGYQKTVDHTKVNS

551 KLSLFFEIKS <560

(is-denileukin diftitox)

SEQ ID NO: 12

-25 MSRKLFASILIGALLGIGAPPSAHAGADDVVDSSKSFVMENFSSYHGTKP

26 GYVDSIQKGIQKPKSGTQGNYDDDWKGFYSIDNKYDAAGYSVDNENPLSG

76 KAGGVVKVTYPGLTKVLALKVDNAETIKKELGLSLTEPLMEQVGTEEFIK

126 RFGDGASRVVLSLPFAEGSSSVEYINNWEQAKALSVELEINFETRGKRGQ

176 DAMYEYMAQACAGNRVRRSVGSSLSCINLDWDVIRDKTKTKIESLKEHGP

226 IKNKMSESPNKTVSEEKAKQYLEEFHQTALEHPELSELKTVTGINPVFAG

276 ANYAAWAVNVAQVIDSETADNLEKTTAALSILPGIGSVMGIADGAVHHNT

326 EEIVAQSIALSSLMVAQAIPLVGELVDIGFAAYNFVESIINLFQVVHNSY

376 NRPAYSPGHKTHAPTSSSTKKTQLQLEHLLLDLQMILNGINNYKNPKLTR

426 MLIFKFYMPKKATELKHLQCLEEELKPLEEVLNLAQSKNFHLRPRDLISN

476 INVIVLELKGSETTFMCEYADETATIVEFLNRWITFCQSIISTLT <520

(ms-denileukin diftitox)

SEQ ID NO: 13

1 GADDVVDSSKSFVMENFSSYHGTKP

26 GYVDSIQKGIQKPKSGTQGNYDDDWKGFYSTDNKYDAAGYSVDNENPLSG

76 KAGGVVKVTYPGLTKVLALKVDNAETIKKELGLSLTEPLMEQVGTEEFIK

126 RFGDGASRVVLSLPFAEGSSSVEYINNWEQAKALSVELEINFETRGKRGQ

176 DAMYEYMAQACAGNRVRRSVGSSLSCINLDWDVIRDKTKTKIESLKEHGP

226 IKNKMSESPNKTVSEEKAKQYLEEFHQTALEHPELSELKTVTGINPVFAG

276 ANYAAWAVNVAQVIDSETADNLEKTTAALSILPGIGSVMGIADGAVHHNT

326 EEIVAQSIALSSLMVAQAIPLVGELVDIGFAAYNFVESIINLFQVVHNSY

376 NRPAYSPGHKTHAPTSSSTKKTQLQLEHLLLDLQMILNGINNYKNPKLTR

426 MLIFKFYMPKKATELKHLQCLEEELKPLEEVLNLAQSKNFHLRPRDLISN

476 INVIVLELKGSETTFMCEYADETATIVEFLNRWITFCQSIISTLT <520

(Protein sequence of is-denileukin diftitox-VLM)

SEQ ID NO: 14

-25 MSRKLFASILIGALLGIGAPPSAHAGADDVADSSKSFVMENFSSYHGTKP

26 GYVDSIQKGIQKPKSGTQGNYDDDWKGFYSTDNKYDAAGYSVDNENPLSG

76 KAGGVVKVTYPGLTKVLALKVDNAETIKKELGLSLTEPLMEQVGTEEFIK

126 RFGDGASRVVLSLPFAEGSSSVEYINNWEQAKALSVELEINFETRGKRGQ

176 DAMYEYMAQACAGNRVRRSVGSSLSCINLDWDVIRDKTKTKIESLKEHGP

-continued

```
226 IKNKMSESPNKTVSEEKAKQYLEEFHQTALEHPELSELKTVTGINPVFAG

276 ANYAAWAVNVAQVIDSETADNLEKTTAALSILPGIGSVMGIADGAVHHNT

326 EEIVAQSIALSSLMVAQAIPLVGELVDIGFAAYNFVESIINLFQVVHNSY

376 NRPAYSPGHKTHAPTSSSTKKTQLQLEHLLLDLQMILNGINNYKNPKLTR

426 MLIFKFYMPKKATELKHLQCLEEELKPLEEVLNLAQSKNFHLRPRDLISN

476 INVIVLELKGSETTFMCEYADETATIVEFLNRWITFCQSIISTLT <520
```

(Protein sequence of ms-denileukin diftitox-VLM)

SEQ ID NO: 15

```
 51 GADDVADSSKSFVMENFSSYHGTKP

 26 GYVDSIQKGIQKPKSGTQGNYDDDWKGFYSTDNKYDAAGYSVDNENPLSG

 76 KAGGVVKVTYPGLTKVLALKVDNAETIKKELGLSLTEPLMEQVGTEEFIK

126 RFGDGASRVVLSLPFAEGSSSVEYINNWEQAKALSVELEINFETRGKRGQ

176 DAMYEYMAQACAGNRVRRSVGSSLSCINLDWDVIRDKTKTKIESLKEHGP

226 IKNKMSESPNKTVSEEKAKQYLEEFHQTALEHPELSELKTVTGTNPVFAG

276 ANYAAWAVNVAQVIDSETADNLEKTTAALSILPGIGSVMGIADGAVHHNT

326 EEIVAQSIALSSLMVAQAIPLVGELVDIGFAAYNFVESIINLFQVVHNSY

376 NRPAYSPGHKTHAPTSSSTKKTQLQLEHLLLDLQMILNGINNYKNPKLTR

426 MLIFKFYMPKKATELKHLQCLEEELKPLEEVLNLAQSKNFHLRPRDLISN

476 INVIVLELKGSETTFMCEYADETATIVEFLNRWITFCQSIISTLT <520
```

(Protein sequence of denileukin diftitox-VLM described in U.S. Pat. No. 8,865,866)

SEQ ID NO: 16

```
  1 MGADDVADSSKSFVMENFSSYHGTKP

 27 GYVDSIQKGIQKPKSGTQGNYDDDWKGFYSTDNKYDAAGYSVDNENPLSG

 77 KAGGVVKVTYPGLTKVLALKVDNAETIKKELGLSLTEPLMEQVGTEEFIK

127 RFGDGASRVVLSLPFAEGSSSVEYINNWEQAKALSVELEINFETRGKRGQ

177 DAMYEYMAQACAGNRVRRSVGSSLSCINLDWDVIRDKTKTKIESLKEHGP

227 IKNKMSESPNKTVSEEKAKQYLEEFHQTALEHPELSELKTVTGTNPVFAG

277 ANYAAWAVNVAQVIDSETADNLEKTTAALSILPGIGSVMGIADGAVHHNT

327 EEIVAQSIALSSLMVAQAIPLVGELVDIGFAAYNFVESIINLFQVVHNSY

377 NRPAYSPGHKTHAPTSSSTKKTQLQLEHLLLDLQMILNGINNYKNPKLTR

427 MLTFKFYMPKKATELKHLLQCLEEELKPLEEVLNLAQSKNFHLRPRDLIS

477 NINVIVLELKGSETTFMCEYADETATIVEFLNRWITFCQSIISTLT <522
```

Protein Alignment of SEQ ID NO: 16 is denileukin diftitox-VLM described in U.S. Pat. No. 8,865,866 that has an extra amino acid (L) at position 445 when compared with SEQ ID NO: 14 is-denileukin diftitox-VLM of the present invention.

```
Similarity: 521/522 (99.81%)
NO: 16   1 M------------------------GADDVADSSKSFVMENFSSYHGTKPGYVDSIQKGI   36
           |########################|||||||||||||||||||||||||||||||||||
NO: 14   1 MSRKLFASILIGALLGIGAPPSAHAGADDVADSSKSFVMENFSSYHGTKPGYVDSIQKGI   60

NO: 16  37 QKPKSGTQGNYDDDWKGFYSTDNKYDAAGYSVDNENPLSGKAGGVVKVTYPGLTKVLALK   96
           ||||||||||||||||II||||||||||||||||||||||||||||||||||||||||||
NO: 14  61 QKPKSGTQGNYDDDWKGFYSTDNKYDAAGYSVDNENPLSGKAGGVVKVTYPGLTKVLALK  120
```

-continued

```
NO: 16  97 VDNAETIKKELGLSLTEPLMEQVGTEEFIKRFGDGASRVVLSLPFAEGSSSVEYINNWEQ 156
           ||||||||||||||||||||||||||||||||||||||||||||||||||||||||||||
NO: 14 121 VDNAETIKKELGLSLTEPLMEQVGTEEFIKRFGDGASRVVLSLPFAEGSSSVEYINNWEQ 180

NO: 16 157 AKALSVELEINFETRGKRGQDAMYEYMAQACAGNRVRRSVGSSLSCINLDWDVIRDKTKT 216
           ||||||||||||||||||||||||||||||||||||||||||||||||||||||||||||
NO: 14 181 AKALSVELEINFETRGKRGQDAMYEYMAQACAGNRVRRSVGSSLSCINLDWDVIRDKTKT 240

NO: 16 217 KIESLKEHGP|KNKMSESPNKTVSEEKAKQYLEEFHQTALEHPELSELKTVTGTNPVFAG 276
           ||||||||||||||||||||||||||||||||||||||||||||||||||||||||||||
NO: 14 241 KIESLKEHGPIKNKMSESPNKTVSEEKAKQYLEEFHQTALEHPELSELKTVTGTNPVFAG 300

NO: 16 277 ANYAAWAVNVAQVIDSETADNLEKTTAALSILPGIGSVMGIADGAVHHNTEEIVAQSIAL 336
           ||||||||||||||||||||||||||||||||||||||||||||||||||||||||||||
NO: 14 301 ANYAAWAVNVAQVIDSETADNLEKTTAALSILPGIGSVMGIADGAVHHNTEEIVAQSIAL 360

NO: 16 337 SSLMVAQAIPLVGELVDIGFAAYNFVESIINLFQVVHNSYNRPAYSPGHKTHAPTSSSTK 396
           ||||||||||||||||||||||||||||||||||||||||||||||||||||||||||||
NO: 14 361 SSLMVAQAIPLVGELVDIGFAAYNFVESIINLFQVVHNSYNRPAYSPGHKTHAPTSSSTK 420

NO: 16 397 KTQLQLEHLLLDLQMILNGINNYKNPKLTRMLTFKFYMPKKATELKHLLQCLEEELKPLE 456
           ||||||||||||||||||||||||||||||||||||||||||||||||#|||||||||||
NO: 14 421 KTQLQLEHLLLDLQMILNGINNYKNPKLTRMLTFKFYMPKKATELKHL-QCLEEELKPLE 479

NO: 16 457 EVLNLAQSKNFHLRPRDLISNINVIVLELKGSETTFMCEYADETATIVEFLNRWITFCQS 516
           ||||||||||||||||||||||||||||||||||||||||||||||||||||||||||||
NO: 14 480 EVLNLAQSKNFHLRPRDLISNINVIVLELKGSETTFMCEYADETATIVEFLNRWITFCQS 539

NO: 16 517 IISTLT                                                       522
           ||||||
NO: 14 540 IISTLT                                                       545
```

Use of DNA Expression Vectors to Manufacture Proteins.

The method using Fe-independent, secreted expression of proteins related to diphtheria toxin described above has several commercial applications in addition to the use of the method to express s-denileukin diftitox. The method can be used to improve (enhance) expression (yield) of:

WT Diphtheria Toxin:

The wild type Diphtheria toxin (SEQ ID NO: 11) used to make diphtheria toxO id, a vaccine for diphtheria which is present in DTP, TDaP, and other combination vaccines may be made using the DNA expression vector of the present invention. The DNA segment encoding SEQ ID NO: 11 may be placed in the DNA expression vector of the present invention and located downstream of the ToxP/mutant ToxO.

Cross-Reacting Material-197 (CRM197) and Cross-Reacting Material-107 (CRM107):

CRM197 and CR107 are mutant proteins of full-length diphtheria toxin which are highly immunogenic but are completely devoid of toxin activity. They are used as carriers for several polysaccharide conjugate vaccines. For example, Wyeth and Pfizer took advantage of this immunogenicity in the 1990s when it conjugated seven polysaccharides from *Streptococcus pneumoniae* to CRM197 to create the original Prevnar vaccine which was FDA approved in February 2000. A 13-polysaccharides Prevnar was FDA-approved in 2010. The meningococcal vaccine Menveo, from Novartis, is four *Neisseria meningitidis* polysaccharides plus CRM197. This vaccine gained FDA approval in 2010. The cancer immunotherapy company Imugene (ASX: IMU) reported dramatic improvements in antibody titers from its B cell peptide cancer immunotherapy targeting HER2 when it used CRM197 as a carrier protein. CRM197 is also being evaluated as a potential drug delivery protein. The Swiss-based Turing Pharmaceuticals is working on CRM197 fusion constructs with therapeutic proteins of up to 1,000 amino acids in length. The DNA expression vectors of the present invention maybe used to produce CRM 197 and CRM 107. One or more of the DNA segment(s) encoding SEQ ID NOs: 18-21 may be placed in the DNA expression vector of the present invention and located downstream of the ToxP/mutant ToxO.

Diphtheria Toxin Based Fusion Proteins with Cleavable Peptide or Protein Tags Used to Enhance Purification.

Cleavable peptide tags (such as $His_6$ (SEQ ID NO: 23) or FLAG [DYKDDDDK] (SEQ ID NO: 24)) or protein tags (such as GST [glutathione S-transferase] or SUMO [Small Ubiquitin-like Modifier protein]) may be fused with specific protease cleavage sites to diphtheria toxin based fusion proteins. Affinity chromatography methods using antibodies or ligands which bind to the tag may be used for rapid purification of the tagged protein. Following purification, the specific cleavage site enables separation of the tag from the desired diphtheria toxin related proteins. Such fusions may enhance purification of diphtheria toxin based fusion proteins of the present invention.

```
(Protein sequence of ms-CRM197)
                              SEQ ID NO: 17
  1 GADDVVDSSKSFVMENFSSYHGTKP

    GYVDSIQKGIQKPKSGTQGNYDDDW

 51 KEFYSIDNKYDAAGYSVDNENPLSG

    KAGGVVKVTYPGLIKVLALKVDNAE

101 TIKKELGLSLTEPLMEQVGTEEFIK

    RFGDGASRVVLSLPFAEGSSSVEYI

151 NNWEQAKALSVELEINFETRGKRGQ

    DAMYEYMAQACAGNRVRRSVGSSLS

201 CINLDWDVIRDKIKTKIESLKEHGP

    IKNKMSESPNKTVSEEKAKQYLEEF
```

-continued

251 HQTALEHPELSELKTVIGINPVFAG

ANYAAWAVNVAQVIDSETADNLEKT

301 TAALSILPGIGSVMGIADGAVHHNT

EEIVAQSIALSSLMVAQAIPLVGEL

351 VDIGFAAYNFVESIINLFQVVHNSY

NRPAYSPGHKTQPFLHDGYAVSWNT

401 VEDSIIRTGFQGESGHDIKITAENT

PLPIAGVLLPTIPGKLDVNKSKTHI 451 aVNGRKIRMRCRAIDGDVTFCRPKS

PVYVGNGVHANLHVAFHRSSSEKIH

501 SNEISSDSIGVLGYQKTVDHTKVNS

KLSLFFEIKS <535

(Protein sequence of is-CRM197)

SEQ ID NO: 18

1 MSRKLFASILIGALLGIGAPPSAHA

GADDVVDSSKSFVMENFSSYHGTKP

51 GYVDSIQKGIQKPKSGTQGNYDDDW

KEFYSIDNKYDAAGYSVDNENPLSG

101 KAGGVVKVTYPGLIKVLALKVDNAE

TIKKELGLSLTEPLMEQVGTEEFIK

151 RFGDGASRVVLSLPFAEGSSSVEYI

NNWEQAKALSVELEINFETRGKRGQ

201 DAMYEYMAQACAGNRVRRSVGSSLS

CINLDWDVIRDKIKTKIESLKEHGP

251 IKNKMSESPNKTVSEEKAKQYLEEF

HQTALEHPELSELKTVIGINPVFAG

301 ANYAAWAVNVAQVIDSETADNLEKT

TAALSILPGIGSVMGIADGAVHHNT

351 EEIVAQSIALSSLMVAQAIPLVGEL

VDIGFAAYNFVESIINLFQVVHNSY

401 NRPAYSPGHKTQPFLHDGYAVSWNI

VEDSIIRTGFQGESGHDIKITAENT

451 PLPIAGVLLPTIPGKLDVNKSKTHI

SVNGRKIRMRCRAIDGDVTFCRPKS

501 PVYVGNGVHANLHVAFHRSSSEKIH

SNEISSDSIGVLGYQKTVDHTKVNS

551 KLSLFFEIKS <560

(Protein sequence of ms-CRM107)

SEQ ID NO: 19

GADDVVDSSKSFVMENFSSYHGTKP

51 GYVDSIQKGIQKPKSGTQGNYDDDW

KGFYSIDNKYDAAGYSVDNENPLSG

-continued

101 KAGGVVKVTYPGLIKVLALKVDNAE

TIKKELGLSLTEPLMEQVGTEEFIK

151 RFGDGASRVVLSLPFAEGSSSVEYI

NNWEQAKALSVELEINFETRGKRGQ

201 DAMYEYMAQACAGNRVRRSVGSSLS

CINLDWDVIRDKIKTKIESLKEHGP

251 IKNKMSESPNKTVSEEKAKQYLEEF

HQTALEHPELSELKTVIGINPVFAG

301 ANYAAWAVNVAQVIDSETADNLEKT

TAALSILPGIGSVMGIADGAVHHNT

351 EEIVAQSIALSSLMVAQAIPLVGEL

VDIGFAAYNFVESIINLFQVVHNSY

401 NRPAYSPGHKTQPFFHDGYAVSWNI

VEDSIIRTGFQGESGHDIKITAENT

451 PLPIAGVLLPTIPGKLDVNKSKTHI

SVNGRKIRMRCRAIDGDVTFCRPKS

501 PVYVGNGVHANLHVAFHRSSSEKIH

SNEISSDSIGVLGYQKTVDHTKVNF

551 KLSLFFEIKS <560

(Protein sequence of is-CRM107)

SEQ ID NO: 20

1 MSRKLFASILIGALLGIGAPPSAHA

GADDVVDSSKSFVMENFSSYHGTKP

51 GYVDSIQKGIQKPKSGTQGNYDDDW

KGFYSIDNKYDAAGYSVDNENPLSG

101 KAGGVVKVTYPGLIKVLALKVDNAE

TIKKELGLSLTEPLMEQVGTEEFIK

151 RFGDGASRVVLSLPFAEGSSSVEYI

NNWEQAKALSVELEINFETRGKRGQ

201 DAMYEYMAQACAGNRVRRSVGSSLS

CINLDWDVIRDKIKTKIESLKEHGP

251 IKNKMSESPNKTVSEEKAKQYLEEF

HQTALEHPELSELKTVIGINPVFAG

301 ANYAAWAVNVAQVIDSETADNLEKT

TAALSILPGIGSVMGIADGAVHHNT

351 EEIVAQSIALSSLMVAQAIPLVGEL

VDIGFAAYNFVESIINLFQVVHNSY

401 NRPAYSPGHKTQPFFHDGYAVSWNI

VEDSIIRTGFQGESGHDIKITAENT

451 PLPIAGVLLPTIPGKLDVNKSKTHI

SVNGRKIRMRCRAIDGDVTFCRPKS

-continued

```
501 PVYVGNGVHANLHVAFHRSSSEKIH

    SNEISSDSIGVLGYQKTVDHTKVNF

551 KLSLFFEIKS <560
```

TABLE 1

| SEQUENCE NUMBER | DESCRIPTION |
|---|---|
| SEQ ID NO: 38 | Protein sequence of N terminal His tag to VLM s-Ontak |
| SEQ ID NO: 39 | Protein sequence of N terminal His tag to VLM s-Ontak after signal sequence is cleaved |
| SEQ ID NO: 40 | Protein sequence of N terminal His tag to VLM s-Ontak after signal sequence is cleaved and TEV site is cleaved |
| SEQ ID NO: 41 | DNA sequence of N terminal His tag to VLM s-Ontak |
| SEQ ID NO: 42 | Protein sequence of C terminal His tag to VLM s-Ontak |
| SEQ ID NO: 43 | Protein sequence of C terminal His tag to VLM s-Ontak after signal sequence is cleaved) |
| SEQ ID NO: 44 | DNA sequence of C terminal His tag to VLM s-Ontak |
| SEQ ID NO: 45 | Protein sequence of C terminal TEV His9 tag to VLM s-Ontak ("His9" disclosed as SEQ ID NO: 48) |
| SEQ ID NO: 46 | Protein sequence of C terminal TEV His9 tag to VLM s-Ontak after signal sequence is cleaved ("His9" disclosed as SEQ ID NO: 48) |
| SEQ ID NO: 30 | Protein sequence of C terminal TEV His9 tag to VLM s-Ontak after signal sequence and Tev protease site are cleaved ("His9" disclosed as SEQ ID NO: 48) |
| SEQ ID NO: 31 | DNA sequence of C terminal His tag to VLM s-Ontak |
| SEQ ID NO: 32 | Secreted *C. diphtheriae* protease 1 amino acid sequence |
| SEQ ID NO: 33 | Secreted *C. diphtheriae* protease 1 DNA sequence |
| SEQ ID NO: 34 | DNA sequence of allelic exchange substrate [AES] for knocking out secreted *C. diphtheriae* protease 1 |
| SEQ ID NO: 35 | Secreted *C. diphtheriae* protease 2 amino acid sequence |
| SEQ ID NO: 36 | Secreted *C. diphtheriae* protease 2 DNA sequence) Protease 2 DNA sequence |
| SEQ ID NO: 37 | DNA sequence of allelic exchange substrate [AES] for knocking out secreted *C. diphtheriae* protease 2 |

Purification of VLM s-Ontak Using His-Tagged Versions of the Polypeptide

In some preparations of VLM s-Ontak produced in *Corynebacterium diphtheriae* C7 slow proteolytic cleavage of the mature 520 amino acid polypeptide occurs. This is probably due to secreted proteases made by *Corynebacterium diphtheriae* C7. This proteolytic cleavage occurs at approximately amino acid 390 of the mature 520 amino acid VLM s-Ontak.

Histidine-tagged (His-tagged) versions of VLM s-Ontak have been constructed for the purpose of accelerating the purification of the desired protein away from the secreted proteases present in the culture supernatant. Tobacco Etch Virus (TEV) nuclear-inclusion-a endopeptidase (EC 3.4.22.44) recognition sites have also been engineered into these His-tagged versions of VLM s-Ontak. The purpose of the TEV cleavage sites is to enable the removal of the poly-His sequences in the final preparation of VLM s-Ontak. TEV is a highly specific endopeptidase which recognizes the amino acid sequence ENLYFQ\X where '\' denotes the cleaved peptide bond, and X represents any small hydrophobic or polar amino acid such as glycine (G) (SEQ ID NO: 49).

N-terminal His-tagged VLM s-Ontak with TEV cleavage site. As shown in SEQ ID: 38 (Protein sequence of N terminal His tag to VLM s-Ontak) it is possible to add the amino sequence HHHHHHENLYFQ (SEQ ID NO: 50) to the immature protein sequence of VLM s-Ontak near its N-terminus. In this version, the sequence HHHHHHENLYFQ (SEQ ID NO: 50) appears immediately after the 26 amino acid signal sequence and immediately before the mature sequence of VLM s-Ontak (GADDVA (SEQ ID NO: 51)). The first glycine of VLM s-Ontak comprises the final recognition residue for the TEV protease which recognizes ENLYFQ\X (SEQ ID NO: 49) with X being any small amino acid. The mature, secreted protein sequence of this N-terminal His-tagged VLM s-Ontak is shown in SEQ ID: 39 (Protein sequence of N terminal His tag to VLM s-Ontak after signal sequence is cleaved) which is a good candidate for Nickel-column affinity purification with its $His_6$ tag (SEQ ID NO: 23). The affinity purified VLM s-Ontak may then be exposed to small amounts of pure TEV protease, leading to enzymatic proteolysis that removes the 13 N-terminal residues MHHHHHHENLYFQ (SEQ ID NO: 52) and releases mature, untagged VLM s-Ontak as is shown in SEQ ID NO: 40 (Protein sequence of N terminal His tag to VLM s-Ontak after signal sequence is cleaved and TEV site is cleaved).

Because the secreted protease(s) of *Corynebacterium diphtheriae* C7 cleave at approximately amino acid 390, N-terminal His-tagging can lead to two species: full length desired VLM s-Ontak (520 amino acids) and a 390-amino acid N-terminal breakdown fragment. These two polypeptides, being relatively close in size (as well as molecular composition) are difficult to separate by size exclusion chromatography. Hence we have also developed C-terminal His-tagged version of VLM s-Ontak.

C-terminal His-tagged VLM s-Ontak without TEV cleavage site. As shown in SEQ ID NO: 42 (Protein sequence of C terminal His tag to VLM s-Ontak) it is possible to add the amino sequence HHHHHH (SEQ ID NO: 23) to the immature protein sequence of VLM s-Ontak at its C-terminus. In this version, the sequence HHHHHH (SEQ ID NO: 23) appears immediately after the C-terminal threonine of VLM s-Ontak ( . . . IISTLT (SEQ ID NO: 53)). The mature, secreted protein sequence of this C-terminal His-tagged VLM s-Ontak is shown in SEQ ID: 43 (Protein sequence of C terminal His tag to VLM s-Ontak after signal sequence is cleaved) which is a good candidate for Nickel-column affinity purification with its $His_6$ tag (SEQ ID NO: 23).

C-terminal His-tagged VLM s-Ontak with TEV cleavage site. In order to avoid having the $His_6$ sequence (SEQ ID NO: 23) in the final polypeptide sequence of the above version of VLM s-Ontak made by C-terminal His-tagging (SEQ ID: 43), it is possible to insert a TEV recognition sequence at the C-terminus to enable removal of the His-tag sequence. In this version, the sequence ENLYFQGHHHHHHHHH (SEQ ID NO: 54) appears immediately after the C-terminal threonine of VLM s-Ontak ( . . . IISTLT (SEQ ID NO: 53)). Since nickel affinity binding is enhanced by poly-His sequences even longer than six amino acids, it is possible to include nine His residues. The amino acid sequence of this C-terminal His-tagged VLM s-Ontak with TEV cleavage site is shown in SEQ ID: 45 (Protein sequence of C terminal TEV His9 tag (SEQ ID NO: 48) to VLM s-Ontak). The mature, secreted protein sequence of this C-terminal His-tagged VLM s-Ontak with TEV cleavage site is shown in SEQ ID: 46 (Protein sequence of C terminal TEV His9 tag (SEQ ID NO: 48) to VLM s-Ontak after signal sequence is cleaved) and is a good candidate for Nickel-column affinity purification with its $His_9$ tag (SEQ ID NO: 48). The affinity purified VLM s-Ontak may then be exposed to small amounts of pure TEV protease, leading to enzymatic proteolysis that removes the 10 C-terminal residues GHHHHHHHHH (SEQ ID NO: 55), and releases mature, untagged VLM s-Ontak as is shown in SEQ ID: 30. Of note, this version of purified VLM s-Ontak (SEQ ID: 30) is 526 amino acids in length rather than 520 amino acids (SEQ ID NO: 15) because it contains six additional amino acids of the TEV protease recognition sequence (ENLYFQ (SEQ ID NO: 56) fused to the usual C-terminus threonine of VLM s-Ontak ( . . . IISTLT (SEQ ID NO: 53)). The end result of this version of C-terminal His-tagged VLM s-Ontak with TEV cleavage site (SEQ ID: 30) is a C-terminal sequence . . . IISTLTENLYFQ (SEQ ID NO: 57).

Manufacturing method for VLM s-Ontak which include His-tags and TEV protease sites. The above three His-tag versions of VLM s-Ontak (N-terminal $His_6$ tag (SEQ ID NO: 23) with TEV protease site, C-terminal $His_6$ tag (SEQ ID NO: 23) without TEV protease site, and C-terminal $His_9$ (SEQ ID NO: 48) tag with TEV protease site) are examples of methods to use His-tag/Nickel column affinity chromatography in the manufacturing method of VLM s-Ontak. Because of secreted proteases from *Corynebacterium diphtheriae* C7 that are present in the culture supernatant, it is important to purify VLM s-Ontak away from other proteins in the culture supernatant rapidly in order to avoid significant loss of the desired product. The inclusion of His-tags and TEV protease sites represents a significant improvement and may enable a rapid, streamlined manufacturing process for VLM s-Ontak Generation of *Corynebacterium diphtheriae* C7 lacking key secreted proteases for improved manufacturing of VLM s-Ontak. The genome sequence of *Corynebacterium diphtheriae* C7 reveals two secreted proteases: Protease 1 is NCBI Reference Sequence WP_014318592.1 (SEQ ID: 32, 33) and Protease 2 is NCBI Reference Sequence WP_014318898.1 (SEQ ID: 35, 36). These proteases may be genetically deleted using the method of Ton-That and Scheewind (Ton-That H, Schneewind O. Assembly of pili on the surface of *Corynebacterium diphtheriae*. Mol Microbiol. 2003 November; 50(4):1429-38. PubMed PMID: 14622427) and also Allen and Schmitt (Allen C E, Schmitt M P. HtaA is an iron-regulated hemin binding protein involved in the utilization of heme iron in *Corynebacterium diphtheriae*. J Bacteriol. 2009 April; 191(8):2638-48. PubMed PMID: 19201805). The allelic exchange substrates to knock out protease 1 and protease 2 are shown in SEQ ID: 34 and SEQ ID: 37, respectively. These sequences when inserted into pk18mobsacB, a conjugative, mating plasmid with sacB counterselection (Schafer A, Tauch A, Jäger W, Kalinowski J, Thierbach G, Pühler A (1994) Small mobilizable multi-purpose cloning vectors derived from the *Escherichia coli* plasmids pK18 and pK19: selection of defined deletions in the chromosome of *Corynebacterium glutumicum*. Gene 145:69-73. PMID: 8045426), lead to constructs which will knockout each protease. A recombinant *Corynebacterium diphtheriae* strain lacking both protease 1 and protease 2 will be a valuable production strain for future manufacturing methods to generate VLM s-Ontak.

Protein Manufacturing Process of Diphtheria Toxin-Based Fusion Proteins

Using the DNA plasmids and expression vectors of the present invention, a novel process was discovered eliminating the problems associated with the conventional method of manufacturing Ontak®. Ontak® is currently expressed using a DNA vector in an *E. coli* expression system. c-denileukin diftitox or Ontak® is 521 amino acids in length and has a molecular weight of 58 kD. The conventional Ontak® manufacturing process results in the formation of Ontak® aggregates of heterogeneous molecular weight, residual DNA, and excessive residual detergent in the final formulation resulting in the FDA placing classic-Ontak® on clinical hold in June 2011. As observed in FIG. 8*a*, Ontak® is expressed from a plasmid in *E. coli* and results in insoluble, cytosolic Ontak® (protein) accumulations known as inclusion body forms. Using the process of the present invention, FIG. 8*b* illustrates the expression of s-denileukin diftitox as an extracellular mature secreted protein in a cell free supernatant that can be easily purified and results in higher protein yields as illustrated in FIG. 9. FIG. 9 shows both a Coomassie Blue stain for total protein and an anti-IL2 immunoblot of s-denileukin diftitox generated using the process of the present invention probed with anti-IL-2.

The novel process of the present invention comprises: 1) transforming bacteria, preferably a *Corynebacterium diphtheriae* strain, with a DNA expression vector of the present invention, 2) forming a transformant; 3) incubating the transformant in a culture medium for a period of time to allow growth and expression of a protein (such as a diphtheria toxin-based fusion protein and CRM typically containing a signal peptide), 4) secretion of the protein into the culture medium (due to a signal peptide attached to the protein); and (8) purifying the diphtheria toxin-based fusion protein from the culture medium. The DNA expression vectors include a ToxP and mutant ToxO that regulate the expression of at least one protein, such as a diphtheria toxin fusion protein, CRM protein, or other protein that may be attached to a signal peptide of the present invention.

Therapeutic Applications of Diphtheria Toxin-Based Fusion Proteins of the Present Invention Clinical efficacy of Ontak® has been demonstrated in cutaneous T cell lymphoma, peripheral T cell lymphoma, steroid-refractory graft versus host disease, methotrexate-refractory psoriasis, and methotrexate-refractory rheumatoid arthritis. Clinical efficacy has also been demonstrated in malignant melanoma and ovarian carcinoma as shown in FIG. 14. The diphtheria toxin-based fusion proteins of the present invention (including s-denileukin diftitox, ms-denileukin diftitox, is-denileukin diftitox-VLM, ms-denileukin diftitox-VLM) produced by the methods of the present invention will perform similarly, or better, than Ontak® that is commercially available with regard to clinical efficacies of treating or preventing disease.

Treatment for Tuberculosis.

As illustrated in FIG. 10, inventors of the present invention believe diphtheria toxin fusion proteins of the present invention will be active against tuberculosis. Denileukin diftitox is known to deplete IL-2-receptor (CD25+)-bearing cells including T regulatory ($T_{regs}$) cells. $T_{regs}$ cells express CD25 as well as FoxP3 and are immunosuppressive by their inhibition of Teffector ($T_{eff}$) cells. Teff cells such as CD4+ Thelper ($T_h$) cells and CD8+ cytotoxic T lymphocytes (CTLs) are needed within a tuberculosis granuloma to contain the *M. tuberculosis* bacterial infection. During tuberculosis infection, cellular lesions called granulomas form to contain the infection but are unable to fully eradicate the bacilli. Regulatory T cells (Tregs) are recruited to granulomas, leading to suppression of effector T cell function, potentially contributing to a permissive environment for *M. tuberculosis* persistence and growth. The diphtheria toxin fusion proteins of the present invention are used to deplete Tregs, which express IL-2 receptor, in order to ameliorate immune suppression by these cells during TB infection. FIG. 11 illustrates diphtheria fusion proteins used in the in vivo treatment of subjects (mice) with *M. tuberculosis*. Mice were infected with M. tb. strain H37Rv by aerosol infection giving an initial implantation of ~2.8 $log_{10}$ CFU counts in lungs on day 0. The groups of mice were treated with 750 ng of c-Ontak® intraperitoneally (IP) or intravenously (IV) as one treatment cycle (1×, dosed at week 2 post-infection) or two treatment cycles (2×, dosed at ~day 3 pre-infection and week 2 post-infection). A treatment cycle of denileukin diftitox is defined as 35 mg/kg (750 ng for a typical mouse) given two times, two days apart. RHZ daily treatment by oral gavage was started at week 2. R is rifampin and was given to mice at 10 mg/kg. H is isoniazid and was given to mice at 10 mg/kg. Z is pyrazinamide and was given to mice at 150 mg/kg. The outcome of this study is illustrated in FIGS. 12 and 13.

Treatment for Cancer

Tregs have also been shown to inhibit anti-tumor immunity, and the cellular expansion of Tregs in tumors generally correlates with poor prognosis in patients. Denileukin diftitox treatment in melanoma patients resulted in transient depletion of Tregs and increased 1 year median overall survival. s-denileukin diftitox and s-denileukin diftitox-VLM of the present invention will be used to deplete Tregs in patients with tumors heavily infiltrated with Tregs as a cancer immunotherapy.

Sequential Immunotherapy Using an IL-2 Receptor Targeted Fusion Toxin Followed by Anti-PD-1 Treatment Inhibits Melanoma Tumor Growth in Mice.

Immune checkpoints are inhibitory pathways that are necessary to prevent autoimmunity but can also dampen beneficial anti-tumor immune responses. Antibody-mediated blockade with checkpoint inhibitors (CPIs) of these pathways, especially of the PD-1/PD-L1 interaction, has shown remarkable long-term efficacy in clinical trials for a subset of cancer patients. However, a number of CPI-treated patients eventually exhibit disease progression and/or treatment refractory disease, and this suggests that additional targets or combinatorial drug regimens may be required to improve clinical outcomes. Denileukin diftitox, or *E. coli*-derived classic Ontak, is a diphtheria fusion toxin approved for the treatment of cutaneous T cell lymphoma by directly targeting cancer cells. Additionally, *E. coli*-derived classic Ontak can transiently deplete regulatory T cells (Tregs) in vivo and has been found to induce tumor regression in patients with metastatic melanoma. The inventors hypothesized that by depleting Tregs, *C. diphtheriae*-derived SEQ ID NO: 43 and *C. diphtheriae*-derived SEQ ID NO: 58 would inhibit B16 melanoma tumor growth and enhance the effector T cell response induced by anti-PD-1 treatment. The inventors found that *C. diphtheriae*-derived SEQ ID NO: 43 (as well as *C. diphtheriae*-derived SEQ ID NO: 58) treatment inhibits tumor growth of established tumors to a greater degree than monotherapy with anti-PD-1 treatment or monotherapy alone and led to increased tumor infiltration by IFNγ+CD8+ lymphocytes. When treatment was delayed, both anti-PD-1 and *C. diphtheriae*-derived SEQ ID NO: 43 (as well as *C. diphtheriae*-derived SEQ ID NO: 58) monotherapy were no longer effective, however sequential therapy of *C. diphtheriae*-derived SEQ ID NO: 43 (as well as *C. diphtheriae*-derived SEQ ID NO: 58) followed by anti-PD-1 treatment was still able to inhibit tumor growth and was superior to either agent alone. Taken together, these data indicate that *C. diphtheriae*-derived SEQ ID NO: 43 induces antitumor immune responses and shows promise as a cancer immunotherapy both alone and in combination with immune checkpoint inhibitors.

*E. coli*-derived classic Ontak (SEQ ID NO: 10) is a diphtheria fusion toxin that directly targets and kills high-affinity IL-2 receptor (CD25) positive cells and is used for the treatment of cutaneous T cell lymphoma (CTCL). Previous work has shown that *E. coli*-derived classic Ontak (SEQ ID NO: 10) can also transiently deplete Tregs, which also express high-affinity IL-2 receptor (Rasku M A, Clem A L, Telang S, Taft B, Gettings K, Gragg H, et al. Transient T cell depletion causes regression of melanoma metastases. J Transl Med. 2008; 6(12). PMID: 18334033). The inventors sought to determine whether depletion of Tregs by *C. diphtheriae*-derived SEQ ID NO: 43 and *C. diphtheriae*-derived SEQ ID NO: 58 could inhibit tumor growth in a murine model of melanoma. Additionally, the inventors assessed whether *C. diphtheriae*-derived SEQ ID NO: 43 and *C. diphtheriae*-derived SEQ ID NO: 58 could enhance immune checkpoint blockade, specifically anti-PD-1. The inventors hypothesized that as anti-PD-1 mainly acts to reverse effector T cell (Teff) exhaustion, that depletion of Tregs by *C. diphtheriae*-derived SEQ ID NO 15 or *C. diphtheriae*-derived SEQ ID NO 43 (or *C. diphtheriae*-derived SEQ ID NO 13 or *C. diphtheriae*-derived SEQ ID NO 58) would remove another mode of immune suppression and improve upon anti-PD-1 anti-tumor activity.

*C. diphtheriae*-Derived SEQ ID 43 and *C. diphtheriae*-Derived SEQ ID NO: 58 Inhibit Tumor Growth and Increases the Frequency of Tumor-Infiltrating Lymphocytes (TILs).

Although *E. coli*-derived classic Ontak (SEQ ID NO: 10) is an FDA approved drug, it has been placed on clinical hold because of misfolded protein aggregates and detergent contaminating the final formulation. *C. diphtheriae*-derived SEQ ID NO: 43, *C. diphtheriae*-derived SEQ ID NO: 15, *C. diphtheriae*-derived SEQ ID NO: 58, and *C. diphtheriae*-derived SEQ ID NO: 13 are novel fusion toxins made with a production method that produces fully folded, active proteins and do not require detergent-treatment to refold the protein. *C. diphtheriae*-derived SEQ ID NO: 43 and *C. diphtheriae*-derived SEQ ID NO: 58 produced by the inventors showed comparable activity to the commercial drug and effectively depleted splenic Tregs in vivo (FIG. 23). The B16F10 murine melanoma model produces poorly immunogenic tumors that are highly infiltrated with Tregs (101). Previous work in DEREG transgenic mice, has shown that targeted Treg depletion leads to inhibition of B16F10 tumor growth. To assess whether *C. diphtheriae*-derived SEQ ID NO: 43 and *C. diphtheriae*-derived SEQ ID NO: 58 can enhance anti-tumor immune responses by depleting Tregs, mice with established B16F10 melanoma tumors were treated with drug and tumor growth was measured over time. With only 2 doses of *C. diphtheriae*-derived SEQ ID NO: 43 (FIG. 24) or 2 doses of *C. diphtheriae*-derived SEQ ID NO: 58 (FIG. 25), tumor growth was significantly inhibited in treated mice when compared to control mice. The inventors then examined how these two treatments affect the frequency of different lymphocytic populations in the tumor and secondary lymphoid organs. CD8+ T cells are cytotoxic lymphocytes that are able to kill tumor cells and infiltration of tumors by CD8+ T cells has been correlated with a more favorable prognosis in patients (Topalian S L, Hodi F S, Brahmer J R, Gettinger S, Smith D C, McDermott D F, et al. Safety, Activity, and Immune Correlates of Anti-PD-1 Antibody in Cancer. N Engl J Med. 2012; 366(26):9-19. PMID: 22658127). Additionally, IFNγ production is essential for induction of cytotoxic CD8+ T cells (Mandai M, Hamanishi J, Abiko K, Matsumura N, Baba T, Konishi I. Dual faces of IFNγ in cancer progression: A Role of PD-L1 Induction in the Determination of Pro- and Antitumor Immunity. Clin Cancer Res. 2016; 22(10):2329-34. PMID: 27016309). The inventors found that mice treated with *C. diphtheriae*-derived SEQ ID NO: 58 had an increased frequency of IFNγ+ CD8+ in their tumors and spleens (FIG. 26).

*C. diphtheriae*-Derived SEQ ID 43 and *C. diphtheriae*-Derived SEQ ID NO: 58 Enhance Anti-Tumor Activity of PD-1 Blockade.

While PD-1 blockade results in reversal of Teff cell exhaustion, tumor Treg frequencies remain unchanged by treatment (Erdag G, Schaefer J T, Smolkin M E, Deacon D H, Shea S M, Dengel L T, et al. Immunotype and Immunohistologic Characteristics of Tumor-Infiltrating Immune Cells Are Associated with Clinical Outcome in Metastatic Melanoma. Cancer Res. 2012; 72(5):1070-81. PMID: 22266112). To determine whether Treg depletion could augment anti-PD-1 anti-tumor activity, mice with established B16F10 tumors were given *C. diphtheriae*-derived SEQ ID NO: 58 on day 7 post tumor injection and anti-PD-1 treatment was initiated 24 hrs later. Sequential therapy was given to avoid *C. diphtheriae*-derived SEQ ID NO: 58-mediated clearance of Teff that upregulate CD25 upon activation. *C. diphtheriae*-derived SEQ ID NO: 58 monotherapy was more effective in inhibiting tumor growth than anti-PD1 treatment, and when sequential therapy was given, the inventors observed tumor reduction greater than that seen with either monotherapy alone (FIG. 25). Similar results were obtained with *C. diphtheriae*-derived SEQ ID NO: 43 (FIG. 24). Previous studies have shown that as tumors grow larger, many immunotherapies such as anti-PD-1 are no longer effective in murine tumor models. To assess efficacy in larger tumors, treatment was initiated on day 10 post tumor injection. When treatment was delayed to day 10 and tumors were more progressed, *C. diphtheriae*-derived SEQ ID NO: 58 and anti-PD-1 monotherapy were no longer as efficacious as in the day 7-start-treatment model; however, sequential therapy remained highly active in tumor growth inhibition (FIG. 27).

These data show that Treg depletion by either *C. diphtheriae*-derived SEQ ID NO: 43 or *C. diphtheriae*-derived SEQ ID NO: 58 coupled with PD-1 blockade leads to potent anti-tumor activity superior to monotherapy with anti-PD-1 alone or to *C. diphtheriae*-derived SEQ ID NO: 43 or *C. diphtheriae*-derived SEQ ID NO: 58 given as monotherapy. The dual therapy is robust, giving potent tumor suppression even when therapy is delayed to day 10 post-tumor cell injection. Not to be held to a particular theory, FIG. 28 provides an overview of the inventors' proposed mechanism of how sequential dual therapy with *C. diphtheriae*-derived SEQ ID NO: 15, *C. diphtheriae*-derived SEQ ID NO: 43, *C. diphtheriae*-derived SEQ ID NO: 13, or *C. diphtheriae*-derived SEQ ID NO: 58 preceding checkpoint inhibitor therapy may be more beneficial than either monotherapy alone. As may be seen, following checkpoint-inhibitor blockade there is a Teff cell autocrine loop in which IL2 secretion drives Teff cell expansion and expression of the IL2-receptor (CD25). Treatment with *C. diphtheriae*-derived SEQ ID NO: 15, *C. diphtheriae*-derived SEQ ID NO: 43, *C. diphtheriae*-derived SEQ ID NO: 13, or *C. diphtheriae*-derived SEQ ID NO: 58 given prior to checkpoint blockade effectively eliminates Tregs prior to the establishment of the IL2/IL2-receptor autocrine loop. The use of *C. diphtheriae*-derived SEQ ID NO: 15, *C. diphtheriae*-derived SEQ ID NO: 43, *C. diphtheriae*-derived SEQ ID NO: 13, or *C. diphtheriae*-derived SEQ ID NO: 58 simultaneously with or after checkpoint inhibitor treatment might lead to killing of Teff cells as well as Tregs and would not be expected to have the same tumor-inhibitory activity that is seen with sequential dual therapy with *C. diphtheriae*-derived SEQ ID NO: 43 or *C. diphtheriae*-derived SEQ ID NO: 58 preceding checkpoint inhibitor therapy.

Unlike the present invention Padron et al. (Age effects of distinct immune checkpoint blockade treatments in a mouse melanoma model. Experimental Gerontology. Published online 28 Dec. 2017 doi.org/10.1016/j.exger.2017.12.025) did not see the same tumor-inhibitory activity of the present invention. Padron et al. reported a comparative analysis of combination therapies of three checkpoint inhibitors (anti-PD1, anti-PDL1, and anti-CTLA4) together with *E. coli*-derived classic Ontak (SEQ ID NO: 10) in the mouse B16F10 melanoma model and found no improvement in tumor volume responses to checkpoint inhibitor therapy when *E. coli*-derived classic Ontak (SEQ ID NO: 10) was added as dual therapy.

Padron et al. treated mice intraperitoneally (IP) with a checkpoint inhibitor (CPI) plus *E. coli*-derived classic Ontak (SEQ ID NO: 10, 3 mg per mouse per dose) simultaneously every 5 days starting on day 7 post-tumor challenge. There are many substantial differences between Padron et al.'s method of treating mice IP with *E. coli*-derived classic Ontak (SEQ ID NO: 10) and the methods of the present invention. For example, Padron et al. simultaneously provided *E. coli*-derived classic Ontak (SEQ ID NO: 10) and specific checkpoint inhibitors to mice resulting in no improvement in tumor volume response. The inventors of the present invention made a surprising discovery by administering to a subject a first agent that depletes a subject's Tregs (such as *C. diphtheriae* derived SEQ ID NO: 43 or as *C. diphtheriae* derived SEQ ID NO: 58) followed by administering to the subject a second agent that is a checkpoint inhibitor (such as anti-PD-1), thereby improving tumor volume response. Also, Padron et al. teaches the use of *E. coli*-derived classic Ontak (SEQ ID NO: 10) which contains ~40% inactive protein aggregates whereas the methods of the present invention used *C. diphtheriae*-derived SEQ ID NO: 15, *C. diphtheriae*-derived SEQ ID NO: 43, *C. diphtheriae*-derived SEQ ID NO: 13, or *C. diphtheriae*-derived SEQ ID NO: 58 (which are fully active, monomeric polypeptides). Unlike Padron et al., the methods of the present invention used 5 mg or in some instance 10 mg of *C. diphtheriae*-derived SEQ ID NO: 43 or *C. diphtheriae*-derived SEQ ID NO: 58 while Padron et al. teaches the use of 3 mg of *E. coli*-derived classic Ontak (SEQ ID NO: 10). The methods of the present invention use a single initial course of *C. diphtheriae*-derived SEQ ID NO: 43 or *C. diphtheriae*-derived SEQ ID NO: 58 with two doses on day 7/day 10 or day 8/day 11 or day 10/day 13 followed by twice weekly CPI until the end of the experiment. FIG. 28 illustrates why the use of CPI simultaneously with *E. coli*-derived classic Ontak (SEQ ID NO: 10) or *C. diphtheriae*-derived Ontak-related molecules (SEQ ID NO: 15, SEQ ID NO: 43, SEQ ID NO: 13, SEQ ID NO: 58) based on the inventors' discoveries, would be expected to have poor effectiveness because of Ontak-mediated killing of Teff cells expressing the IL2-receptor.

Promoter Operator Strain Combinations Increase Expression.

The incorporation of the native diphtheria tox promoter with mutant tox operator sequences allow for the constitutive expression of tox gene products in medium that contains high concentrations of iron. This is in contrast to constructs that carry the wild type tox operator sequence, a 19 bp inverted palindromic sequence immediately downstream from the tox promoter. In the case of the wild type tox operator, the iron activated diphtheria tox repressor, DtxR, binds to the operator and represses the expression of tox gene products. The activation of apo-DtxR by iron causes the repressor to bind to the tox operator and repress expression of tox. When iron becomes the growth rate limiting substrate, iron disassociates from the repressor and apo-DtxR no longer binds to the tox operator, thereby allowing derepression of tox and the production of tox gene products. Accordingly, the incorporation of mutant tox operator sequences into each of the fusion protein toxin genetic constructs (SEQ ID NO: 2) allows for their constitutive expression and secretion into the culture medium in moderate yield.

Figure 29:
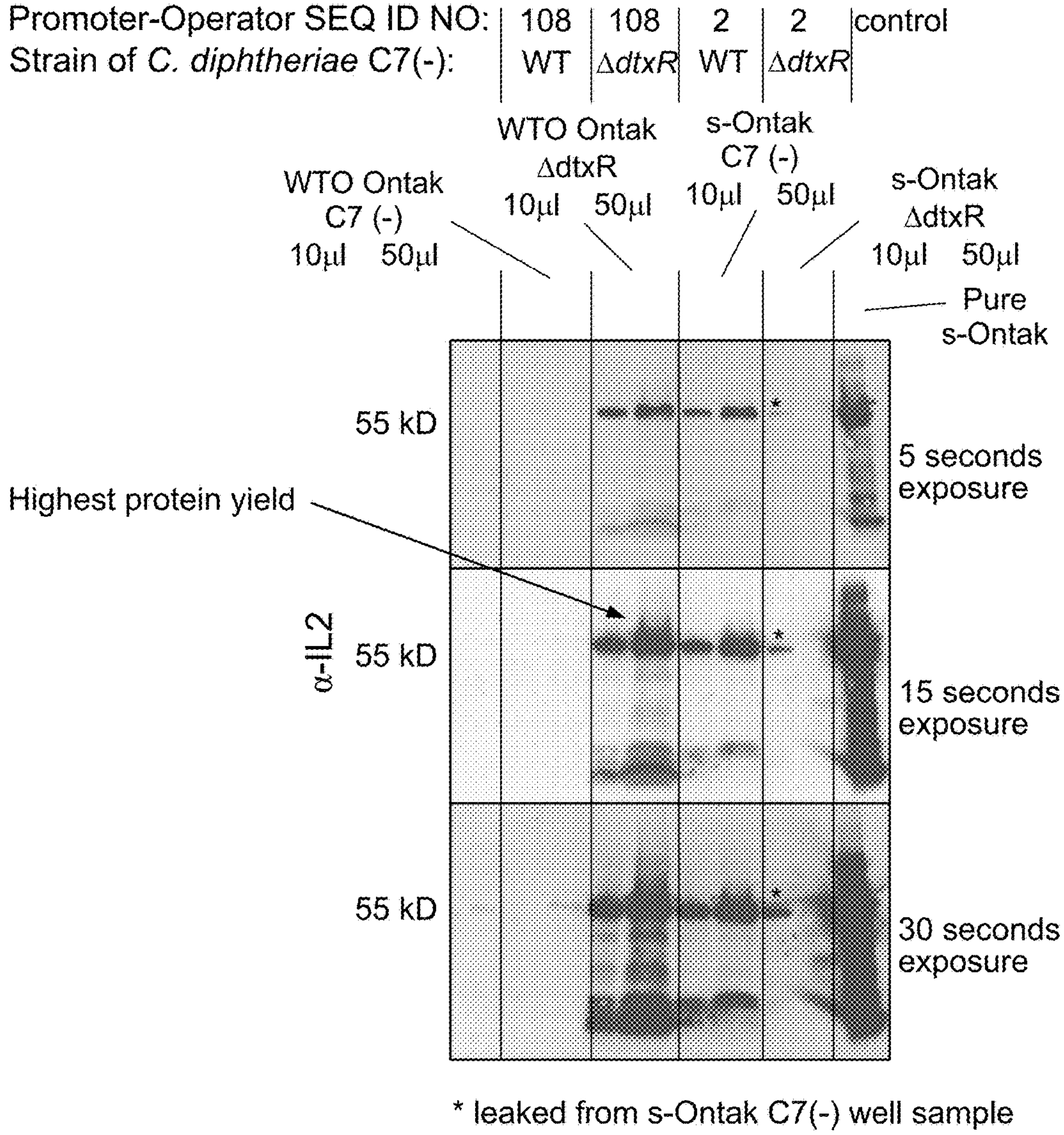

The inventors also studied expression of s-Ontak-related proteins in the *C. diphtheriae* C7(−) ΔdtxR mutant strain. There is some overlap between the −10 promoter consensus sequence and the inverted repeats that form the tox operator. Considering this the inventors studied whether expression of s-Ontak-related proteins would be increased by using the ΔdtxR mutant strain with the wild type promoter-operator sequences. As may be seen in FIG. 29, the combination of WT promoter operator (SEQ ID NO: 108) expressed in the ΔdtxR mutant strain increased protein yield by ~50% as compared with the mutant operator (SEQ ID NO: 2) being expressed in WT *C. diphtheriae.*

Purification Strategies Using Hydrophobic Interaction Chromatography (HIC) and Mimetic Blue Affinity Chromatographic Matrix.

The diphtheria toxin-related fusion protein toxins described in this application all carry the native diphtheria toxin translocation domain. This domain is largely hydrophobic and as such under conditions of high salt (1M NaCl) allows the binding of these proteins to Phenyl-Sepharose chromatography (hydrophobic interaction chromatography, HIC) medium. These proteins then are partially purified by employing a reverse gradient reducing the salt concentration in the elution buffer. In the case of s-$DAB_{1-389}$-IL2-V6A (SEQ ID NO: 15), the fusion protein toxin is eluted from the matrix at a salt concentration of 100 mM NaCl, and showed partial enrichment (FIG. 30). Thus, hydrophobic interaction chromatography (HIC) is a promising approach to purify s-Ontak-related proteins which lack $His_6$-tags (SEQ ID NO: 23) and to avoid the use of nickel column chromatography.

In addition, Mimetic Blue affinity chromatography is used to selectively bind proteins that contain interleukin 2 sequences. In this instance, s-$DAB_{1-389}$-IL2-V6A (SEQ ID NO: 15), and related mutant proteins selectively bind to the Mimetic Blue and are eluted from the matrix by an increasing gradient of NaCl in Tris-HCl buffer at pH 7.0. In these instances, IL-2 is selectively bound to Mimetic Blus resin and is eluted from the column matrix when the concentration of NaCl in the eluate reaches approximately 600 mM.

Combinations of HIC, Mimetic Blue chromatography, and ion-exchange chromatography are promising methods to purify s-Ontak-related proteins which lack $His_6$-tags (SEQ ID NO: 23) and to avoid the use of nickel column chromatography.

V6A Leads to Transient Treg Depletion.

The inventors have shown that treatment of murine models of melanoma (B16F10) and triple negative breast cancer (4T1) with s-$DAB_{1-389}$-IL2-V6A-$His_6$ (SEQ ID NO: 43) result in a transient depletion of activated T regulatory cells in the tumor microenvironment. For example, in the case of established 4T1 tumors in the mammary fat pad, within 3 days following the administration of s-$DAB_{1-389}$-IL2-V6A-$His_6$ (SEQ ID NO: 43) the inventors have found a 71% reduction of activated Tregs in the tumor (see FIG. 31). This reduction is transient and within one week of administration, the total T regulatory cell count rebounds to normal levels. It is important to note that the biologic half-life of s-$DAB_{1-389}$-IL2-V6A-$His_6$ (SEQ ID NO: 43) in circulation is only 60 minutes (FIG. 43), and because of this there are no long-term immunologic deficits (induction of autoimmune disease, activation of latent tuberculosis, etc.) associated with this transient depletion.

Early clinical trials with s-$DAB_{1-389}$-IL2-V6A-$His_6$ (SEQ ID NO: 43) or related proteins may therefore find it attractive to use depletion of circulating Treg cells as a biomarker for drug efficacy.

Fully Sequential Dual Therapy of s-Ontak-Related Proteins with Anti-PD1 Leads to Potent Anti-Tumor Effects.

Previously disclosed data on dual sequential therapy of s-Ontak-related proteins with anti-PD1 used treatment regimens in mice in which dosing of the s-Ontak-related proteins overlapped with the anti-PD1 checkpoint inhibitor (FIG. 24, 25, 27), and thus the drugs were not dosed in a fully sequential manner. In new data in FIG. 32, the inventors show that fully sequential (no overlap) dual therapy of s-$DAB_{1-389}$-IL2-V6A-$His_6$ (SEQ ID NO: 43) followed by anti-PD1 results in potent anti-tumor effects.

The inventors further observed that dual sequential therapy was active in the B16 melanoma model even when therapy was started late (day 10 post-tumor implantation) as may be seen in FIG. 33.

s-$DAB_{1-389}$-IL2-V6A-$His_6$ (SEQ ID NO: 43) is Active in Three Additional Tumor Types in Mice in Addition to Melanoma The inventors demonstrated that s-$DAB_{1-389}$-IL2-V6A-$His_6$ (SEQ ID NO: 43) has potent anti-tumor activity as monotherapy in three mouse tumor models: (i) syngeneic CT26 colon carcinoma (FIG. 34), (ii) syngeneic RENCA renal cell carcinoma (FIG. 35), and (iii) orthotopic 4T1 triple negative breast cancer (FIG. 49).

The inventors also demonstrated that s-$DAB_{1-389}$-IL2-V6A-$His_6$ (SEQ ID NO: 43) has potent anti-tumor activity as dual sequential therapy with anti-PD1 in two mouse tumor models: (i) syngeneic CT26 colon carcinoma (FIG. 34), (ii) syngeneic RENCA renal cell carcinoma (FIG. 35).

D3E Substitution Leads to More Stable s-Ontak-Related Proteins and Results in Prolonged Half-Life, Reduced Vascular Leak, Retained Potency, and Higher Expression Levels in *C. diphtheriae* C7(−).

A major part of this invention is the discovery that the D3E mutant version of s-Ontak is associated with (i) prolonged half-life, (ii) reduced vascular leak, (iii) high potency (84% as active as s-Ontak), and (iv) 4-fold higher expression in *C. diphtheriae* C7(−).

The inventors used protein structure algorithms, which are based on the 3-dimensional crystal structure of full-length diphtheria toxin. In particular, the inventors focused on the vascular leak associated-tripeptide motif (x)D(y) where x is valine, isoleucine, leucine, or glycine and y is serine, leucine, or valine. The sequence of s-Ontak contains two such (x)D(y) motifs near its amino terminus: $V_6D_7S_8$ and $V_{28}D_{29}S_{30}$.

As may be seen in FIG. 36, the inventors noticed that $V_6D_7S_8$ appears at the end of the second alpha helix of the s-Ontak 3-dimensional structure and that it forms hydrogen bond interactions with the first alpha-helical loop. Specifically $D_3$ in the first helix forms a hydrogen bond with $S_8$ in the second helix. The inventors hypothesized that substitution of Glu for Asp at residue 3, or D3E substitution, would result in a tighter H-bonding interaction between the two helices. Further, the inventors hypothesized that with a stronger H-bond in place, the D3E substitution mutant would be less able to expose the $V_6D_7S_8$ motif to vascular endothelium and produce vascular leak.

Indeed, the inventors found that s-Ontak-D3E-$His_6$ (Tm=45.5) had greater thermal stability than s-Ontak-$His_6$ (Tm 43.0) and s-Ontak-V6A-$His_6$ (Tm 40.0) as shown in FIG. 37. Binding of the substrate NAD further increased the thermal stability of s-Ontak-D3E-$His_6$ and s-Ontak-$His_6$, but did not alter the thermal stability of the other substituted forms of s-Ontak (FIG. 38).

Expression of s-Ontak-D3E-$His_6$ in *C. diphtheriae* C7(−) was ~4-fold greater than that of s-Ontak (FIG. 40), most likely because of the protein's enhanced stability. In addition, of s-Ontak-D3E-$His_6$ demonstrated a longer serum half-life (240 min) than either s-Ontak-$His_6$, (150 min) or s-Ontak-V6A-$His_6$ (60 min) as shown in FIG. 43—probably due to its increased stability.

The inventors found that s-Ontak-D3E-$His_6$ showed high potency for killing CD25+ cells with 84% of the activity of s-Ontak-$His_6$, while s-Ontak-V6A-$His_6$ demonstrated killing activity that was 20% of that of s-Ontak-$His_6$ (FIG. 40). s-Ontak-D3E-$His_6$ also showed significantly less vascular leak as measured by HUVEC permeation assay than s-Ontak-$His_6$ (FIG. 41).

Using peptides to study vascular leak by HUVEC permeation assay, the inventors observed that in addition to V6A and D3E substation, alteration of the second VDS sequence ($V_{28}D_{29}S_{30}$) with a D29E substitution also resulted in reduced vascular leak (FIG. 42).

Overall, the use of D3E substitution offers a promising avenue towards making s-Ontak-related proteins with (i) prolonged half-life, (ii) reduced vascular leak, (iii) and high potency. D3E substituted s-Ontak related proteins also demonstrate higher expression in *C. diphtheriae* C7(−) and therefore may be easier to manufacture.

s-$DAB_{1-389}$-mIL4-$His_6$ (SEQ ID NO: 134) and Related Proteins are Active in Killing CD124 Positive Cells Including Myeloid Derived Suppressor Cells (MDSCs) and Tumors that Bear CD124 (e.g., Triple Negative Breast Cancer, TNBC)

The inventors used their *C. diphtheriae* expression system to generate s-$DAB_{1-389}$-mIL4-$His_6$ (SEQ ID NO: 134) as may be seen in FIG. 46. The inventors showed that it has an $IC_{50}$ of 10 pM for 4T1 CD124+ TNBC tumor cells (FIG. 47).

s-$DAB_{1-389}$-mIL4-$His_6$ (SEQ ID NO: 134) showed potent anti-tumor activity as monotherapy in the orthotopic mouse model of 4T1 triple negative breast cancer, where it showed clear-cut dose dependent tumor inhibition (FIG. 48). The anti-tumor activity was associated with depletion of myeloid derived suppressor cells (CD124+) which are known to suppress anti-tumor immunity (FIG. 48). Moreover, s-$DAB_{1-389}$-mIL4-$His_6$ (SEQ ID NO: 134) was active in preventing metastases to the lung (FIG. 48).

The inventors tested the combination of s-$DAB_{1-389}$-mIL4-$His_6$ (SEQ ID NO: 134) followed by s-$DAB_{1-389}$-IL2-$His_6$ (SEQ ID NO: 43) in the orthotopic mouse model of 4T1 triple negative breast cancer. The two agents showed additive effects as measured by tumor volume and tumor weight (FIG. 49). Both monotherapies and combination therapy reduced CD124+ tumor cells (FIG. 50). Both monotherapies and combination therapy reduced CD124+ MDSC cells in the spleens of mice (FIG. 51).

Overall, s-$DAB_{1-389}$-mIL4-$His_6$ (SEQ ID NO: 134) is a promising agent to deplete MDSCs in the tumor microenvironment (MDSCs are known to inhibit anti-tumor immunity) as well as tumors that express CD124 (such as triple negative breast cancer).

s-$DAB_{1-389}$-EGF-$His_6$ (SEQ ID NO: 106) and Related Proteins are Active in Killing EGFR Positive Cells The inventors used their *C. diphtheriae* expression system to generate s-$DAB_{1-389}$-EGF-$His_6$ (SEQ ID NO: 106) as may be seen in FIG. 52. The inventors showed that it has an $IC_{50}$ of 300 pM for the A431 epidermoid carcinoma cell line 4T1 which is positive for the EGF receptor (EGFR) as may be seen in FIG. 53. An important application of s-$DAB_{1-389}$-EGF-$His_6$ (SEQ ID NO: 106) and related proteins would be for the treatment of glioblastoma multiforme—a tumor which commonly expresses high levels of the EGF-receptor.

Animal Studies and Treatments

C57BL/6 mice were purchased from the Charles Rivers Laboratory, and animal studies were performed according to IACUC approved protocols at Johns Hopkins University. Mice were administered 2 doses of 5 μg of *C. diphtheriae*-derived SEQ ID NO: 43 or *C. diphtheriae*-derived SEQ ID NO: 58 preceding checkpoint inhibitor therapy by intraperitoneal injection in a volume of 100 μl on specified days. For melanoma experiments, mice were given subcutaneous injections of $1\times10^5$ B16F10 cells in the right flank. 100 μg per mouse per dose of anti-mouse PD1 antibody (clone J43 purchased from Bio X Cell, Cat #BE0033-2) was given IP in a volume of 100 μl on specified days. Tumors were measured by electronic caliper, and tumor volume was calculated using the following equation: tumor volume=length×width×height 0.5326. Mice were sacrificed at specified time points, and lymph nodes, spleens and tumors were isolated. Single cell suspensions were prepared by dissociation through 100 μm filters.

Materials and Methods. Flow Cytometry and Cell Stimulations

Single cell suspensions were stained for viability using the LIVE/DEAD Fixable Aqua Dead Cell Stain Kit (Thermo Fisher Scientific). Cells were incubated with Purified Rat Anti-mouse CD16/32 (BD) and labeled in FACS buffer (PBS, 2% heat-inactivated FBS, 0.1% HEPES, 0.1%) sodium azide) with the following antibodies (BD unless otherwise noted): Ax700 anti-CD8, APC anti-CD4, and BV421 CD25. Intracellular staining was performed using the Transcription Buffer Set (BD Biosciences) according to manufacturer's protocol and labeled with FITC FoxP3. For in vitro stimulations, cells were incubated with PMA (50 ng/mL) and ionomycin (1 μM) with Golgistop (BD) for 4 hours at 37° C. Surface staining was performed as above, and intracellular staining was performed with the Fixation/Permeabilization Solution Kit (BD) according to manufacturer's protocol and labeled with FITC IFNγ. Samples were acquired on an LSRII (BD) and data was analyzed using FlowJo (Tree Star).

Nucleic Acid and Protein Sequences of s-Ontak-$His_6$ ("$His_6$" Disclosed as SEQ ID NO: 23)

Protein Sequence of *C. diphtheriae* derived s-Ontak-$His_6$ ("$His_6$" disclosed as SEQ ID NO: 23) (theoretical MW 58339) (IL2 portion in Boldface) (SEQ ID NO: 58):

```
GADDVVDSSKSFVMENFSSYHGTKP
GYVDSIQKGIQKPKSGTQGNYDDDW
KGFYSTDNKYDAAGYSVDNENPLSG
KAGGVVKVTYPGLTKVLALKVDNAE
TIKKELGLSLTEPLMEQVGTEEFIK
RFGDGASRVVLSLPFAEGSSSVEYI
```

-continued

NNWEQAKALSVELEINFETRGKRGQ

DAMYEYMAQACAGNRVRRSVGSSLS

CINLDWDVIRDKTKTKIESLKEHGP

IKNKMSESPNKTVSEEKAKQYLEEF

HQTALEHPELSELKTVTGTNPVFAG

ANYAAWAVNVAQVIDSETADNLEKT

TAALSILPGIGSVMGIADGAVHHNT

EEIVAQSIALSSLMVAQAIPLVGEL

VDIGFAAYNFVESIINLFQVVHNSY

NRPAYSPGHKTHAPTSSSTKKTQLQ

-continued

LEHLLLDLQMILNGINNYKNPKLTR

MLTEKEYMPKKATELKHLQCLEEEL

KPLEEVLNLAQSKNEHLRPRDLISN

INVIVLELKGSETTFMCEYADETAT

IVEFLNRWITFCQSIISTLTHHHHH

H

DNA sequence for *C. diphtheriae*-derived s-Ontak-$His_6$ ("$His_6$" disclosed as SEQ ID NO: 23) (SEQ ID NO: 59). Alterations to promoter/operator are starred with boldface. The underlined portion encodes the signal sequence. The first codon of mature s-Ontak-$His_6$ ("$His_6$" disclosed as SEQ ID NO: 23) begins at base 149 in larger font and italicized. The codons for the C-terminal $His_6$ ("$His_6$" disclosed as SEQ ID NO: 23) begin at base 1709 in larger font and italicized.

```
                                            **** * *
   1 TTGATTTCAGAGCACCCTTATAATTAGGATAGCTAAGTCCATTATTTTAT

  51 GAGTCCTGGTAAGGGGATACGTTGTGAGCAGAAAACTGTTTGCGTCAATC

 101 TTAATAGGGGCGCTACTGGGGATAGGGGCCCCACCTTCAGCCCATGCAGG

 151 CGCTGATGATGTTGTTGATTCTTCTAAATCTTTTGTGATGGAAAACTTTT

 201 CTTCGTACCACGGGACTAAACCTGGTTATGTAGATTCCATTCAAAAAGGT

 251 ATACAAAAGCCAAAATCTGGTACACAAGGAAATTATGACGATGATTGGAA

 301 AGGGTTTTATAGTACCGACAATAAATACGACGCTGCGGGATACTCTGTAG

 351 ATAATGAAAACCCGCTCTCTGGAAAAGCTGGAGGCGTGGTCAAAGTGACG

 401 TATCCAGGACTGACGAAGGTTCTCGCACTAAAAGTGGATAATGCCGAAAC

 451 TATTAAGAAAGAGTTAGGTTTAAGTCTCACTGAACCGTTGATGGAGCAAG

 501 TCGGAACGGAAGAGTTTATCAAAAGGTTCGGTGATGGTGCTTCGCGTGTA

 551 GTGCTCAGCCTTCCCTTCGCTGAGGGGAGTTCTAGCGTTGAATATATTAA

 601 TAACTGGGAACAGGCGAAAGCGTTAAGCGTAGAACTTGAGATTAATTTTG

 651 AAACCCGTGGAAAACGTGGCCAAGATGCGATGTATGAGTATATGGCTCAA

 701 GCCTGTGCAGGAAATCGTGTCAGGCGATCAGTAGGTAGCTCATTGTCATG

 751 CATCAACCTGGATTGGGATGTTATCCGTGATAAAACTAAAACTAAGATCG

 801 AATCTCTGAAAGAACACGGTCCGATCAAAAACAAAATGAGCGAAAGCCCG

 851 AACAAAACTGTATCTGAAGAAAAAGCTAAACAGTACCTGGAAGAATTCCA

 901 CCAGACTGCACTGGAACACCCGGAACTGTCTGAACTTAAGACCGTTACTG

 951 GTACCAACCCGGTATTCGCTGGTGCTAACTACGCTGCTTGGGCAGTAAAC

1001 GTTGCTCAGGTTATCGATAGCGAAACTGCTGATAACCTGGAAAAAACTAC

1051 CGCGGCTCTGTCTATCCTGCCGGGTATCGGTAGCGTAATGGGCATCGCAG

1101 ACGGCGCCGTTCACCACAACACTGAAGAAATCGTTGCACAGTCTATCGCT

1151 CTGAGCTCTCTGATGGTTGCTCAGGCCATCCCGCTGGTAGGTGAACTGGT

1201 TGATATCGGTTTCGCTGCATACAACTTCGTTGAAAGCATCATCAACCTGT

1251 TCCAGGTTGTTCACAACTCTTACAACCGCCCGGCTTACTCTCCGGGTCAC

1301 AAGACGCATGCACCTACTTCTAGCTCTACCAAGAAAACCCAGCTGCAGCT

1351 CGAGCACCTGCTGCTGGATTTGCAGATGATCCTGAACGGTATCAACAATT
```

-continued

```
1401 ACAAGAACCCGAAACTGACGCGTATGCTGACCTTCAAGTTCTACATGCCG

1451 AAGAAGGCCACCGAACTGAAACACCTGCAGTGTCTAGAAGAAGAACTGAA

1501 ACCGCTGGAGGAAGTTCTGAACCTGGCTCAGTCTAAAAACTTCCACCTGC

1551 GGCCGCGTGACCTGATCTCTAACATCAACGTAATCGTTCTGGAACTGAAG

1601 GGCTCTGAAACCACCTTCATGTGTGAATACGCTGATGAGACCGCAACCAT

1651 CGTAGAATTCCTGAACCGTTGGATCACCTTCTGTCAGTCTATCATCTCTA

1701 CCCTGACCCACCATCACCATCATCACTGA <1711
```

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the described elements of the invention in all possible variations thereof is encompassed by the invention unless otherwise indicated herein or otherwise clearly contradicted by context.

Embodiments of the disclosure concern methods and/or compositions for treating and/or preventing disorders such as cancer and tuberculosis in which a subject is administered a composition of the present invention comprising a nucleic acid or protein sequence such as anyone of SEQ ID NOs: 11-15, or fusion proteins thereof.

An individual known to having disease such as cancer and/or tuberculosis, suspected of having such a disease, or at risk for having such a disease may be provided an effective amount of a composition of the present invention comprising a nucleic acid or protein sequence such as anyone of SEQ ID NOs: 11-15, or fusion proteins thereof. Those at risk for cancer or tuberculosis may be those individuals having one or more genetic factors, may be of advancing age, and/or may have a family history, for example.

In particular embodiments of the disclosure, an individual is given an agent for cancer and/or tuberculosis therapy in addition to a composition of the present invention comprising a nucleic acid or protein sequence such as anyone of SEQ ID NOs: 11-15, or fusion proteins thereof. Such additional therapy may include chemotherapy or antimicrobial agents, for example. When combination therapy is employed with a composition of the present invention comprising a nucleic acid or protein sequence such as anyone of SEQ ID NOs: 11-15, or fusion proteins thereof, the additional therapy may be given prior to, at the same time as, and/or subsequent to a composition of the present invention comprising a nucleic acid or protein sequence such as anyone of SEQ ID NOs: 11-15, or fusion proteins thereof Pharmaceutical Preparations Pharmaceutical compositions of the present invention comprise an effective amount of one or more composition of the present invention comprising a nucleic acid or protein sequence such as anyone of SEQ ID NOs: 11-15, or fusion proteins thereof, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one composition of the present invention comprising a nucleic acid or protein sequence such as any one of SEQ ID NOs: 11-15, or fusion proteins thereof, or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The one or more compositions of the present invention comprising a nucleic acid or protein sequence such as anyone of SEQ ID NOs: 11-15, or fusion proteins thereof, may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The one or more compositions of the present invention comprising a nucleic acid or protein sequence such as any one of SEQ ID NOs: 11-15, or fusion proteins thereof, may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle composition that includes one or more composition of the present invention comprising a nucleic acid or protein sequence such as anyone of SEQ ID NOs: 11-15, or fusion proteins thereof, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the one or more compositions of the present invention comprising a nucleic acid or protein sequence such as anyone of SEQ ID NOs: 11-15, or fusion proteins thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In further embodiments, a pharmaceutical composition of the invention as described in any of the previous embodiments comprises greater than about 80% purity of a polypeptide of the invention. In other embodiments, the pharmaceutical composition comprises greater than about 81%, greater than about 82%, greater than about 83%, greater than about 84%, greater than about 85%, greater than about 86%, greater than about 87%, greater than about 88%, greater than about 89%, greater than about 90%, greater than about 91%, greater than about 92%, greater than about 93%, greater than about 94%, greater than about 95%, greater than about 95%, greater than about 96%, greater than about 97%, greater than about 98%, greater than about 99%, or about 100% purity of a polypeptide of the invention. In other embodiments, the pharmaceutical composition comprises about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% purity of a polypeptide of the invention. In other embodiments, the pharmaceutical composition comprises from about 80% to about 100%, from about 80% to about 97%, from about 80% to about 95%, from about 80% to about 90%, from about 80% to about 85%, from about 85% to about 100%, from about 85% to about 97%, from about 85% to about 95%, from about 85% to about 90%, from about 90% to about 100%, from about 90% to about 97%, from about 90% to about 95%, from about 95% to about 100%, or from about 95% to about 97% purity of a polypeptide of the invention, or any other range thereof.

In further embodiments, a pharmaceutical composition of the invention as described in any of the previous embodiments comprises greater than about 80% aggregate-free, full-length, monomeric polypeptide of the invention. In other embodiments, the pharmaceutical composition comprises greater than about 81%, greater than about 82%, greater than about 83%, greater than about 84%, greater than about 85%, greater than about 86%, greater than about 87%, greater than about 88%, greater than about 89%, greater than about 90%, greater than about 91%, greater than about 92%, greater than about 93%, greater than about 94%, greater than about 95%, greater than about 95%, greater than about 96%, greater than about 97%, greater than about 98%, greater than about 99%, or about 100% aggregate-free, full-length, monomeric polypeptide of the invention. In other embodiments, the pharmaceutical composition comprises about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% aggregate-free, full-length, monomeric polypeptide of the invention. In other embodiments, the pharmaceutical composition comprises from about 80% to about 100%, from about 80% to about 97%, from about 80% to about 95%, from about 80% to about 90%, from about 80% to about 85%, from about 85% to about 100%, from about 85% to about 97%, from about 85% to about 95%, from about 85% to about 90%, from about 90% to about 100%, from about 90% to about 97%, from about 90% to about 95%, from about 95% to about 100%, or from about 95% to about 97% aggregate-free, full-length, monomeric polypeptide of the invention, or any other range thereof.

In further embodiments, a pharmaceutical composition of the invention comprises greater than about 80% purity of a polypeptide of the invention (or any other range or amount described herein) and greater than about 80% aggregate-free, full-length, monomeric polypeptide of the invention (or any other range or amount described herein).

In further embodiments, a polypeptide of such pharmaceutical compositions comprises a histidine (His) tag. In some embodiments, the His tag has six or nine His residues (SEQ ID NOS 23 and 48, respectively). In other embodiments, the His tag is at the C-terminus of the polypeptide. In other embodiments, a polypeptide of such pharmaceutical compositions does not comprise a His tag.

Alimentary Compositions and Formulations

In one embodiment of the present disclosure, the one or more compositions of the present invention comprising a nucleic acid or protein sequence such as anyone of SEQ ID NOs: 11-15, or fusion proteins thereof, are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup or elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, one or more composition of the present invention comprising a nucleic acid or protein sequence such as anyone of SEQ ID NOs: 11-15, or fusion proteins thereof, may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,737,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the one or more compositions of the present invention comprising a nucleic acid or protein sequence such as anyone of SEQ ID NOs: 11-15, or fusion proteins thereof, may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, one or more composition of the present invention comprising a nucleic acid or protein sequence such as anyone of SEQ ID NOs: 11-15, SEQ ID NO: 43, SEQ ID NO: 58, or fusion proteins thereof, may be comprised in a kit.

The kits may comprise a suitably aliquoted of one or more compositions of the present invention comprising a nucleic acid or protein sequence such as anyone of SEQ ID NOs: 11-15, SEQ ID NO: 43, SEQ ID NO: 58 or fusion proteins thereof, and in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the one or more compositions of the present invention comprising a nucleic acid or protein sequence such as anyone of SEQ ID NOs: 11-15, SEQ ID NO: 43, SEQ ID NO: 58, or fusion proteins thereof, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The one or more compositions of the present invention comprising a nucleic acid or protein sequence such as anyone of SEQ ID NOs: 11-15, SEQ ID NO: 43, SEQ ID NO: 58, or fusion proteins thereof, may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

SEQUENCE LISTING

```
<160> NUMBER OF SEQ ID NOS: 140

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 1
ttaggatagc taagtccat 19

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
ttgatttcag agcaccctta taattaggat agctaagtcc at 42

<210> SEQ ID NO 3
<211> LENGTH: 1711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
ttgatttcag agcaccctta taattaggat agctaagtcc attattttat gagtcctggt 60
aaggggatac gttgtgagca gaaaactgtt tgcgtcaatc ttaatagggg cgctactggg 120
gataggggcc ccaccttcag cccatgcagg cgctgatgat gttgttgatt cttctaaatc 180
ttttgtgatg gaaaactttt cttcgtacca cgggactaaa cctggttatg tagattccat 240
tcaaaaaggt atacaaaagc caaaatctgg tacacaagga aattatgacg atgattggaa 300
agggttttat agtaccgaca ataaatacga cgctgcggga tactctgtag ataatgaaaa 360
cccgctctct ggaaaagctg gaggcgtggt caaagtgacg tatccaggac tgacgaaggt 420
tctcgcacta aaagtggata atgccgaaac tattaagaaa gagttaggtt taagtctcac 480
tgaaccgttg atggagcaag tcggaacgga agagtttatc aaaaggttcg gtgatggtgc 540
ttcgcgtgta gtgctcagcc ttcccttcgc tgaggggagt tctagcgttg aatatattaa 600
taactgggaa caggcgaaag cgttaagcgt agaacttgag attaattttg aaacccgtgg 660
aaaacgtggc caagatgcga tgtatgagta tatggctcaa gcctgtgcag gaaatcgtgt 720
caggcgatca gtaggtagct cattgtcatg catcaacctg gattgggatg ttatccgtga 780
taaaactaaa actaagatcg aatctctgaa agaacacggt ccgatcaaaa acaaaatgag 840
cgaaagcccg aacaaaactg tatctgaaga aaaagctaaa cagtacctgg aagaattcca 900
ccagactgca ctggaacacc cggaactgtc tgaacttaag accgttactg gtaccaaccc 960
ggtattcgct ggtgctaact acgctgcttg ggcagtaaac gttgctcagg ttatcgatag 1020
cgaaactgct gataacctgg aaaaaactac cgcggctctg tctatcctgc cgggtatcgg 1080
tagcgtaatg ggcatcgcag acggcgccgt tcaccacaac actgaagaaa tcgttgcaca 1140
gtctatcgct ctgagctctc tgatggttgc tcaggccatc ccgctggtag gtgaactggt 1200
tgatatcggt ttcgctgcat acaacttcgt tgaaagcatc atcaacctgt tccaggttgt 1260
tcacaactct tacaaccgcc cggcttactc tccgggtcac aagacgcatg cacctacttc 1320
tagctctacc aagaaaaccc agctgcagct cgagcacctg ctgctggatt tgcagatgat 1380
cctgaacggt atcaacaatt acaagaaccc gaaactgacg cgtatgctga ccttcaagtt 1440
ctacatgccg aagaaggcca ccgaactgaa acacctgcag tgtctagaag aagaactgaa 1500

-continued

```
accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgacctg a                                  1711
```

<210> SEQ ID NO 4
<211> LENGTH: 75
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4

```
gtgagcagaa aactgtttgc gtcaatctta ataggggcgc tactggggat aggggcccca     60

ccttcagccc atgca                                                      75
```

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

```
Met Ser Arg Lys Leu Phe Ala Ser Ile Leu Ile Gly Ala Leu Leu Gly
1               5                   10                  15

Ile Gly Ala Pro Pro Ser Ala His Ala
            20                  25
```

<210> SEQ ID NO 6
<211> LENGTH: 1566
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atgggcgctg atgatgttgt tgattcttct aaatcttttg tgatggaaaa cttttcttcg     60

taccacggga ctaaacctgg ttatgtagat tccattcaaa aaggtataca aaagccaaaa    120

tctggtacac aaggaaatta tgacgatgat tggaaagggt tttatagtac cgacaataaa    180

tacgacgctg cgggatactc tgtagataat gaaaacccgc tctctggaaa agctggaggc    240

gtggtcaaag tgacgtatcc aggactgacg aaggttctcg cactaaaagt ggataatgcc    300

gaaactatta agaaagagtt aggtttaagt ctcactgaac cgttgatgga gcaagtcgga    360

acggaagagt ttatcaaaag gttcggtgat ggtgcttcgc gtgtagtgct cagccttccc    420

ttcgctgagg ggagttctag cgttgaatat attaataact gggaacaggc gaaagcgtta    480

agcgtagaac ttgagattaa ttttgaaacc cgtggaaaac gtggccaaga tgcgatgtat    540

gagtatatgg ctcaagcctg tgcaggaaat cgtgtcaggc gatcagtagg tagctcattg    600

tcatgcatca acctggattg ggatgttatc cgtgataaaa ctaaaactaa gatcgaatct    660

ctgaaagaac acggtccgat caaaaacaaa atgagcgaaa gcccgaacaa aactgtatct    720

gaagaaaaag ctaaacagta cctggaagaa ttccaccaga ctgcactgga acacccggaa    780

ctgtctgaac ttaagaccgt tactggtacc aacccggtat tcgctggtgc taactacgct    840
```

-continued

```
gcttgggcag taaacgttgc tcaggttatc gatagcgaaa ctgctgataa cctggaaaaa    900

actaccgcgg ctctgtctat cctgccgggt atcggtagcg taatgggcat cgcagacggc    960

gccgttcacc acaacactga agaaatcgtt gcacagtcta tcgctctgag ctctctgatg   1020

gttgctcagg ccatcccgct ggtaggtgaa ctggttgata tcggtttcgc tgcatacaac   1080

ttcgttgaaa gcatcatcaa cctgttccag gttgttcaca actcttacaa ccgcccggct   1140

tactctccgg gtcacaagac gcatgcacct acttctagct ctaccaagaa aacccagctg   1200

cagctcgagc acctgctgct ggatttgcag atgatcctga acggtatcaa caattacaag   1260

aacccgaaac tgacgcgtat gctgaccttc aagttctaca tgccgaagaa ggccaccgaa   1320

ctgaaacacc tgcagtgtct agaagaagaa ctgaaaccgc tggaggaagt tctgaacctg   1380

gctcagtcta aaaacttcca cctgcggccg cgtgacctga tctctaacat caacgtaatc   1440

gttctggaac tgaagggctc tgaaaccacc ttcatgtgtg aatacgctga tgagaccgca   1500

accatcgtag aattcctgaa ccgttggatc accttctgtc agtctatcat ctctaccctg   1560

acctga                                                              1566
```

<210> SEQ ID NO 7
<211> LENGTH: 1566
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7

```
atgggcgctg atgatgttgc tgattcttct aaatcttttg tgatggaaaa cttttcttcg     60

taccacggga ctaaacctgg ttatgtagat tccattcaaa aaggtataca aaagccaaaa    120

tctggtacac aaggaaatta tgacgatgat tggaaagggt tttatagtac cgacaataaa    180

tacgacgctg cgggatactc tgtagataat gaaaacccgc tctctggaaa agctggaggc    240

gtggtcaaag tgacgtatcc aggactgacg aaggttctcg cactaaaagt ggataatgcc    300

gaaactatta agaaagagtt aggtttaagt ctcactgaac cgttgatgga gcaagtcgga    360

acggaagagt ttatcaaaag gttcggtgat ggtgcttcgc gtgtagtgct cagccttccc    420

ttcgctgagg ggagttctag cgttgaatat attaataact gggaacaggc gaaagcgtta    480

agcgtagaac ttgagattaa ttttgaaacc cgtggaaaac gtggccaaga tgcgatgtat    540

gagtatatgg ctcaagcctg tgcaggaaat cgtgtcaggc gatcagtagg tagctcattg    600

tcatgcatca acctggattg ggatgttatc cgtgataaaa ctaaaactaa gatcgaatct    660

ctgaaagaac acggtccgat caaaaacaaa atgagcgaaa gcccgaacaa aactgtatct    720

gaagaaaaag ctaaacagta cctggaagaa ttccaccaga ctgcactgga acacccggaa    780

ctgtctgaac ttaagaccgt tactggtacc aacccggtat tcgctggtgc taactacgct    840

gcttgggcag taaacgttgc tcaggttatc gatagcgaaa ctgctgataa cctggaaaaa    900

actaccgcgg ctctgtctat cctgccgggt atcggtagcg taatgggcat cgcagacggc    960

gccgttcacc acaacactga agaaatcgtt gcacagtcta tcgctctgag ctctctgatg   1020

gttgctcagg ccatcccgct ggtaggtgaa ctggttgata tcggtttcgc tgcatacaac   1080

ttcgttgaaa gcatcatcaa cctgttccag gttgttcaca actcttacaa ccgcccggct   1140

tactctccgg gtcacaagac gcatgcacct acttctagct ctaccaagaa aacccagctg   1200

cagctcgagc acctgctgct ggatttgcag atgatcctga acggtatcaa caattacaag   1260
```

-continued

```
aacccgaaac tgacgcgtat gctgaccttc aagttctaca tgccgaagaa ggccaccgaa   1320

ctgaaacacc tgctgcagtg tctagaagaa gaactgaaac cgctggagga agttctgaac   1380

ctggctcagt ctaaaaactt ccacctgcgg ccgcgtgacc tgatctctaa catcaacgta   1440

atcgttctgg aactgaaggg ctctgaaacc accttcatgt gtgaatacgc tgatgagacc   1500

gcaaccatcg tagaattcct gaaccgttgg atcaccttct gtcagtctat catctctacc   1560

ctgacc                                                              1566


<210> SEQ ID NO 8
<211> LENGTH: 1638
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

gtgagcagaa aactgtttgc gtcaatctta ataggggcgc tactggggat aggggcccca     60

ccttcagccc atgcaggcgc tgatgatgtt gctgattctt ctaaatcttt tgtgatggaa    120

aacttttctt cgtaccacgg gactaaacct ggttatgtag attccattca aaaaggtata    180

caaaagccaa aatctggtac acaaggaaat tatgacgatg attggaaagg gttttatagt    240

accgacaata aatacgacgc tgcgggatac tctgtagata atgaaaaccc gctctctgga    300

aaagctggag gcgtggtcaa agtgacgtat ccaggactga cgaaggttct cgcactaaaa    360

gtggataatg ccgaaactat taagaaagag ttaggtttaa gtctcactga accgttgatg    420

gagcaagtcg gaacggaaga gtttatcaaa aggttcggtg atggtgcttc gcgtgtagtg    480

ctcagccttc ccttcgctga ggggagttct agcgttgaat atattaataa ctgggaacag    540

gcgaaagcgt taagcgtaga acttgagatt aattttgaaa cccgtggaaa acgtggccaa    600

gatgcgatgt atgagtatat ggctcaagcc tgtgcaggaa atcgtgtcag gcgatcagta    660

ggtagctcat tgtcatgcat caacctggat tgggatgtta tccgtgataa aactaaaact    720

aagatcgaat ctctgaaaga acacggtccg atcaaaaaca aaatgagcga aagcccgaac    780

aaaactgtat ctgaagaaaa agctaaacag tacctggaag aattccacca gactgcactg    840

gaacacccgg aactgtctga acttaagacc gttactggta ccaacccggt attcgctggt    900

gctaactacg ctgcttgggc agtaaacgtt gctcaggtta tcgatagcga aactgctgat    960

aacctggaaa aaactaccgc ggctctgtct atcctgccgg gtatcggtag cgtaatgggc   1020

atcgcagacg gcgccgttca ccacaacact gaagaaatcg ttgcacagtc tatcgctctg   1080

agctctctga tggttgctca ggccatcccg ctggtaggtg aactggttga tatcggtttc   1140

gctgcataca acttcgttga aagcatcatc aacctgttcc aggttgttca caactcttac   1200

aaccgcccgg cttactctcc gggtcacaag acgcatgcac ctacttctag ctctaccaag   1260

aaaacccagc tgcagctcga gcacctgctg ctggatttgc agatgatcct gaacggtatc   1320

aacaattaca agaacccgaa actgacgcgt atgctgacct tcaagttcta catgccgaag   1380

aaggccaccg aactgaaaca cctgcagtgt ctagaagaag aactgaaacc gctggaggaa   1440

gttctgaacc tggctcagtc taaaaacttc cacctgcggc cgcgtgacct gatctctaac   1500

atcaacgtaa tcgttctgga actgaagggc tctgaaacca ccttcatgtg tgaatacgct   1560

gatgagaccg caaccatcgt agaattcctg aaccgttgga tcaccttctg tcagtctatc   1620

atctctaccc tgacctga                                                 1638
```

<210> SEQ ID NO 9
<211> LENGTH: 402
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
gcacctactt ctagctctac caagaaaacc cagctgcagc tcgagcacct gctgctggat 60
ttgcagatga tcctgaacgg tatcaacaat tacaagaacc cgaaactgac gcgtatgctg 120
accttcaagt tctacatgcc gaagaaggcc accgaactga aacacctgca gtgtctagaa 180
gaagaactga aaccgctgga ggaagttctg aacctggctc agtctaaaaa cttccacctg 240
cggccgcgtg acctgatctc taacatcaac gtaatcgttc tggaactgaa gggctctgaa 300
accaccttca tgtgtgaata cgctgatgag accgcaacca tcgtagaatt cctgaaccgt 360
tggatcacct tctgtcagtc tatcatctct accctgacct ga 402

<210> SEQ ID NO 10
<211> LENGTH: 521
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Met Gly Ala Asp Asp Val Val Asp Ser Ser Lys Ser Phe Val Met Glu
1 5 10 15

Asn Phe Ser Ser Tyr His Gly Thr Lys Pro Gly Tyr Val Asp Ser Ile
20 25 30

Gln Lys Gly Ile Gln Lys Pro Lys Ser Gly Thr Gln Gly Asn Tyr Asp
35 40 45

Asp Asp Trp Lys Gly Phe Tyr Ser Thr Asp Asn Lys Tyr Asp Ala Ala
50 55 60

Gly Tyr Ser Val Asp Asn Glu Asn Pro Leu Ser Gly Lys Ala Gly Gly
65 70 75 80

Val Val Lys Val Thr Tyr Pro Gly Leu Thr Lys Val Leu Ala Leu Lys
85 90 95

Val Asp Asn Ala Glu Thr Ile Lys Lys Glu Leu Gly Leu Ser Leu Thr
100 105 110

Glu Pro Leu Met Glu Gln Val Gly Thr Glu Glu Phe Ile Lys Arg Phe
115 120 125

Gly Asp Gly Ala Ser Arg Val Val Leu Ser Leu Pro Phe Ala Glu Gly
130 135 140

Ser Ser Ser Val Glu Tyr Ile Asn Asn Trp Glu Gln Ala Lys Ala Leu
145 150 155 160

Ser Val Glu Leu Glu Ile Asn Phe Glu Thr Arg Gly Lys Arg Gly Gln
165 170 175

Asp Ala Met Tyr Glu Tyr Met Ala Gln Ala Cys Ala Gly Asn Arg Val
180 185 190

Arg Arg Ser Val Gly Ser Ser Leu Ser Cys Ile Asn Leu Asp Trp Asp
195 200 205

Val Ile Arg Asp Lys Thr Lys Thr Lys Ile Glu Ser Leu Lys Glu His
210 215 220

Gly Pro Ile Lys Asn Lys Met Ser Glu Ser Pro Asn Lys Thr Val Ser

-continued

```
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr His Ala Pro Thr Ser Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
            420                 425                 430

Tyr Met Pro Lys Lys Ala Thr Glu Leu Lys His Leu Gln Cys Leu Glu
        435                 440                 445

Glu Glu Leu Lys Pro Leu Glu Glu Val Leu Asn Leu Ala Gln Ser Lys
    450                 455                 460

Asn Phe His Leu Arg Pro Arg Asp Leu Ile Ser Asn Ile Asn Val Ile
465                 470                 475                 480

Val Leu Glu Leu Lys Gly Ser Glu Thr Thr Phe Met Cys Glu Tyr Ala
                485                 490                 495

Asp Glu Thr Ala Thr Ile Val Glu Phe Leu Asn Arg Trp Ile Thr Phe
            500                 505                 510

Cys Gln Ser Ile Ile Ser Thr Leu Thr
        515                 520


<210> SEQ ID NO 11
<211> LENGTH: 560
<212> TYPE: PRT
<213> ORGANISM: Corynebacterium diphtheriae

<400> SEQUENCE: 11

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80
```

-continued

```
Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
        355                 360                 365

Ile Pro Leu Val Gly Glu Leu Val Asp Ile Gly Phe Ala Ala Tyr Asn
    370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
            420                 425                 430

Thr Gly Phe Gln Gly Glu Ser Gly His Asp Ile Lys Ile Thr Ala Glu
        435                 440                 445

Asn Thr Pro Leu Pro Ile Ala Gly Val Leu Leu Pro Thr Ile Pro Gly
    450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
```

```
            500                 505                 510

His Val Ala Phe His Arg Ser Ser Ser Glu Lys Ile His Ser Asn Glu
        515                 520                 525

Ile Ser Ser Asp Ser Ile Gly Val Leu Gly Tyr Gln Lys Thr Val Asp
    530                 535                 540

His Thr Lys Val Asn Ser Lys Leu Ser Leu Phe Phe Glu Ile Lys Ser
545                 550                 555                 560


<210> SEQ ID NO 12
<211> LENGTH: 545
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300
```

Ala Trp Ala Val Asn Val Ala Gln Val Ile Asp Ser Glu Thr Ala Asp
305 310 315 320

Asn Leu Glu Lys Thr Thr Ala Ala Leu Ser Ile Leu Pro Gly Ile Gly
325 330 335

Ser Val Met Gly Ile Ala Asp Gly Ala Val His His Asn Thr Glu Glu
340 345 350

Ile Val Ala Gln Ser Ile Ala Leu Ser Ser Leu Met Val Ala Gln Ala
355 360 365

Ile Pro Leu Val Gly Glu Leu Val Asp Ile Gly Phe Ala Ala Tyr Asn
370 375 380

Phe Val Glu Ser Ile Ile Asn Leu Phe Gln Val Val His Asn Ser Tyr
385 390 395 400

Asn Arg Pro Ala Tyr Ser Pro Gly His Lys Thr His Ala Pro Thr Ser
405 410 415

Ser Ser Thr Lys Lys Thr Gln Leu Gln Leu Glu His Leu Leu Leu Asp
420 425 430

Leu Gln Met Ile Leu Asn Gly Ile Asn Asn Tyr Lys Asn Pro Lys Leu
435 440 445

Thr Arg Met Leu Thr Phe Lys Phe Tyr Met Pro Lys Lys Ala Thr Glu
450 455 460

Leu Lys His Leu Gln Cys Leu Glu Glu Glu Leu Lys Pro Leu Glu Glu
465 470 475 480

Val Leu Asn Leu Ala Gln Ser Lys Asn Phe His Leu Arg Pro Arg Asp
485 490 495

Leu Ile Ser Asn Ile Asn Val Ile Val Leu Glu Leu Lys Gly Ser Glu
500 505 510

Thr Thr Phe Met Cys Glu Tyr Ala Asp Glu Thr Ala Thr Ile Val Glu
515 520 525

Phe Leu Asn Arg Trp Ile Thr Phe Cys Gln Ser Ile Ile Ser Thr Leu
530 535 540

Thr
545

<210> SEQ ID NO 13
<211> LENGTH: 520
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 13

Gly Ala Asp Asp Val Val Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

-continued

```
Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520
```

<210> SEQ ID NO 14
<211> LENGTH: 545
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

```
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Ala Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
        355                 360                 365
```

Ile Pro Leu Val Gly Glu Leu Val Asp Ile Gly Phe Ala Ala Tyr Asn
370 375 380

Phe Val Glu Ser Ile Ile Asn Leu Phe Gln Val Val His Asn Ser Tyr
385 390 395 400

Asn Arg Pro Ala Tyr Ser Pro Gly His Lys Thr His Ala Pro Thr Ser
405 410 415

Ser Ser Thr Lys Lys Thr Gln Leu Gln Leu Glu His Leu Leu Leu Asp
420 425 430

Leu Gln Met Ile Leu Asn Gly Ile Asn Asn Tyr Lys Asn Pro Lys Leu
435 440 445

Thr Arg Met Leu Thr Phe Lys Phe Tyr Met Pro Lys Lys Ala Thr Glu
450 455 460

Leu Lys His Leu Gln Cys Leu Glu Glu Glu Leu Lys Pro Leu Glu Glu
465 470 475 480

Val Leu Asn Leu Ala Gln Ser Lys Asn Phe His Leu Arg Pro Arg Asp
485 490 495

Leu Ile Ser Asn Ile Asn Val Ile Val Leu Glu Leu Lys Gly Ser Glu
500 505 510

Thr Thr Phe Met Cys Glu Tyr Ala Asp Glu Thr Ala Thr Ile Val Glu
515 520 525

Phe Leu Asn Arg Trp Ile Thr Phe Cys Gln Ser Ile Ile Ser Thr Leu
530 535 540

Thr
545

<210> SEQ ID NO 15
<211> LENGTH: 520
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Gly Ala Asp Asp Val Ala Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp

-continued

```
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520
```

<210> SEQ ID NO 16
<211> LENGTH: 522
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

-continued

```
Met Gly Ala Asp Asp Val Ala Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr His Ala Pro Thr Ser Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
```

```
            420                 425                 430

Tyr Met Pro Lys Lys Ala Thr Glu Leu Lys His Leu Leu Gln Cys Leu
        435                 440                 445

Glu Glu Glu Leu Lys Pro Leu Glu Glu Val Leu Asn Leu Ala Gln Ser
    450                 455                 460

Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
                485                 490                 495

Ala Asp Glu Thr Ala Thr Ile Val Glu Phe Leu Asn Arg Trp Ile Thr
            500                 505                 510

Phe Cys Gln Ser Ile Ile Ser Thr Leu Thr
        515                 520


<210> SEQ ID NO 17
<211> LENGTH: 535
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255
```

-continued

```
His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535


<210> SEQ ID NO 18
<211> LENGTH: 560
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Glu Phe Tyr Ser
65                  70                  75                  80
```

-continued

```
Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
        355                 360                 365

Ile Pro Leu Val Gly Glu Leu Val Asp Ile Gly Phe Ala Ala Tyr Asn
    370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
            420                 425                 430

Thr Gly Phe Gln Gly Glu Ser Gly His Asp Ile Lys Ile Thr Ala Glu
        435                 440                 445

Asn Thr Pro Leu Pro Ile Ala Gly Val Leu Leu Pro Thr Ile Pro Gly
    450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
                485                 490                 495
```

```
Arg Pro Lys Ser Pro Val Tyr Val Gly Asn Gly Val His Ala Asn Leu
            500                 505                 510

His Val Ala Phe His Arg Ser Ser Ser Glu Lys Ile His Ser Asn Glu
        515                 520                 525

Ile Ser Ser Asp Ser Ile Gly Val Leu Gly Tyr Gln Lys Thr Val Asp
    530                 535                 540

His Thr Lys Val Asn Ser Lys Leu Ser Leu Phe Phe Glu Ile Lys Ser
545                 550                 555                 560


<210> SEQ ID NO 19
<211> LENGTH: 535
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300
```

```
Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Phe His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Phe Lys Leu Ser
        515                 520                 525

Leu Phe Phe Glu Ile Lys Ser
    530                 535


<210> SEQ ID NO 20
<211> LENGTH: 560
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
```

-continued

```
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
        355                 360                 365

Ile Pro Leu Val Gly Glu Leu Val Asp Ile Gly Phe Ala Ala Tyr Asn
    370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Phe His
                405                 410                 415

Asp Gly Tyr Ala Val Ser Trp Asn Thr Val Glu Asp Ser Ile Ile Arg
            420                 425                 430

Thr Gly Phe Gln Gly Glu Ser Gly His Asp Ile Lys Ile Thr Ala Glu
        435                 440                 445

Asn Thr Pro Leu Pro Ile Ala Gly Val Leu Leu Pro Thr Ile Pro Gly
    450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
            500                 505                 510

His Val Ala Phe His Arg Ser Ser Ser Glu Lys Ile His Ser Asn Glu
        515                 520                 525

Ile Ser Ser Asp Ser Ile Gly Val Leu Gly Tyr Gln Lys Thr Val Asp
    530                 535                 540
```

```
His Thr Lys Val Asn Phe Lys Leu Ser Leu Phe Phe Glu Ile Lys Ser
545                 550                 555                 560


<210> SEQ ID NO 21
<211> LENGTH: 6402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

ggcgagtgct ttgaatgctt gggcttcttc acggcgggtc ttgaccgcgt tgataagttc     60

gcggccagag ctgaattgct ggcgtggggt ggggttgaac tggtcgtgtc ctgccatatc    120

ccttacctgc tttatcaagt ctccaaggcg catcacccgg ttgtgctgcc tataccaacg    180

ataagcggta ggggctttgc ctgtgtagaa cgggttgcgg ctaaagcggt gggaaaagtg    240

cgggtcatgg tctaaaagct cacccagcac acgcgtggtt gctgcaagaa gcttcatctg    300

cgcagattta ccgttacggt cagcgtagac agggtcaata agccatatga actgggcttt    360

gccgttagtt gggttaatac ccacccaggc tggcccgacg ctatgagtaa tcagtgagcg    420

caccacgtcg cggacgtacg ggtttaagtc tgcggggtca ccgcctgcgg tacctacttg    480

gtcaacgtct acgaccagga cggcggcgta ctgcttggtg gtgagcatgg cgtactcgca    540

ccgtcctaaa gcatcagtct cgaagcgata catacgcggc gagttcgtgc cgtcagcgtt    600

gcgtcgatag gccttttaa agtctcgtgt gactgaaccg tggagtacat cgcggcctag    660

atgatcgcgt aaaaggtcgc ggtcactggc agatgctggg gtgttgtcca gtccaccacg    720

gtcgcgctcg acgcgggtag gtgttttagt gtgcgcattc tgcgcatgag tctgtaaact    780

catgaccgtg ctttctccca ggtgtgtgct gggtgataag cgaaagtcat cgggttgccg    840

cccggtggct ttcttcgttt ttcattgtct ttccctgact ctaaatgaca ccggtgttat    900

ttactagcca tgacacgcga aaaatatgcc ttttacctgc ggttacgtat ggctagacat    960

atggcaagct atacgtaacc gcgtttcagc tgcacagggc tgtctgcgca gatttaccat   1020

cacgggactt ttcccagttc aggctgcgca tatttacgca tacaacgaaa gcggttgcgc   1080

agatttacca cacactctgc gctgatttac cgatacgcag aaaaagcgtg cgcagattta   1140

cccatacggt ggcgaattat ccagagcaat aggtatacag caatacagta atacaggtgc   1200

cataaacctg tattactgta ttgctgtatg cctgtaaacc tttatttatt gttgtggacg   1260

tattcttcga ggtaggtgct aacaatctcg cggatggtca cgcctttttg ggcggcgatg   1320

actttaagtt ctgcgtgaag gtcgcggtcg atttcaatcg tcatcttctt gacgtagtcg   1380

cggcctgtgg gttggtggaa tgcgcttcgc actgttttct tctcggctgc tggagttagc   1440

ttcgtggctt ttttcattga ggttcgcggg ccttgctgcg ccctggcgcg ttctttactg   1500

gtgctcattt catcatctcc atgagttcgt cggcgacgtg gtcgtagccg tgcatgtcgg   1560

ggcctgggca gtatccaaac gctaggtgca tatcttcgcg tagcgggatt tcggttttaa   1620

agtgcggcat gtgttccgcg tcgagcgctt ctcgtgccgc gtcaagggcg ctggtgcctt   1680

tcctggcgaa cgtcagtaag actgcatgag gtgttccgtt gactgcgtcg cgcagctccc   1740

atactcggga gaggtcggca gcagcagaac gggtcggaag aatgatgaag tcgctgactg   1800

cgattgctgc ttcgatagcg ttctcgtctc ctggcggcac atcgataccg actgggcgat   1860

ggcccactac gtgaaccatc accctaatca agttttttgg ggtcgaggtg ccgtaaagca   1920
```

-continued

```
ctaaatcgga accctaaagg gagcccccga tttagagctt gacggggaaa gccggcgaac   1980
gtggcgagaa aggaagggaa gaaagcgaaa ggagcgggcg ctagggcgct ggcaagtgta   2040
gcggtcacgc tgcgcgtaac caccacaccc gccgcgctta atgcgccgct acagggcgct   2100
cccattcgcc attcaggctg cgcaactgtt gggaagggcg atcggtgcgg gcctcttcgc   2160
tattacgcca gctggcgaaa gggggatgtg ctgcaaggcg attaagttgg gtaacgccag   2220
ggttttccca gtcacgacgt tgtaaaacga cggccagtga attgtaatac gactcactat   2280
agggcgaatt ggagctccac cgcggtggcg gccgctctag aactagtgga tccagggcat   2340
tgatttcaga gcacccttat aattaggata gctaagtcca ttattttatg agtcctggta   2400
aggggatacg ttgtgagcag aaaactgttt gcgtcaatct taatagggc gctactgggg   2460
atagggggccc caccttcagc ccatgcaggc gctgatgatg ttgttgattc ttctaaatct   2520
tttgtgatgg aaaacttttc ttcgtaccac gggactaaac ctggttatgt agattccatt   2580
caaaaaggta tacaaaagcc aaaatctggt acacaaggaa attatgacga tgattggaaa   2640
gggttttata gtaccgacaa taaatacgac gctgcgggat actctgtaga taatgaaaac   2700
ccgctctctg gaaaagctgg aggcgtggtc aaagtgacgt atccaggact gacgaaggtt   2760
ctcgcactaa aagtggataa tgccgaaact attaagaaag agttaggttt aagtctcact   2820
gaaccgttga tggagcaagt cggaacggaa gagtttatca aaaggttcgg tgatggtgct   2880
tcgcgtgtag tgctcagcct tcccttcgct gaggggagtt ctagcgttga atatattaat   2940
aactgggaac aggcgaaagc gttaagcgta gaacttgaga ttaattttga aacccgtgga   3000
aaacgtggcc aagatgcgat gtatgagtat atggctcaag cctgtgcagg aaatcgtgtc   3060
aggcgatcag taggtagctc attgtcatgc atcaacctgg attgggatgt tatccgtgat   3120
aaaactaaaa ctaagatcga atctctgaaa gaacacggtc cgatcaaaaa caaaatgagc   3180
gaaagcccga acaaaactgt atctgaagaa aaagctaaac agtacctgga agaattccac   3240
cagactgcac tggaacaccc ggaactgtct gaacttaaga ccgttactgg taccaacccg   3300
gtattcgctg gtgctaacta cgctgcttgg gcagtaaacg ttgctcaggt tatcgatagc   3360
gaaactgctg ataacctgga aaaaactacc gcggctctgt ctatcctgcc gggtatcggt   3420
agcgtaatgg gcatcgcaga cggcgccgtt caccacaaca ctgaagaaat cgttgcacag   3480
tctatcgctc tgagctctct gatggttgct caggccatcc cgctggtagg tgaactggtt   3540
gatatcggtt tcgctgcata caacttcgtt gaaagcatca tcaacctgtt ccaggttgtt   3600
cacaactctt acaaccgccc ggcttactct ccgggtcaca agacgcatgc acctacttct   3660
agctctacca agaaaaccca gctgcagctc gagcacctgc tgctggattt gcagatgatc   3720
ctgaacggta tcaacaatta caagaacccg aaactgacgc gtatgctgac cttcaagttc   3780
tacatgccga agaaggccac cgaactgaaa cacctgcagt gtctagaaga agaactgaaa   3840
ccgctggagg aagttctgaa cctggctcag tctaaaaact tccacctgcg gccgcgtgac   3900
ctgatctcta acatcaacgt aatcgttctg gaactgaagg gctctgaaac caccttcatg   3960
tgtgaatacg ctgatgagac cgcaaccatc gtagaattcc tgaaccgttg gatcaccttc   4020
tgtcagtcta tcatctctac cctgacctga ggatcccccg ggctgcagga attcgatatc   4080
aagcttatcg ataccgtcga cctcgagggg gggcccggta ccagcttttg ttccctttag   4140
tgagggttaa tttcgagctt ggcgtaatca tggtcatagc tgtttcctgt gtgaaattgt   4200
tatccgctca caattccaca caacatacga gccggaagca taaagtgtaa agcctggggt   4260
gcctaatgag tgagtccccg atccgtcgag ctcgacctgc aggggggggg gggcgctgag   4320
```

-continued

```
gtctgcctcg tgaagaaggt gttgctgact cataccaggc ctgaatcgcc ccatcatcca   4380

gccagaaagt gagggagcca cggttgatga gagctttgtt gtaggtggac cagttggtga   4440

ttttgaactt ttgctttgcc acggaacggt ctgcgttgtc gggaagatgc gtgatctgat   4500

ccttcaactc agcaaaagtt cgatttattc aacaaagccg ccgtcccgtc aagtcagcgt   4560

aatgctctgc cagtgttaca accaattaac caattctgat tagaaaaact catcgagcat   4620

caaatgaaac tgcaatttat tcatatcagg attatcaata ccatattttt gaaaaagccg   4680

tttctgtaat gaaggagaaa actcaccgag gcagttccat aggatggcaa gatcctggta   4740

tcggtctgcg attccgactc gtccaacatc aatacaacct attaatttcc cctcgtcaaa   4800

aataaggtta tcaagtgaga aatcaccatg agtgacgact gaatccggtg agaatggcaa   4860

aagcttatgc atttctttcc agacttgttc aacaggccag ccattacgct cgtcatcaaa   4920

atcactcgca tcaaccaaac cgttattcat tcgtgattgc gcctgagcga gacgaaatac   4980

gcgatcgctg ttaaaaggac aattacaaac aggaatcgaa tgcaaccggc gcaggaacac   5040

tgccagcgca tcaacaatat tttcacctga atcaggatat tcttctaata cctggaatgc   5100

tgttttcccg gggatcgcag tggtgagtaa ccatgcatca tcaggagtac ggataaaatg   5160

cttgatggtc ggaagaggca taaattccgt cagccagttt agtctgacca tctcatctgt   5220

aacatcattg gcaacgctac ctttgccatg tttcagaaac aactctggcg catcgggctt   5280

cccatacaat cgatagattg tcgcacctga ttgcccgaca ttatcgcgag cccatttata   5340

cccatataaa tcagcatcca tgttggaatt taatcgcggc ctcgagcaag acgtttcccg   5400

ttgaatatgg ctcataacac cccttgtatt actgtttatg taagcagaca gttttattgt   5460

tcatgatgat atatttttat cttgtgcaat gtaacatcag agattttgag acacaacgtg   5520

gctttccccc cccccccctgc aggtcgagct cgacggatcg ggctgcagga attcggtgag   5580

gttatggcgg agggttgcga ggtctaggag aacagaggaa gtcatgcttt gaagcatata   5640

agctgccctg cccctcaagg ttttcttcaa gtgaggtttt atctaactgc ctaacggcag   5700

gggaaccgta tattgcttac ggtatgagac cccttaaacg tccggatagt caccgctctt   5760

ctttagctcc gcgacatgcc tagcaaccgt ggcgcgagag actcctacct ctgcccctat   5820

ttcagcccac gtgggaactg tccctgtctg gaaatactga tcgttcacca tttggctaat   5880

acgggacttc gtagatcgtc cttgagcctt tttcttacgg tgcgtctttt caagcttcga   5940

cctttgtgct tgcgcatatt tgccctcggg gtctgttttc cagcgttgtg cggcttttg    6000

tccgcctctg cgtcccatcg tggccaaggc tttccgctcg ctgctggtgg ctttacctgg   6060

tgcgttagag ccgctgtagg tctcgctctt ggattgggcg acatacccgc gcacgcgcct   6120

tgccatggtt tggcggtcgc gcatgggtgg catctcgttg tcgcggcctg caccgccgtg   6180

ggtgtgtgcg acgttgtagg cgtgctcata ggcgtcgatg attgctgcgt ctgtcaggcg   6240

ttggccttgc tggcgcaagc ggtggccagt cttaagcgca tgtctaaagg ctgtttcgtc   6300

gcgtgctgcg gttccttgga caatccagag cacacgcaca ccgtcgataa gttccgggtc   6360

atactggtcg agaccaccgg cgatttccgc gtctacgtcc tg                      6402
```

<210> SEQ ID NO 22
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Ser Arg Lys Leu Phe Ala Ser Ile Leu Ile Gly Ala Leu Leu Gly
1               5                   10                  15

Ile Gly Ala Pro Pro Ser Ala His Ala
            20                  25

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Tyr Lys Asp Asp Asp Asp Lys
1               5

<210> SEQ ID NO 25
<211> LENGTH: 19
<212> TYPE: DNA
<213> ORGANISM: Unknown
<220> FEATURE:
<223> OTHER INFORMATION: Description of Unknown:
      wild-type toxO sequence

<400> SEQUENCE: 25
ttaggatagc tttacctaa                                                19

<210> SEQ ID NO 26
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Ser Arg Lys Leu Phe Ala Ser Ile Leu Ile Gly Ala Leu Leu Gly 1 5 10 15

Ile Gly Ala Pro Pro Ser Ala His Ala Gly Ala Asp Asp Val Val
20 25 30

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Met Gly Ala Asp Asp
1 5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Gly Ala Asp Asp
1

<210> SEQ ID NO 30
<211> LENGTH: 526
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Gly Ala Asp Asp Val Ala Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

```
Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr Glu Asn Leu Tyr Phe Gln
        515                 520                 525
```

<210> SEQ ID NO 31
<211> LENGTH: 1686
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
gtgagcagaa aactgtttgc gtcaatctta ataggggcgc tactggggat aggggcccca      60

ccttcagccc atgcaggcgc tgatgatgtt gctgattctt ctaaatcttt tgtgatggaa     120
```

aacttttctt cgtaccacgg gactaaacct ggttatgtag attccattca aaaaggtata 180
caaaagccaa aatctggtac acaaggaaat tatgacgatg attggaaagg gttttatagt 240
accgacaata aatacgacgc tgcgggatac tctgtagata atgaaaaccc gctctctgga 300
aaagctggag gcgtggtcaa agtgacgtat ccaggactga cgaaggttct cgcactaaaa 360
gtggataatg ccgaaactat taagaaagag ttaggtttaa gtctcactga accgttgatg 420
gagcaagtcg gaacggaaga gtttatcaaa aggttcggtg atggtgcttc gcgtgtagtg 480
ctcagccttc ccttcgctga ggggagttct agcgttgaat atattaataa ctgggaacag 540
gcgaaagcgt taagcgtaga acttgagatt aattttgaaa cccgtggaaa acgtggccaa 600
gatgcgatgt atgagtatat ggctcaagcc tgtgcaggaa atcgtgtcag gcgatcagta 660
ggtagctcat tgtcatgcat caacctggat tgggatgtta tccgtgataa aactaaaact 720
aagatcgaat ctctgaaaga acacggtccg atcaaaaaca aaatgagcga aagcccgaac 780
aaaactgtat ctgaagaaaa agctaaacag tacctggaag aattccacca gactgcactg 840
gaacacccgg aactgtctga acttaagacc gttactggta ccaacccggt attcgctggt 900
gctaactacg ctgcttgggc agtaaacgtt gctcaggtta tcgatagcga aactgctgat 960
aacctggaaa aaactaccgc ggctctgtct atcctgccgg gtatcggtag cgtaatgggc 1020
atcgcagacg gcgccgttca ccacaacact gaagaaatcg ttgcacagtc tatcgctctg 1080
agctctctga tggttgctca ggccatcccg ctggtaggtg aactggttga tatcggtttc 1140
gctgcataca acttcgttga aagcatcatc aacctgttcc aggttgttca caactcttac 1200
aaccgcccgg cttactctcc gggtcacaag acgcatgcac ctacttctag ctctaccaag 1260
aaaacccagc tgcagctcga gcacctgctg ctggatttgc agatgatcct gaacggtatc 1320
aacaattaca agaacccgaa actgacgcgt atgctgacct tcaagttcta catgccgaag 1380
aaggccaccg aactgaaaca cctgcagtgt ctagaagaag aactgaaacc gctggaggaa 1440
gttctgaacc tggctcagtc taaaaacttc cacctgcggc cgcgtgacct gatctctaac 1500
atcaacgtaa tcgttctgga actgaagggc tctgaaacca ccttcatgtg tgaatacgct 1560
gatgagaccg caaccatcgt agaattcctg aaccgttgga tcaccttctg tcagtctatc 1620
atctctaccc tgaccgagaa cctgtacttc cagggccatc accaccacca ccaccatcat 1680
cactag 1686

<210> SEQ ID NO 32
<211> LENGTH: 250
<212> TYPE: PRT
<213> ORGANISM: Corynebacterium diphtheriae

<400> SEQUENCE: 32

Met Arg Lys Ile Val Thr Leu Ala Ala Ala Ser Leu Leu Gly Ile Ala
1 5 10 15

Gly Thr Ser Gly Val Leu Gly Ala Ala Thr Ala Thr Ala Leu Thr Asn
20 25 30

Gly Thr Pro Val Ser Pro Glu Asp Asp Thr Ala Ala Glu Gly Val Val
35 40 45

Gln Val Ala Ser Cys Thr Gly Thr Val Val Ala Ser Gln Trp Val Leu
50 55 60

Thr Ala Gln His Cys Val Glu Val Pro Asn Leu Gln Arg Pro Val Tyr
65 70 75 80

Val Gly Thr Thr Arg Glu Gln Gln Gln Arg Glu Glu Asn Thr Phe Thr
85 90 95

-continued

```
Ser Asp Tyr Ala Val Trp Ala Pro His Gly Asp Val Ala Leu Val His
            100                 105                 110

Val Thr Asp Ala Leu Pro Gln Arg Leu Val Arg Ala Val Arg Arg Ala
        115                 120                 125

Pro Val Ser Phe Gly Glu Gln Gly Arg Val Tyr Gly Trp Gly Ala Gly
    130                 135                 140

Thr Gly Glu Thr Leu Gln Tyr Ala Arg Ala Ala Val Gly Lys Thr Ser
145                 150                 155                 160

Ser Gly Val Arg Pro Gln Gly Asn Gln His Gly Ala Phe Ile Val Gln
                165                 170                 175

Tyr Leu Asp Glu Ala Lys Ala Gly Arg Gly Asp Ser Gly Gly Pro Leu
            180                 185                 190

Phe Val Asn Gly Glu Val Ala Gly Val Thr Ser Phe Lys Ala Pro Gln
        195                 200                 205

Gly Gly Gly Arg Phe Ser Leu Phe Ala Ser Leu His Gly Leu Gly Asp
    210                 215                 220

Trp Ile Ala Gln Thr Thr Ala Ala Lys Pro Glu Asn Pro Asn Ser Lys
225                 230                 235                 240

Asn Gln Gln Ser Gln Gln Pro Arg Arg Pro
                245                 250
```

<210> SEQ ID NO 33
<211> LENGTH: 753
<212> TYPE: DNA
<213> ORGANISM: Corynebacterium diphtheriae

<400> SEQUENCE: 33

```
atgcggaaaa ttgttactct tgctgcagca agcttgctgg gtattgcggg taccagcggt     60

gttcttggtg cggcaacagc caccgcactg acaaatggca cgcccgtctc ccctgaggac    120

gataccgctg ccgaaggcgt ggttcaagtg gctagttgta ctggcaccgt ggttgcttct    180

cagtgggtgc tgaccgccca gcattgcgtc gaggtgccca atttgcagcg gccggtctat    240

gttggcacca cccgcgagca gcaacaacgg gaagaaaata cgttcacctc ggattacgca    300

gtgtgggcac cgcacggcga tgtggcgttg gtgcatgtca ccgatgcgct gccgcagcgt    360

ctggtccgcg cggttcgccg cgcaccggtg agctttggtg agcagggacg cgtgtacggc    420

tggggtgctg gcaccggcga gacgctgcag tatgcccgcg ctgcggttgg taaaacttct    480

tccggagttc ggccgcaggg caaccagcat ggtgcattca tcgtgcagta tttggacgag    540

gctaaagccg ggcgtggcga ttccggcggg ccgctttttg tcaacggtga ggttgctggg    600

gtgacctcgt ttaaggctcc tcaaggtggt gggcgtttct cgctgtttgc ttcgctgcat    660

gggctaggcg attggattgc gcagaccacc gccgccaagc ccgagaaccc gaattccaag    720

aatcaacagt cccagcaacc acgtagaccg tag                                 753
```

<210> SEQ ID NO 34
<211> LENGTH: 1012
<212> TYPE: DNA
<213> ORGANISM: Corynebacterium diphtheriae

<400> SEQUENCE: 34

```
ggatccgcaa ttgcgggaat cgtcgtgctt tttagccgaa attttcttgc agccagcgct     60

atgcttatcg cctcagggtt agccgctgac atttaccgct tgaggaataa tatgagtgga    120

aatcaacggt aatttcagaa gacttgccta cacctttagc tagcgaccac cattggtggt    180
```

-continued

```
cgctagcttt ttgatggctt aagggacatt tgggcatccg tgtatcgcac attagtcata    240

caggaaatcc tccaagattt cgtccgcatg cccgaccaga cactacagca cccacatagc    300

ttctcgattg tcttgcggag cgggagtagg tagctcacgt gctaccgcac ggggaaccgt    360

atattgctta tggtgtgccc attacccacc gttggtgcta tgatccgaac ggaaaaagtc    420

agtcgtatta gtgaatcacc gttccgccgc gcgagaacgc agggctccaa caagcgtgtg    480

gttccacaag attgcaagga tgtgtacggt gctggtggcg gtggctccag cctgggtctg    540

tcgtcttctt agcaagtctg cattcacggt tccctaggca atctttgagc aaatccctgt    600

ttaacgcccc tgtacgttcg gcgccgcaga aacctgccgg atcgtgatgt taatcctgcc    660

ttgttccagc ccgcagccgt cgggaagcgt ggcatcattc acgcgcacca ccccgtgata    720

agcaaaacgc ttcggcccac cgaaaaccac caagtcgccg gagcacagag tcacatcgtc    780

ccagggttgg gtgcgtgatt cggtgtgtcc catccgaaac agtgcttcgt cgccaatcga    840

tactgaaatg accggcgccc gcgattcctc aaattcatcg acgtgcatgc ccatcccgga    900

acccggcgga tagtagttga ccagcaccat ctctgtcacg aaggcctcta cccacggggc    960

tagttcttcg gcaacctccg ctgctgcgcg caacgctgcc ggcgccggat cc          1012
```

<210> SEQ ID NO 35
<211> LENGTH: 242
<212> TYPE: PRT
<213> ORGANISM: Corynebacterium diphtheriae

<400> SEQUENCE: 35

```
Met Lys Lys Leu Arg Thr Leu Ala Val Thr Leu Thr Ala Ile Ala Ala
1               5                   10                  15

Ser Thr Met Ala Thr Met Pro Ala Gln Ala Val Ile Ser Pro Thr Pro
            20                  25                  30

Ser His Gln Val Ser Leu Ala Tyr Val Ser Phe Asp Asn Met Gln Cys
        35                  40                  45

Thr Gly Thr Leu Val Ser Pro Thr Ala Val Leu Thr Ala Arg His Cys
    50                  55                  60

Leu Asn Gly Gly Leu Gly His Val Arg Leu Gly Ala Asp His Phe Thr
65                  70                  75                  80

Ala Val Arg Ala Val Ala His Pro Gln Ala Asp Leu Ala Val Leu His
                85                  90                  95

Leu Asp Arg Pro Ala Pro Ile Ala Pro Ser Ala Ile Ser Gly Arg His
            100                 105                 110

Thr Gln Pro Gly Asn Arg Phe Gly Val Ala Gly Tyr Gly Ser Thr Phe
        115                 120                 125

Thr Gly Ile Pro Met Ala Ala Ala Ala Thr Met Gln Arg Arg Val Thr
    130                 135                 140

Asp Val Pro Ser Pro Asp Arg Gln Ala Val Met Ile Glu Asn His Ile
145                 150                 155                 160

Ser Gln Gly Val Leu Arg Pro Gly Asp Ser Gly Gly Pro Leu Leu Glu
                165                 170                 175

Gly Asn His Val Ile Gly Val Leu Ser Met Ser Ser Ala Ser Gly Arg
            180                 185                 190

Val Gly Trp Tyr Ile Pro Thr Ala Glu His Ala Asp Trp Ile Ala Ala
        195                 200                 205

Ala Ala Gly Ile Pro Ala Pro Gly Ser Val Asp Lys Pro Ala Pro Leu
    210                 215                 220

Val Asp Ala Thr Ala Phe Pro Thr Gln Glu Pro Ser Leu Ala Ser Leu
```

-continued 225 230 235 240

Ser Ser

<210> SEQ ID NO 36
<211> LENGTH: 729
<212> TYPE: DNA
<213> ORGANISM: Corynebacterium diphtheriae
<400> SEQUENCE: 36
atgaagaaac ttcgtaccct agccgtaacc ctgaccgcaa tcgcagcatc aaccatggcg 60
accatgccag cacaagcagt gattagtccg acaccgtcac atcaagtttc gctagcgtac 120
gtcagttttg acaacatgca gtgcaccggc acactcgtca gccccaccgc cgtgctcaca 180
gcacgacact gcctcaacgg cggcctcggc cacgtccgac tcggcgccga tcacttcacc 240
gccgtacgtg ccgtggcaca cccccaagca gaccttgccg tcctccacct cgatcgccca 300
gcgccaatag cgccatccgc aatctctgga cgtcacaccc aaccaggtaa ccgcttcgga 360
gttgccggct acggaagcac cttcaccggc atccccatgg cagcagctgc aaccatgcaa 420
cgccgcgtca ccgacgtccc cagccccgac cgccaagcag tcatgatcga aaaccacatc 480
agccaaggtg tactacgccc aggcgactct ggcggccccc tcctagaggg caatcacgtc 540
ataggagtac tcagcatgag cagtgcatcc ggccgcgtcg gctggtacat ccccaccgca 600
gaacacgccg actggatcgc ggcggcagcc ggaatccccg caccgggaag cgtcgacaag 660
cccgctccgc tcgtcgacgc cacagccttc ccgacgcaag agccaagcct cgctagccta 720
tcctcctag 729

<210> SEQ ID NO 37
<211> LENGTH: 1012
<212> TYPE: DNA
<213> ORGANISM: Corynebacterium diphtheriae
<400> SEQUENCE: 37
ggatccgggc ttatcaccgc agaagacgcc gaaaaagcca tcgatgccac cctcctagcc 60
gtcgacggca tcacacgcca taacgacgac cccatggcat ggctcgccgc tatgggatac 120
ccactaacat gggcaaaaaa catcacgctt aaggaggccg aatgattacc gtctatcaca 180
acccccgctg ctccacctcg cgcaaagcct tggagtacat agaacaacac agcgacgacg 240
aggtgaccat catccgctac ctcgacgccc ctcctagtga acaagagctg cgcactttgc 300
ttgccgacgc ccacctcagc ccgcacgacg caatccgcac caaagaagcc gaatacaaag 360
aactcggact cagctccacc acccccgaat cagagctaat caaggccatg gtcacccacc 420
cacgcctcat tcagcgccca attgtggcaa catgcaaggg aacgcggatc gcccgaccaa 480
ccgaaattct gaaagaaatt ctctagccga atcgccagcg atctcggaag ccaaggaatc 540
cttcggcatg ttaaaaaatg taaaagttta atgcgggcac aaacgcgttg aaagagcaac 600
acaccaccat cgttgaacat acttgattat ttcccacttt ccagaatttt aatgagcatg 660
cccagctcga catcaagaac gcagggaaga tctcactagc aatcgacgat aggcccttct 720
tcgacaaccc ggaacatctt gccacgtacg acggaactac actggcagga tcgtcaatat 780
gtggtgaatt ccctgttaaa gtaggaagaa cagagggtgt cagtccgttt gtgtacgggg 840
actgacaccc tctgttcaaa tgattcatcg aagacggttt cacttttcta gcaaaacagc 900
aagacccgca agatttcata tattggtcaa gcgcagccac aaactatcac tcatagctat 960
gtagccccct attaattcat atctcaaaga gtatccaagc actttgggat cc 1012

<210> SEQ ID NO 38
<211> LENGTH: 558
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 38

```
Met Ser Arg Lys Leu Phe Ala Ser Ile Leu Ile Gly Ala Leu Leu Gly
1               5                   10                  15

Ile Gly Ala Pro Pro Ser Ala His Ala Met His His His His His His
            20                  25                  30

Glu Asn Leu Tyr Phe Gln Gly Ala Asp Asp Val Ala Asp Ser Ser Lys
        35                  40                  45

Ser Phe Val Met Glu Asn Phe Ser Ser Tyr His Gly Thr Lys Pro Gly
    50                  55                  60

Tyr Val Asp Ser Ile Gln Lys Gly Ile Gln Lys Pro Lys Ser Gly Thr
65                  70                  75                  80

Gln Gly Asn Tyr Asp Asp Asp Trp Lys Gly Phe Tyr Ser Thr Asp Asn
                85                  90                  95

Lys Tyr Asp Ala Ala Gly Tyr Ser Val Asp Asn Glu Asn Pro Leu Ser
            100                 105                 110

Gly Lys Ala Gly Gly Val Val Lys Val Thr Tyr Pro Gly Leu Thr Lys
        115                 120                 125

Val Leu Ala Leu Lys Val Asp Asn Ala Glu Thr Ile Lys Lys Glu Leu
    130                 135                 140

Gly Leu Ser Leu Thr Glu Pro Leu Met Glu Gln Val Gly Thr Glu Glu
145                 150                 155                 160

Phe Ile Lys Arg Phe Gly Asp Gly Ala Ser Arg Val Val Leu Ser Leu
                165                 170                 175

Pro Phe Ala Glu Gly Ser Ser Ser Val Glu Tyr Ile Asn Asn Trp Glu
            180                 185                 190

Gln Ala Lys Ala Leu Ser Val Glu Leu Glu Ile Asn Phe Glu Thr Arg
        195                 200                 205

Gly Lys Arg Gly Gln Asp Ala Met Tyr Glu Tyr Met Ala Gln Ala Cys
    210                 215                 220

Ala Gly Asn Arg Val Arg Arg Ser Val Gly Ser Ser Leu Ser Cys Ile
225                 230                 235                 240

Asn Leu Asp Trp Asp Val Ile Arg Asp Lys Thr Lys Thr Lys Ile Glu
                245                 250                 255

Ser Leu Lys Glu His Gly Pro Ile Lys Asn Lys Met Ser Glu Ser Pro
            260                 265                 270

Asn Lys Thr Val Ser Glu Glu Lys Ala Lys Gln Tyr Leu Glu Glu Phe
        275                 280                 285

His Gln Thr Ala Leu Glu His Pro Glu Leu Ser Glu Leu Lys Thr Val
    290                 295                 300

Thr Gly Thr Asn Pro Val Phe Ala Gly Ala Asn Tyr Ala Ala Trp Ala
305                 310                 315                 320

Val Asn Val Ala Gln Val Ile Asp Ser Glu Thr Ala Asp Asn Leu Glu
                325                 330                 335

Lys Thr Thr Ala Ala Leu Ser Ile Leu Pro Gly Ile Gly Ser Val Met
            340                 345                 350

Gly Ile Ala Asp Gly Ala Val His His Asn Thr Glu Glu Ile Val Ala
```

```
        355                 360                 365

Gln Ser Ile Ala Leu Ser Ser Leu Met Val Ala Gln Ala Ile Pro Leu
    370                 375                 380

Val Gly Glu Leu Val Asp Ile Gly Phe Ala Ala Tyr Asn Phe Val Glu
385                 390                 395                 400

Ser Ile Ile Asn Leu Phe Gln Val Val His Asn Ser Tyr Asn Arg Pro
                405                 410                 415

Ala Tyr Ser Pro Gly His Lys Thr His Ala Pro Thr Ser Ser Ser Thr
            420                 425                 430

Lys Lys Thr Gln Leu Gln Leu Glu His Leu Leu Leu Asp Leu Gln Met
        435                 440                 445

Ile Leu Asn Gly Ile Asn Asn Tyr Lys Asn Pro Lys Leu Thr Arg Met
    450                 455                 460

Leu Thr Phe Lys Phe Tyr Met Pro Lys Lys Ala Thr Glu Leu Lys His
465                 470                 475                 480

Leu Gln Cys Leu Glu Glu Glu Leu Lys Pro Leu Glu Glu Val Leu Asn
                485                 490                 495

Leu Ala Gln Ser Lys Asn Phe His Leu Arg Pro Arg Asp Leu Ile Ser
            500                 505                 510

Asn Ile Asn Val Ile Val Leu Glu Leu Lys Gly Ser Glu Thr Thr Phe
        515                 520                 525

Met Cys Glu Tyr Ala Asp Glu Thr Ala Thr Ile Val Glu Phe Leu Asn
    530                 535                 540

Arg Trp Ile Thr Phe Cys Gln Ser Ile Ile Ser Thr Leu Thr
545                 550                 555


<210> SEQ ID NO 39
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met His His His His His His Glu Asn Leu Tyr Phe Gln Gly Ala Asp
1               5                   10                  15

Asp Val Ala Asp Ser Ser Lys Ser Phe Val Met Glu Asn Phe Ser Ser
            20                  25                  30

Tyr His Gly Thr Lys Pro Gly Tyr Val Asp Ser Ile Gln Lys Gly Ile
        35                  40                  45

Gln Lys Pro Lys Ser Gly Thr Gln Gly Asn Tyr Asp Asp Asp Trp Lys
    50                  55                  60

Gly Phe Tyr Ser Thr Asp Asn Lys Tyr Asp Ala Ala Gly Tyr Ser Val
65                  70                  75                  80

Asp Asn Glu Asn Pro Leu Ser Gly Lys Ala Gly Gly Val Val Lys Val
                85                  90                  95

Thr Tyr Pro Gly Leu Thr Lys Val Leu Ala Leu Lys Val Asp Asn Ala
            100                 105                 110

Glu Thr Ile Lys Lys Glu Leu Gly Leu Ser Leu Thr Glu Pro Leu Met
        115                 120                 125

Glu Gln Val Gly Thr Glu Glu Phe Ile Lys Arg Phe Gly Asp Gly Ala
    130                 135                 140

Ser Arg Val Val Leu Ser Leu Pro Phe Ala Glu Gly Ser Ser Ser Val
145                 150                 155                 160
```

-continued

```
Glu Tyr Ile Asn Asn Trp Glu Gln Ala Lys Ala Leu Ser Val Glu Leu
            165                 170                 175

Glu Ile Asn Phe Glu Thr Arg Gly Lys Arg Gly Gln Asp Ala Met Tyr
            180                 185                 190

Glu Tyr Met Ala Gln Ala Cys Ala Gly Asn Arg Val Arg Arg Ser Val
        195                 200                 205

Gly Ser Ser Leu Ser Cys Ile Asn Leu Asp Trp Asp Val Ile Arg Asp
    210                 215                 220

Lys Thr Lys Thr Lys Ile Glu Ser Leu Lys Glu His Gly Pro Ile Lys
225                 230                 235                 240

Asn Lys Met Ser Glu Ser Pro Asn Lys Thr Val Ser Glu Glu Lys Ala
            245                 250                 255

Lys Gln Tyr Leu Glu Glu Phe His Gln Thr Ala Leu Glu His Pro Glu
            260                 265                 270

Leu Ser Glu Leu Lys Thr Val Thr Gly Thr Asn Pro Val Phe Ala Gly
        275                 280                 285

Ala Asn Tyr Ala Ala Trp Ala Val Asn Val Ala Gln Val Ile Asp Ser
    290                 295                 300

Glu Thr Ala Asp Asn Leu Glu Lys Thr Thr Ala Ala Leu Ser Ile Leu
305                 310                 315                 320

Pro Gly Ile Gly Ser Val Met Gly Ile Ala Asp Gly Ala Val His His
            325                 330                 335

Asn Thr Glu Glu Ile Val Ala Gln Ser Ile Ala Leu Ser Ser Leu Met
            340                 345                 350

Val Ala Gln Ala Ile Pro Leu Val Gly Glu Leu Val Asp Ile Gly Phe
        355                 360                 365

Ala Ala Tyr Asn Phe Val Glu Ser Ile Ile Asn Leu Phe Gln Val Val
    370                 375                 380

His Asn Ser Tyr Asn Arg Pro Ala Tyr Ser Pro Gly His Lys Thr His
385                 390                 395                 400

Ala Pro Thr Ser Ser Ser Thr Lys Lys Thr Gln Leu Gln Leu Glu His
            405                 410                 415

Leu Leu Leu Asp Leu Gln Met Ile Leu Asn Gly Ile Asn Asn Tyr Lys
            420                 425                 430

Asn Pro Lys Leu Thr Arg Met Leu Thr Phe Lys Phe Tyr Met Pro Lys
        435                 440                 445

Lys Ala Thr Glu Leu Lys His Leu Gln Cys Leu Glu Glu Glu Leu Lys
    450                 455                 460

Pro Leu Glu Glu Val Leu Asn Leu Ala Gln Ser Lys Asn Phe His Leu
465                 470                 475                 480

Arg Pro Arg Asp Leu Ile Ser Asn Ile Asn Val Ile Val Leu Glu Leu
            485                 490                 495

Lys Gly Ser Glu Thr Thr Phe Met Cys Glu Tyr Ala Asp Glu Thr Ala
            500                 505                 510

Thr Ile Val Glu Phe Leu Asn Arg Trp Ile Thr Phe Cys Gln Ser Ile
        515                 520                 525

Ile Ser Thr Leu Thr
    530
```

<210> SEQ ID NO 40
<211> LENGTH: 520
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 40

```
Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400
```

-continued

```
Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520
```

```
<210> SEQ ID NO 41
<211> LENGTH: 1677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

gtgagcagaa aactgtttgc gtcaatctta ataggggcgc tactggggat aggggcccca     60

ccttcagccc atgcaatgca tcaccaccac caccacgaga acctgtactt ccagggcgct    120

gatgatgttg ctgattcttc taaatctttt gtgatggaaa acttttcttc gtaccacggg    180

actaaacctg gttatgtaga ttccattcaa aaaggtatac aaaagccaaa atctggtaca    240

caaggaaatt atgacgatga ttggaaaggg ttttatagta ccgacaataa atacgacgct    300

gcgggatact ctgtagataa tgaaaacccg ctctctggaa aagctggagg cgtggtcaaa    360

gtgacgtatc caggactgac gaaggttctc gcactaaaag tggataatgc cgaaactatt    420

aagaaagagt taggtttaag tctcactgaa ccgttgatgg agcaagtcgg aacggaagag    480

tttatcaaaa ggttcggtga tggtgcttcg cgtgtagtgc tcagccttcc cttcgctgag    540

gggagttcta gcgttgaata tattaataac tgggaacagg cgaaagcgtt aagcgtagaa    600

cttgagatta attttgaaac ccgtggaaaa cgtggccaag atgcgatgta tgagtatatg    660

gctcaagcct gtgcaggaaa tcgtgtcagg cgatcagtag gtagctcatt gtcatgcatc    720

aacctggatt gggatgttat ccgtgataaa actaaaacta agatcgaatc tctgaaagaa    780

cacggtccga tcaaaaacaa aatgagcgaa agcccgaaca aaactgtatc tgaagaaaaa    840

gctaaacagt acctggaaga attccaccag actgcactgg aacacccgga actgtctgaa    900

cttaagaccg ttactggtac caacccggta ttcgctggtg ctaactacgc tgcttgggca    960

gtaaacgttg ctcaggttat cgatagcgaa actgctgata acctggaaaa aactaccgcg   1020

gctctgtcta tcctgccggg tatcggtagc gtaatgggca tcgcagacgg cgccgttcac   1080

cacaacactg aagaaatcgt tgcacagtct atcgctctga gctctctgat ggttgctcag   1140

gccatcccgc tggtaggtga actggttgat atcggtttcg ctgcatacaa cttcgttgaa   1200

agcatcatca acctgttcca ggttgttcac aactcttaca accgcccggc ttactctccg   1260

ggtcacaaga cgcatgcacc tacttctagc tctaccaaga aaacccagct gcagctcgag   1320
```

```
cacctgctgc tggatttgca gatgatcctg aacggtatca acaattacaa gaacccgaaa   1380

ctgacgcgta tgctgacctt caagttctac atgccgaaga aggccaccga actgaaacac   1440

ctgcagtgtc tagaagaaga actgaaaccg ctggaggaag ttctgaacct ggctcagtct   1500

aaaaacttcc acctgcggcc gcgtgacctg atctctaaca tcaacgtaat cgttctggaa   1560

ctgaagggct ctgaaaccac cttcatgtgt gaatacgctg atgagaccgc aaccatcgta   1620

gaattcctga accgttggat caccttctgt cagtctatca tctctaccct gacctga      1677
```

```
<210> SEQ ID NO 42
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Ala Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300
```

```
Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
        355                 360                 365

Ile Pro Leu Val Gly Glu Leu Val Asp Ile Gly Phe Ala Ala Tyr Asn
    370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr His Ala Pro Thr Ser
                405                 410                 415

Ser Ser Thr Lys Lys Thr Gln Leu Gln Leu Glu His Leu Leu Leu Asp
            420                 425                 430

Leu Gln Met Ile Leu Asn Gly Ile Asn Asn Tyr Lys Asn Pro Lys Leu
        435                 440                 445

Thr Arg Met Leu Thr Phe Lys Phe Tyr Met Pro Lys Lys Ala Thr Glu
    450                 455                 460

Leu Lys His Leu Gln Cys Leu Glu Glu Glu Leu Lys Pro Leu Glu Glu
465                 470                 475                 480

Val Leu Asn Leu Ala Gln Ser Lys Asn Phe His Leu Arg Pro Arg Asp
                485                 490                 495

Leu Ile Ser Asn Ile Asn Val Ile Val Leu Glu Leu Lys Gly Ser Glu
            500                 505                 510

Thr Thr Phe Met Cys Glu Tyr Ala Asp Glu Thr Ala Thr Ile Val Glu
        515                 520                 525

Phe Leu Asn Arg Trp Ile Thr Phe Cys Gln Ser Ile Ile Ser Thr Leu
    530                 535                 540

Thr His His His His His His
545                 550


<210> SEQ ID NO 43
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
```

-continued

```
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 44
<211> LENGTH: 1656
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 44
gtgagcagaa aactgtttgc gtcaatctta ataggggcgc tactggggat aggggcccca 60
ccttcagccc atgcaggcgc tgatgatgtt gctgattctt ctaaatcttt tgtgatggaa 120
aacttttctt cgtaccacgg gactaaacct ggttatgtag attccattca aaaaggtata 180
caaaagccaa aatctggtac acaaggaaat tatgacgatg attggaaagg gttttatagt 240
accgacaata aatacgacgc tgcgggatac tctgtagata atgaaaaccc gctctctgga 300
aaagctggag gcgtggtcaa agtgacgtat ccaggactga cgaaggttct cgcactaaaa 360
gtggataatg ccgaaactat taagaaagag ttaggtttaa gtctcactga accgttgatg 420
gagcaagtcg gaacggaaga gtttatcaaa aggttcggtg atggtgcttc gcgtgtagtg 480
ctcagccttc ccttcgctga ggggagttct agcgttgaat atattaataa ctgggaacag 540
gcgaaagcgt taagcgtaga acttgagatt aattttgaaa cccgtggaaa acgtggccaa 600
gatgcgatgt atgagtatat ggctcaagcc tgtgcaggaa atcgtgtcag gcgatcagta 660
ggtagctcat tgtcatgcat caacctggat tgggatgtta tccgtgataa aactaaaact 720
aagatcgaat ctctgaaaga acacggtccg atcaaaaaca aaatgagcga aagcccgaac 780
aaaactgtat ctgaagaaaa agctaaacag tacctggaag aattccacca gactgcactg 840
gaacacccgg aactgtctga acttaagacc gttactggta ccaacccggt attcgctggt 900
gctaactacg ctgcttgggc agtaaacgtt gctcaggtta tcgatagcga aactgctgat 960
aacctggaaa aaactaccgc ggctctgtct atcctgccgg gtatcggtag cgtaatgggc 1020
atcgcagacg gcgccgttca ccacaacact gaagaaatcg ttgcacagtc tatcgctctg 1080
agctctctga tggttgctca ggccatcccg ctggtaggtg aactggttga tatcggtttc 1140
gctgcataca acttcgttga aagcatcatc aacctgttcc aggttgttca caactcttac 1200
aaccgcccgg cttactctcc gggtcacaag acgcatgcac ctacttctag ctctaccaag 1260
aaaacccagc tgcagctcga gcacctgctg ctggatttgc agatgatcct gaacggtatc 1320
aacaattaca agaacccgaa actgacgcgt atgctgacct tcaagttcta catgccgaag 1380
aaggccaccg aactgaaaca cctgcagtgt ctagaagaag aactgaaacc gctggaggaa 1440
gttctgaacc tggctcagtc taaaaacttc cacctgcggc cgcgtgacct gatctctaac 1500
atcaacgtaa tcgttctgga actgaagggc tctgaaacca ccttcatgtg tgaatacgct 1560
gatgagaccg caaccatcgt agaattcctg aaccgttgga tcaccttctg tcagtctatc 1620
atctctaccc tgacccacca tcaccatcat cactga 1656

<210> SEQ ID NO 45
<211> LENGTH: 561
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 45

-continued

```
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Ala Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
        355                 360                 365

Ile Pro Leu Val Gly Glu Leu Val Asp Ile Gly Phe Ala Ala Tyr Asn
    370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr His Ala Pro Thr Ser
                405                 410                 415

Ser Ser Thr Lys Lys Thr Gln Leu Gln Leu Glu His Leu Leu Leu Asp
```

```
            420                 425                 430

Leu Gln Met Ile Leu Asn Gly Ile Asn Asn Tyr Lys Asn Pro Lys Leu
        435                 440                 445

Thr Arg Met Leu Thr Phe Lys Phe Tyr Met Pro Lys Lys Ala Thr Glu
    450                 455                 460

Leu Lys His Leu Gln Cys Leu Glu Glu Glu Leu Lys Pro Leu Glu Glu
465                 470                 475                 480

Val Leu Asn Leu Ala Gln Ser Lys Asn Phe His Leu Arg Pro Arg Asp
                485                 490                 495

Leu Ile Ser Asn Ile Asn Val Ile Val Leu Glu Leu Lys Gly Ser Glu
            500                 505                 510

Thr Thr Phe Met Cys Glu Tyr Ala Asp Glu Thr Ala Thr Ile Val Glu
        515                 520                 525

Phe Leu Asn Arg Trp Ile Thr Phe Cys Gln Ser Ile Ile Ser Thr Leu
    530                 535                 540

Thr Glu Asn Leu Tyr Phe Gln Gly His His His His His His His His
545                 550                 555                 560

His


<210> SEQ ID NO 46
<211> LENGTH: 536
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
```

-continued

```
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr Glu Asn Leu Tyr Phe Gln Gly His
        515                 520                 525

His His His His His His His His
    530                 535
```

<210> SEQ ID NO 47
<211> LENGTH: 4679
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
ggatccccccg ggctgcagga attcgatatc aagcttatcg ataccgtcga cctcgagggg     60

gggcccggta ccagcttttg ttccctttag tgagggttaa tttcgagctt ggcgtaatca    120

tggtcatagc tgtttcctgt gtgaaattgt tatccgctca caattccaca caacatacga    180
```

-continued

```
gccggaagca taaagtgtaa agcctggggt gcctaatgag tgagtccccg atccgtcgag    240
ctcgacctgc aggggggggg gggcgctgag gtctgcctcg tgaagaaggt gttgctgact    300
cataccaggc ctgaatcgcc ccatcatcca gccagaaagt gagggagcca cggttgatga    360
gagctttgtt gtaggtggac cagttggtga ttttgaactt ttgctttgcc acggaacggt    420
ctgcgttgtc gggaagatgc gtgatctgat ccttcaactc agcaaaagtt cgatttattc    480
aacaaagccg ccgtcccgtc aagtcagcgt aatgctctgc cagtgttaca accaattaac    540
caattctgat tagaaaaact catcgagcat caaatgaaac tgcaatttat tcatatcagg    600
attatcaata ccatattttt gaaaaagccg tttctgtaat gaaggagaaa actcaccgag    660
gcagttccat aggatggcaa gatcctggta tcggtctgcg attccgactc gtccaacatc    720
aatacaacct attaatttcc cctcgtcaaa aataaggtta tcaagtgaga aatcaccatg    780
agtgacgact gaatccggtg agaatggcaa aagcttatgc atttctttcc agacttgttc    840
aacaggccag ccattacgct cgtcatcaaa atcactcgca tcaaccaaac cgttattcat    900
tcgtgattgc gcctgagcga gacgaaatac gcgatcgctg ttaaaaggac aattacaaac    960
aggaatcgaa tgcaaccggc gcaggaacac tgccagcgca tcaacaatat tttcacctga   1020
atcaggatat tcttctaata cctggaatgc tgttttcccg gggatcgcag tggtgagtaa   1080
ccatgcatca tcaggagtac ggataaaatg cttgatggtc ggaagaggca taaattccgt   1140
cagccagttt agtctgacca tctcatctgt aacatcattg gcaacgctac ctttgccatg   1200
tttcagaaac aactctggcg catcgggctt cccatacaat cgatagattg tcgcacctga   1260
ttgcccgaca ttatcgcgag cccatttata cccatataaa tcagcatcca tgttggaatt   1320
taatcgcggc ctcgagcaag acgtttcccg ttgaatatgg ctcataacac cccttgtatt   1380
actgtttatg taagcagaca gttttattgt tcatgatgat atatttttat cttgtgcaat   1440
gtaacatcag agattttgag acacaacgtg gctttccccc cccccccctgc aggtcgagct   1500
cgacggatcg ggctgcagga attcggtgag gttatggcgg agggttgcga ggtctaggag   1560
aacagaggaa gtcatgcttt gaagcatata agctgccctg cccctcaagg ttttcttcaa   1620
gtgaggtttt atctaactgc ctaacggcag gggaaccgta tattgcttac ggtatgagac   1680
cccttaaacg tccggatagt caccgctctt ctttagctcc gcgacatgcc tagcaaccgt   1740
ggcgcgagag actcctacct ctgcccctat ttcagcccac gtgggaactg tccctgtctg   1800
gaaatactga tcgttcacca tttggctaat acgggacttc gtagatcgtc cttgagcctt   1860
tttcttacgg tgcgtctttt caagcttcga cctttgtgct tgcgcatatt tgccctcggg   1920
gtctgttttc cagcgttgtg cggctttttg tccgcctctg cgtcccatcg tggccaaggc   1980
tttccgctcg ctgctggtgg ctttacctgg tgcgttagag ccgctgtagg tctcgctctt   2040
ggattgggcg acatacccgc gcacgcgcct tgccatggtt tggcggtcgc gcatgggtgg   2100
catctcgttg tcgcggcctg caccgccgtg ggtgtgtgcg acgttgtagg cgtgctcata   2160
ggcgtcgatg attgctgcgt ctgtcaggcg ttggccttgc tggcgcaagc ggtggccagt   2220
cttaagcgca tgtctaaagg ctgtttcgtc gcgtgctgcg gttccttgga caatccagag   2280
cacacgcaca ccgtcgataa gttccgggtc atactggtcg agaccaccgg cgatttccgc   2340
gtctacgtcc tgggcgagtg ctttgaatgc ttgggcttct tcacggcggg tcttgaccgc   2400
gttgataagt tcgcggccag agctgaattg ctggcgtggg gtggggttga actggtcgtg   2460
tcctgccata tcccttacct gctttatcaa gtctccaagg cgcatcaccc ggttgtgctg   2520
cctataccaa cgataagcgg taggggcttt gcctgtgtag aacgggttgc ggctaaagcg   2580
```

```
gtgggaaaag tgcgggtcat ggtctaaaag ctcacccagc acacgcgtgg ttgctgcaag   2640
aagcttcatc tgcgcagatt taccgttacg gtcagcgtag acagggtcaa taagccatat   2700
gaactgggct ttgccgttag ttgggttaat acccacccag gctggcccga cgctatgagt   2760
aatcagtgag cgcaccacgt cgcggacgta cgggtttaag tctgcggggt caccgcctgc   2820
ggtacctact tggtcaacgt ctacgaccag gacggcggcg tactgcttgg tggtgagcat   2880
ggcgtactcg caccgtccta aagcatcagt ctcgaagcga tacatacgcg gcgagttcgt   2940
gccgtcagcg ttgcgtcgat aggccttttt aaagtctcgt gtgactgaac cgtggagtac   3000
atcgcggcct agatgatcgc gtaaaaggtc gcggtcactg gcagatgctg gggtgttgtc   3060
cagtccacca cggtcgcgct cgacgcgggt aggtgtttta gtgtgcgcat tctgcgcatg   3120
agtctgtaaa ctcatgaccg tgctttctcc caggtgtgtg ctgggtgata agcgaaagtc   3180
atcgggttgc cgcccggtgg ctttcttcgt tttcattgt ctttccctga ctctaaatga   3240
caccggtgtt atttactagc catgacacgc gaaaaatatg ccttttacct gcggttacgt   3300
atggctagac atatggcaag ctatacgtaa ccgcgtttca gctgcacagg gctgtctgcg   3360
cagatttacc atcacgggac ttttcccagt tcaggctgcg catatttacg catacaacga   3420
aagcggttgc gcagatttac cacacactct gcgctgattt accgatacgc agaaaaagcg   3480
tgcgcagatt tacccatacg gtggcgaatt atccagagca ataggtatac agcaatacag   3540
taatacaggt gccataaacc tgtattactg tattgctgta tgcctgtaaa cctttattta   3600
ttgttgtgga cgtattcttc gaggtaggtg ctaacaatct cgcggatggt cacgcctttt   3660
tgggcggcga tgactttaag ttctgcgtga aggtcgcggt cgatttcaat cgtcatcttc   3720
ttgacgtagt cgcggcctgt gggttggtgg aatgcgcttc gcactgtttt cttctcggct   3780
gctggagtta gcttcgtggc ttttttcatt gaggttcgcg ggccttgctg cgccctggcg   3840
cgttctttac tggtgctcat ttcatcatct ccatgagttc gtcggcgacg tggtcgtagc   3900
cgtgcatgtc ggggcctggg cagtatccaa acgctaggtg catatcttcg cgtagcggga   3960
tttcggtttt aaagtgcggc atgtgttccg cgtcgagcgc ttctcgtgcc gcgtcaaggg   4020
cgctggtgcc tttcctggcg aacgtcagta agactgcatg aggtgttccg ttgactgcgt   4080
cgcgcagctc ccatactcgg gagaggtcgg cagcagcaga acgggtcgga agaatgatga   4140
agtcgctgac tgcgattgct gcttcgatag cgttctcgtc tcctggcggc acatcgatac   4200
cgactgggcg atggcccact acgtgaacca tcaccctaat caagtttttt ggggtcgagg   4260
tgccgtaaag cactaaatcg gaaccctaaa gggagccccc gatttagagc ttgacgggga   4320
aagccggcga acgtggcgag aaaggaaggg aagaaagcga aaggagcggg cgctagggcg   4380
ctggcaagtg tagcggtcac gctgcgcgta accaccacac ccgccgcgct taatgcgccg   4440
ctacagggcg ctcccattcg ccattcaggc tgcgcaactg ttgggaaggg cgatcggtgc   4500
gggcctcttc gctattacgc cagctggcga aaggggggatg tgctgcaagg cgattaagtt   4560
gggtaacgcc agggttttcc cagtcacgac gttgtaaaac gacggccagt gaattgtaat   4620
acgactcact atagggcgaa ttggagctcc accgcggtgg cggccgctct agaactagt    4679
```

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      9xHis tag

<400> SEQUENCE: 48

His His His His His His His His His
1               5

<210> SEQ ID NO 49
<211> LENGTH: 7
<212> TYPE: PRT
<213> ORGANISM: Unknown
<220> FEATURE:
<223> OTHER INFORMATION: Description of Unknown:
      TEV cleavage site peptide sequence
<220> FEATURE:
<221> NAME/KEY: MOD_RES
<222> LOCATION: (7)..(7)
<223> OTHER INFORMATION: Any small hydrophobic or polar amino acid

<400> SEQUENCE: 49

Glu Asn Leu Tyr Phe Gln Xaa
1               5

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His His His His His His Glu Asn Leu Tyr Phe Gln
1               5                   10

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Ala Asp Asp Val Ala
1               5

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Met His His His His His His Glu Asn Leu Tyr Phe Gln
1               5                   10

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ile Ile Ser Thr Leu Thr
1               5

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Glu Asn Leu Tyr Phe Gln Gly His His His His His His His His His
1 5 10 15

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Gly His His His His His His His His His
1 5 10

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Glu Asn Leu Tyr Phe Gln
1 5

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Ile Ile Ser Thr Leu Thr Glu Asn Leu Tyr Phe Gln
1 5 10

<210> SEQ ID NO 58
<211> LENGTH: 526
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 58

Gly Ala Asp Asp Val Val Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

-continued

```
Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480
```

-continued

Leu Glu Leu Lys Gly Ser Glu Thr Thr Phe Met Cys Glu Tyr Ala Asp
485 490 495

Glu Thr Ala Thr Ile Val Glu Phe Leu Asn Arg Trp Ile Thr Phe Cys
500 505 510

Gln Ser Ile Ile Ser Thr Leu Thr His His His His His His
515 520 525

<210> SEQ ID NO 59
<211> LENGTH: 1729
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 59
ttgatttcag agcaccctta taattaggat agctaagtcc attattttat gagtcctggt 60
aaggggatac gttgtgagca gaaaactgtt tgcgtcaatc ttaatagggg cgctactggg 120
gataggggcc ccaccttcag cccatgcagg cgctgatgat gttgttgatt cttctaaatc 180
ttttgtgatg gaaaactttt cttcgtacca cgggactaaa cctggttatg tagattccat 240
tcaaaaaggt atacaaaagc caaaatctgg tacacaagga aattatgacg atgattggaa 300
agggttttat agtaccgaca ataaatacga cgctgcggga tactctgtag ataatgaaaa 360
cccgctctct ggaaaagctg gaggcgtggt caaagtgacg tatccaggac tgacgaaggt 420
tctcgcacta aaagtggata atgccgaaac tattaagaaa gagttaggtt taagtctcac 480
tgaaccgttg atggagcaag tcggaacgga agagtttatc aaaaggttcg gtgatggtgc 540
ttcgcgtgta gtgctcagcc ttcccttcgc tgaggggagt tctagcgttg aatatattaa 600
taactgggaa caggcgaaag cgttaagcgt agaacttgag attaattttg aaacccgtgg 660
aaaacgtggc caagatgcga tgtatgagta tatggctcaa gcctgtgcag gaaatcgtgt 720
caggcgatca gtaggtagct cattgtcatg catcaacctg gattgggatg ttatccgtga 780
taaaactaaa actaagatcg aatctctgaa agaacacggt ccgatcaaaa acaaaatgag 840
cgaaagcccg aacaaaactg tatctgaaga aaaagctaaa cagtacctgg aagaattcca 900
ccagactgca ctggaacacc cggaactgtc tgaacttaag accgttactg gtaccaaccc 960
ggtattcgct ggtgctaact acgctgcttg ggcagtaaac gttgctcagg ttatcgatag 1020
cgaaactgct gataacctgg aaaaaactac cgcggctctg tctatcctgc cgggtatcgg 1080
tagcgtaatg ggcatcgcag acggcgccgt tcaccacaac actgaagaaa tcgttgcaca 1140
gtctatcgct ctgagctctc tgatggttgc tcaggccatc ccgctggtag gtgaactggt 1200
tgatatcggt ttcgctgcat acaacttcgt tgaaagcatc atcaacctgt tccaggttgt 1260
tcacaactct tacaaccgcc cggcttactc tccgggtcac aagacgcatg cacctacttc 1320
tagctctacc aagaaaaccc agctgcagct cgagcacctg ctgctggatt tgcagatgat 1380
cctgaacggt atcaacaatt acaagaaccc gaaactgacg cgtatgctga ccttcaagtt 1440
ctacatgccg aagaaggcca ccgaactgaa acacctgcag tgtctagaag aagaactgaa 1500
accgctggag gaagttctga acctggctca gtctaaaaac ttccacctgc ggccgcgtga 1560
cctgatctct aacatcaacg taatcgttct ggaactgaag ggctctgaaa ccaccttcat 1620
gtgtgaatac gctgatgaga ccgcaaccat cgtagaattc ctgaaccgtt ggatcacctt 1680
ctgtcagtct atcatctcta ccctgaccca ccatcaccat catcactga 1729

<210> SEQ ID NO 60
<211> LENGTH: 520
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 60

```
Gly Ala Glu Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365
```

-continued

```
Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520
```

<210> SEQ ID NO 61
<211> LENGTH: 1711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgaagat gttgttgatt cttctaaatc    180

ttttgtgatg gaaaactttt cttcgtacca cgggactaaa cctggttatg tagattccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140
```

```
gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgacctg a                                   1711
```

```
<210> SEQ ID NO 62
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gly Ala Glu Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255
```

-continued

```
His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 63
<211> LENGTH: 1729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
ttgatttcag agcaccctta taattaggat agctaagtcc attattttat gagtcctggt      60

aaggggatac gttgtgagca gaaaactgtt tgcgtcaatc ttaatagggg cgctactggg     120

gataggggcc ccaccttcag cccatgcagg cgctgaagat gttgttgatt cttctaaatc     180

ttttgtgatg gaaaactttt cttcgtacca cgggactaaa cctggttatg tagattccat     240

tcaaaaaggt atacaaaagc caaaatctgg tacacaagga aattatgacg atgattggaa     300

agggttttat agtaccgaca ataaatacga cgctgcggga tactctgtag ataatgaaaa     360

cccgctctct ggaaaagctg gaggcgtggt caaagtgacg tatccaggac tgacgaaggt     420

tctcgcacta aaagtggata atgccgaaac tattaagaaa gagttaggtt taagtctcac     480

tgaaccgttg atggagcaag tcggaacgga agagtttatc aaaaggttcg gtgatggtgc     540
```

```
ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgaccca ccatcaccat catcactga               1729
```

<210> SEQ ID NO 64
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Gly Ala Glu Asp Val Val Glu Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140
```

-continued

```
Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520
```

<210> SEQ ID NO 65
<211> LENGTH: 1711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65
ttgatttcag agcaccctta taattaggat agctaagtcc attattttat gagtcctggt 60
aaggggatac gttgtgagca gaaaactgtt tgcgtcaatc ttaatagggg cgctactggg 120
gataggggcc ccaccttcag cccatgcagg cgctgatgat gttgttgaat cttctaaatc 180
ttttgtgatg gaaaactttt cttcgtacca cgggactaaa cctggttatg tagattccat 240
tcaaaaaggt atacaaaagc caaaatctgg tacacaagga aattatgacg atgattggaa 300
agggttttat agtaccgaca ataaatacga cgctgcggga tactctgtag ataatgaaaa 360
cccgctctct ggaaaagctg gaggcgtggt caaagtgacg tatccaggac tgacgaaggt 420
tctcgcacta aaagtggata atgccgaaac tattaagaaa gagttaggtt taagtctcac 480
tgaaccgttg atggagcaag tcggaacgga agagtttatc aaaaggttcg gtgatggtgc 540
ttcgcgtgta gtgctcagcc ttcccttcgc tgaggggagt tctagcgttg aatatattaa 600
taactgggaa caggcgaaag cgttaagcgt agaacttgag attaattttg aaacccgtgg 660
aaaacgtggc caagatgcga tgtatgagta tatggctcaa gcctgtgcag gaaatcgtgt 720
caggcgatca gtaggtagct cattgtcatg catcaacctg gattgggatg ttatccgtga 780
taaaactaaa actaagatcg aatctctgaa agaacacggt ccgatcaaaa acaaaatgag 840
cgaaagcccg aacaaaactg tatctgaaga aaaagctaaa cagtacctgg aagaattcca 900
ccagactgca ctggaacacc cggaactgtc tgaacttaag accgttactg gtaccaaccc 960
ggtattcgct ggtgctaact acgctgcttg ggcagtaaac gttgctcagg ttatcgatag 1020
cgaaactgct gataacctgg aaaaaactac cgcggctctg tctatcctgc cgggtatcgg 1080
tagcgtaatg ggcatcgcag acggcgccgt tcaccacaac actgaagaaa tcgttgcaca 1140
gtctatcgct ctgagctctc tgatggttgc tcaggccatc ccgctggtag gtgaactggt 1200
tgatatcggt ttcgctgcat acaacttcgt tgaaagcatc atcaacctgt tccaggttgt 1260
tcacaactct tacaaccgcc cggcttactc tccgggtcac aagacgcatg cacctacttc 1320
tagctctacc aagaaaaccc agctgcagct cgagcacctg ctgctggatt tgcagatgat 1380
cctgaacggt atcaacaatt acaagaaccc gaaactgacg cgtatgctga ccttcaagtt 1440
ctacatgccg aagaaggcca ccgaactgaa acacctgcag tgtctagaag aagaactgaa 1500
accgctggag gaagttctga acctggctca gtctaaaaac ttccacctgc ggccgcgtga 1560
cctgatctct aacatcaacg taatcgttct ggaactgaag ggctctgaaa ccaccttcat 1620
gtgtgaatac gctgatgaga ccgcaaccat cgtagaattc ctgaaccgtt ggatcacctt 1680
ctgtcagtct atcatctcta ccctgacctg a 1711

<210> SEQ ID NO 66
<211> LENGTH: 526
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 66

Gly Ala Glu Asp Val Val Glu Ser Ser Lys Ser Phe Val Met Glu Asn
1 5 10 15

Phe Ser Ser Tyr His Gly Thr Lys Pro Gly Tyr Val Asp Ser Ile Gln
20 25 30

-continued

```
Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
```

```
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 67
<211> LENGTH: 1729
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
ttgatttcag agcaccctta taattaggat agctaagtcc attattttat gagtcctggt     60
aaggggatac gttgtgagca gaaaactgtt tgcgtcaatc ttaatagggg cgctactggg    120
gataggggcc ccaccttcag cccatgcagg cgctgatgat gttgttgaat cttctaaatc    180
ttttgtgatg gaaaactttt cttcgtacca cgggactaaa cctggttatg tagattccat    240
tcaaaaaggt atacaaaagc caaaatctgg tacacaagga aattatgacg atgattggaa    300
agggttttat agtaccgaca ataaatacga cgctgcggga tactctgtag ataatgaaaa    360
cccgctctct ggaaaagctg gaggcgtggt caaagtgacg tatccaggac tgacgaaggt    420
tctcgcacta aaagtggata atgccgaaac tattaagaaa gagttaggtt taagtctcac    480
tgaaccgttg atggagcaag tcggaacgga agagtttatc aaaaggttcg gtgatggtgc    540
ttcgcgtgta gtgctcagcc ttcccttcgc tgaggggagt tctagcgttg aatatattaa    600
taactgggaa caggcgaaag cgttaagcgt agaacttgag attaattttg aaacccgtgg    660
aaaacgtggc caagatgcga tgtatgagta tatggctcaa gcctgtgcag gaaatcgtgt    720
caggcgatca gtaggtagct cattgtcatg catcaacctg gattgggatg ttatccgtga    780
taaaactaaa actaagatcg aatctctgaa agaacacggt ccgatcaaaa acaaaatgag    840
cgaaagcccg aacaaaactg tatctgaaga aaaagctaaa cagtacctgg aagaattcca    900
ccagactgca ctggaacacc cggaactgtc tgaacttaag accgttactg gtaccaaccc    960
ggtattcgct ggtgctaact acgctgcttg ggcagtaaac gttgctcagg ttatcgatag   1020
cgaaactgct gataacctgg aaaaaactac cgcggctctg tctatcctgc cgggtatcgg   1080
tagcgtaatg ggcatcgcag acggcgccgt tcaccacaac actgaagaaa tcgttgcaca   1140
gtctatcgct ctgagctctc tgatggttgc tcaggccatc ccgctggtag gtgaactggt   1200
tgatatcggt ttcgctgcat acaacttcgt tgaaagcatc atcaacctgt tccaggttgt   1260
tcacaactct tacaaccgcc cggcttactc tccgggtcac aagacgcatg cacctacttc   1320
tagctctacc aagaaaaccc agctgcagct cgagcacctg ctgctggatt tgcagatgat   1380
cctgaacggt atcaacaatt acaagaaccc gaaactgacg cgtatgctga ccttcaagtt   1440
ctacatgccg aagaaggcca ccgaactgaa acacctgcag tgtctagaag aagaactgaa   1500
accgctggag gaagttctga acctggctca gtctaaaaac ttccacctgc ggccgcgtga   1560
cctgatctct aacatcaacg taatcgttct ggaactgaag ggctctgaaa ccaccttcat   1620
```

gtgtgaatac gctgatgaga ccgcaaccat cgtagaattc ctgaaccgtt ggatcacctt 1680
ctgtcagtct atcatctcta ccctgaccca ccatcaccat catcactga 1729

<210> SEQ ID NO 68
<211> LENGTH: 520
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 68

Gly Ala Glu Asp Val Val Asp Thr Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly
210 215 220

Pro Ile Lys Asn Lys Met Ser Glu Ser Pro Asn Lys Thr Val Ser Glu
225 230 235 240

Glu Lys Ala Lys Gln Tyr Leu Glu Glu Phe His Gln Thr Ala Leu Glu
245 250 255

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

Ile Asp Ser Glu Thr Ala Asp Asn Leu Glu Lys Thr Thr Ala Ala Leu
290 295 300

Ser Ile Leu Pro Gly Ile Gly Ser Val Met Gly Ile Ala Asp Gly Ala
305 310 315 320

Val His His Asn Thr Glu Glu Ile Val Ala Gln Ser Ile Ala Leu Ser
325 330 335

Ser Leu Met Val Ala Gln Ala Ile Pro Leu Val Gly Glu Leu Val Asp

-continued

```
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520


<210> SEQ ID NO 69
<211> LENGTH: 1711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgatgat gttgttgata cttctaaatc    180

ttttgtgatg gaaaactttt cttcgtacca cgggactaaa cctggttatg tagattccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020
```

```
cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgacctg a                                  1711
```

<210> SEQ ID NO 70
<211> LENGTH: 526
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Gly Ala Glu Asp Val Val Asp Thr Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
```

-continued

```
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 71
<211> LENGTH: 1732
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 71

```
ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgatgat gttgttgata cttctaaatc    180

ttttgtgatg gaaaactttt cttcgtacca cgggactaaa cctggttatg tagattccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360
```

```
cccgctctct ggaaaagctg gaggcgtggt caaagtgacg tatccaggac tgacgaaggt    420
tctcgcacta aaagtggata atgccgaaac tattaagaaa gagttaggtt taagtctcac    480
tgaaccgttg atggagcaag tcggaacgga agagtttatc aaaaggttcg gtgatggtgc    540
ttcgcgtgta gtgctcagcc ttcccttcgc tgaggggagt tctagcgttg aatatattaa    600
taactgggaa caggcgaaag cgttaagcgt agaacttgag attaattttg aaacccgtgg    660
aaaacgtggc caagatgcga tgtatgagta tatggctcaa gcctgtgcag gaaatcgtgt    720
caggcgatca gtaggtagct cattgtcatg catcaacctg gattgggatg ttatccgtga    780
taaaactaaa actaagatcg aatctctgaa agaacacggt ccgatcaaaa acaaaatgag    840
cgaaagcccg aacaaaactg tatctgaaga aaaagctaaa cagtacctgg aagaattcca    900
ccagactgca ctggaacacc cggaactgtc tgaacttaag accgttactg gtaccaaccc    960
ggtattcgct ggtgctaact acgctgcttg ggcagtaaac gttgctcagg ttatcgatag   1020
cgaaactgct gataacctgg aaaaaactac cgcggctctg tctatcctgc cgggtatcgg   1080
tagcgtaatg ggcatcgcag acggcgccgt tcaccacaac actgaagaaa tcgttgcaca   1140
gtctatcgct ctgagctctc tgatggttgc tcaggccatc ccgctggtag gtgaactggt   1200
tgatatcggt ttcgctgcat acaacttcgt tgaaagcatc atcaacctgt tccaggttgt   1260
tcacaactct tacaaccgcc cggcttactc tccgggtcac aagacgcatg cacctacttc   1320
tagctctacc aagaaaaccc agctgcagct cgagcacctg ctgctggatt tgcagatgat   1380
cctgaacggt atcaacaatt acaagaaccc gaaactgacg cgtatgctga ccttcaagtt   1440
ctacatgccg aagaaggcca ccgaactgaa acacctgcag tgtctagaag aagaactgaa   1500
accgctggag gaagttctga acctggctca gtctaaaaac ttccacctgc ggccgcgtga   1560
cctgatctct aacatcaacg taatcgttct ggaactgaag ggctctgaaa ccaccttcat   1620
gtgtgaatac gctgatgaga ccgcaaccat cgtagaattc ctgaaccgtt ggatcacctt   1680
ctgtcagtct atcatctcta ccctgacctg acaccatcac catcatcact ga           1732
```

<210> SEQ ID NO 72
<211> LENGTH: 520
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Gly Ala Glu Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
```

-continued

```
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520
```

<210> SEQ ID NO 73

<211> LENGTH: 1711
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 73

```
ttgatttcag agcaccctta taattaggat agctaagtcc attattttat gagtcctggt     60
aaggggatac gttgtgagca gaaaactgtt tgcgtcaatc ttaatagggg cgctactggg    120
gataggggcc ccaccttcag cccatgcagg cgctgaagat gttgctgatt cttctaaatc    180
ttttgtgatg gaaaactttt cttcgtacca cgggactaaa cctggttatg tagattccat    240
tcaaaaaggt atacaaaagc caaaatctgg tacacaagga aattatgacg atgattggaa    300
agggttttat agtaccgaca ataaatacga cgctgcggga tactctgtag ataatgaaaa    360
cccgctctct ggaaaagctg gaggcgtggt caaagtgacg tatccaggac tgacgaaggt    420
tctcgcacta aaagtggata atgccgaaac tattaagaaa gagttaggtt taagtctcac    480
tgaaccgttg atggagcaag tcggaacgga agagtttatc aaaaggttcg gtgatggtgc    540
ttcgcgtgta gtgctcagcc ttcccttcgc tgaggggagt tctagcgttg aatatattaa    600
taactgggaa caggcgaaag cgttaagcgt agaacttgag attaattttg aaacccgtgg    660
aaaacgtggc caagatgcga tgtatgagta tatggctcaa gcctgtgcag gaaatcgtgt    720
caggcgatca gtaggtagct cattgtcatg catcaacctg gattgggatg ttatccgtga    780
taaaactaaa actaagatcg aatctctgaa agaacacggt ccgatcaaaa acaaaatgag    840
cgaaagcccg aacaaaactg tatctgaaga aaaagctaaa cagtacctgg aagaattcca    900
ccagactgca ctggaacacc cggaactgtc tgaacttaag accgttactg gtaccaaccc    960
ggtattcgct ggtgctaact acgctgcttg ggcagtaaac gttgctcagg ttatcgatag   1020
cgaaactgct gataacctgg aaaaaactac cgcggctctg tctatcctgc cgggtatcgg   1080
tagcgtaatg ggcatcgcag acggcgccgt tcaccacaac actgaagaaa tcgttgcaca   1140
gtctatcgct ctgagctctc tgatggttgc tcaggccatc ccgctggtag gtgaactggt   1200
tgatatcggt ttcgctgcat acaacttcgt tgaaagcatc atcaacctgt tccaggttgt   1260
tcacaactct tacaaccgcc cggcttactc tccgggtcac aagacgcatg cacctacttc   1320
tagctctacc aagaaaaccc agctgcagct cgagcacctg ctgctggatt tgcagatgat   1380
cctgaacggt atcaacaatt acaagaaccc gaaactgacg cgtatgctga ccttcaagtt   1440
ctacatgccg aagaaggcca ccgaactgaa acacctgcag tgtctagaag aagaactgaa   1500
accgctggag gaagttctga acctggctca gtctaaaaac ttccacctgc ggccgcgtga   1560
cctgatctct aacatcaacg taatcgttct ggaactgaag ggctctgaaa ccaccttcat   1620
gtgtgaatac gctgatgaga ccgcaaccat cgtagaattc ctgaaccgtt ggatcacctt   1680
ctgtcagtct atcatctcta ccctgacctg a                                  1711
```

<210> SEQ ID NO 74
<211> LENGTH: 526
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 74

Gly Ala Glu Asp Val Ala Asp Ser Ser Lys Ser Phe Val Met Glu Asn

-continued

```
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430
```

```
Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525


<210> SEQ ID NO 75
<211> LENGTH: 1729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgaagat gttgctgatt cttctaaatc    180

ttttgtgatg gaaaactttt cttcgtacca cgggactaaa cctggttatg tagattccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500
```

```
accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgaccca ccatcaccat catcactga               1729


<210> SEQ ID NO 76
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gly Ala Glu Asp Val Val Glu Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320
```

-continued

```
Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520
```

<210> SEQ ID NO 77
<211> LENGTH: 1711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77

```
ttgatttcag agcaccctta taattaggat agctaagtcc attattttat gagtcctggt      60

aaggggatac gttgtgagca gaaaactgtt tgcgtcaatc ttaatagggg cgctactggg     120

gataggggcc ccaccttcag cccatgcagg cgctgaagat gttgttgaat cttctaaatc     180

ttttgtgatg gaaaactttt cttcgtacca cgggactaaa cctggttatg tagattccat     240

tcaaaaaggt atacaaaagc caaaatctgg tacacaagga aattatgacg atgattggaa     300

agggttttat agtaccgaca ataaatacga cgctgcggga tactctgtag ataatgaaaa     360

cccgctctct ggaaaagctg gaggcgtggt caaagtgacg tatccaggac tgacgaaggt     420

tctcgcacta aaagtggata atgccgaaac tattaagaaa gagttaggtt taagtctcac     480

tgaaccgttg atggagcaag tcggaacgga agagtttatc aaaaggttcg gtgatggtgc     540

ttcgcgtgta gtgctcagcc ttcccttcgc tgaggggagt tctagcgttg aatatattaa     600

taactgggaa caggcgaaag cgttaagcgt agaacttgag attaattttg aaacccgtgg     660

aaaacgtggc caagatgcga tgtatgagta tatggctcaa gcctgtgcag gaaatcgtgt     720

caggcgatca gtaggtagct cattgtcatg catcaacctg gattgggatg ttatccgtga     780

taaaactaaa actaagatcg aatctctgaa agaacacggt ccgatcaaaa acaaaatgag     840
```

```
cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgacctg a                                  1711
```

<210> SEQ ID NO 78
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Gly Ala Glu Asp Val Val Glu Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205
```

```
Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 79
<211> LENGTH: 1729
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
ttgatttcag agcaccctta taattaggat agctaagtcc attattttat gagtcctggt      60

aaggggatac gttgtgagca gaaaactgtt tgcgtcaatc ttaatagggg cgctactggg     120

gataggggcc ccaccttcag cccatgcagg cgctgaagat gttgttgaat cttctaaatc     180

ttttgtgatg gaaaactttt cttcgtacca cgggactaaa cctggttatg tagattccat     240
```

```
tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgaccca ccatcaccat catcactga              1729
```

```
<210> SEQ ID NO 80
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gly Ala Glu Asp Val Val Asp Thr Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95
```

```
Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510
```

Gln Ser Ile Ile Ser Thr Leu Thr
515 520

<210> SEQ ID NO 81
<211> LENGTH: 1711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81
ttgatttcag agcaccctta taattaggat agctaagtcc attattttat gagtcctggt 60
aaggggatac gttgtgagca gaaaactgtt tgcgtcaatc ttaatagggg cgctactggg 120
gataggggcc ccaccttcag cccatgcagg cgctgaagat gttgttgata cttctaaatc 180
ttttgtgatg gaaaactttt cttcgtacca cgggactaaa cctggttatg tagattccat 240
tcaaaaaggt atacaaaagc caaaatctgg tacacaagga aattatgacg atgattggaa 300
agggttttat agtaccgaca ataaatacga cgctgcggga tactctgtag ataatgaaaa 360
cccgctctct ggaaaagctg gaggcgtggt caaagtgacg tatccaggac tgacgaaggt 420
tctcgcacta aaagtggata atgccgaaac tattaagaaa gagttaggtt taagtctcac 480
tgaaccgttg atggagcaag tcggaacgga agagtttatc aaaaggttcg gtgatggtgc 540
ttcgcgtgta gtgctcagcc ttcccttcgc tgaggggagt tctagcgttg aatatattaa 600
taactgggaa caggcgaaag cgttaagcgt agaacttgag attaattttg aaacccgtgg 660
aaaacgtggc caagatgcga tgtatgagta tatggctcaa gcctgtgcag gaaatcgtgt 720
caggcgatca gtaggtagct cattgtcatg catcaacctg gattgggatg ttatccgtga 780
taaaactaaa actaagatcg aatctctgaa agaacacggt ccgatcaaaa acaaaatgag 840
cgaaagcccg aacaaaactg tatctgaaga aaaagctaaa cagtacctgg aagaattcca 900
ccagactgca ctggaacacc cggaactgtc tgaacttaag accgttactg gtaccaaccc 960
ggtattcgct ggtgctaact acgctgcttg ggcagtaaac gttgctcagg ttatcgatag 1020
cgaaactgct gataacctgg aaaaaactac cgcggctctg tctatcctgc cgggtatcgg 1080
tagcgtaatg ggcatcgcag acggcgccgt tcaccacaac actgaagaaa tcgttgcaca 1140
gtctatcgct ctgagctctc tgatggttgc tcaggccatc ccgctggtag gtgaactggt 1200
tgatatcggt ttcgctgcat acaacttcgt tgaaagcatc atcaacctgt tccaggttgt 1260
tcacaactct tacaaccgcc cggcttactc tccgggtcac aagacgcatg cacctacttc 1320
tagctctacc aagaaaaccc agctgcagct cgagcacctg ctgctggatt tgcagatgat 1380
cctgaacggt atcaacaatt acaagaaccc gaaactgacg cgtatgctga ccttcaagtt 1440
ctacatgccg aagaaggcca ccgaactgaa acacctgcag tgtctagaag aagaactgaa 1500
accgctggag gaagttctga acctggctca gtctaaaaac ttccacctgc ggccgcgtga 1560
cctgatctct aacatcaacg taatcgttct ggaactgaag ggctctgaaa ccaccttcat 1620
gtgtgaatac gctgatgaga ccgcaaccat cgtagaattc ctgaaccgtt ggatcacctt 1680
ctgtcagtct atcatctcta ccctgacctg a 1711

<210> SEQ ID NO 82
<211> LENGTH: 526
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Gly Ala Glu Asp Val Val Asp Thr Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400
```

-continued

```
Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 83
<211> LENGTH: 1732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgaagat gttgttgata cttctaaatc    180

ttttgtgatg gaaaactttt cttcgtacca cgggactaaa cctggttatg tagattccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320
```

```
tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgacctg acaccatcac catcatcact ga           1732
```

<210> SEQ ID NO 84
<211> LENGTH: 520
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Gly Ala Asp Asp Val Ala Glu Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285
```

-continued

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520

<210> SEQ ID NO 85
<211> LENGTH: 1711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
ttgatttcag agcaccctta taattaggat agctaagtcc attattttat gagtcctggt      60
aaggggatac gttgtgagca gaaaactgtt tgcgtcaatc ttaatagggg cgctactggg     120
gataggggcc ccaccttcag cccatgcagg cgctgatgat gttgctgaat cttctaaatc     180
ttttgtgatg gaaaactttt cttcgtacca cgggactaaa cctggttatg tagattccat     240
tcaaaaaggt atacaaaagc caaaatctgg tacacaagga aattatgacg atgattggaa     300
agggttttat agtaccgaca ataaatacga cgctgcggga tactctgtag ataatgaaaa     360
cccgctctct ggaaaagctg gaggcgtggt caaagtgacg tatccaggac tgacgaaggt     420
tctcgcacta aaagtggata atgccgaaac tattaagaaa gagttaggtt taagtctcac     480
tgaaccgttg atggagcaag tcggaacgga agagtttatc aaaaggttcg gtgatggtgc     540
ttcgcgtgta gtgctcagcc ttcccttcgc tgaggggagt tctagcgttg aatatattaa     600
taactgggaa caggcgaaag cgttaagcgt agaacttgag attaattttg aaacccgtgg     660
aaaacgtggc caagatgcga tgtatgagta tatggctcaa gcctgtgcag gaaatcgtgt     720

```
caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgacctg a                                  1711
```

```
<210> SEQ ID NO 86
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gly Ala Glu Asp Val Ala Glu Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175
```

```
Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 87
<211> LENGTH: 1729
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87
ttgatttcag agcaccctta taattaggat agctaagtcc attattttat gagtcctggt 60

```
aaggggatac gttgtgagca gaaaactgtt tgcgtcaatc ttaatagggg cgctactggg    120

gataggggcc ccaccttcag cccatgcagg cgctgatgat gttgctgaat cttctaaatc    180

ttttgtgatg gaaaactttt cttcgtacca cgggactaaa cctggttatg tagattccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgaccca ccatcaccat catcactga               1729
```

<210> SEQ ID NO 88
<211> LENGTH: 520
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Gly Ala Glu Asp Val Ala Asp Thr Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60
```

-continued

```
Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
```

-continued

```
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520
```

<210> SEQ ID NO 89
<211> LENGTH: 1711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgatgat gttgctgata cttctaaatc    180

ttttgtgatg gaaaactttt cttcgtacca cgggactaaa cctggttatg tagattccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgacctg a                                  1711
```

<210> SEQ ID NO 90

<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Gly Ala Glu Asp Val Ala Asp Thr Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
```

```
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 91
<211> LENGTH: 1732
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

```
ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgatgat gttgctgata cttctaaatc    180

ttttgtgatg gaaaactttt cttcgtacca cgggactaaa cctggttatg tagattccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200
```

```
tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgacctg acaccatcac catcatcact ga           1732
```

```
<210> SEQ ID NO 92
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Ala Glu Asp Val Val Glu Thr Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
```

-continued

```
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520
```

<210> SEQ ID NO 93
<211> LENGTH: 1711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
ttgatttcag agcaccctta taattaggat agctaagtcc attattttat gagtcctggt      60

aaggggatac gttgtgagca gaaaactgtt tgcgtcaatc ttaatagggg cgctactggg     120

gataggggcc ccaccttcag cccatgcagg cgctgatgat gttgttgaaa cttctaaatc     180

ttttgtgatg gaaaactttt cttcgtacca cgggactaaa cctggttatg tagattccat     240

tcaaaaaggt atacaaaagc caaaatctgg tacacaagga aattatgacg atgattggaa     300

agggttttat agtaccgaca ataaatacga cgctgcggga tactctgtag ataatgaaaa     360

cccgctctct ggaaaagctg gaggcgtggt caaagtgacg tatccaggac tgacgaaggt     420

tctcgcacta aaagtggata atgccgaaac tattaagaaa gagttaggtt taagtctcac     480

tgaaccgttg atggagcaag tcggaacgga agagtttatc aaaaggttcg gtgatggtgc     540
```

ttcgcgtgta gtgctcagcc ttcccttcgc tgaggggagt tctagcgttg aatatattaa 600
taactgggaa caggcgaaag cgttaagcgt agaacttgag attaattttg aaacccgtgg 660
aaaacgtggc caagatgcga tgtatgagta tatggctcaa gcctgtgcag gaaatcgtgt 720
caggcgatca gtaggtagct cattgtcatg catcaacctg gattgggatg ttatccgtga 780
taaaactaaa actaagatcg aatctctgaa agaacacggt ccgatcaaaa acaaaatgag 840
cgaaagcccg aacaaaactg tatctgaaga aaaagctaaa cagtacctgg aagaattcca 900
ccagactgca ctggaacacc cggaactgtc tgaacttaag accgttactg gtaccaaccc 960
ggtattcgct ggtgctaact acgctgcttg ggcagtaaac gttgctcagg ttatcgatag 1020
cgaaactgct gataacctgg aaaaaactac cgcggctctg tctatcctgc cgggtatcgg 1080
tagcgtaatg ggcatcgcag acggcgccgt tcaccacaac actgaagaaa tcgttgcaca 1140
gtctatcgct ctgagctctc tgatggttgc tcaggccatc ccgctggtag gtgaactggt 1200
tgatatcggt ttcgctgcat acaacttcgt tgaaagcatc atcaacctgt tccaggttgt 1260
tcacaactct tacaaccgcc cggcttactc tccgggtcac aagacgcatg cacctacttc 1320
tagctctacc aagaaaaccc agctgcagct cgagcacctg ctgctggatt tgcagatgat 1380
cctgaacggt atcaacaatt acaagaaccc gaaactgacg cgtatgctga ccttcaagtt 1440
ctacatgccg aagaaggcca ccgaactgaa acacctgcag tgtctagaag aagaactgaa 1500
accgctggag gaagttctga acctggctca gtctaaaaac ttccacctgc ggccgcgtga 1560
cctgatctct aacatcaacg taatcgttct ggaactgaag ggctctgaaa ccaccttcat 1620
gtgtgaatac gctgatgaga ccgcaaccat cgtagaattc ctgaaccgtt ggatcacctt 1680
ctgtcagtct atcatctcta ccctgacctg a 1711

<210> SEQ ID NO 94
<211> LENGTH: 526
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 94

Gly Ala Glu Asp Val Val Glu Thr Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser

-continued

```
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 95
<211> LENGTH: 1729
<212> TYPE: DNA
<213> ORGANISM: Artificial Sequence
<220> FEATURE:
<223> OTHER INFORMATION: Description of Artificial Sequence: Synthetic
polynucleotide -continued

<400> SEQUENCE: 95
ttgatttcag agcaccctta taattaggat agctaagtcc attattttat gagtcctggt 60
aaggggatac gttgtgagca gaaaactgtt tgcgtcaatc ttaatagggg cgctactggg 120
gataggggcc ccaccttcag cccatgcagg cgctgatgat gttgttgaaa cttctaaatc 180
ttttgtgatg gaaaactttt cttcgtacca cgggactaaa cctggttatg tagattccat 240
tcaaaaaggt atacaaaagc caaaatctgg tacacaagga aattatgacg atgattggaa 300
agggttttat agtaccgaca ataaatacga cgctgcggga tactctgtag ataatgaaaa 360
cccgctctct ggaaaagctg gaggcgtggt caaagtgacg tatccaggac tgacgaaggt 420
tctcgcacta aaagtggata atgccgaaac tattaagaaa gagttaggtt taagtctcac 480
tgaaccgttg atggagcaag tcggaacgga agagtttatc aaaaggttcg gtgatggtgc 540
ttcgcgtgta gtgctcagcc ttcccttcgc tgaggggagt tctagcgttg aatatattaa 600
taactgggaa caggcgaaag cgttaagcgt agaacttgag attaattttg aaacccgtgg 660
aaaacgtggc caagatgcga tgtatgagta tatggctcaa gcctgtgcag gaaatcgtgt 720
caggcgatca gtaggtagct cattgtcatg catcaacctg gattgggatg ttatccgtga 780
taaaactaaa actaagatcg aatctctgaa agaacacggt ccgatcaaaa acaaaatgag 840
cgaaagcccg aacaaaactg tatctgaaga aaaagctaaa cagtacctgg aagaattcca 900
ccagactgca ctggaacacc cggaactgtc tgaacttaag accgttactg gtaccaaccc 960
ggtattcgct ggtgctaact acgctgcttg ggcagtaaac gttgctcagg ttatcgatag 1020
cgaaactgct gataacctgg aaaaaactac cgcggctctg tctatcctgc cgggtatcgg 1080
tagcgtaatg ggcatcgcag acggcgccgt tcaccacaac actgaagaaa tcgttgcaca 1140
gtctatcgct ctgagctctc tgatggttgc tcaggccatc ccgctggtag gtgaactggt 1200
tgatatcggt ttcgctgcat acaacttcgt tgaaagcatc atcaacctgt tccaggttgt 1260
tcacaactct tacaaccgcc cggcttactc tccgggtcac aagacgcatg cacctacttc 1320
tagctctacc aagaaaaccc agctgcagct cgagcacctg ctgctggatt tgcagatgat 1380
cctgaacggt atcaacaatt acaagaaccc gaaactgacg cgtatgctga ccttcaagtt 1440
ctacatgccg aagaaggcca ccgaactgaa acacctgcag tgtctagaag aagaactgaa 1500
accgctggag gaagttctga acctggctca gtctaaaaac ttccacctgc ggccgcgtga 1560
cctgatctct aacatcaacg taatcgttct ggaactgaag ggctctgaaa ccaccttcat 1620
gtgtgaatac gctgatgaga ccgcaaccat cgtagaattc ctgaaccgtt ggatcacctt 1680
ctgtcagtct atcatctcta ccctgaccca ccatcaccat catcactga 1729

<210> SEQ ID NO 96
<211> LENGTH: 506
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Gly Ala Asp Asp Val Ala Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp

```
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ile His Gly Cys Asp Lys Asn His Leu Arg Glu Ile Ile
385                 390                 395                 400

Gly Ile Leu Asn Glu Val Thr Gly Glu Gly Thr Pro Cys Thr Glu Met
                405                 410                 415

Asp Val Pro Asn Val Leu Thr Ala Thr Lys Asn Thr Thr Glu Ser Glu
            420                 425                 430

Leu Val Cys Arg Ala Ser Lys Val Leu Arg Ile Phe Tyr Leu Lys His
        435                 440                 445

Gly Lys Thr Pro Cys Leu Lys Lys Asn Ser Ser Val Leu Met Glu Leu
    450                 455                 460
```

Gln Arg Leu Phe Arg Ala Phe Arg Cys Leu Asp Ser Ser Ile Ser Cys
465 470 475 480

Thr Met Asn Glu Ser Lys Ser Thr Ser Leu Lys Asp Phe Leu Glu Ser
485 490 495

Leu Lys Ser Ile Met Gln Met Asp Tyr Ser
500 505

<210> SEQ ID NO 97
<211> LENGTH: 1596
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97
gtgagcagaa aactgtttgc gtcaatctta ataggggcgc tactggggat aggggcccca 60
ccttcagccc atgcaggcgc tgatgatgtt gctgattctt ctaaatcttt tgtgatggaa 120
aacttttctt cgtaccacgg gactaaacct ggttatgtag attccattca aaaaggtata 180
caaaagccaa aatctggtac acaaggaaat tatgacgatg attggaaagg gttttatagt 240
accgacaata aatacgacgc tgcgggatac tctgtagata atgaaaaccc gctctctgga 300
aaagctggag gcgtggtcaa agtgacgtat ccaggactga cgaaggttct cgcactaaaa 360
gtggataatg ccgaaactat taagaaagag ttaggtttaa gtctcactga accgttgatg 420
gagcaagtcg gaacggaaga gtttatcaaa aggttcggtg atggtgcttc gcgtgtagtg 480
ctcagccttc ccttcgctga ggggagttct agcgttgaat atattaataa ctgggaacag 540
gcgaaagcgt taagcgtaga acttgagatt aattttgaaa cccgtggaaa acgtggccaa 600
gatgcgatgt atgagtatat ggctcaagcc tgtgcaggaa atcgtgtcag gcgatcagta 660
ggtagctcat tgtcatgcat caacctggat tgggatgtta tccgtgataa aactaaaact 720
aagatcgaat ctctgaaaga acacggtccg atcaaaaaca aaatgagcga aagcccgaac 780
aaaactgtat ctgaagaaaa agctaaacag tacctggaag aattccacca gactgcactg 840
gaacacccgg aactgtctga acttaagacc gttactggta ccaacccggt attcgctggt 900
gctaactacg ctgcttgggc agtaaacgtt gctcaggtta tcgatagcga aactgctgat 960
aacctggaaa aaactaccgc ggctctgtct atcctgccgg gtatcggtag cgtaatgggc 1020
atcgcagacg gcgccgttca ccacaacact gaagaaatcg ttgcacagtc tatcgctctg 1080
agctctctga tggttgctca ggccatcccg ctggtaggtg aactggttga tatcggtttc 1140
gctgcataca acttcgttga aagcatcatc aacctgttcc aggttgttca caactcttac 1200
aaccgcccgg cttactctcc gggtcacaag acgcatattc atggctgcga taaaaaccat 1260
ctgcgcgaaa ttattggcat tctgaacgaa gtgaccggcg aaggcacccc gtgcaccgaa 1320
atggatgtgc cgaacgtgct gaccgcgacc aaaaacacca ccgaaagcga actggtgtgc 1380
cgcgcgagca aagtgctgcg catttttat ctgaaacatg gcaaaacccc gtgcctgaaa 1440
aaaaacagca gcgtgctgat ggaactgcag cgcctgtttc gcgcgtttcg ctgcctggat 1500
agcagcatta gctgcaccat gaacgaaagc aaaagcacca gcctgaaaga ttttctggaa 1560
agcctgaaaa gcattatgca gatggattat agctag 1596

<210> SEQ ID NO 98
<211> LENGTH: 519
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 98

```
Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380
```

-continued

```
Lys Thr His Ile His Gly Cys Asp Lys Asn His Leu Arg Glu Ile Ile
385                 390                 395                 400

Gly Ile Leu Asn Glu Val Thr Gly Glu Gly Thr Pro Cys Thr Glu Met
                405                 410                 415

Asp Val Pro Asn Val Leu Thr Ala Thr Lys Asn Thr Thr Glu Ser Glu
            420                 425                 430

Leu Val Cys Arg Ala Ser Lys Val Leu Arg Ile Phe Tyr Leu Lys His
        435                 440                 445

Gly Lys Thr Pro Cys Leu Lys Lys Asn Ser Ser Val Leu Met Glu Leu
    450                 455                 460

Gln Arg Leu Phe Arg Ala Phe Arg Cys Leu Asp Ser Ser Ile Ser Cys
465                 470                 475                 480

Thr Met Asn Glu Ser Lys Ser Thr Ser Leu Lys Asp Phe Leu Glu Ser
                485                 490                 495

Leu Lys Ser Ile Met Gln Met Asp Tyr Ser Glu Asn Leu Tyr Phe Gln
            500                 505                 510

Gly His His His His His His
        515
```

<210> SEQ ID NO 99
<211> LENGTH: 1635
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99

```
gtgagcagaa aactgtttgc gtcaatctta ataggggcgc tactggggat aggggcccca     60

ccttcagccc atgcaggcgc tgatgatgtt gctgattctt ctaaatcttt tgtgatggaa    120

aacttttctt cgtaccacgg gactaaacct ggttatgtag attccattca aaaaggtata    180

caaaagccaa aatctggtac acaaggaaat tatgacgatg attggaaagg gttttatagt    240

accgacaata aatacgacgc tgcgggatac tctgtagata atgaaaaccc gctctctgga    300

aaagctggag gcgtggtcaa agtgacgtat ccaggactga cgaaggttct cgcactaaaa    360

gtggataatg ccgaaactat taagaaagag ttaggtttaa gtctcactga accgttgatg    420

gagcaagtcg gaacggaaga gtttatcaaa aggttcggtg atggtgcttc gcgtgtagtg    480

ctcagccttc ccttcgctga ggggagttct agcgttgaat atattaataa ctgggaacag    540

gcgaaagcgt taagcgtaga acttgagatt aattttgaaa cccgtggaaa acgtggccaa    600

gatgcgatgt atgagtatat ggctcaagcc tgtgcaggaa atcgtgtcag gcgatcagta    660

ggtagctcat tgtcatgcat caacctggat tgggatgtta tccgtgataa aactaaaact    720

aagatcgaat ctctgaaaga acacggtccg atcaaaaaca aaatgagcga aagcccgaac    780

aaaactgtat ctgaagaaaa agctaaacag tacctggaag aattccacca gactgcactg    840

gaacacccgg aactgtctga acttaagacc gttactggta ccaacccggt attcgctggt    900

gctaactacg ctgcttgggc agtaaacgtt gctcaggtta tcgatagcga aactgctgat    960

aacctggaaa aaactaccgc ggctctgtct atcctgccgg gtatcggtag cgtaatgggc   1020

atcgcagacg gcgccgttca ccacaacact gaagaaatcg ttgcacagtc tatcgctctg   1080

agctctctga tggttgctca ggccatcccg ctggtaggtg aactggttga tatcggtttc   1140

gctgcataca acttcgttga aagcatcatc aacctgttcc aggttgttca caactcttac   1200

aaccgcccgg cttactctcc gggtcacaag acgcatattc atggctgcga taaaaaccat   1260
```

-continued

```
ctgcgcgaaa ttattggcat tctgaacgaa gtgaccggcg aaggcacccc gtgcaccgaa   1320

atggatgtgc cgaacgtgct gaccgcgacc aaaaacacca ccgaaagcga actggtgtgc   1380

cgcgcgagca aagtgctgcg catttttat ctgaaacatg gcaaaacccc gtgcctgaaa   1440

aaaaacagca gcgtgctgat ggaactgcag cgcctgtttc gcgcgtttcg ctgcctggat   1500

agcagcatta gctgcaccat gaacgaaagc aaaagcacca gcctgaaaga ttttctggaa   1560

agcctgaaaa gcattatgca gatggattat agcgagaacc tgtacttcca gggccatcac   1620

caccaccacc actag                                                    1635


<210> SEQ ID NO 100
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285
```

```
Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His His Lys Cys Asp Ile Thr Leu Gln Glu Ile Ile Lys Thr
385                 390                 395                 400

Leu Asn Ser Leu Thr Glu Gln Lys Thr Leu Cys Thr Glu Leu Thr Val
                405                 410                 415

Thr Asp Ile Phe Ala Ala Ser Lys Asn Thr Thr Glu Lys Glu Thr Phe
            420                 425                 430

Cys Arg Ala Ala Thr Val Leu Arg Gln Phe Tyr Ser His His Glu Lys
        435                 440                 445

Asp Thr Arg Cys Leu Gly Ala Thr Ala Gln Gln Phe His Arg His Lys
    450                 455                 460

Gln Leu Ile Arg Phe Leu Lys Arg Leu Asp Arg Asn Leu Trp Gly Leu
465                 470                 475                 480

Ala Gly Leu Asn Ser Cys Pro Val Lys Glu Ala Asn Gln Ser Thr Leu
                485                 490                 495

Glu Asn Phe Leu Glu Arg Leu Lys Thr Ile Met Arg Glu Lys Tyr Ser
            500                 505                 510

Lys Cys Ser Ser
        515
```

<210> SEQ ID NO 101
<211> LENGTH: 1626
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
gtgagcagaa aactgtttgc gtcaatctta ataggggcgc tactggggat aggggcccca     60

ccttcagccc atgcaggcgc tgatgatgtt gctgattctt ctaaatcttt tgtgatggaa    120

aacttttctt cgtaccacgg gactaaacct ggttatgtag attccattca aaaaggtata    180

caaaagccaa aatctggtac acaaggaaat tatgacgatg attggaaagg gttttatagt    240

accgacaata aatacgacgc tgcgggatac tctgtagata atgaaaaccc gctctctgga    300

aaagctggag gcgtggtcaa agtgacgtat ccaggactga cgaaggttct cgcactaaaa    360

gtggataatg ccgaaactat taagaaagag ttaggtttaa gtctcactga accgttgatg    420

gagcaagtcg gaacggaaga gtttatcaaa aggttcggtg atggtgcttc gcgtgtagtg    480

ctcagccttc ccttcgctga ggggagttct agcgttgaat atattaataa ctgggaacag    540

gcgaaagcgt taagcgtaga acttgagatt aattttgaaa cccgtggaaa acgtggccaa    600

gatgcgatgt atgagtatat ggctcaagcc tgtgcaggaa atcgtgtcag gcgatcagta    660
```

-continued

```
ggtagctcat tgtcatgcat caacctggat tgggatgtta tccgtgataa aactaaaact    720

aagatcgaat ctctgaaaga acacggtccg atcaaaaaca aaatgagcga aagcccgaac    780

aaaactgtat ctgaagaaaa agctaaacag tacctggaag aattccacca gactgcactg    840

gaacacccgg aactgtctga acttaagacc gttactggta ccaacccggt attcgctggt    900

gctaactacg ctgcttgggc agtaaacgtt gctcaggtta tcgatagcga aactgctgat    960

aacctggaaa aaactaccgc ggctctgtct atcctgccgg gtatcggtag cgtaatgggc   1020

atcgcagacg gcgccgttca ccacaacact gaagaaatcg ttgcacagtc tatcgctctg   1080

agctctctga tggttgctca ggccatcccg ctggtaggtg aactggttga tatcggtttc   1140

gctgcataca acttcgttga aagcatcatc aacctgttcc aggttgttca caactcttac   1200

aaccgcccgg cttactctcc gggtcacaag acgcatcaca agtgcgatat caccttgcag   1260

gaaatcatca agaccctcaa ctcgttgacc gaacaaaaaa ccttgtgcac cgagctgacc   1320

gtgaccgaca tcttcgcagc ctctaagaac accaccgaaa aagagacctt ctgccgcgct   1380

gcgaccgttc tgcgtcagtt ttactcccac cacgagaaag atacccgctg ccttggcgca   1440

accgcccagc aattccaccg ccacaagcaa ctcatccgtt ttctgaaacg ccttgaccgt   1500

aacctctggg gcttggctgg tctgaactct tgcccagtga aggaagcgaa ccagtccacc   1560

ctcgaaaact ttcttgagcg cctcaaaacc atcatgcgtg agaagtactc gaaatgctcc   1620

tcgtaa                                                              1626
```

<210> SEQ ID NO 102
<211> LENGTH: 529
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

```
Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
```

```
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His His Lys Cys Asp Ile Thr Leu Gln Glu Ile Ile Lys Thr
385                 390                 395                 400

Leu Asn Ser Leu Thr Glu Gln Lys Thr Leu Cys Thr Glu Leu Thr Val
                405                 410                 415

Thr Asp Ile Phe Ala Ala Ser Lys Asn Thr Thr Glu Lys Glu Thr Phe
            420                 425                 430

Cys Arg Ala Ala Thr Val Leu Arg Gln Phe Tyr Ser His His Glu Lys
        435                 440                 445

Asp Thr Arg Cys Leu Gly Ala Thr Ala Gln Gln Phe His Arg His Lys
    450                 455                 460

Gln Leu Ile Arg Phe Leu Lys Arg Leu Asp Arg Asn Leu Trp Gly Leu
465                 470                 475                 480

Ala Gly Leu Asn Ser Cys Pro Val Lys Glu Ala Asn Gln Ser Thr Leu
                485                 490                 495

Glu Asn Phe Leu Glu Arg Leu Lys Thr Ile Met Arg Glu Lys Tyr Ser
            500                 505                 510

Lys Cys Ser Ser Glu Asn Leu Tyr Phe Gln Gly His His His His His
        515                 520                 525

His
```

<210> SEQ ID NO 103
<211> LENGTH: 1665
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 103
gtgagcagaa aactgtttgc gtcaatctta ataggggcgc tactggggat aggggcccca 60

```
ccttcagccc atgcaggcgc tgatgatgtt gctgattctt ctaaatcttt tgtgatggaa    120

aacttttctt cgtaccacgg gactaaacct ggttatgtag attccattca aaaaggtata    180

caaaagccaa aatctggtac acaaggaaat tatgacgatg attggaaagg gttttatagt    240

accgacaata aatacgacgc tgcgggatac tctgtagata atgaaaaccc gctctctgga    300

aaagctggag gcgtggtcaa agtgacgtat ccaggactga cgaaggttct cgcactaaaa    360

gtggataatg ccgaaactat taagaaagag ttaggtttaa gtctcactga accgttgatg    420

gagcaagtcg gaacggaaga gtttatcaaa aggttcggtg atggtgcttc gcgtgtagtg    480

ctcagccttc ccttcgctga ggggagttct agcgttgaat atattaataa ctgggaacag    540

gcgaaagcgt taagcgtaga acttgagatt aattttgaaa cccgtggaaa acgtggccaa    600

gatgcgatgt atgagtatat ggctcaagcc tgtgcaggaa atcgtgtcag gcgatcagta    660

ggtagctcat tgtcatgcat caacctggat tgggatgtta tccgtgataa aactaaaact    720

aagatcgaat ctctgaaaga acacggtccg atcaaaaaca aaatgagcga aagcccgaac    780

aaaactgtat ctgaagaaaa agctaaacag tacctggaag aattccacca gactgcactg    840

gaacacccgg aactgtctga acttaagacc gttactggta ccaacccggt attcgctggt    900

gctaactacg ctgcttgggc agtaaacgtt gctcaggtta tcgatagcga aactgctgat    960

aacctggaaa aaactaccgc ggctctgtct atcctgccgg gtatcggtag cgtaatgggc   1020

atcgcagacg gcgccgttca ccacaacact gaagaaatcg ttgcacagtc tatcgctctg   1080

agctctctga tggttgctca ggccatcccg ctggtaggtg aactggttga tatcggtttc   1140

gctgcataca acttcgttga aagcatcatc aacctgttcc aggttgttca caactcttac   1200

aaccgcccgg cttactctcc gggtcacaag acgcatcaca agtgcgatat caccttgcag   1260

gaaatcatca agaccctcaa ctcgttgacc gaacaaaaaa ccttgtgcac cgagctgacc   1320

gtgaccgaca tcttcgcagc ctctaagaac accaccgaaa aagagacctt ctgccgcgct   1380

gcgaccgttc tgcgtcagtt ttactcccac cacgagaaag atacccgctg ccttggcgca   1440

accgcccagc aattccaccg ccacaagcaa ctcatccgtt ttctgaaacg ccttgaccgt   1500

aacctctggg gcttggctgg tctgaactct tgcccagtga aggaagcgaa ccagtccacc   1560

ctcgaaaact ttcttgagcg cctcaaaacc atcatgcgtg agaagtactc gaaatgctcc   1620

tcggaaaacc tctacttcca gggccaccac caccaccacc actaa                   1665
```

```
<210> SEQ ID NO 104
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
```

```
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Met Asn Ser Asp Ser Glu Cys Pro Leu Ser His Asp
385                 390                 395                 400

Gly Tyr Cys Leu His Asp Gly Val Cys Met Tyr Ile Glu Ala Leu Asp
                405                 410                 415

Lys Tyr Ala Cys Asn Cys Val Val Gly Tyr Ile Gly Glu Arg Cys Gln
            420                 425                 430

Tyr Arg Asp Leu Lys Trp Trp Glu Leu Arg
        435                 440
```

<210> SEQ ID NO 105
<211> LENGTH: 1332
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 105
ggcgctgatg atgttgctga ttcttctaaa tcttttgtga tggaaaactt ttcttcgtac 60
cacgggacta aacctggtta tgtagattcc attcaaaaag gtatacaaaa gccaaaatct 120
ggtacacaag gaaattatga cgatgattgg aaagggtttt atagtaccga caataaatac 180
gacgctgcgg gatactctgt agataatgaa aacccgctct ctggaaaagc tggaggcgtg 240
gtcaaagtga cgtatccagg actgacgaag gttctcgcac taaaagtgga taatgccgaa 300
actattaaga aagagttagg tttaagtctc actgaaccgt tgatggagca agtcggaacg 360
gaagagttta tcaaaaggtt cggtgatggt gcttcgcgtg tagtgctcag ccttcccttc 420
gctgagggga gttctagcgt tgaatatatt aataactggg aacaggcgaa agcgttaagc 480
gtagaacttg agattaattt tgaaacccgt ggaaaacgtg gccaagatgc gatgtatgag 540
tatatggctc aagcctgtgc aggaaatcgt gtcaggcgat cagtaggtag ctcattgtca 600
tgcatcaacc tggattggga tgttatccgt gataaaacta aaactaagat cgaatctctg 660
aaagaacacg gtccgatcaa aaacaaaatg agcgaaagcc cgaacaaaac tgtatctgaa 720
gaaaaagcta aacagtacct ggaagaattc caccagactg cactggaaca cccggaactg 780
tctgaactta agaccgttac tggtaccaac ccggtattcg ctggtgctaa ctacgctgct 840
tgggcagtaa acgttgctca ggttatcgat agcgaaactg ctgataacct ggaaaaaact 900
accgcggctc tgtctatcct gccgggtatc ggtagcgtaa tgggcatcgc agacggcgcc 960
gttcaccaca acactgaaga aatcgttgca cagtctatcg ctctgagctc tctgatggtt 1020
gctcaggcca tcccgctggt aggtgaactg gttgatatcg gtttcgctgc atacaacttc 1080
gttgaaagca tcatcaacct gttccaggtt gttcacaact cttacaaccg cccggcttac 1140
tctccgggtc acaagacgca tgcaatgaac tccgactccg agtgcccgct ctcccacgac 1200
ggttactgcc tccacgacgg tgtctgcatg tacatcgagg ccctcgacaa gtacgcctgc 1260
aactgcgtcg tcggttacat cggtgagcgc tgccagtacc gcgacctgaa gtggtgggag 1320
ctccgctgat ga 1332

<210> SEQ ID NO 106
<211> LENGTH: 448
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 106

Gly Ala Asp Asp Val Ala Asp Ser Ser Lys Ser Phe Val Met Glu Asn
1 5 10 15

Phe Ser Ser Tyr His Gly Thr Lys Pro Gly Tyr Val Asp Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu

```
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Met Asn Ser Asp Ser Glu Cys Pro Leu Ser His Asp
385                 390                 395                 400

Gly Tyr Cys Leu His Asp Gly Val Cys Met Tyr Ile Glu Ala Leu Asp
                405                 410                 415

Lys Tyr Ala Cys Asn Cys Val Val Gly Tyr Ile Gly Glu Arg Cys Gln
            420                 425                 430

Tyr Arg Asp Leu Lys Trp Trp Glu Leu Arg His His His His His His
        435                 440                 445
```

<210> SEQ ID NO 107
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

```
ggcgctgatg atgttgctga ttcttctaaa tcttttgtga tggaaaactt ttcttcgtac      60

cacgggacta aacctggtta tgtagattcc attcaaaaag gtatacaaaa gccaaaatct     120
```

```
ggtacacaag gaaattatga cgatgattgg aaagggtttt atagtaccga caataaatac    180

gacgctgcgg gatactctgt agataatgaa aacccgctct ctggaaaagc tggaggcgtg    240

gtcaaagtga cgtatccagg actgacgaag gttctcgcac taaaagtgga taatgccgaa    300

actattaaga aagagttagg tttaagtctc actgaaccgt tgatggagca agtcggaacg    360

gaagagttta tcaaaaggtt cggtgatggt gcttcgcgtg tagtgctcag ccttcccttc    420

gctgagggga gttctagcgt tgaatatatt aataactggg aacaggcgaa agcgttaagc    480

gtagaacttg agattaattt tgaaacccgt ggaaaacgtg gccaagatgc gatgtatgag    540

tatatggctc aagcctgtgc aggaaatcgt gtcaggcgat cagtaggtag ctcattgtca    600

tgcatcaacc tggattggga tgttatccgt gataaaacta aaactaagat cgaatctctg    660

aaagaacacg gtccgatcaa aaacaaaatg agcgaaagcc cgaacaaaac tgtatctgaa    720

gaaaaagcta aacagtacct ggaagaattc caccagactg cactggaaca cccggaactg    780

tctgaactta agaccgttac tggtaccaac ccggtattcg ctggtgctaa ctacgctgct    840

tgggcagtaa acgttgctca ggttatcgat agcgaaactg ctgataacct ggaaaaaact    900

accgcggctc tgtctatcct gccgggtatc ggtagcgtaa tgggcatcgc agacggcgcc    960

gttcaccaca acactgaaga aatcgttgca cagtctatcg ctctgagctc tctgatggtt   1020

gctcaggcca tcccgctggt aggtgaactg gttgatatcg gtttcgctgc atacaacttc   1080

gttgaaagca tcatcaacct gttccaggtt gttcacaact cttacaaccg cccggcttac   1140

tctccgggtc acaagacgca tgcaatgaac tccgactccg agtgcccgct ctcccacgac   1200

ggttactgcc tccacgacgg tgtctgcatg tacatcgagg ccctcgacaa gtacgcctgc   1260

aactgcgtcg tcggttacat cggtgagcgc tgccagtacc gcgacctgaa gtggtgggag   1320

ctccgccacc atcaccatca tcactgatga                                     1350
```

<210> SEQ ID NO 108
<211> LENGTH: 89
<212> TYPE: DNA
<213> ORGANISM: Unknown
<220> FEATURE:
<223> OTHER INFORMATION: Description of Unknown:
wild-type toxO sequence

<400> SEQUENCE: 108

```
ggatccaggg cattgatttc agagcaccct tataattagg atagctttac ctaattattt     60

tatgagtcct ggtaagggga tacgttgtg                                        89
```

<210> SEQ ID NO 109
<211> LENGTH: 244
<212> TYPE: DNA
<213> ORGANISM: Mycobacterium leprae

<400> SEQUENCE: 109

```
ggatccttct agaattccgg aattgcactc gccttagggg agtgctaaaa atgatcctgg     60

cactcgcgat cagcgagtgc caggtcggga cggtgagacc cagccagcaa gctgtggtcg    120

tccgtcgcgg gcactgcacc cggccagcgt aagtaatggg ggttgtcggc acccggtgac    180

ctagacacat gcatgcatgc ttaattaatt aagcgatatc cggaggaatc acttccatat    240

gatg                                                                 244
```

<210> SEQ ID NO 110
<211> LENGTH: 125

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 110
ttgacaatta atcatcggct cgtataatgt gtggaattgt gagcggataa caatttcaca 60
caggaaacag ccagtccgtt taggtgtttt cacgagcact tcaccaacaa ggaccataga 120
ttgtg 125

<210> SEQ ID NO 111
<211> LENGTH: 520
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 111

Gly Ala Asp Asp Val Val Asp Ser Ser Lys Ser Phe Val Met Glu Asn
1 5 10 15

Phe Ser Ser Tyr His Gly Thr Lys Pro Gly Tyr Val Glu Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

Asp Gly Ala Ser Arg Val Val Leu Ser Leu Pro Phe Ala Glu Gly Ser
130 135 140

Ser Ser Val Glu Tyr Ile Asn Asn Trp Glu Gln Ala Lys Ala Leu Ser
145 150 155 160

Val Glu Leu Glu Ile Asn Phe Glu Thr Arg Gly Lys Arg Gly Gln Asp
165 170 175

Ala Met Tyr Glu Tyr Met Ala Gln Ala Cys Ala Gly Asn Arg Val Arg
180 185 190

Arg Ser Val Gly Ser Ser Leu Ser Cys Ile Asn Leu Asp Trp Asp Val
195 200 205

Ile Arg Asp Lys Thr Lys Thr Lys Ile Glu Ser Leu Lys Glu His Gly
210 215 220

Pro Ile Lys Asn Lys Met Ser Glu Ser Pro Asn Lys Thr Val Ser Glu
225 230 235 240

Glu Lys Ala Lys Gln Tyr Leu Glu Glu Phe His Gln Thr Ala Leu Glu
245 250 255

His Pro Glu Leu Ser Glu Leu Lys Thr Val Thr Gly Thr Asn Pro Val
260 265 270

Phe Ala Gly Ala Asn Tyr Ala Ala Trp Ala Val Asn Val Ala Gln Val
275 280 285

```
Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520
```

<210> SEQ ID NO 112
<211> LENGTH: 1711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112

```
ttgatttcag agcaccctta taattaggat agctaagtcc attattttat gagtcctggt      60

aaggggatac gttgtgagca gaaaactgtt tgcgtcaatc ttaatagggg cgctactggg     120

gataggggcc ccaccttcag cccatgcagg cgctgatgat gttgttgatt cttctaaatc     180

ttttgtgatg gaaaactttt cttcgtacca cgggactaaa cctggttatg tagagtccat     240

tcaaaaaggt atacaaaagc caaaatctgg tacacaagga aattatgacg atgattggaa     300

agggttttat agtaccgaca ataaatacga cgctgcggga tactctgtag ataatgaaaa     360

cccgctctct ggaaaagctg gaggcgtggt caaagtgacg tatccaggac tgacgaaggt     420

tctcgcacta aaagtggata atgccgaaac tattaagaaa gagttaggtt taagtctcac     480

tgaaccgttg atggagcaag tcggaacgga agagtttatc aaaaggttcg gtgatggtgc     540

ttcgcgtgta gtgctcagcc ttcccttcgc tgaggggagt tctagcgttg aatatattaa     600

taactgggaa caggcgaaag cgttaagcgt agaacttgag attaattttg aaacccgtgg     660

aaaacgtggc caagatgcga tgtatgagta tatggctcaa gcctgtgcag gaaatcgtgt     720
```

```
caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgacctg a                                  1711
```

```
<210> SEQ ID NO 113
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Glu Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175
```

-continued

```
Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 114
<211> LENGTH: 1729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
ttgatttcag agcaccctta taattaggat agctaagtcc attattttat gagtcctggt      60
```

-continued

```
aaggggatac gttgtgagca gaaaactgtt tgcgtcaatc ttaatagggg cgctactggg    120

gataggggcc ccaccttcag cccatgcagg cgctgatgat gttgttgatt cttctaaatc    180

ttttgtgatg gaaaactttt cttcgtacca cgggactaaa cctggttatg tagagtccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgaccca ccatcaccat catcactga               1729
```

```
<210> SEQ ID NO 115
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gly Ala Glu Asp Val Val Asp Ser Ser Lys Ser Phe Val Met Glu Asn
1               5                   10                  15

Phe Ser Ser Tyr His Gly Thr Lys Pro Gly Tyr Val Glu Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60
```

```
Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
```

```
            485                 490                 495

Glu Thr Ala Thr Ile Val Glu Phe Leu Asn Arg Trp Ile Thr Phe Cys
        500                 505                 510

Gln Ser Ile Ile Ser Thr Leu Thr
    515                 520


<210> SEQ ID NO 116
<211> LENGTH: 1711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgaagat gttgttgatt cttctaaatc    180

ttttgtgatg gaaaactttt cttcgtacca cgggactaaa cctggttatg tagagtccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgacctg a                                  1711


<210> SEQ ID NO 117
```

```
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gly Ala Glu Asp Val Val Asp Ser Ser Lys Ser Phe Val Met Glu Asn
1               5                   10                  15

Phe Ser Ser Tyr His Gly Thr Lys Pro Gly Tyr Val Glu Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
```

```
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525


<210> SEQ ID NO 118
<211> LENGTH: 1729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgaagat gttgttgatt cttctaaatc    180

ttttgtgatg gaaaactttt cttcgtacca cgggactaaa cctggttatg tagagtccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200
```

```
tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgaccca ccatcaccat catcactga              1729
```

<210> SEQ ID NO 119
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Gly Ala Glu Asp Val Val Glu Ser Ser Lys Ser Phe Val Met Glu Asn
1               5                   10                  15

Phe Ser Ser Tyr His Gly Thr Lys Pro Gly Tyr Val Glu Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
```

```
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520
```

<210> SEQ ID NO 120
<211> LENGTH: 1711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 120

```
ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgatgat gttgttgaat cttctaaatc    180

ttttgtgatg gaaaactttt cttcgtacca cgggactaaa cctggttatg tagagtccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540
```

-continued

```
ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgacctg a                                  1711
```

```
<210> SEQ ID NO 121
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gly Ala Glu Asp Val Val Glu Ser Ser Lys Ser Phe Val Met Glu Asn
1               5                   10                  15

Phe Ser Ser Tyr His Gly Thr Lys Pro Gly Tyr Val Glu Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
```

-continued

```
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 122
<211> LENGTH: 1729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
ttgatttcag agcaccctta taattaggat agctaagtcc attattttat gagtcctggt     60
aaggggatac gttgtgagca gaaaactgtt tgcgtcaatc ttaatagggg cgctactggg    120
gataggggcc ccaccttcag cccatgcagg cgctgatgat gttgttgaat cttctaaatc    180
ttttgtgatg gaaaactttt cttcgtacca cgggactaaa cctggttatg tagagtccat    240
tcaaaaaggt atacaaaagc caaaatctgg tacacaagga aattatgacg atgattggaa    300
agggttttat agtaccgaca ataaatacga cgctgcggga tactctgtag ataatgaaaa    360
cccgctctct ggaaaagctg gaggcgtggt caaagtgacg tatccaggac tgacgaaggt    420
tctcgcacta aaagtggata atgccgaaac tattaagaaa gagttaggtt taagtctcac    480
tgaaccgttg atggagcaag tcggaacgga agagtttatc aaaaggttcg gtgatggtgc    540
ttcgcgtgta gtgctcagcc ttcccttcgc tgaggggagt tctagcgttg aatatattaa    600
taactgggaa caggcgaaag cgttaagcgt agaacttgag attaattttg aaacccgtgg    660
aaaacgtggc caagatgcga tgtatgagta tatggctcaa gcctgtgcag gaaatcgtgt    720
caggcgatca gtaggtagct cattgtcatg catcaacctg gattgggatg ttatccgtga    780
taaaactaaa actaagatcg aatctctgaa agaacacggt ccgatcaaaa acaaaatgag    840
cgaaagcccg aacaaaactg tatctgaaga aaaagctaaa cagtacctgg aagaattcca    900
ccagactgca ctggaacacc cggaactgtc tgaacttaag accgttactg gtaccaaccc    960
ggtattcgct ggtgctaact acgctgcttg ggcagtaaac gttgctcagg ttatcgatag   1020
cgaaactgct gataacctgg aaaaaactac cgcggctctg tctatcctgc cgggtatcgg   1080
tagcgtaatg ggcatcgcag acggcgccgt tcaccacaac actgaagaaa tcgttgcaca   1140
gtctatcgct ctgagctctc tgatggttgc tcaggccatc ccgctggtag gtgaactggt   1200
tgatatcggt ttcgctgcat acaacttcgt tgaaagcatc atcaacctgt tccaggttgt   1260
tcacaactct tacaaccgcc cggcttactc tccgggtcac aagacgcatg cacctacttc   1320
tagctctacc aagaaaaccc agctgcagct cgagcacctg ctgctggatt tgcagatgat   1380
cctgaacggt atcaacaatt acaagaaccc gaaactgacg cgtatgctga ccttcaagtt   1440
ctacatgccg aagaaggcca ccgaactgaa acacctgcag tgtctagaag aagaactgaa   1500
accgctggag gaagttctga acctggctca gtctaaaaac ttccacctgc ggccgcgtga   1560
cctgatctct aacatcaacg taatcgttct ggaactgaag ggctctgaaa ccaccttcat   1620
gtgtgaatac gctgatgaga ccgcaaccat cgtagaattc ctgaaccgtt ggatcacctt   1680
ctgtcagtct atcatctcta ccctgaccca ccatcaccat catcactga               1729
```

<210> SEQ ID NO 123
<211> LENGTH: 520
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

```
Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Glu Ser Ile Gln
            20                  25                  30

Lys Gly Ile Gln Lys Pro Lys Ser Gly Thr Gln Gly Asn Tyr Asp Asp
```

```
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460
```

```
Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520


<210> SEQ ID NO 124
<211> LENGTH: 1711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgatgat gttgctgatt cttctaaatc    180

ttttgtgatg gaaaactttt cttcgtacca cgggactaaa cctggttatg tagagtccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020

cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680
```

ctgtcagtct atcatctcta ccctgacctg a 1711

<210> SEQ ID NO 125
<211> LENGTH: 526
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

```
Gly Ala Glu Asp Val Ala Asp Ser Ser Lys Ser Phe Val Met Glu Asn
1               5                   10                  15

Phe Ser Ser Tyr His Gly Thr Lys Pro Gly Tyr Val Glu Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350
```

```
Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 126
<211> LENGTH: 1729
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126

```
ttgatttcag agcaccctta taattaggat agctaagtcc attattttat gagtcctggt     60

aaggggatac gttgtgagca gaaaactgtt tgcgtcaatc ttaatagggg cgctactggg    120

gataggggcc ccaccttcag cccatgcagg cgctgatgat gttgctgatt cttctaaatc    180

ttttgtgatg gaaaactttt cttcgtacca cgggactaaa cctggttatg tagagtccat    240

tcaaaaaggt atacaaaagc caaaatctgg tacacaagga aattatgacg atgattggaa    300

agggttttat agtaccgaca ataaatacga cgctgcggga tactctgtag ataatgaaaa    360

cccgctctct ggaaaagctg gaggcgtggt caaagtgacg tatccaggac tgacgaaggt    420

tctcgcacta aaagtggata atgccgaaac tattaagaaa gagttaggtt taagtctcac    480

tgaaccgttg atggagcaag tcggaacgga agagtttatc aaaaggttcg gtgatggtgc    540

ttcgcgtgta gtgctcagcc ttcccttcgc tgaggggagt tctagcgttg aatatattaa    600

taactgggaa caggcgaaag cgttaagcgt agaacttgag attaattttg aaacccgtgg    660

aaaacgtggc caagatgcga tgtatgagta tatggctcaa gcctgtgcag gaaatcgtgt    720

caggcgatca gtaggtagct cattgtcatg catcaacctg gattgggatg ttatccgtga    780

taaaactaaa actaagatcg aatctctgaa agaacacggt ccgatcaaaa acaaaatgag    840

cgaaagcccg aacaaaactg tatctgaaga aaaagctaaa cagtacctgg aagaattcca    900

ccagactgca ctggaacacc cggaactgtc tgaacttaag accgttactg gtaccaaccc    960

ggtattcgct ggtgctaact acgctgcttg ggcagtaaac gttgctcagg ttatcgatag   1020
```

```
cgaaactgct gataacctgg aaaaaactac cgcggctctg tctatcctgc cgggtatcgg   1080

tagcgtaatg ggcatcgcag acggcgccgt tcaccacaac actgaagaaa tcgttgcaca   1140

gtctatcgct ctgagctctc tgatggttgc tcaggccatc ccgctggtag gtgaactggt   1200

tgatatcggt ttcgctgcat acaacttcgt tgaaagcatc atcaacctgt tccaggttgt   1260

tcacaactct tacaaccgcc cggcttactc tccgggtcac aagacgcatg cacctacttc   1320

tagctctacc aagaaaaccc agctgcagct cgagcacctg ctgctggatt tgcagatgat   1380

cctgaacggt atcaacaatt acaagaaccc gaaactgacg cgtatgctga ccttcaagtt   1440

ctacatgccg aagaaggcca ccgaactgaa acacctgcag tgtctagaag aagaactgaa   1500

accgctggag gaagttctga acctggctca gtctaaaaac ttccacctgc ggccgcgtga   1560

cctgatctct aacatcaacg taatcgttct ggaactgaag ggctctgaaa ccaccttcat   1620

gtgtgaatac gctgatgaga ccgcaaccat cgtagaattc ctgaaccgtt ggatcacctt   1680

ctgtcagtct atcatctcta ccctgaccca ccatcaccat catcactga              1729
```

```
<210> SEQ ID NO 127
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gly Ala Glu Asp Val Val Asp Thr Ser Lys Ser Phe Val Met Glu Asn
1               5                   10                  15

Phe Ser Ser Tyr His Gly Thr Lys Pro Gly Tyr Val Glu Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240
```

```
Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520


<210> SEQ ID NO 128
<211> LENGTH: 1711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128

ttgatttcag agcaccctta taattaggat agctaagtcc attattttat gagtcctggt      60

aaggggatac gttgtgagca gaaaactgtt tgcgtcaatc ttaatagggg cgctactggg     120

gataggggcc ccaccttcag cccatgcagg cgctgatgat gttgttgata cttctaaatc     180

ttttgtgatg gaaaactttt cttcgtacca cgggactaaa cctggttatg tagagtccat     240

tcaaaaaggt atacaaaagc caaaatctgg tacacaagga aattatgacg atgattggaa     300

agggttttat agtaccgaca ataaatacga cgctgcggga tactctgtag ataatgaaaa     360

cccgctctct ggaaaagctg gaggcgtggt caaagtgacg tatccaggac tgacgaaggt     420
```

tctcgcacta aaagtggata atgccgaaac tattaagaaa gagttaggtt taagtctcac 480
tgaaccgttg atggagcaag tcggaacgga agagtttatc aaaaggttcg gtgatggtgc 540
ttcgcgtgta gtgctcagcc ttcccttcgc tgaggggagt tctagcgttg aatatattaa 600
taactgggaa caggcgaaag cgttaagcgt agaacttgag attaattttg aaacccgtgg 660
aaaacgtggc caagatgcga tgtatgagta tatggctcaa gcctgtgcag gaaatcgtgt 720
caggcgatca gtaggtagct cattgtcatg catcaacctg gattgggatg ttatccgtga 780
taaaactaaa actaagatcg aatctctgaa agaacacggt ccgatcaaaa acaaaatgag 840
cgaaagcccg aacaaaactg tatctgaaga aaaagctaaa cagtacctgg aagaattcca 900
ccagactgca ctggaacacc cggaactgtc tgaacttaag accgttactg gtaccaaccc 960
ggtattcgct ggtgctaact acgctgcttg ggcagtaaac gttgctcagg ttatcgatag 1020
cgaaactgct gataacctgg aaaaaactac cgcggctctg tctatcctgc cgggtatcgg 1080
tagcgtaatg ggcatcgcag acggcgccgt tcaccacaac actgaagaaa tcgttgcaca 1140
gtctatcgct ctgagctctc tgatggttgc tcaggccatc ccgctggtag gtgaactggt 1200
tgatatcggt ttcgctgcat acaacttcgt tgaaagcatc atcaacctgt tccaggttgt 1260
tcacaactct tacaaccgcc cggcttactc tccgggtcac aagacgcatg cacctacttc 1320
tagctctacc aagaaaaccc agctgcagct cgagcacctg ctgctggatt tgcagatgat 1380
cctgaacggt atcaacaatt acaagaaccc gaaactgacg cgtatgctga ccttcaagtt 1440
ctacatgccg aagaaggcca ccgaactgaa acacctgcag tgtctagaag aagaactgaa 1500
accgctggag gaagttctga acctggctca gtctaaaaac ttccacctgc ggccgcgtga 1560
cctgatctct aacatcaacg taatcgttct ggaactgaag ggctctgaaa ccaccttcat 1620
gtgtgaatac gctgatgaga ccgcaaccat cgtagaattc ctgaaccgtt ggatcacctt 1680
ctgtcagtct atcatctcta ccctgacctg a 1711

<210> SEQ ID NO 129
<211> LENGTH: 526
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

Gly Ala Glu Asp Val Val Asp Thr Ser Lys Ser Phe Val Met Glu Asn
1 5 10 15

Phe Ser Ser Tyr His Gly Thr Lys Pro Gly Tyr Val Glu Ser Ile Gln
20 25 30

Lys Gly Ile Gln Lys Pro Lys Ser Gly Thr Gln Gly Asn Tyr Asp Asp
35 40 45

Asp Trp Lys Gly Phe Tyr Ser Thr Asp Asn Lys Tyr Asp Ala Ala Gly
50 55 60

Tyr Ser Val Asp Asn Glu Asn Pro Leu Ser Gly Lys Ala Gly Gly Val
65 70 75 80

Val Lys Val Thr Tyr Pro Gly Leu Thr Lys Val Leu Ala Leu Lys Val
85 90 95

Asp Asn Ala Glu Thr Ile Lys Lys Glu Leu Gly Leu Ser Leu Thr Glu
100 105 110

Pro Leu Met Glu Gln Val Gly Thr Glu Glu Phe Ile Lys Arg Phe Gly
115 120 125

```
Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525
```

<210> SEQ ID NO 130
<211> LENGTH: 1732

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 130

```
ttgatttcag agcaccctta taattaggat agctaagtcc attattttat gagtcctggt     60
aaggggatac gttgtgagca gaaaactgtt tgcgtcaatc ttaatagggg cgctactggg    120
gataggggcc ccaccttcag cccatgcagg cgctgatgat gttgttgata cttctaaatc    180
ttttgtgatg gaaaactttt cttcgtacca cgggactaaa cctggttatg tagagtccat    240
tcaaaaaggt atacaaaagc caaaatctgg tacacaagga aattatgacg atgattggaa    300
agggttttat agtaccgaca ataaatacga cgctgcggga tactctgtag ataatgaaaa    360
cccgctctct ggaaaagctg gaggcgtggt caaagtgacg tatccaggac tgacgaaggt    420
tctcgcacta aaagtggata atgccgaaac tattaagaaa gagttaggtt taagtctcac    480
tgaaccgttg atggagcaag tcggaacgga agagtttatc aaaaggttcg gtgatggtgc    540
ttcgcgtgta gtgctcagcc ttcccttcgc tgaggggagt tctagcgttg aatatattaa    600
taactgggaa caggcgaaag cgttaagcgt agaacttgag attaattttg aaacccgtgg    660
aaaacgtggc caagatgcga tgtatgagta tatggctcaa gcctgtgcag gaaatcgtgt    720
caggcgatca gtaggtagct cattgtcatg catcaacctg gattgggatg ttatccgtga    780
taaaactaaa actaagatcg aatctctgaa agaacacggt ccgatcaaaa acaaaatgag    840
cgaaagcccg aacaaaactg tatctgaaga aaaagctaaa cagtacctgg aagaattcca    900
ccagactgca ctggaacacc cggaactgtc tgaacttaag accgttactg gtaccaaccc    960
ggtattcgct ggtgctaact acgctgcttg ggcagtaaac gttgctcagg ttatcgatag   1020
cgaaactgct gataacctgg aaaaaactac cgcggctctg tctatcctgc cgggtatcgg   1080
tagcgtaatg ggcatcgcag acggcgccgt tcaccacaac actgaagaaa tcgttgcaca   1140
gtctatcgct ctgagctctc tgatggttgc tcaggccatc ccgctggtag gtgaactggt   1200
tgatatcggt ttcgctgcat acaacttcgt tgaaagcatc atcaacctgt tccaggttgt   1260
tcacaactct tacaaccgcc cggcttactc tccgggtcac aagacgcatg cacctacttc   1320
tagctctacc aagaaaaccc agctgcagct cgagcacctg ctgctggatt tgcagatgat   1380
cctgaacggt atcaacaatt acaagaaccc gaaactgacg cgtatgctga ccttcaagtt   1440
ctacatgccg aagaaggcca ccgaactgaa acacctgcag tgtctagaag aagaactgaa   1500
accgctggag gaagttctga acctggctca gtctaaaaac ttccacctgc ggccgcgtga   1560
cctgatctct aacatcaacg taatcgttct ggaactgaag ggctctgaaa ccaccttcat   1620
gtgtgaatac gctgatgaga ccgcaaccat cgtagaattc ctgaaccgtt ggatcacctt   1680
ctgtcagtct atcatctcta ccctgacctg acaccatcac catcatcact ga           1732
```

<210> SEQ ID NO 131
<211> LENGTH: 108
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 131

```
ttgacaatta atcatcggct cgtataatgt gtggaatttc acacaggaaa cagccagtcc     60
```

```
gtttaggtgt tttcacgagc acttcaccaa caaggaccat agattgtg                108


<210> SEQ ID NO 132
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350
```

-continued

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ile His Gly Cys Asp Lys Asn His Leu Arg Glu Ile Ile
385                 390                 395                 400

Gly Ile Leu Asn Glu Val Thr Gly Glu Gly Thr Pro Cys Thr Glu Met
                405                 410                 415

Asp Val Pro Asn Val Leu Thr Ala Thr Lys Asn Thr Thr Glu Ser Glu
            420                 425                 430

Leu Val Cys Arg Ala Ser Lys Val Leu Arg Ile Phe Tyr Leu Lys His
        435                 440                 445

Gly Lys Thr Pro Cys Leu Lys Lys Asn Ser Ser Val Leu Met Glu Leu
    450                 455                 460

Gln Arg Leu Phe Arg Ala Phe Arg Cys Leu Asp Ser Ser Ile Ser Cys
465                 470                 475                 480

Thr Met Asn Glu Ser Lys Ser Thr Ser Leu Lys Asp Phe Leu Glu Ser
                485                 490                 495

Leu Lys Ser Ile Met Gln Met Asp Tyr Ser
            500                 505

<210> SEQ ID NO 133
<211> LENGTH: 1596
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
gtgagcagaa aactgtttgc gtcaatctta ataggggcgc tactggggat aggggcccca     60
ccttcagccc atgcaggcgc tgatgatgtt gttgattctt ctaaatcttt tgtgatggaa    120
aacttttctt cgtaccacgg gactaaacct ggttatgtag attccattca aaaaggtata    180
caaaagccaa aatctggtac acaaggaaat tatgacgatg attggaaagg gttttatagt    240
accgacaata aatacgacgc tgcgggatac tctgtagata atgaaaaccc gctctctgga    300
aaagctggag gcgtggtcaa agtgacgtat ccaggactga cgaaggttct cgcactaaaa    360
gtggataatg ccgaaactat taagaaagag ttaggtttaa gtctcactga accgttgatg    420
gagcaagtcg gaacggaaga gtttatcaaa aggttcggtg atggtgcttc gcgtgtagtg    480
ctcagccttc ccttcgctga ggggagttct agcgttgaat atattaataa ctgggaacag    540
gcgaaagcgt taagcgtaga acttgagatt aattttgaaa cccgtggaaa acgtggccaa    600
gatgcgatgt atgagtatat ggctcaagcc tgtgcaggaa atcgtgtcag gcgatcagta    660
ggtagctcat tgtcatgcat caacctggat tgggatgtta tccgtgataa aactaaaact    720
aagatcgaat ctctgaaaga acacggtccg atcaaaaaca aaatgagcga aagcccgaac    780
aaaactgtat ctgaagaaaa agctaaacag tacctggaag aattccacca gactgcactg    840
gaacacccgg aactgtctga acttaagacc gttactggta ccaacccggt attcgctggt    900
gctaactacg ctgcttgggc agtaaacgtt gctcaggtta tcgatagcga aactgctgat    960
aacctggaaa aaactaccgc ggctctgtct atcctgccgg gtatcggtag cgtaatgggc   1020
atcgcagacg gcgccgttca ccacaacact gaagaaatcg ttgcacagtc tatcgctctg   1080
agctctctga tggttgctca ggccatcccg ctggtaggtg aactggttga tatcggtttc   1140

```
gctgcataca acttcgttga aagcatcatc aacctgttcc aggttgttca caactcttac   1200

aaccgcccgg cttactctcc gggtcacaag acgcatattc atggctgcga taaaaaccat   1260

ctgcgcgaaa ttattggcat tctgaacgaa gtgaccggcg aaggcacccc gtgcaccgaa   1320

atggatgtgc cgaacgtgct gaccgcgacc aaaaacacca ccgaaagcga actggtgtgc   1380

cgcgcgagca aagtgctgcg catttttat ctgaaacatg gcaaaacccc gtgcctgaaa    1440

aaaaacagca gcgtgctgat ggaactgcag cgcctgtttc gcgcgtttcg ctgcctggat   1500

agcagcatta gctgcaccat gaacgaaagc aaaagcacca gcctgaaaga ttttctggaa   1560

agcctgaaaa gcattatgca gatggattat agctag                             1596


<210> SEQ ID NO 134
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
```

```
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ile His Gly Cys Asp Lys Asn His Leu Arg Glu Ile Ile
385                 390                 395                 400

Gly Ile Leu Asn Glu Val Thr Gly Glu Gly Thr Pro Cys Thr Glu Met
                405                 410                 415

Asp Val Pro Asn Val Leu Thr Ala Thr Lys Asn Thr Thr Glu Ser Glu
            420                 425                 430

Leu Val Cys Arg Ala Ser Lys Val Leu Arg Ile Phe Tyr Leu Lys His
        435                 440                 445

Gly Lys Thr Pro Cys Leu Lys Lys Asn Ser Ser Val Leu Met Glu Leu
    450                 455                 460

Gln Arg Leu Phe Arg Ala Phe Arg Cys Leu Asp Ser Ser Ile Ser Cys
465                 470                 475                 480

Thr Met Asn Glu Ser Lys Ser Thr Ser Leu Lys Asp Phe Leu Glu Ser
                485                 490                 495

Leu Lys Ser Ile Met Gln Met Asp Tyr Ser Glu Asn Leu Tyr Phe Gln
            500                 505                 510

Gly His His His His His His
        515


<210> SEQ ID NO 135
<211> LENGTH: 1635
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

gtgagcagaa aactgtttgc gtcaatctta ataggggcgc tactggggat aggggcccca      60

ccttcagccc atgcaggcgc tgatgatgtt gttgattctt ctaaatcttt tgtgatggaa     120

aacttttctt cgtaccacgg gactaaacct ggttatgtag attccattca aaaaggtata     180

caaaagccaa aatctggtac acaaggaaat tatgacgatg attggaaagg gttttatagt     240

accgacaata aatacgacgc tgcgggatac tctgtagata atgaaaaccc gctctctgga     300

aaagctggag gcgtggtcaa agtgacgtat ccaggactga cgaaggttct cgcactaaaa     360

gtggataatg ccgaaactat taagaaagag ttaggtttaa gtctcactga accgttgatg     420

gagcaagtcg gaacggaaga gtttatcaaa aggttcggtg atggtgcttc gcgtgtagtg     480

ctcagccttc ccttcgctga ggggagttct agcgttgaat atattaataa ctgggaacag     540

gcgaaagcgt taagcgtaga acttgagatt aattttgaaa cccgtggaaa acgtggccaa     600

gatgcgatgt atgagtatat ggctcaagcc tgtgcaggaa atcgtgtcag gcgatcagta     660
```

```
ggtagctcat tgtcatgcat caacctggat tgggatgtta tccgtgataa aactaaaact    720

aagatcgaat ctctgaaaga acacggtccg atcaaaaaca aaatgagcga aagcccgaac    780

aaaactgtat ctgaagaaaa agctaaacag tacctggaag aattccacca gactgcactg    840

gaacacccgg aactgtctga acttaagacc gttactggta ccaacccggt attcgctggt    900

gctaactacg ctgcttgggc agtaaacgtt gctcaggtta tcgatagcga aactgctgat    960

aacctggaaa aaactaccgc ggctctgtct atcctgccgg gtatcggtag cgtaatgggc   1020

atcgcagacg gcgccgttca ccacaacact gaagaaatcg ttgcacagtc tatcgctctg   1080

agctctctga tggttgctca ggccatcccg ctggtaggtg aactggttga tatcggtttc   1140

gctgcataca acttcgttga aagcatcatc aacctgttcc aggttgttca caactcttac   1200

aaccgcccgg cttactctcc gggtcacaag acgcatattc atggctgcga taaaaaccat   1260

ctgcgcgaaa ttattggcat tctgaacgaa gtgaccggcg aaggcacccc gtgcaccgaa   1320

atggatgtgc cgaacgtgct gaccgcgacc aaaaacacca ccgaaagcga actggtgtgc   1380

cgcgcgagca aagtgctgcg catttttat ctgaaacatg gcaaaacccc gtgcctgaaa   1440

aaaaacagca gcgtgctgat ggaactgcag cgcctgtttc gcgcgtttcg ctgcctggat   1500

agcagcatta gctgcaccat gaacgaaagc aaaagcacca gcctgaaaga ttttctggaa   1560

agcctgaaaa gcattatgca gatggattat agcgagaacc tgtacttcca gggccatcac   1620

caccaccacc actag                                                    1635
```

<210> SEQ ID NO 136
<211> LENGTH: 15
<212> TYPE: PRT
<213> ORGANISM: Corynebacterium diphtheriae

<400> SEQUENCE: 136

```
Gly Ala Asp Asp Val Val Asp Ser Ser Lys Ser Phe Val Met Glu
1               5                   10                  15
```

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

```
Gly Ala Asp Asp Val Ala Asp Ser Ser Lys Ser Phe Val Met Glu
1               5                   10                  15
```

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

```
Gly Ala Glu Asp Val Val Asp Ser Ser Lys Ser Phe Val Met Glu
1               5                   10                  15
```

<210> SEQ ID NO 139
<211> LENGTH: 15
<212> TYPE: PRT
<213> ORGANISM: Corynebacterium diphtheriae -continued

```
<400> SEQUENCE: 139

Thr Lys Pro Gly Tyr Val Asp Ser Ile Gln Lys Gly Ile Gln Lys
1               5                   10                  15


<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Thr Lys Pro Gly Tyr Val Glu Ser Ile Gln Lys Gly Ile Gln Lys
1               5                   10                  15
```

The invention claimed is:

1. A method of treating cancer in a subject comprising:

(a) administering to a subject having cancer a first agent that depletes the subject's regulatory T cells (Tregs) comprising a diphtheria toxin fusion protein which comprises a diphtheria toxin fragment A; a diphtheria toxin fragment B; or a combination thereof, wherein the first agent comprises (i) SEQ ID NO: 58; SEQ ID NO: 15, SEQ ID NO: 43; or a combination thereof or (ii) an expression vector encoding a protein sequence comprising SEQ ID NO: 58; SEQ ID NO: 15, SEQ ID NO: 43; or a combination thereof; followed by (b) administering to the subject a second agent comprising a checkpoint inhibitor, wherein the cancer is a Tregs infiltrated cancer, thereby treating cancer in the subject.

2. The method of claim 1 wherein the cancer is melanoma, breast cancer, colon cancer, renal cell cancer, glioblastoma multiforme, lung cancer or epidermoid carcinoma.

3. The method of claim 1 wherein the diphtheria toxin fusion protein comprises human interleukin sequences.

4. The method of claim 3 wherein the human interleukin sequences consist of an IL-2 protein or functional parts thereof.

5. The method of claim 3 wherein the diphtheria toxin fusion protein, comprising a mutant diphtheria toxin protein, causes reduced vascular leakage as compared to a reference diphtheria toxin fusion protein comprising a wild-type diphtheria toxin protein.

6. The method of claim 1 wherein the checkpoint inhibitor is an anti-CTLA-4 antibody, an anti-PD-1 antibody, an anti-PD-L1 antibody, or a combination thereof.

7. The method of claim 1 wherein the checkpoint inhibitor is selected from the group consisting of ipilimumab (anti-CTLA-4), nivolumab (anti-PD-1), pembrolizumab (anti-PD-1), atezolizumab (anti-PD-L1), avelumab (anti-PD-L1), and durvalumab (anti-PD-L1), or a combination thereof.

8. The method of claim 1 wherein the second agent is an anti-PD1 antibody.

9. A method of treating cancer in a subject comprising:

(a) administering to a subject having cancer a first agent that depletes the subject's regulatory T cells (Tregs) comprising a diphtheria toxin fusion protein, wherein the first agent comprises (i) SEQ ID NO: 58; or SEQ ID NO: 43; or (ii) an expression vector encoding a protein sequence comprising SEQ ID NO: 58; or SEQ ID NO: 43; followed by (b) administering to the subject a second agent comprising a checkpoint inhibitor, wherein the checkpoint inhibitor is an anti-PD-1 antibody, wherein the cancer is a Tregs infiltrated cancer, thereby treating cancer in the subject.

* * * * *